(12) United States Patent
Vazquez et al.

(10) Patent No.: US 11,072,616 B2
(45) Date of Patent: *Jul. 27, 2021

(54) CYCLIC PEPTIDES TARGETING ALPHA-4-BETA-7 INTEGRIN

(71) Applicants: Zealand Pharma A/S, Søborg (DK); UNIVERSITE DE MONTREAL, Montreal (CA)

(72) Inventors: Manuel Perez Vazquez, Milton (CA); M. Monzur Morshed, Mississauga (CA); Jennifer L. Hickey, Toronto (CA); Adam Paul Kafal, Toronto (CA); James Gillard, Rosemere (CA); Narendra Patel, Brampton (CA); Sai Kumar Chakka, Brampton (CA); Andrew L. Roughton, Port Hope (CA); Marc-André Poupart, Laval (CA); Gaoqiang Yang, Montreal (CA)

(73) Assignees: Universite de Montreal, Montreal (CA); Zealand Pharma A/S, Søborg (DK)

(*) Notice: Subject to any disclaimer, the term of this patent is extended or adjusted under 35 U.S.C. 154(b) by 90 days.

This patent is subject to a terminal disclaimer.

(21) Appl. No.: 15/775,309

(22) PCT Filed: Nov. 14, 2016

(86) PCT No.: PCT/CA2016/000274
§ 371 (c)(1),
(2) Date: May 10, 2018

(87) PCT Pub. No.: WO2017/079820
PCT Pub. Date: May 18, 2017

(65) Prior Publication Data
US 2020/0165300 A1    May 28, 2020

Related U.S. Application Data

(60) Provisional application No. 62/254,003, filed on Nov. 11, 2015.

(51) Int. Cl.
C07D 487/04    (2006.01)
C07C 271/18    (2006.01)
(Continued)

(52) U.S. Cl.
CPC ............. *C07D 487/04* (2013.01); *A61P 1/04* (2018.01); *C07C 271/18* (2013.01);
(Continued)

(58) Field of Classification Search
CPC .... A61K 38/00; A61K 9/0014; A61K 9/0053; A61P 11/02; A61P 11/06; A61P 11/08;
(Continued)

(56) References Cited

U.S. PATENT DOCUMENTS 5,296,604 A    3/1994    Hanko et al.
5,693,325 A    12/1997    Kahn
(Continued)

FOREIGN PATENT DOCUMENTS

CA    2427046 A1    11/2003
DE    3219113        11/1983
(Continued)

OTHER PUBLICATIONS

Walker et al., New Naturally Occurring Amino Acids, Angew. Chem. Int. Ed. Engl., vol. 22:816-828 (1983) (Year: 1983).*
(Continued)

*Primary Examiner* — Randall L Beane
(74) *Attorney, Agent, or Firm* — Clark & Elbing LLP

(57) ABSTRACT

There is described herein antagonists of α4β7 integrin, and more particularly to cyclic peptide antagonists. Accordingly, there is described herein a compound of formula (I) wherein $R^1$, $R^2$, $R^3$, $R^4$, $R^5$, $R^6$, $R^7$ and $R^8$ are various substituents; stereocentres 1*, 2* and 3* are each independently selected from R and S; n is 1, 2, 3, or 4 and where n is 2-4, Z is an
(Continued)

amino terminus of an amino acid; —C═O— adjacent L is the carboxy terminus of an amino acid; and L along with Z and —C═O— is a peptide.

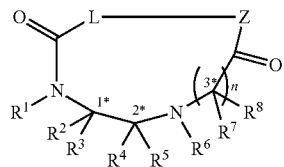

(I)

40 Claims, 47 Drawing Sheets

Specification includes a Sequence Listing.

(51) Int. Cl.
| | |
|---|---|
| C07C 271/22 | (2006.01) |
| C07D 207/16 | (2006.01) |
| C07K 7/06 | (2006.01) |
| C07K 7/56 | (2006.01) |
| A61P 1/04 | (2006.01) |
| C07K 7/54 | (2006.01) |
| C07K 7/64 | (2006.01) |
| A61K 9/00 | (2006.01) |
| A61K 38/00 | (2006.01) |
| C07K 1/107 | (2006.01) |

(52) U.S. Cl.
CPC .......... C07C 271/22 (2013.01); C07D 207/16 (2013.01); C07K 1/1075 (2013.01); C07K 7/06 (2013.01); C07K 7/54 (2013.01); C07K 7/56 (2013.01); C07K 7/64 (2013.01); A61K 9/0014 (2013.01); A61K 9/0053 (2013.01); A61K 38/00 (2013.01); C07C 2603/18 (2017.05)

(58) Field of Classification Search
CPC .......... A61P 15/14; A61P 19/02; A61P 19/10; A61P 1/00; A61P 1/04; A61P 1/14; A61P 1/16; A61P 1/18; A61P 25/00; A61P 25/04; A61P 25/24; A61P 25/28; A61P 29/00; A61P 31/12
See application file for complete search history.

(56) References Cited

U.S. PATENT DOCUMENTS

| | | | |
|---|---|---|---|
| 5,693,612 | A | 12/1997 | Jonczyk et al. |
| 5,693,750 | A | 12/1997 | Ohki et al. |
| 5,696,084 | A | 12/1997 | Lartey et al. |
| 5,705,481 | A | 1/1998 | Jonczyk et al. |
| 5,731,286 | A | 3/1998 | Harbeson et al. |
| 6,492,553 | B1 | 12/2002 | Hulme et al. |
| 2008/0200398 | A1 | 8/2008 | Smyth et al. |
| 2011/0251247 | A1 | 10/2011 | Chubb et al. |
| 2014/0193465 | A1 | 7/2014 | Bhandari et al. |
| 2016/0159862 | A1 | 6/2016 | Bhandari et al. |
| 2019/0077805 | A1 | 3/2019 | Vazquez et al. |

FOREIGN PATENT DOCUMENTS

| | | | | |
|---|---|---|---|---|
| WO | WO-9620216 A1 * | 7/1996 | ............. | A61P 29/00 |
| WO | WO 2001/010799 | 2/2001 | | |
| WO | WO-02/066500 A2 | 8/2002 | | |
| WO | WO 2008/046232 | 4/2008 | | |
| WO | WO 2009/141687 | 11/2009 | | |
| WO | WO 2010/105363 | 9/2010 | | |
| WO | WO 2010/107832 | 9/2010 | | |
| WO | WO-2014/59213 A1 | 4/2014 | | |
| WO | WO-2016/054411 A1 | 4/2016 | | |
| WO | WO-2016/054445 A1 | 4/2016 | | |
| WO | WO 2017/079820 | 5/2017 | | |
| WO | WO 2017/079821 | 5/2017 | | |

OTHER PUBLICATIONS

Achmatowicz & Jurczak, "The Synthesis of L-Proline Derived Hexaazamacrocyclic Ligands of C3 Symmetry Via Intramolecular Methyl Ester Aminolysis," *Tetrahedron: Assymetry*, 12(3): 487-495, 2001.

Baktharaman, et al., "Amino Carbonyl Compounds in Organic Synthesis," *Aldrichimica Acta*, 41: 109-117, 2008.

Burden et al., "Synthesis and biological activities of YkFA analogues: effects of position 4 substitutions and altered ring size on in vitro opioid activity," *Bioorganic & Medicinal Chemistry Letters*, 12 (2002) 213-216.

Couturier et al., "Aziridinium from N,N-dibenzyl Serine Methyl Ester: Synthesis of Enantiomerically Pure β-amino and α,β-diamino Esters" *Organic Letters*, 8(10):2183-2186, 2006.

Hili & Yudin, et al., "Readily Available Unprotected Amino Aldehydes," *Journal of the American Chemical Society*, 128(46): 14772-14773, 2006.

Hili, et al., Macrocyclization of Linear Peptides Enabled by Amphoteric Molecules, *Journal of the American Chemical Society*, 132: 2889-2891, 2010.

Hirose et al., "Total Synthesis and Determination of the Absolute Configuration of Guadinomines Band C2," *Chemistry—A European Journal*, 14:8220-8238, 2008.

International Search Report and Written Opinion Issued in Corresponding PCT Application No. PCT/CA2016/000275, dated Feb. 28, 2017.

International Search Report and Written Opinion Issued in Corresponding PCT Application No. PCT/CA2017/000244, dated Feb. 8, 2018.

International Search Report and Written Opinion Issued in Corresponding PCT Application No. PCT/CA2016/000274, dated Dec. 19, 2016.

Mohan et al., "Synthesis and Biological Activity of Angiotensin II Analog Containing a Val-His Replacement, Val.psi. [CH(CONH2)HN]His" *Journal of Medicinal Chemistry*, 34(8):2402-2410, 1991.

Murray et al., "The Synthesis of Cyclic Tetrapeptoid Analogues of the Antiprotozoal Natural Product Apicidin," *Bioorganic & Medicinal Chemistry Letters*, 22: 773-776, 2001.

Pil et al., "Synthesis and Electrophysiological Characterization of Cyclic Morphiceptin Analogues," *Biochem. Pharma.*, 67, 1887-1895, 2004.

Quartara et al., "Influence of Lipophilicity on the Biological Activity of Cyclic Pseudopeptide NK-2 Receptor Antagonists," *Journal of Medicinal Chemistry*, 37:3630-3638, 1994.

Rotstein, "Synthesis of Peptide Macrocycles Using Unprotected Amino Aldehydes," *Nature Protocols*, 5(11): 1813-1822, 2010.

Slama et al., "Convenient Synthesis of 1,2-Diamines from β-Chloro Amines: Precursors of New Substituted Piperazin-2-ones" *Synthetic Communications*, 43(17):2286-2293, 2013.

Suarez-Gea et al., "General Method for the Synthesis of Carbamoylmethyleneamino Pseudopeptides" *Journal of Organic Chemistry*, 1994, 59(13):3600-3603.

Vercillo, et al., "Design and Synthesis of Cyclic RGD Pentapeptoids by Consecutive Ugi Reactions," *Organic Letters*, 10: 205-208, 2007.

Yudin & Hili, "Overcoming the Demons of Protecting Groups with Amphoteric Molecules," *Chemistry—A European Journal*, 13:6539-6542, 2007.

Tamamura et al., "Stereoselective synthesis of [L-Arg-L/D-3-(2-naphthyl)alanine]-type (E)-alkene dipeptide isosteres and its appli-

(56) References Cited

OTHER PUBLICATIONS cation to the synthesis and biological evaluation of pseudopeptide analogues of the CXCR4 antagonist FC131," J Med Chem. 48(2):380-91 (2005).
International Search Report and Written Opinion Issued in PCT Application No. PCT/CA2018/000087, dated Aug. 7, 2018.
Tal-Gan et al., "Backbone cyclic peptide inhibitors of protein kinase B (PKB/Akt)," J Med Chem. 54(14):5154-64 (2011).
Verheijen et al., "An expeditious liquid-phase synthesis of cyclic peptide nucleic acids," Tetrahedron Letters. 41(20):3991-5 (2000).
Naveh et al., "Developing potent backbone cyclic peptides bearing the shared epitope sequence as rheumatoid arthritis drug-leads," Bioorg Med Chem Lett. 22(1):493-6 (2012).
Chen et al., "Synthesis of 12-membered macrocyclic templates and library analogs for PPI," Tetrahedron Letters. 54(25):3298-301 (2013).
Extended European Search Report for European Application No. 16863253.7, dated Oct. 17, 2019 (6 pages).
Greene et al., "Preface," *Protective Groups in Organic Synthesis*, Third Edition. John Wiley & Sons, Inc., v-vi (1999) (6 pages).
Dutta et al., "Potent cyclic monomeric and dimeric peptide inhibitors of VLA-4 (alpha4beta1 integrin)-mediated cell adhesion based on the Ile-Leu-Asp-Val tetrapeptide," J Pept Sci. 6(7):321-41 (2000).
Zaragoza Dorwald, "Side Reactions of Organic Synthesis: A Guide to Successful Synthesis Design," Weinheim: Wiley-VCH Verlag Gmbh & Co. KGaA, 2005, Preface.

U.S. Appl. No. 16/985,096, Vazquez et al.
Boer et al., "Design and synthesis of potent and selective alpha(4)beta(7) integrin antagonists," J Med Chem. 44(16):2586-92 (2001).
Examination Report for Indian Application No. 201817021544, dated May 18, 2020 (6 pages).
Extended European Search Report for European Application No. 17870529.9, dated Jul. 28, 2020 (14 pages).
Partial Supplementary European Search Report for European Application No. 17870529.9, dated Apr. 23, 2020 (10 pages).
Patil et al., "Second generation, arginine-rich (R-X'-R)(4)-type cell-penetrating alpha-omega-alpha-peptides with constrained, chiral omega-amino acids (X') for enhanced cargo delivery into cells," Bioorg Med Chem Lett. 24(17):4198-202 (Sep. 1, 2014, Epub Jul. 19, 2014).
Supporting Information for Patil et al., "Second generation, arginine-rich (R-X'-R)(4)-type cell-penetrating alpha-omega-alpha-peptides with constrained, chiral omega-amino acids (X') for enhanced cargo delivery into cells," Bioorg Med Chem Lett. 24(17):4198-202 (Sep. 1, 2014, Epub Jul. 19, 2014).
Treder et al., "Solid-phase synthesis of piperazinones via disrupted Ugi condensation," Org Lett. 16(17):4674-7 (Sep. 5, 2014, Epub Aug. 25, 2014).
Gottschling et al., "Synthesis and NMR structure of peptidomimetic alpha-4-beta-7-integrin antagonists," Chembiochem. 3(6):575-8 (2002).

* cited by examiner

| | a4b7 IC50 (uM) |
|---|---|
| Leu | 0.375 |
| Cha | 0.609 |
| vinyl-Br-Leu | 0.785 |
| Nle | 1.703 |
| HomoLeu | 3.025 |
| cyclopropylAla | 3.358 |
| CF3-(d/l)Leu | 3.668 |
| Nle | 3.615 |
| (d/l)Leu | 3.896 |
| Cha | 30.00 |
| Phe | 40.00 |
| Trp | |

| | a4b7 IC50 (uM) |
|---|---|
| Asp | 27.726 |
| Asp(alcohol) | 40 |
| Asp(OBn) | 50 (27 cell) |
| Asp(OEt) | |

| | a4b7 IC50 (uM) |
|---|---|
| Thr | 0.026 |
| Ile | 0.036 |
| Thr(OBn) | 0.042 |
| Thr(OEt) | 0.063 |
| Thr(OMe) | 0.113 |
| Pen | 0.109 |
| Val | 0.262 |
| dCys-Me ether | 0.389 |
| cyclohexylGly | 0.475 |
| allo-Ile | 1.00 |
| Cys | 1.00 |
| Cys(Acm) | 1.00 |
| thio-dPro | 1.088 |
| tBu-Gly | 4.00 |
| Asn | 15 |
| Gln | 45.3 |
| His | 56.6 |
| 2-aza-dPhe | |

| | a4b7 IC50 (uM) |
|---|---|
| "Tyr" | 0.005 |
| Met | 0.009 |
| Tyr(O-allyl) | 0.011 |
| CycloLeu | 0.016 |
| Aic | 0.019 |
| Pro | 0.021 |
| dTiq | 0.022 |
| dTic | 0.023 |
| dArg | 0.026 |
| 1Nal | 0.03 |
| 4-aza-dPhe | 0.03 |
| dHomoPro | 0.04 |
| 3-aza-dPhe | 0.035 |
| 4-amino-dPhe | 0.04 |
| Orn(ethylCarb) | 0.036 |
| dTyr(O-allyl) | 0.039 |
| Orn(Ac) | 0.04 |
| 2Nal | 0.042 |
| Phe | 0.046 |
| dTrp | 0.05 |
| dTyr(O-Bn) | 0.051 |
| Trp | 0.052 |
| 4-aminoMe-dPhe | 0.053 |
| benzthiophenyl-dAla | 0.053 |
| Lys | 0.054 |
| 2-thiophenyl-dAla | 0.057 |
| t-Disc | 0.057 |
| Tyr(4-CO2H diaryl ether) | 0.243 |
| Met-sulfoxide | 0.825 |
| P-Gt-LDT | 0.873 |
| Dab | 0.963 |
| Gly | 0.995 |
| Ser(OBn) | 1.05 |
| Tic | 1.078 |
| Asn | 1.496 |
| Glu | 3.832 |
| Asp | 3.664 |
| D-Disc | 6.935 |
| Asp-acyl-methanesulfonamide | |

PYLDT / ET00696
a4b7 ELISA IC50 = 0.129 uM
a4b1 ELISA IC50 = 0.357 uM (2.8X)
RPMI 8866 cell IC50 = 11.782 uM

Figure 2

| Parameter | Unit | Estimate |
|---|---|---|
| $t_{max}$ | h | 3.00 |
| $C_{max}$ | ng/mL | 581 |
| Apparent $t_{1/2}$ | h | nc |
| $AUC_{0-tlast}$ | h*ng/mL | 589 |
| $AUC_{0-inf}$ | h*ng/mL | nc |
| $MRT_{0-tlast}$ | h | 2.77 |

Summary of PK Parameters for ET01792-03

Measurement of colon length (A), lesion length (B) and colon/lesion length ratio in percentage (C) from DSS-induced UC mice, receiving vehicle or treatments either by oral or i.p. route.

Macroscopic inflammation score x colon/lesion length ratio calculated for the different groups of DSS-induced UC mice, receiving vehicle or treatments either by oral or i.p. route.

Figure 14
Compound No. 9
¹H NMR @ 25 °C
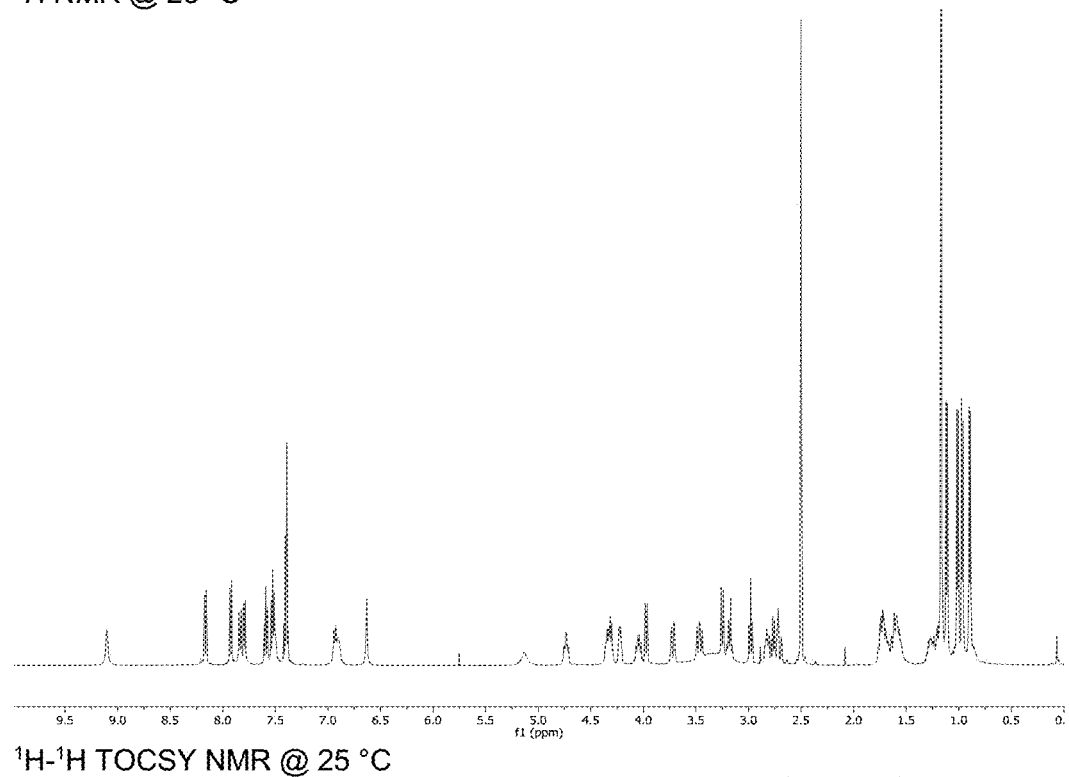
¹H-¹H TOCSY NMR @ 25 °C
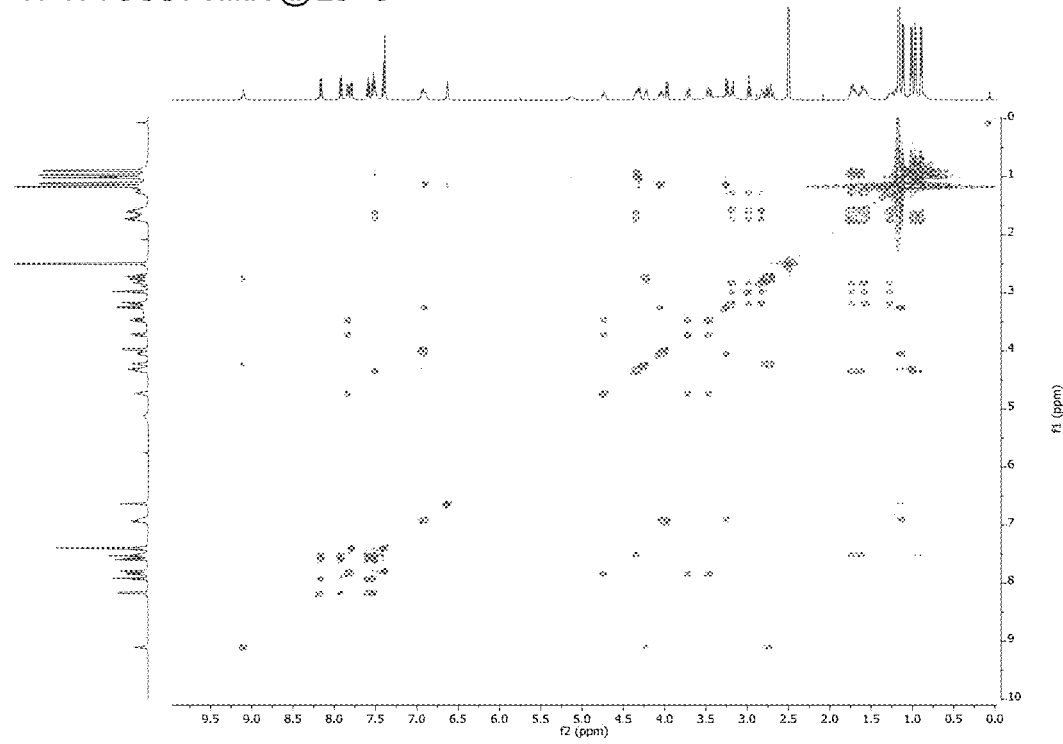

Figure 15
Compound No. 10
¹H NMR @ 25 °C
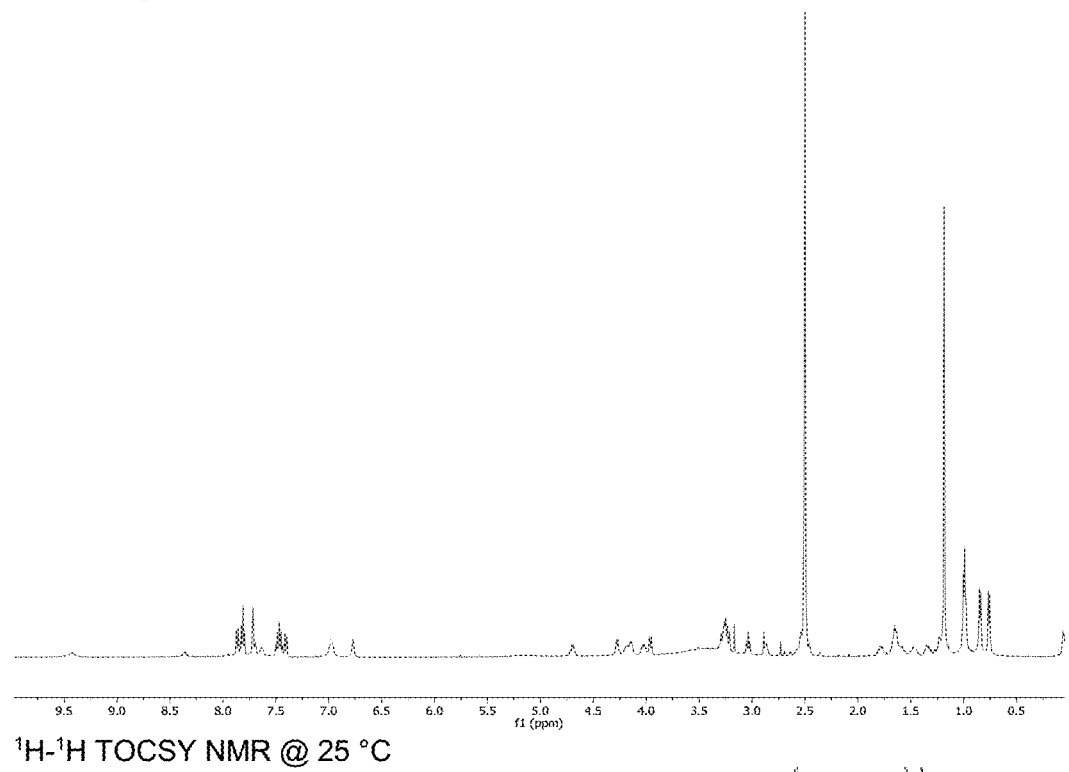
¹H-¹H TOCSY NMR @ 25 °C
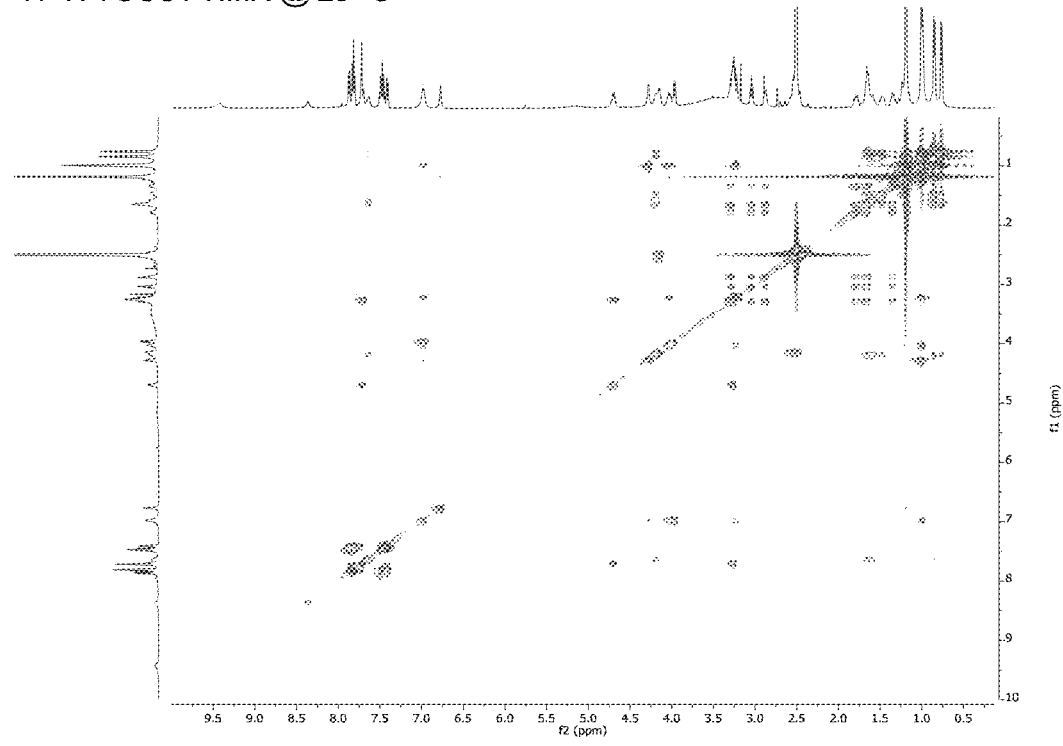

Figure 16
Compound No. 11
¹H NMR @ 25 °C
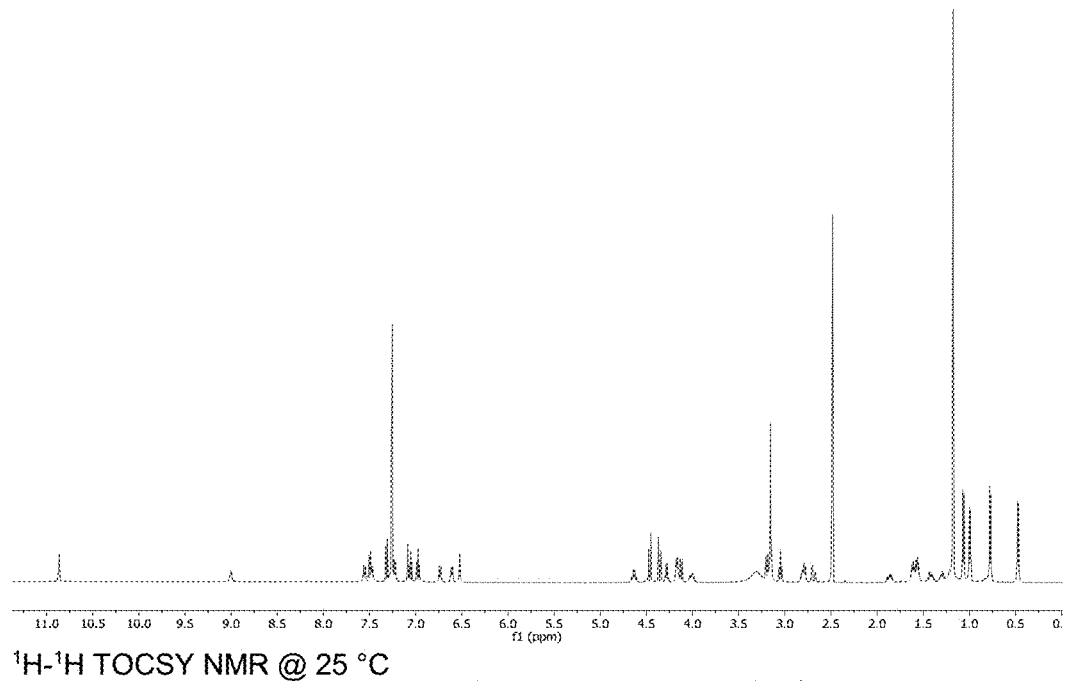
¹H-¹H TOCSY NMR @ 25 °C
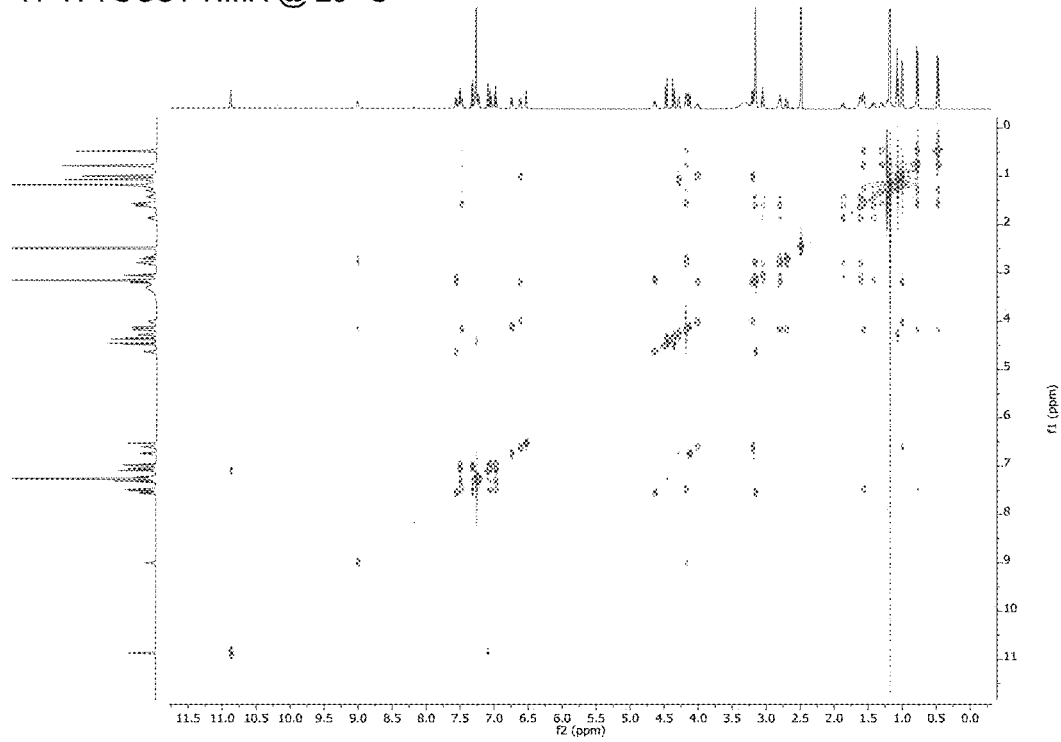

Figure 17
Compound No. 12
¹H NMR @ 25 °C
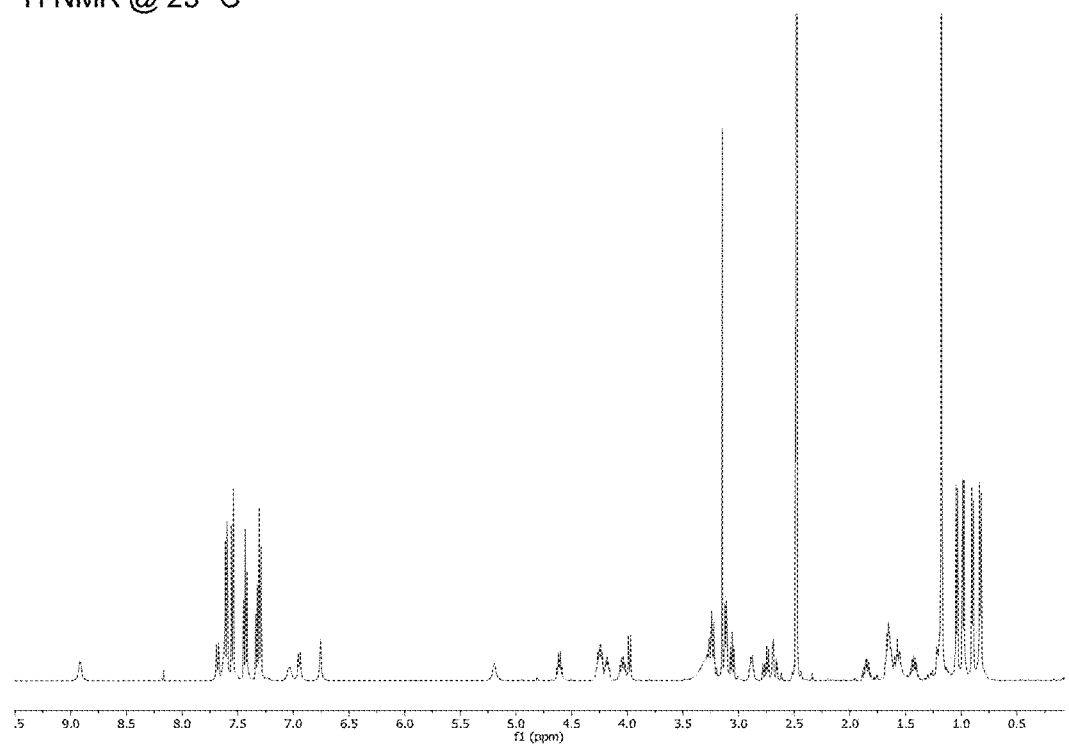
¹H-¹H TOCSY NMR @ 25 °C
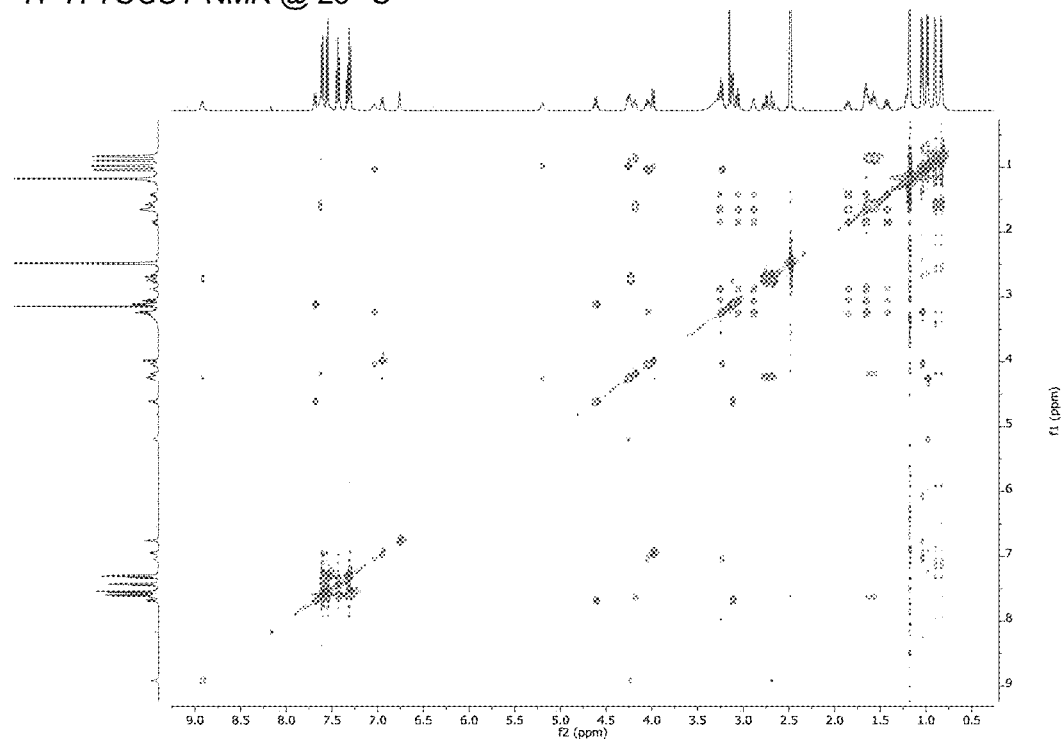

Figure 18
Compound No. 14
¹H NMR @ 25 °C
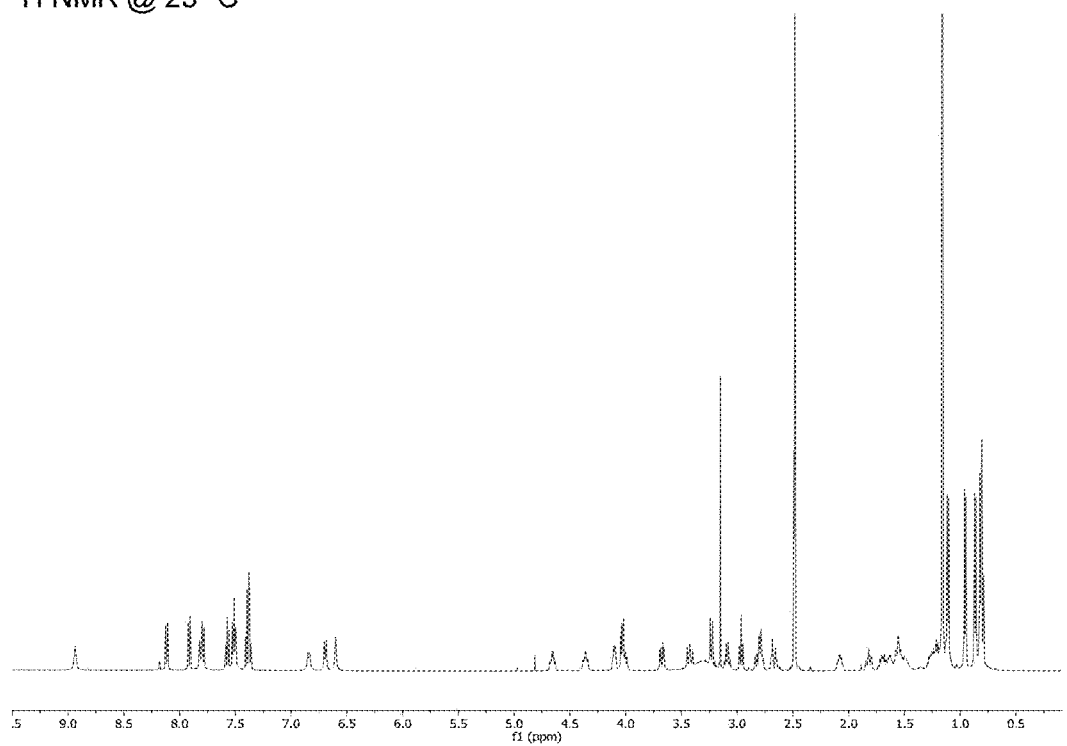
¹H-¹H TOCSY NMR @ 25 °C
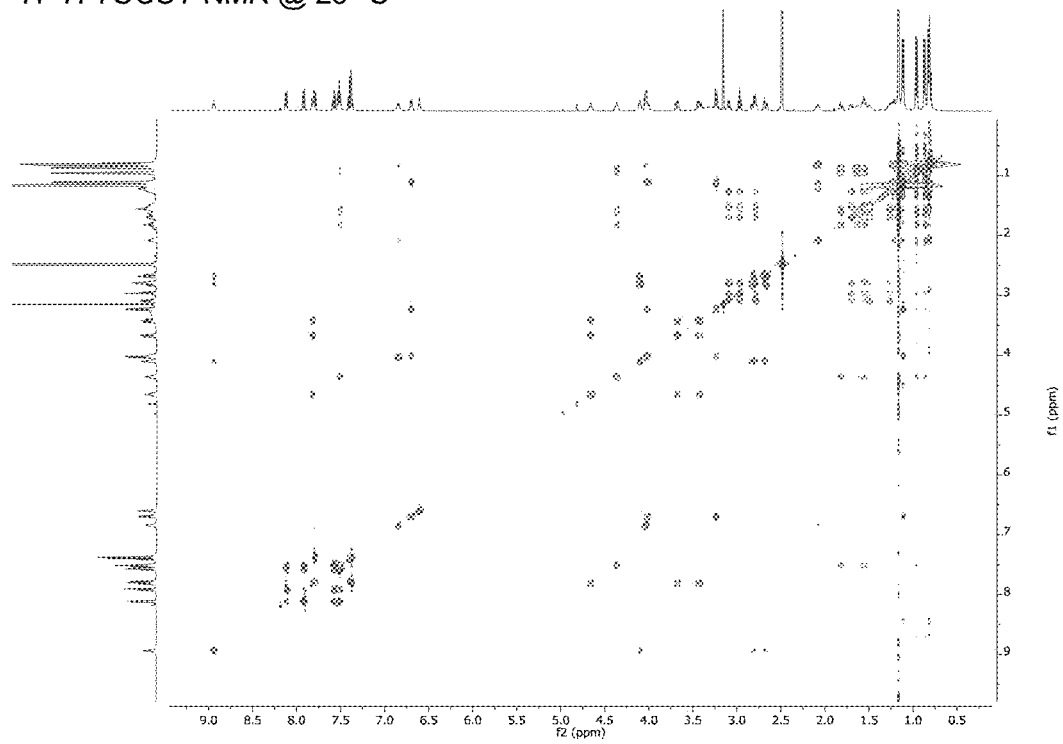

Figure 19
Compound No. 15
¹H NMR @ 25 °C
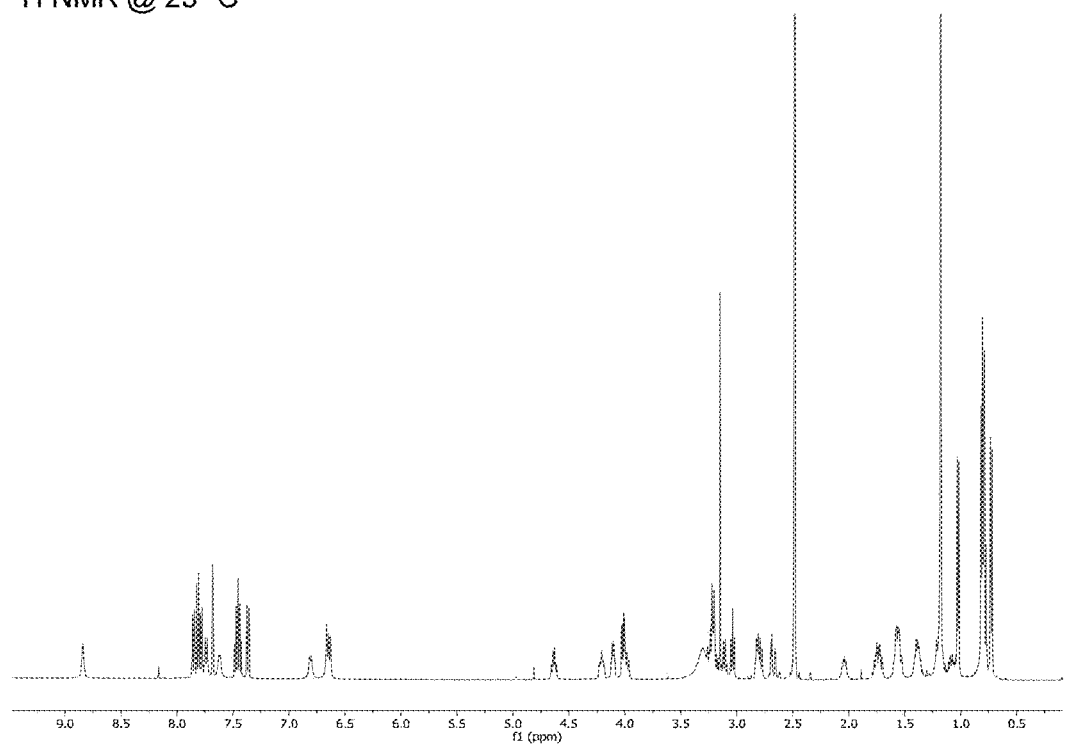
¹H-¹H TOCSY NMR @ 25 °C
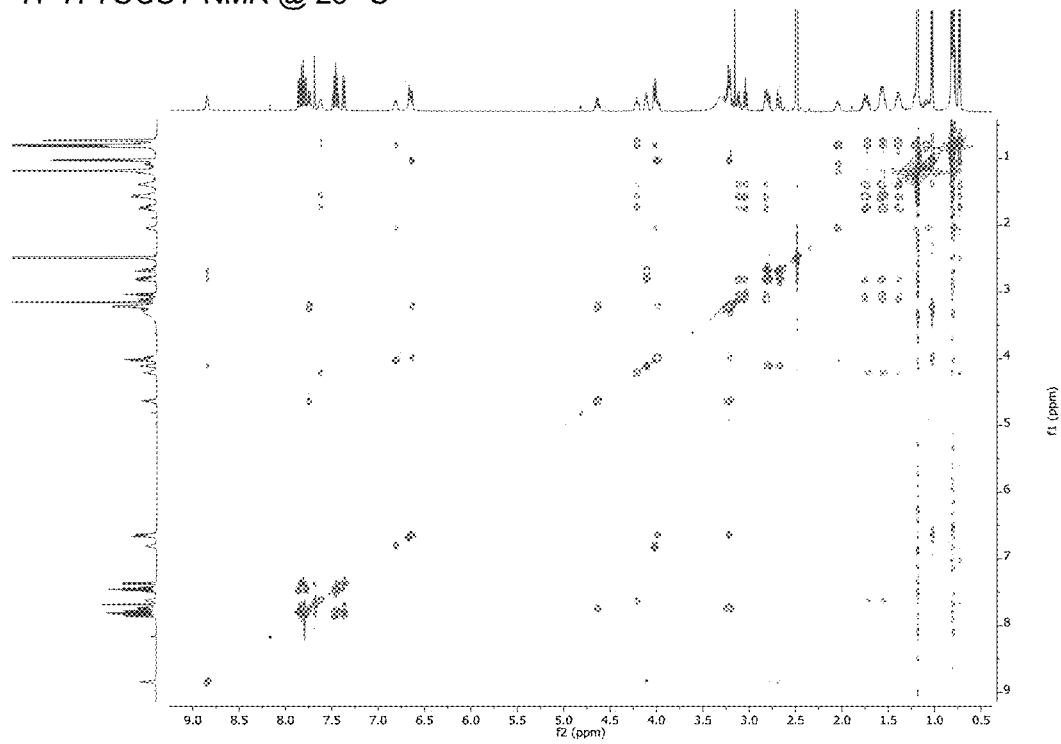

Figure 20
Compound No. 34
¹H NMR @ 25 °C
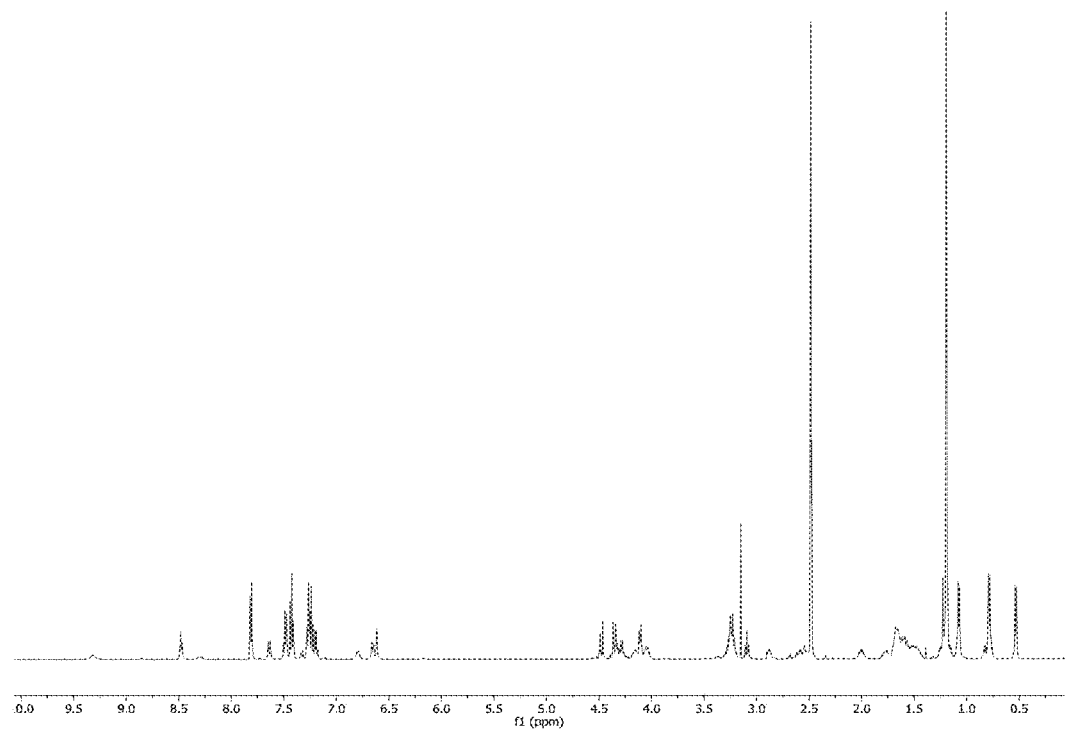
¹H-¹H TOCSY NMR @ 25 °C
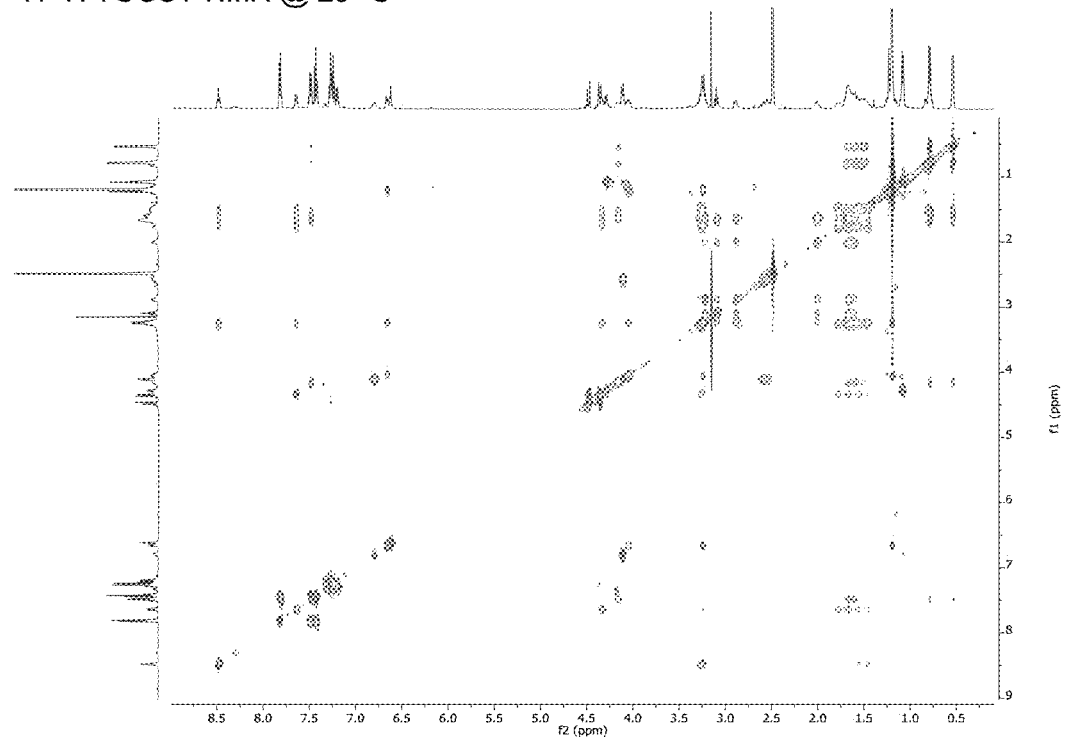

Figure 21
Compound No. 40
¹H NMR @ 25 °C
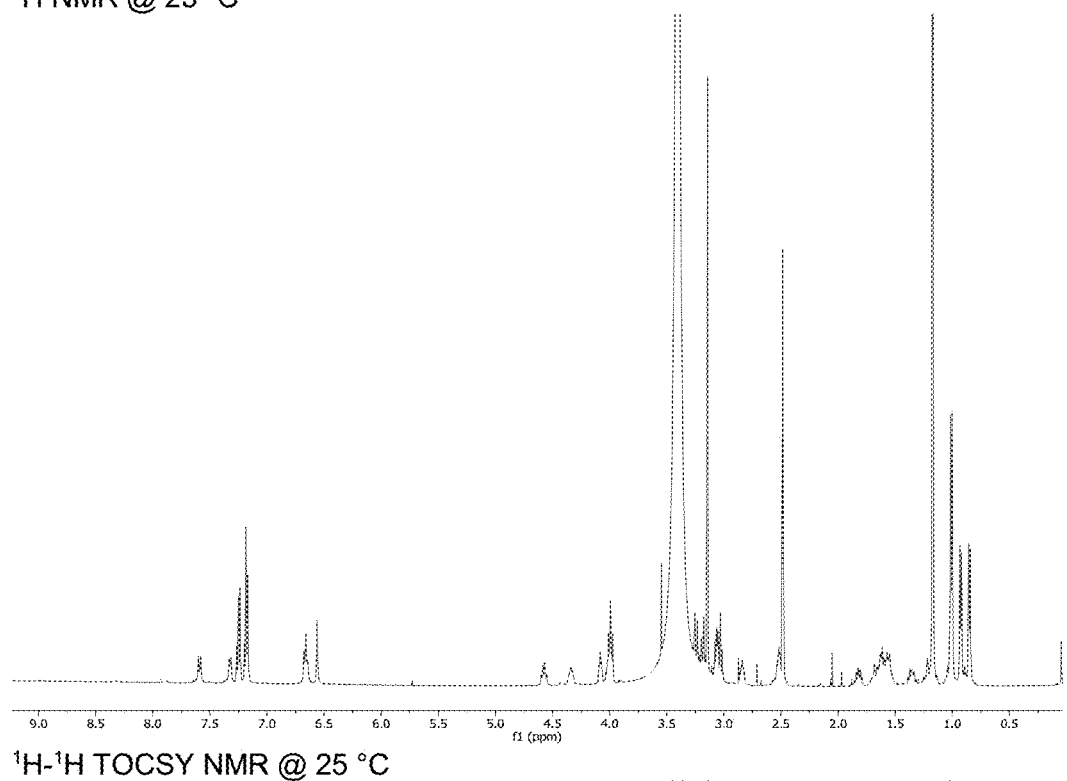
¹H-¹H TOCSY NMR @ 25 °C
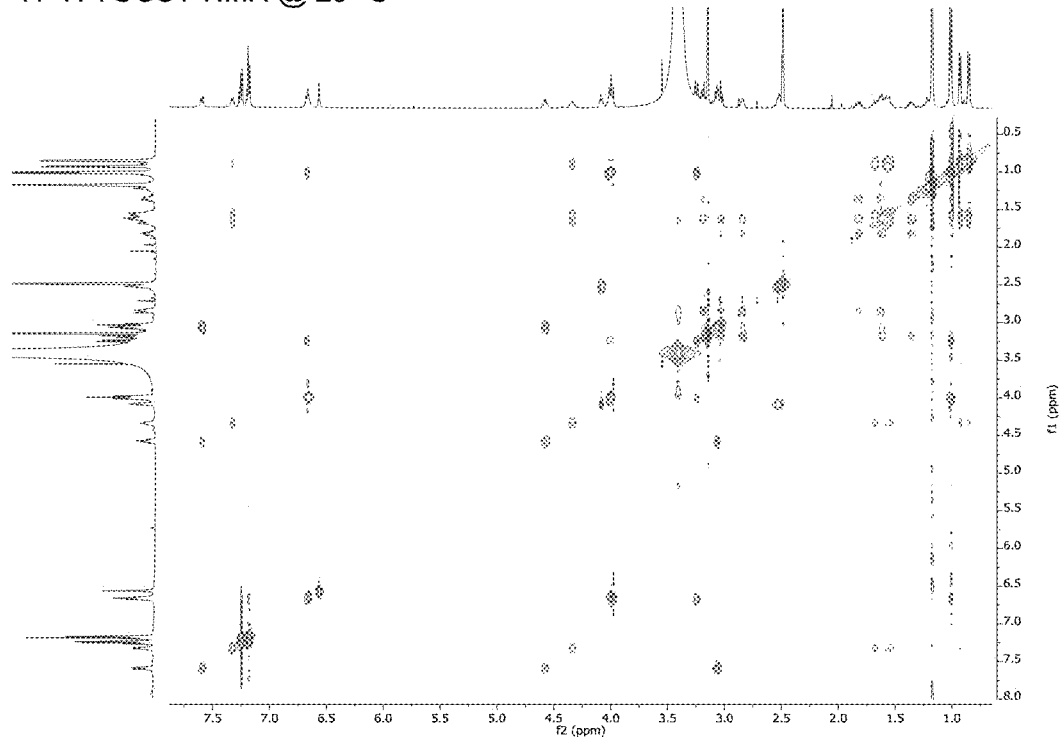

Figure 22
Compound No. 41
¹H NMR @ 25 °C
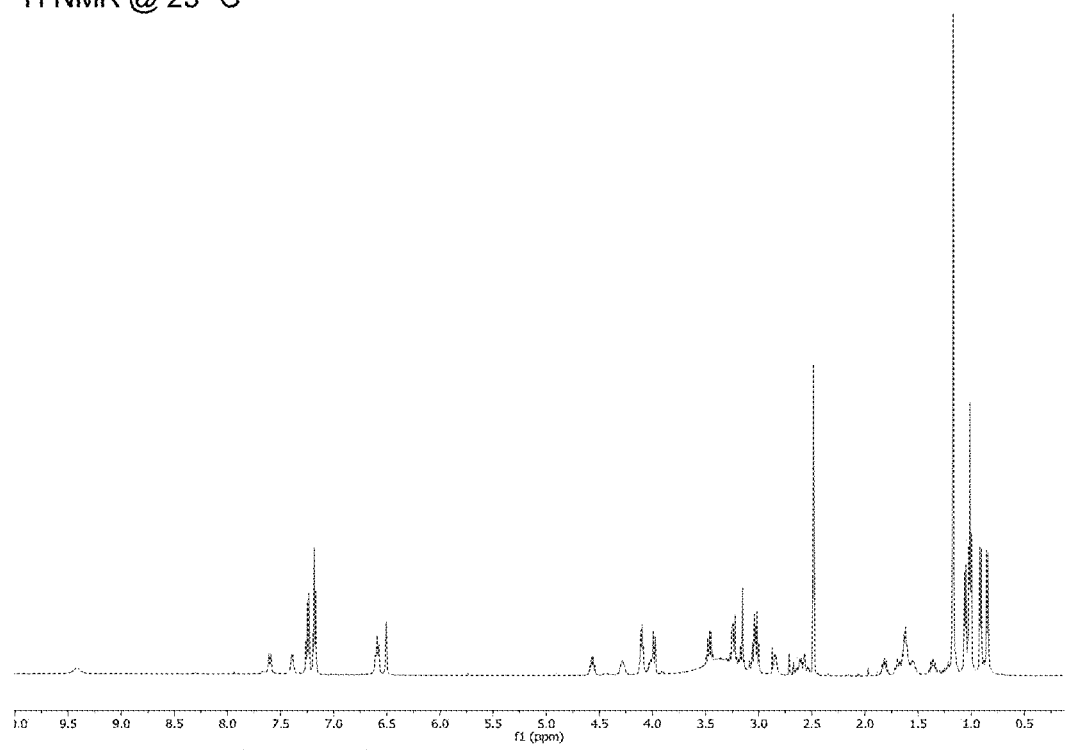
¹H-¹H TOCSY NMR @ 25 °C
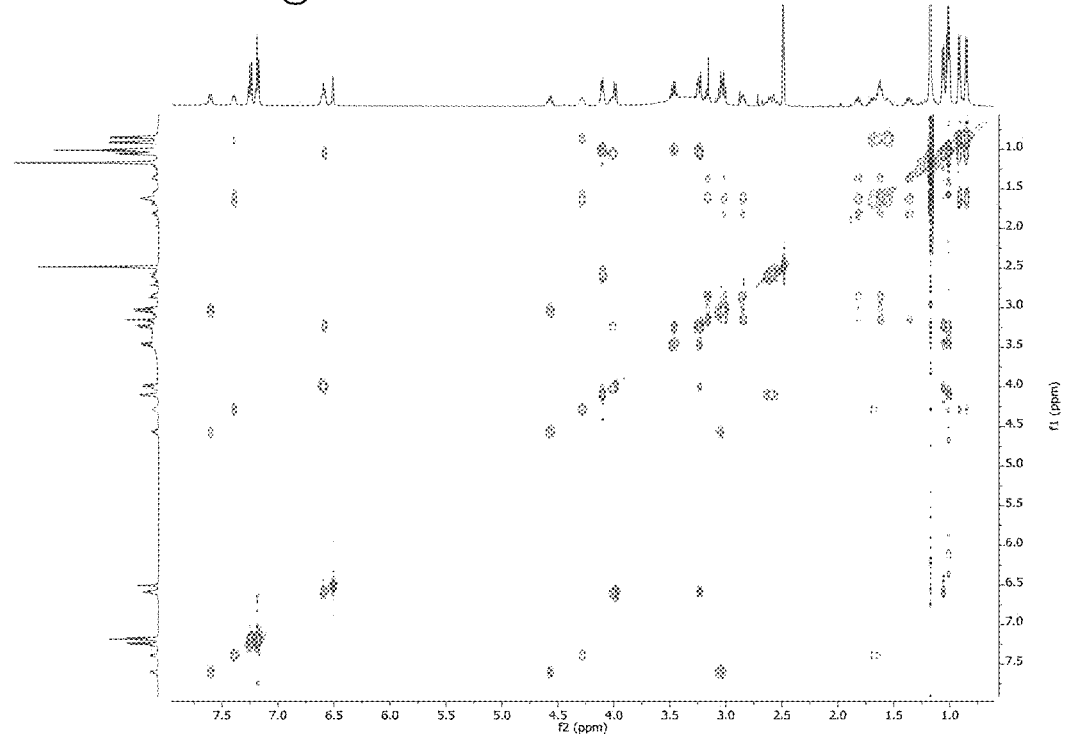

Figure 23
Compound No. 42
¹H NMR @ 25 °C
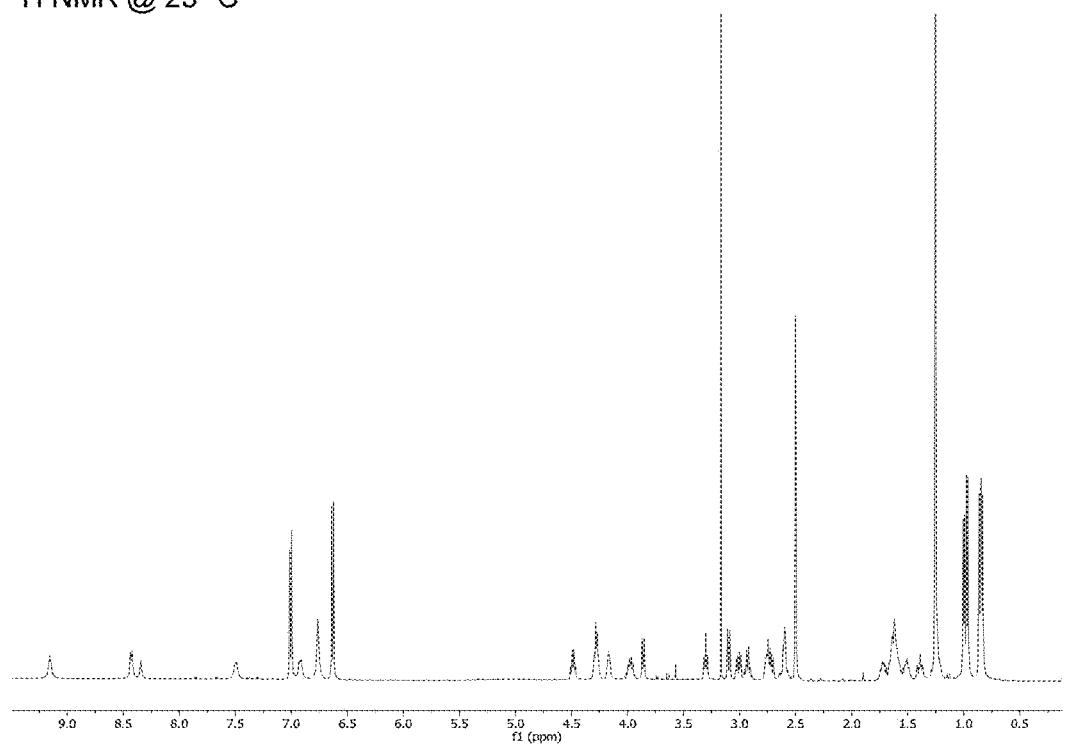
¹H-¹H TOCSY NMR @ 25 °C
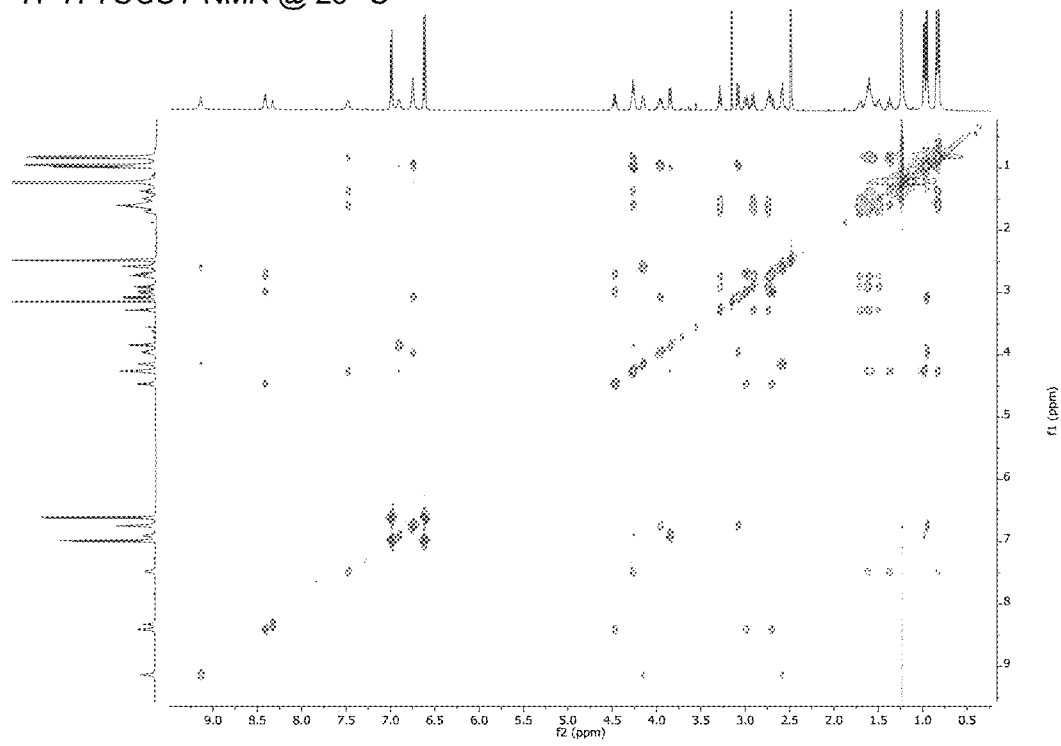

Figure 24
Compound No. 43
¹H NMR @ 25 °C
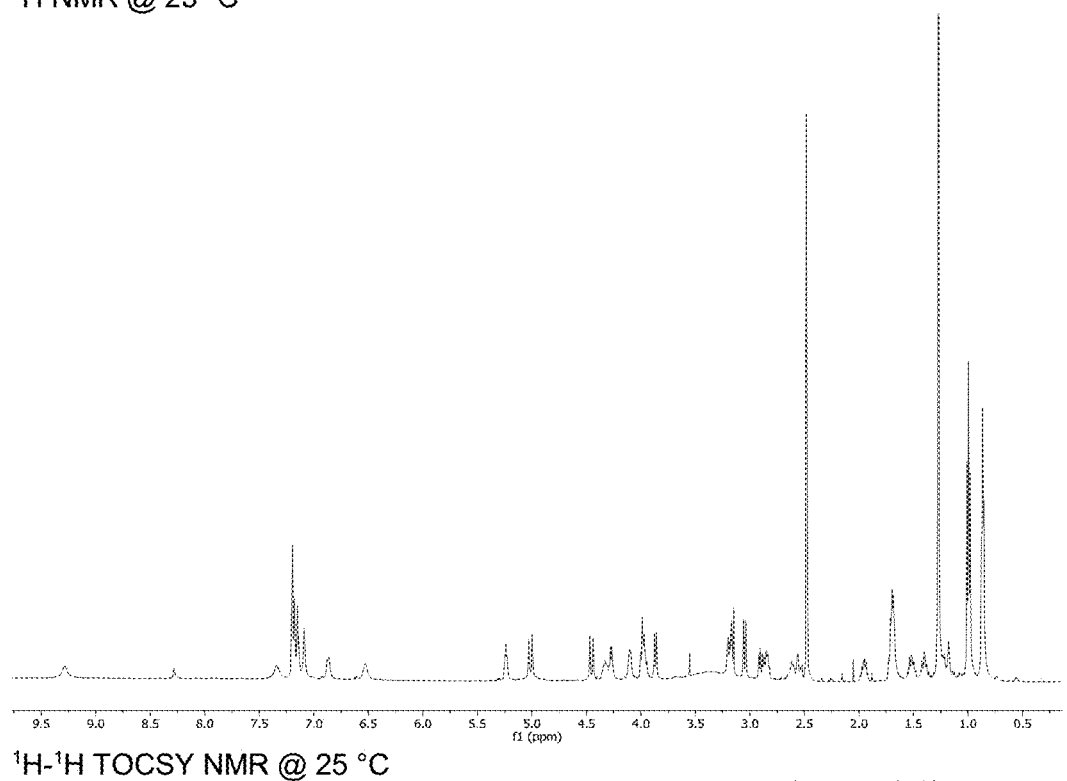
¹H-¹H TOCSY NMR @ 25 °C
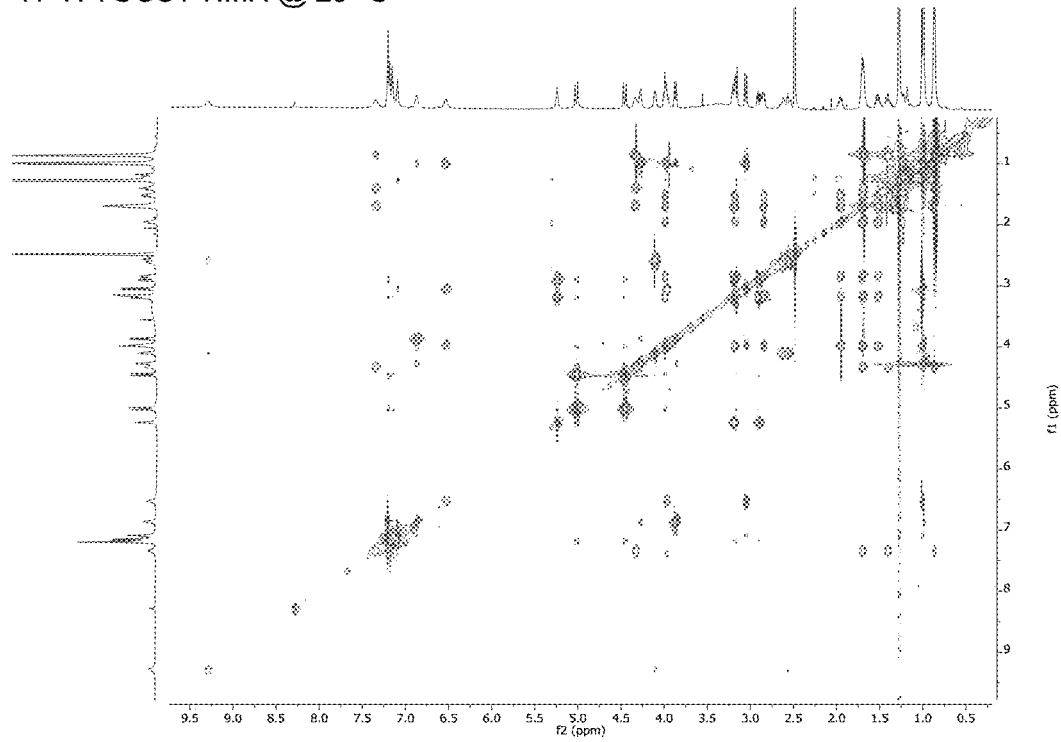

Figure 25
Compound No. 45
¹H NMR @ 25 °C
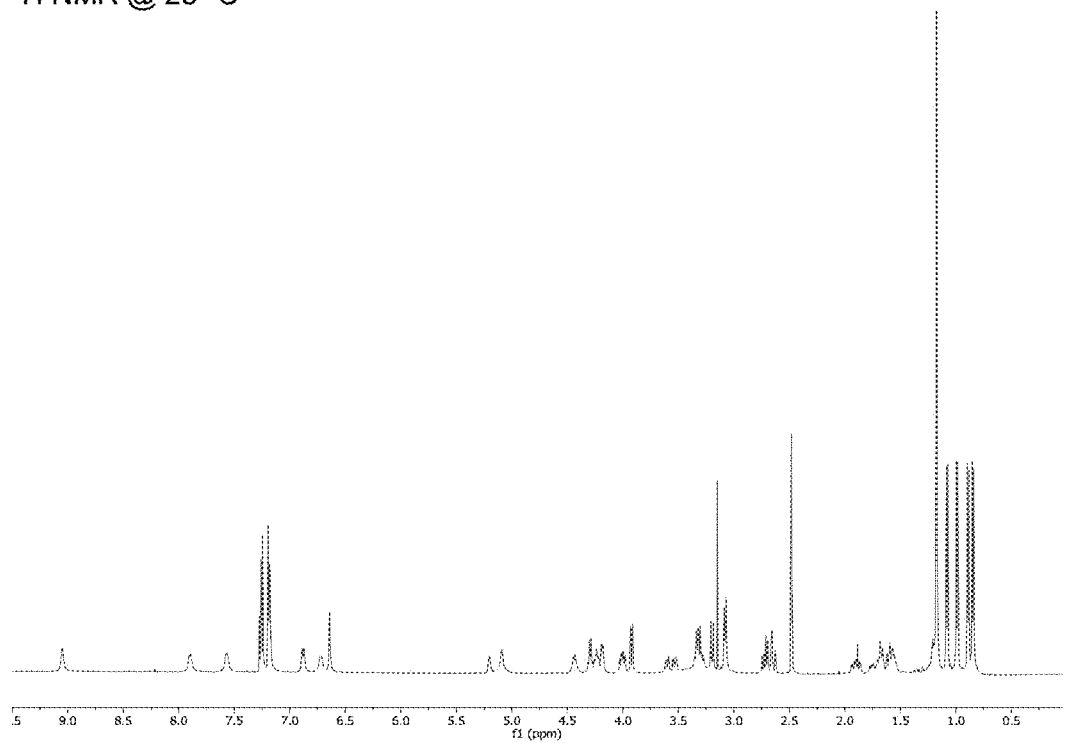
¹H-¹H TOCSY NMR @ 25 °C
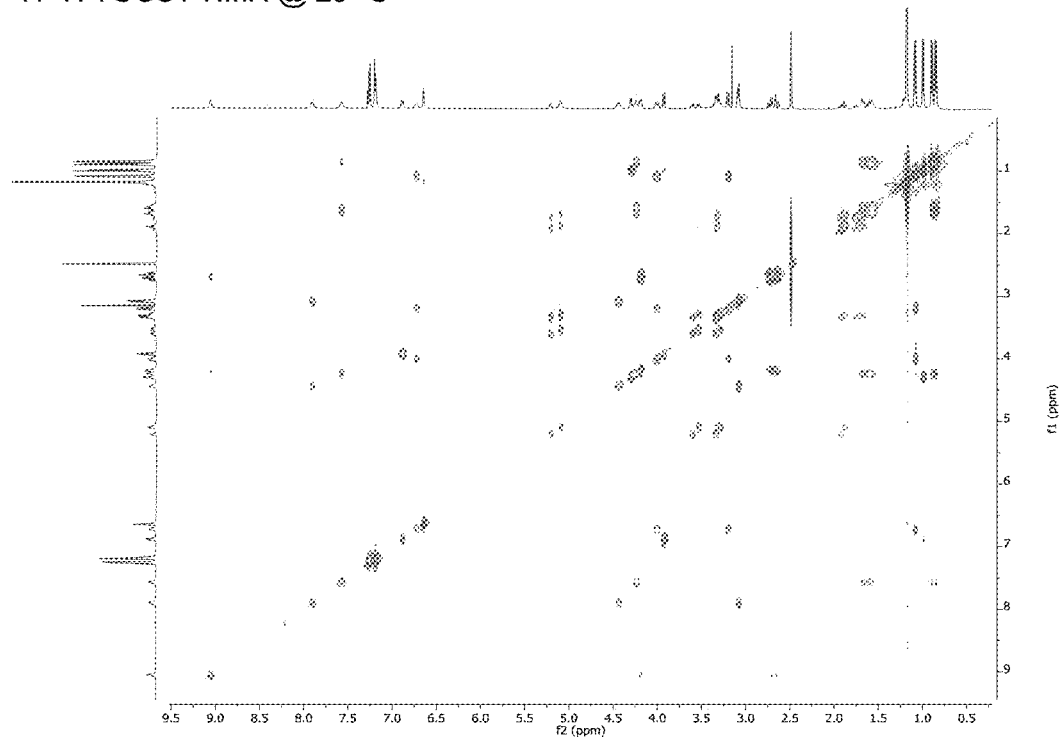

Figure 26
Compound No. 47
¹H NMR @ 25 °C
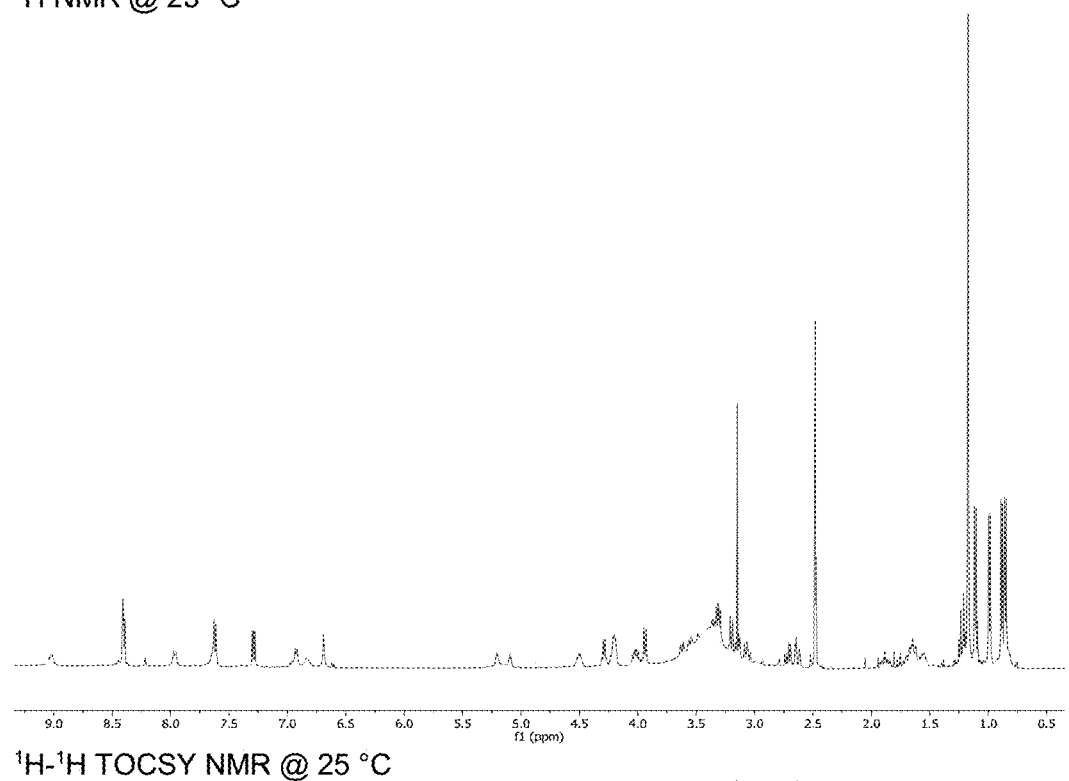
¹H-¹H TOCSY NMR @ 25 °C
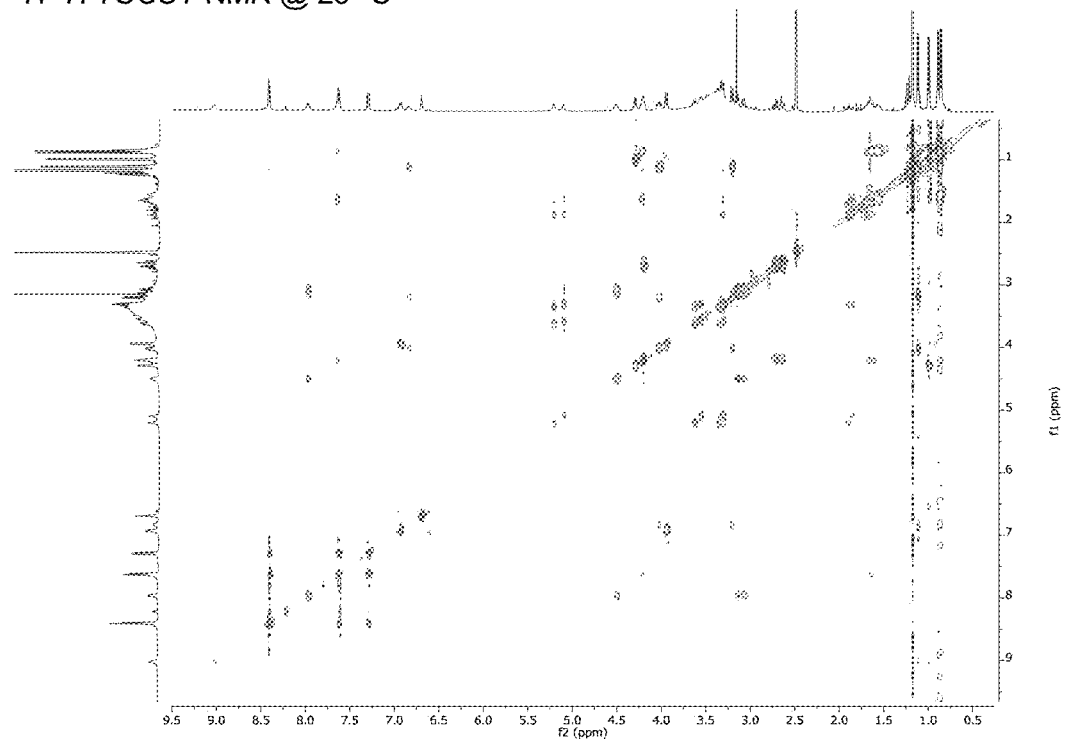

Figure 27
Compound No. 50
¹H NMR @ 25 °C
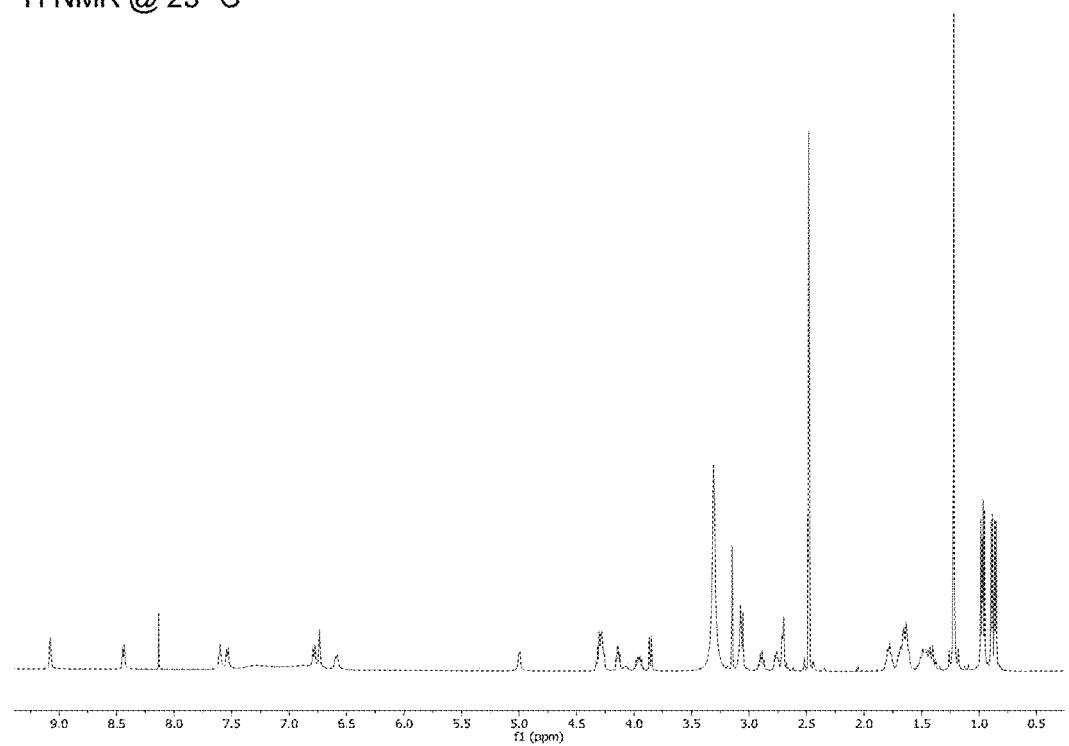
¹H-¹H TOCSY NMR @ 25 °C
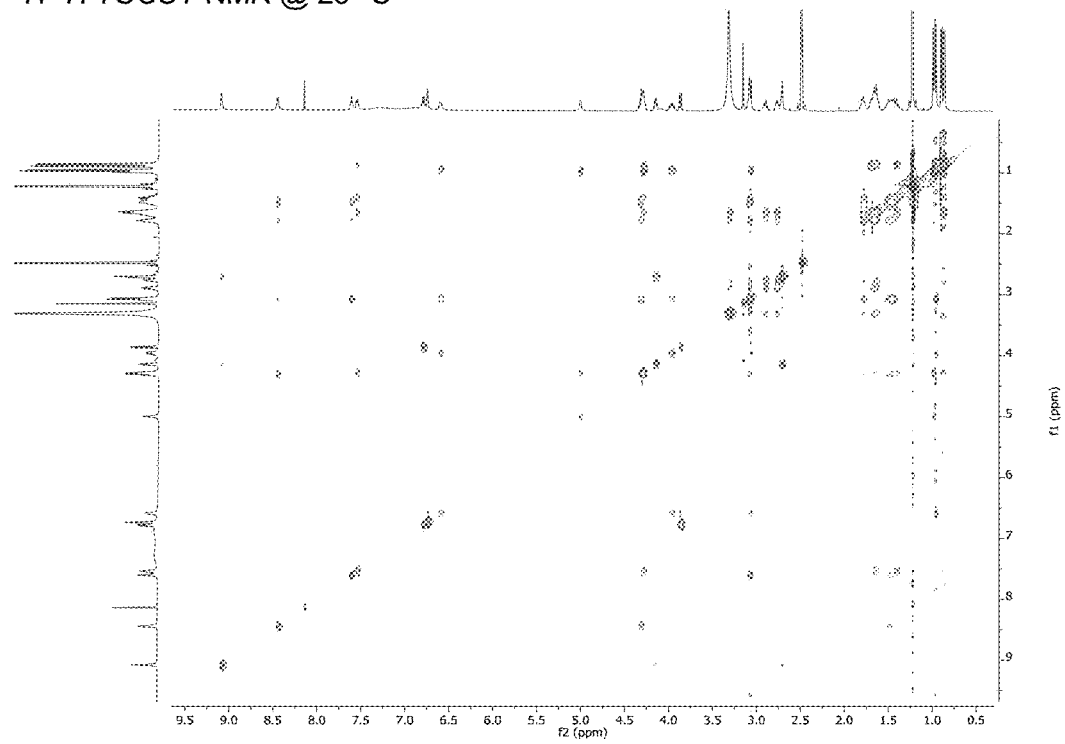

Figure 28
Compound No. 100
¹H NMR @ 25 °C
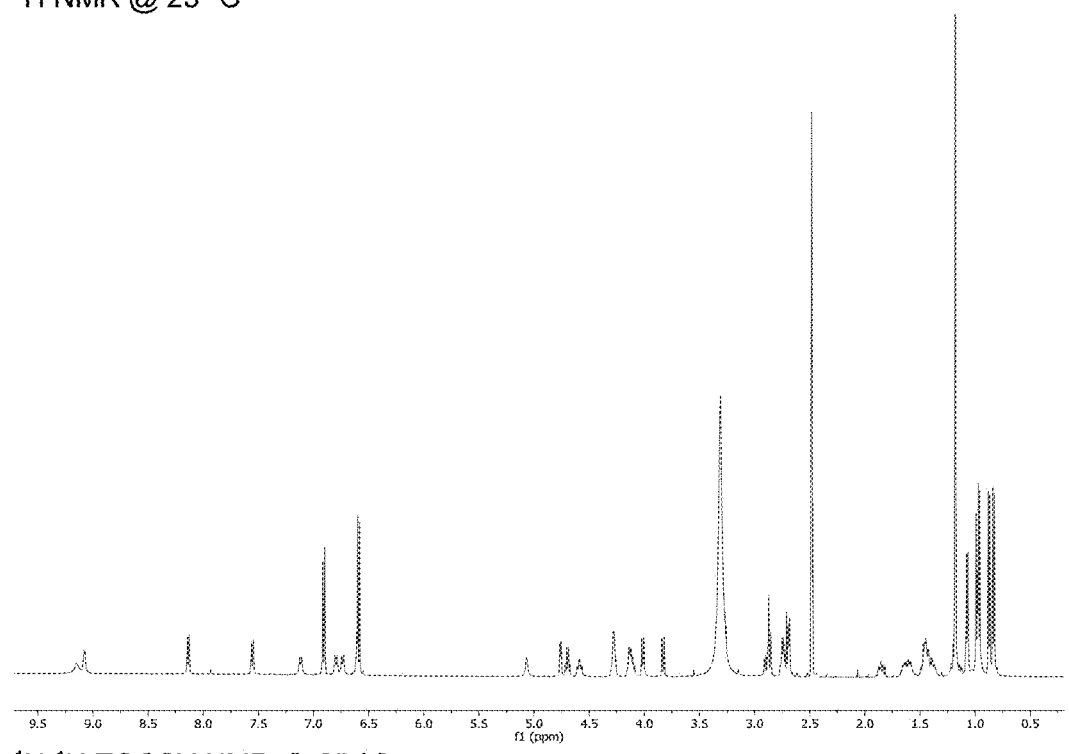
¹H-¹H TOCSY NMR @ 25 °C
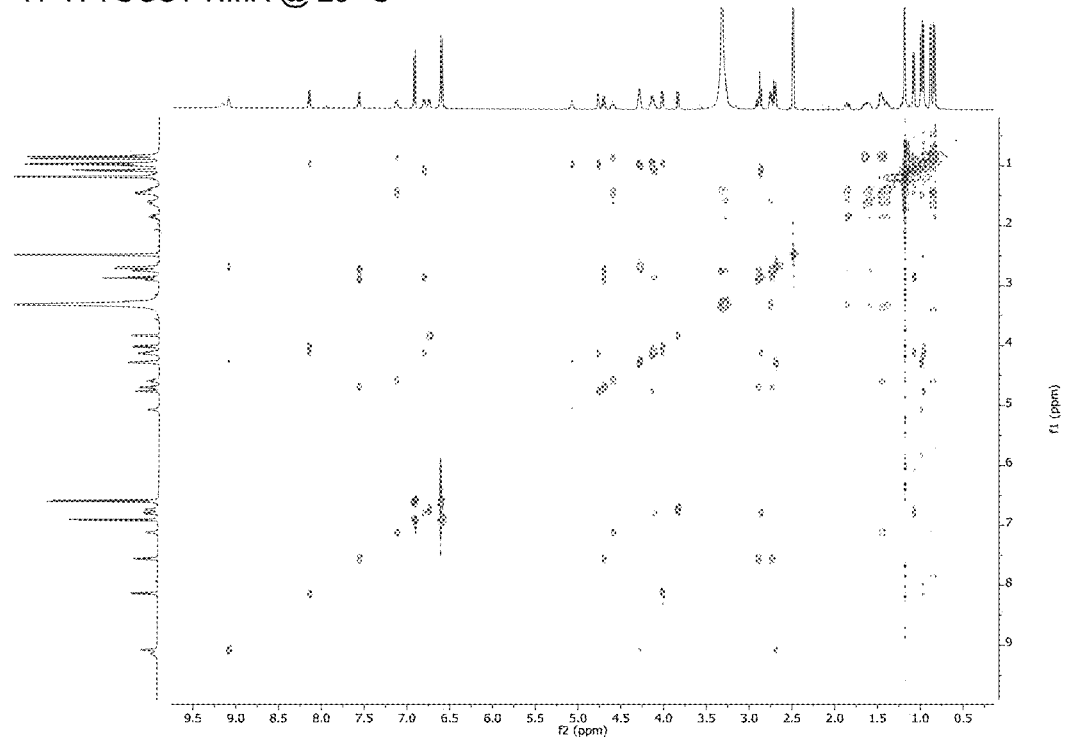

Figure 29
Compound No. 101
¹H NMR @ 25 °C
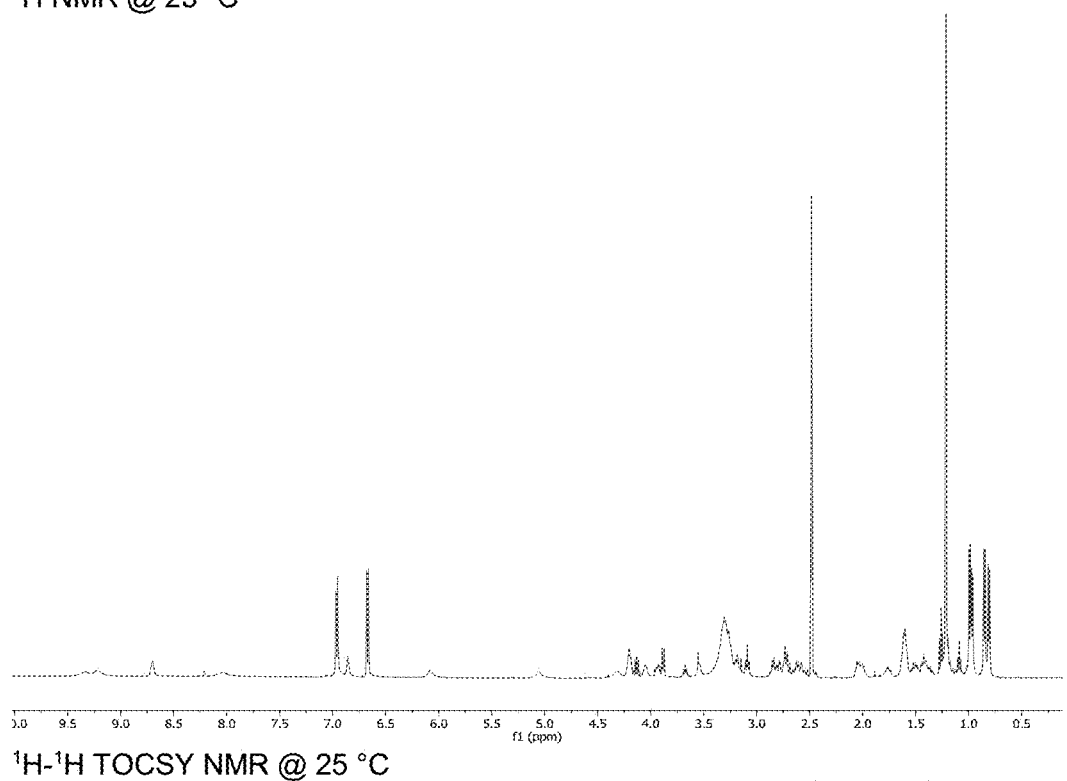
¹H-¹H TOCSY NMR @ 25 °C
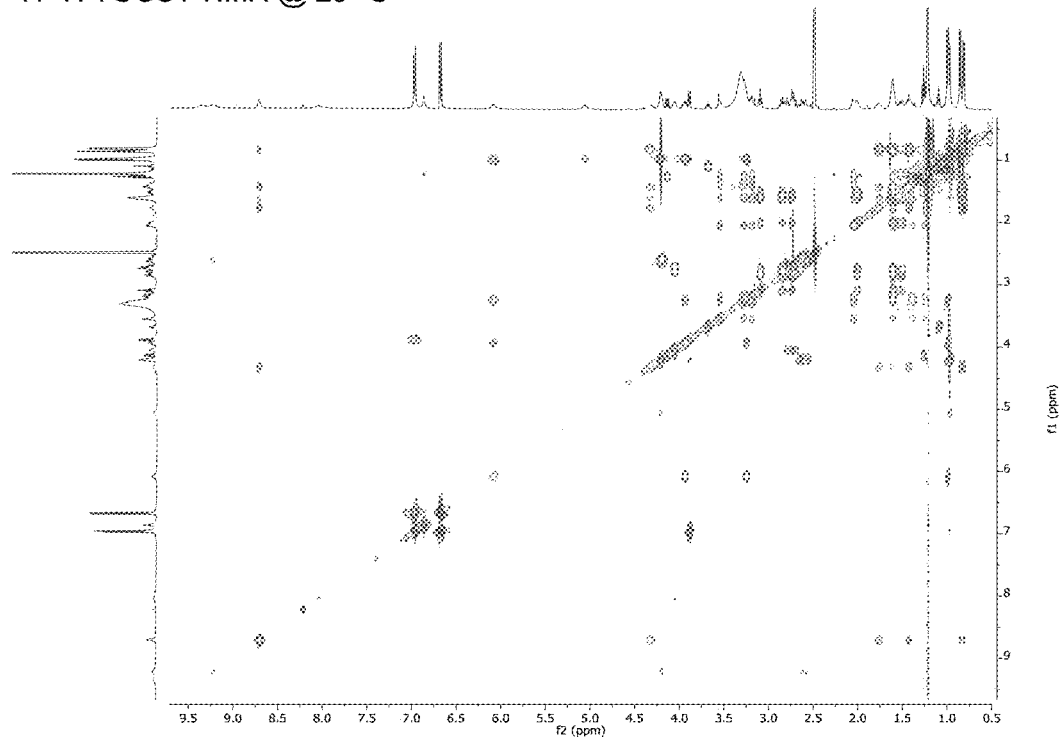

Figure 30
Compound No. 103
¹H NMR @ 25 °C
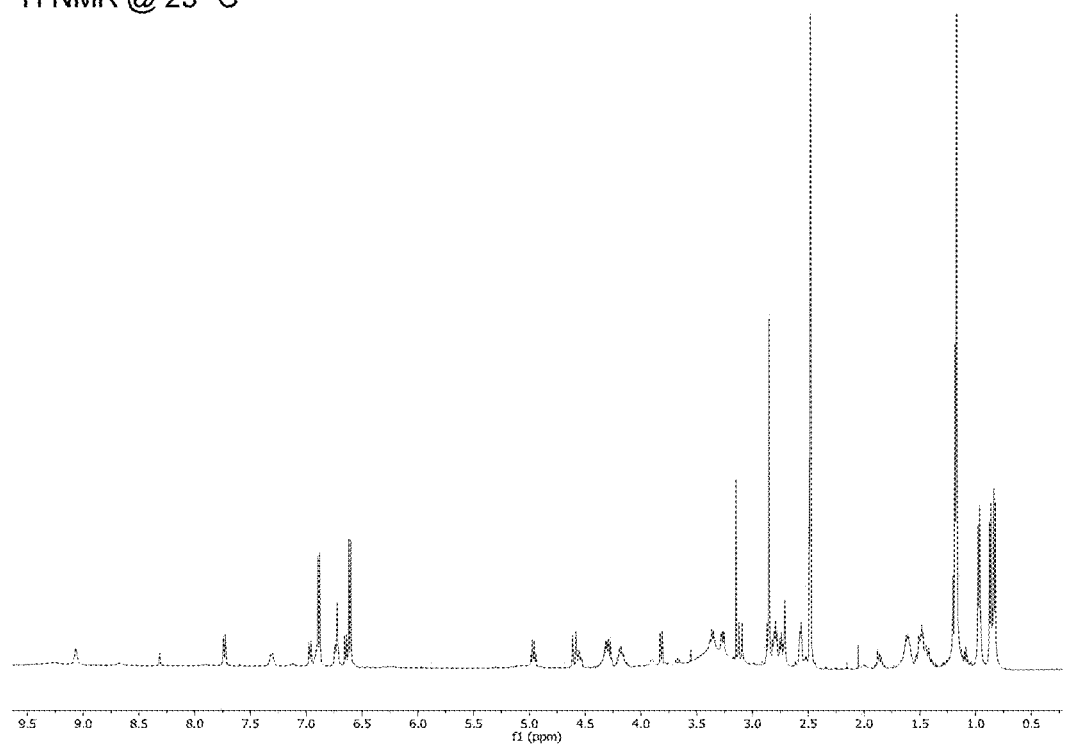
¹H-¹H TOCSY NMR @ 25 °C
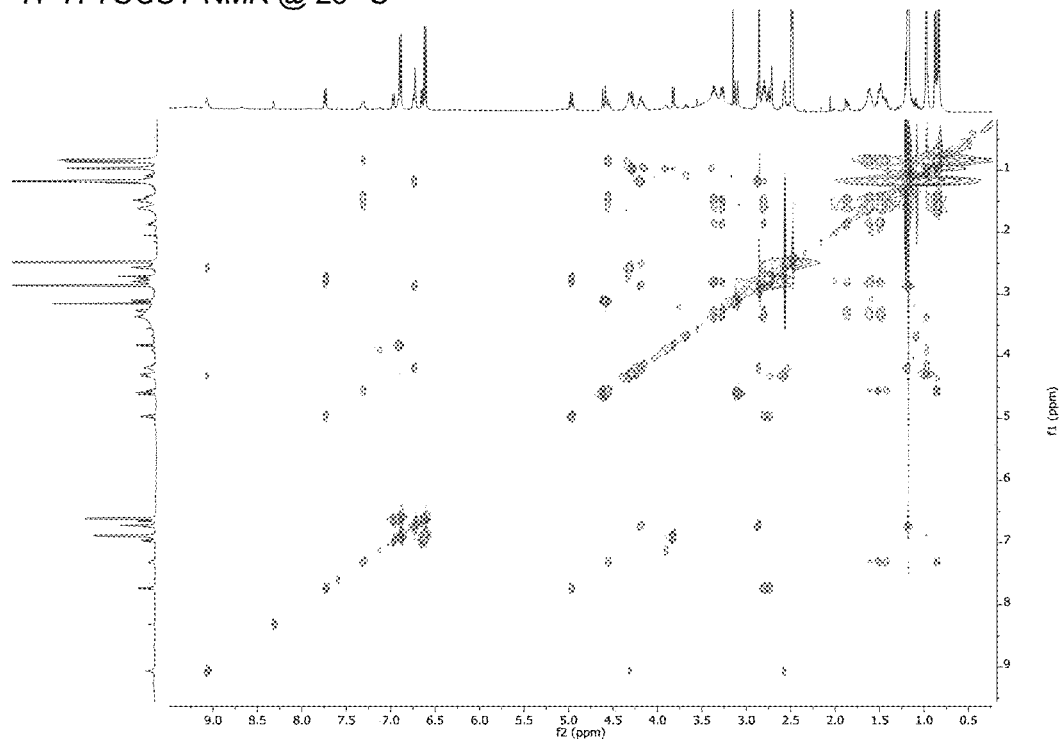

Figure 31
Compound No. 104
¹H NMR @ 25 °C
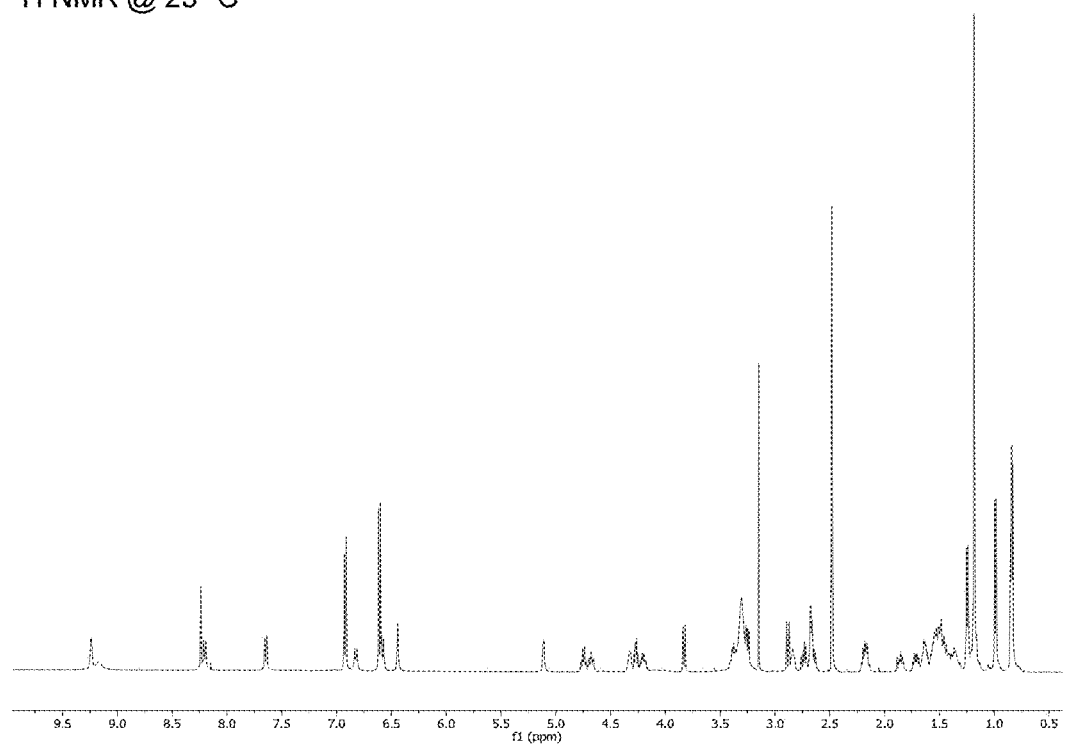
¹H-¹H TOCSY NMR @ 25 °C
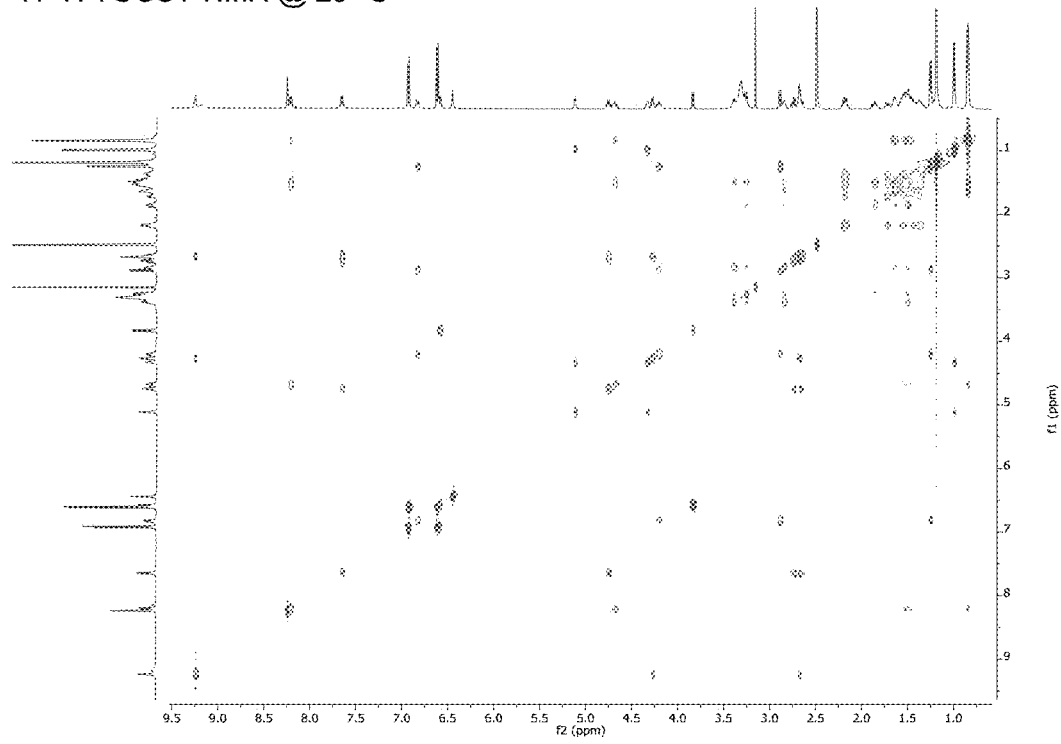

Figure 32
Compound No. 106
¹H NMR @ 25 °C
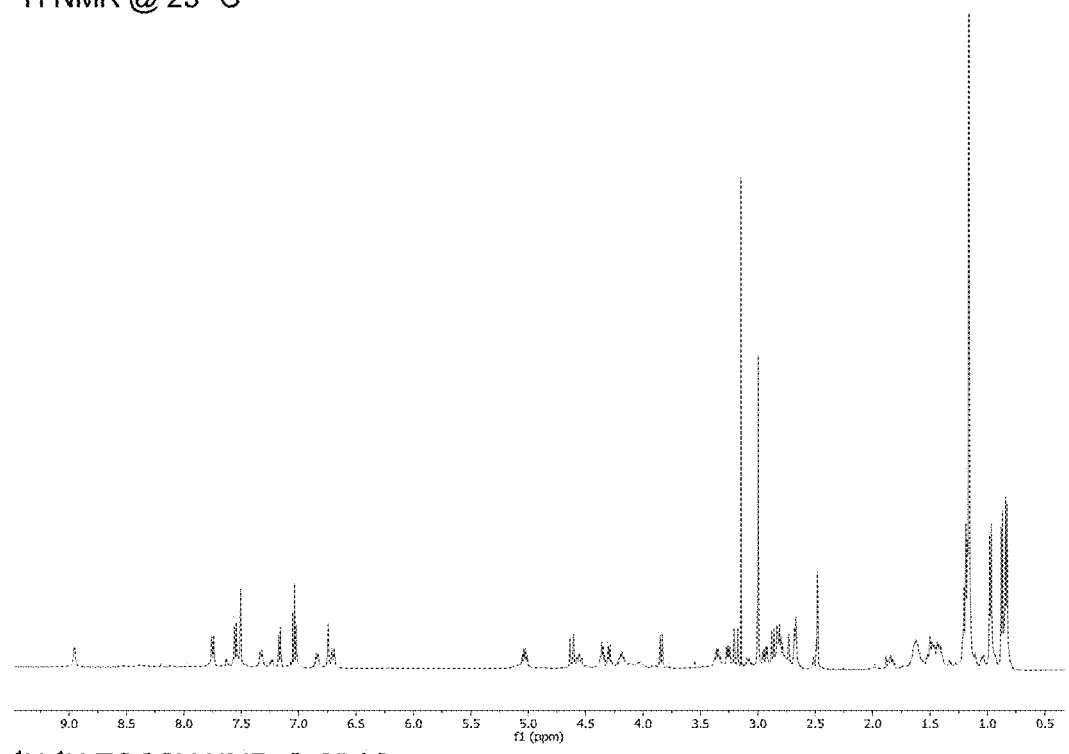
¹H-¹H TOCSY NMR @ 25 °C
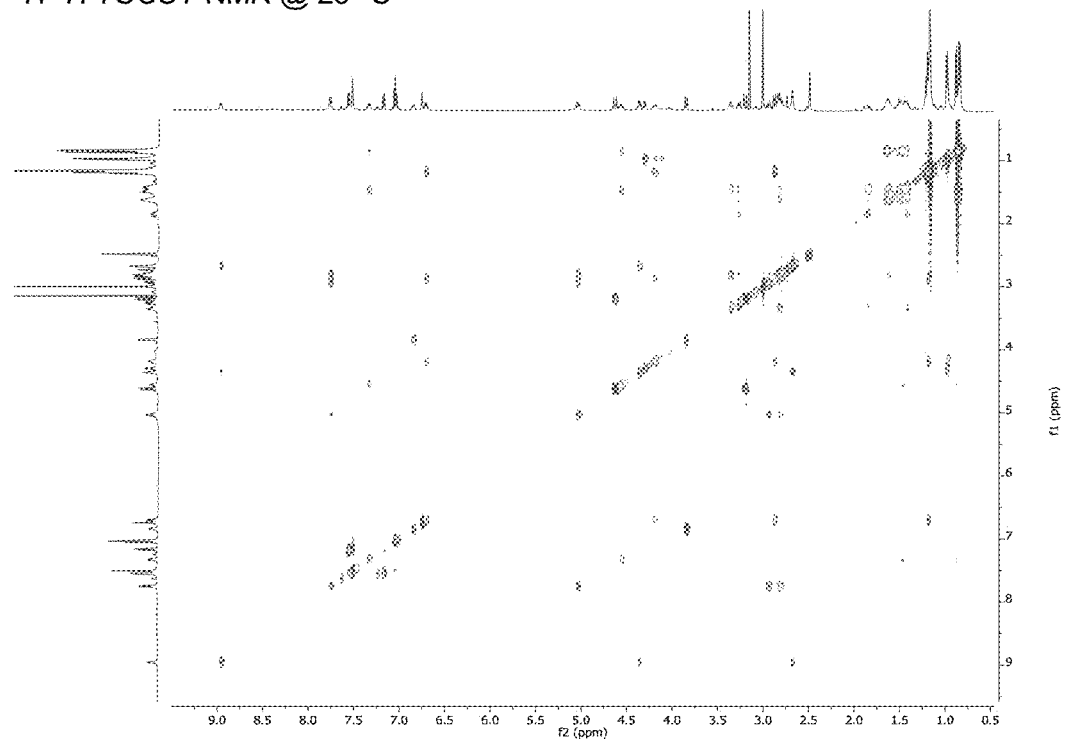

Figure 33
Compound No. 107
¹H NMR @ 25 °C
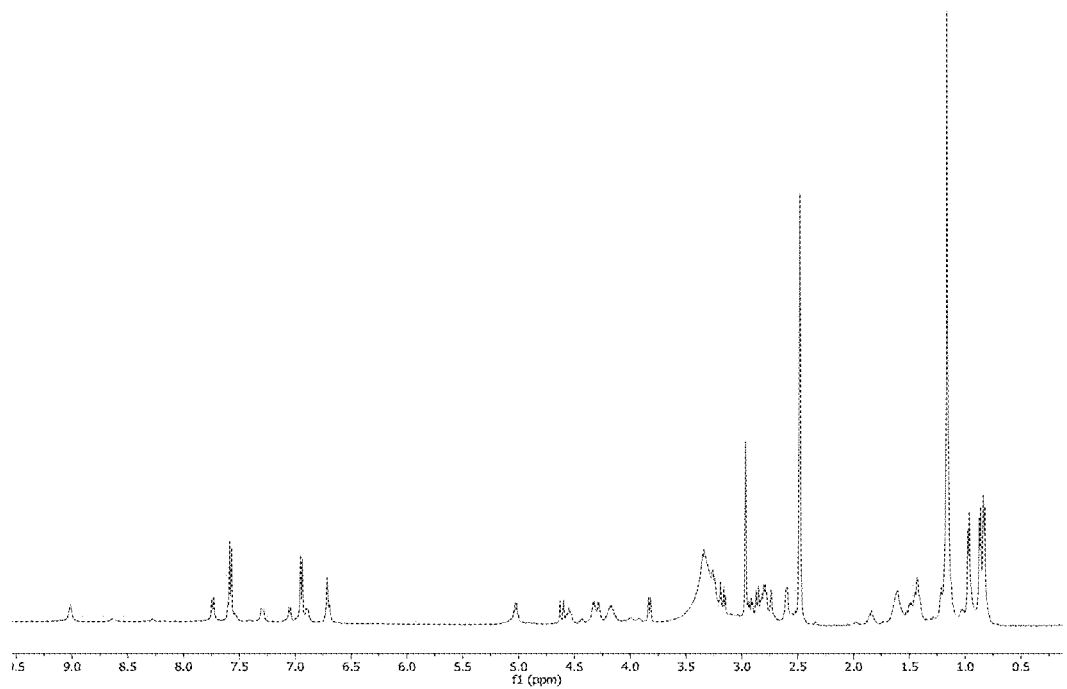
¹H-¹H TOCSY NMR @ 25 °C
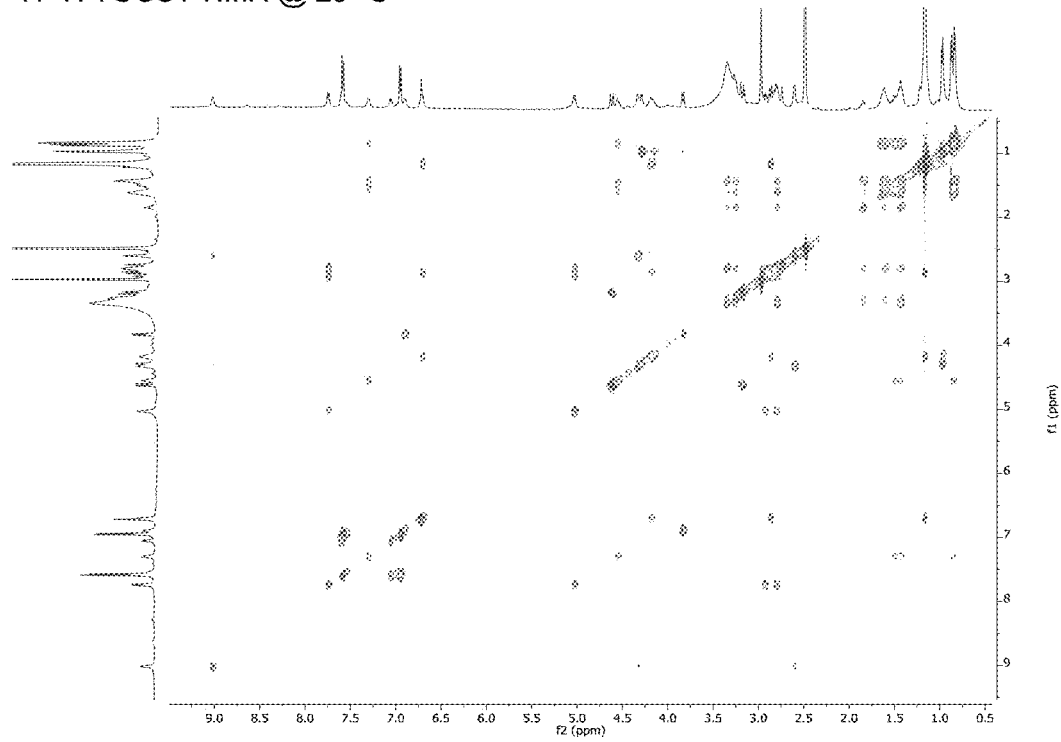

Figure 34
Compound No. 108
¹H NMR @ 25 °C
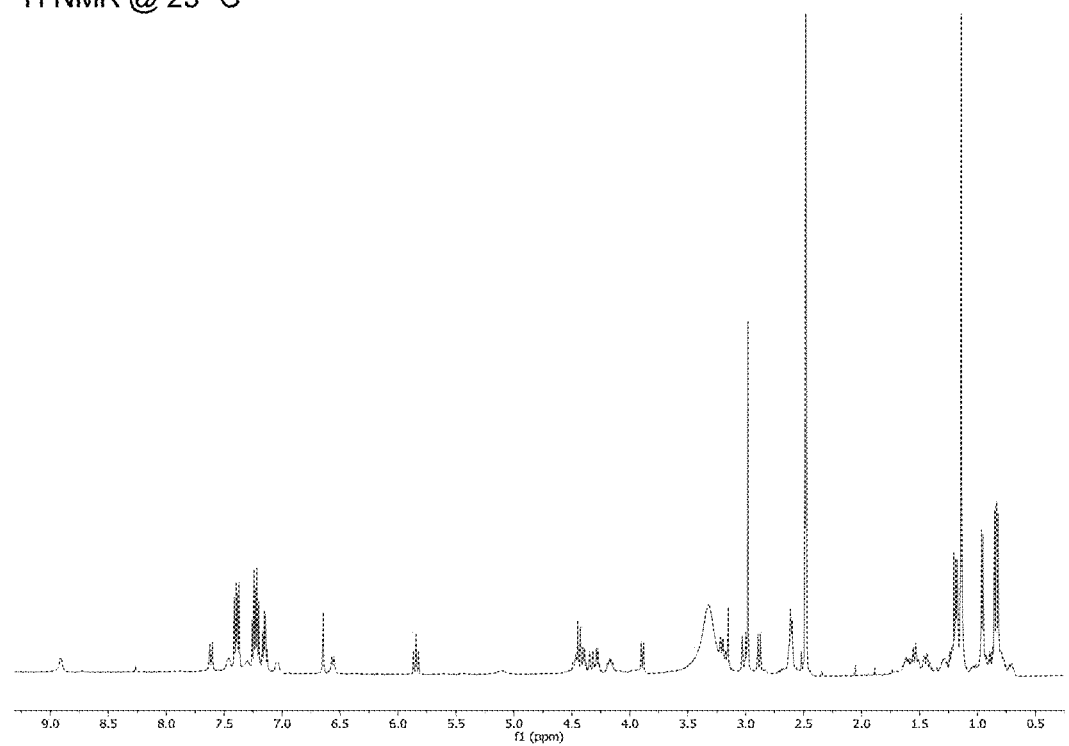
¹H-¹H TOCSY NMR @ 25 °C
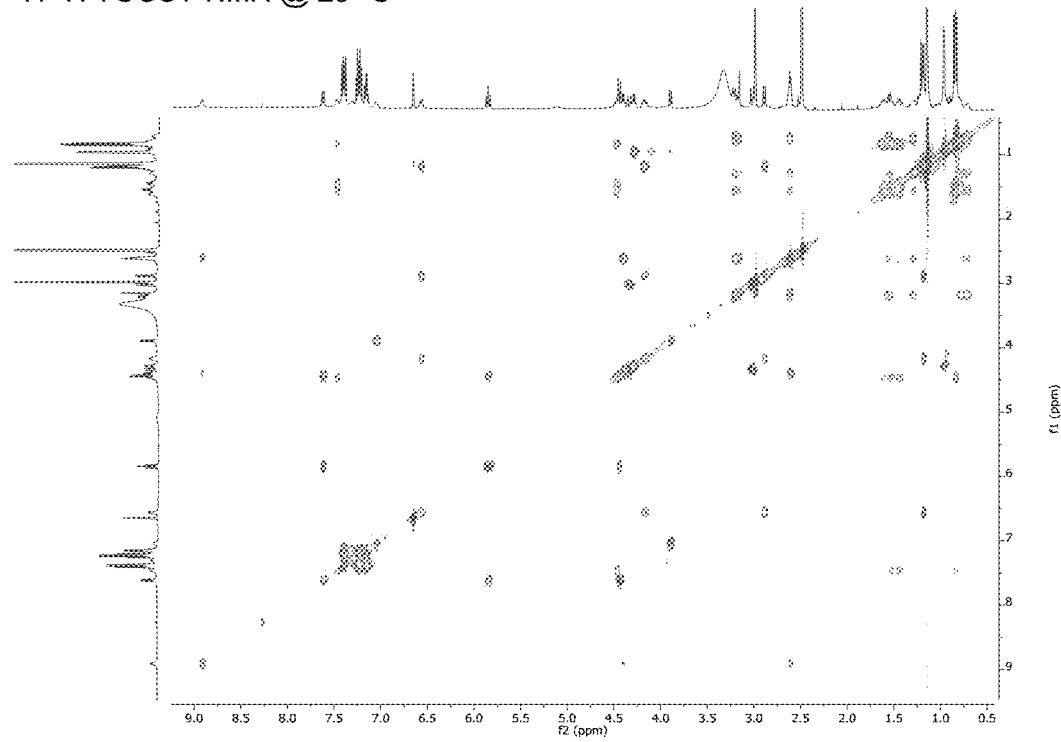

Figure 35
Compound No. 109
¹H NMR @ 25 °C
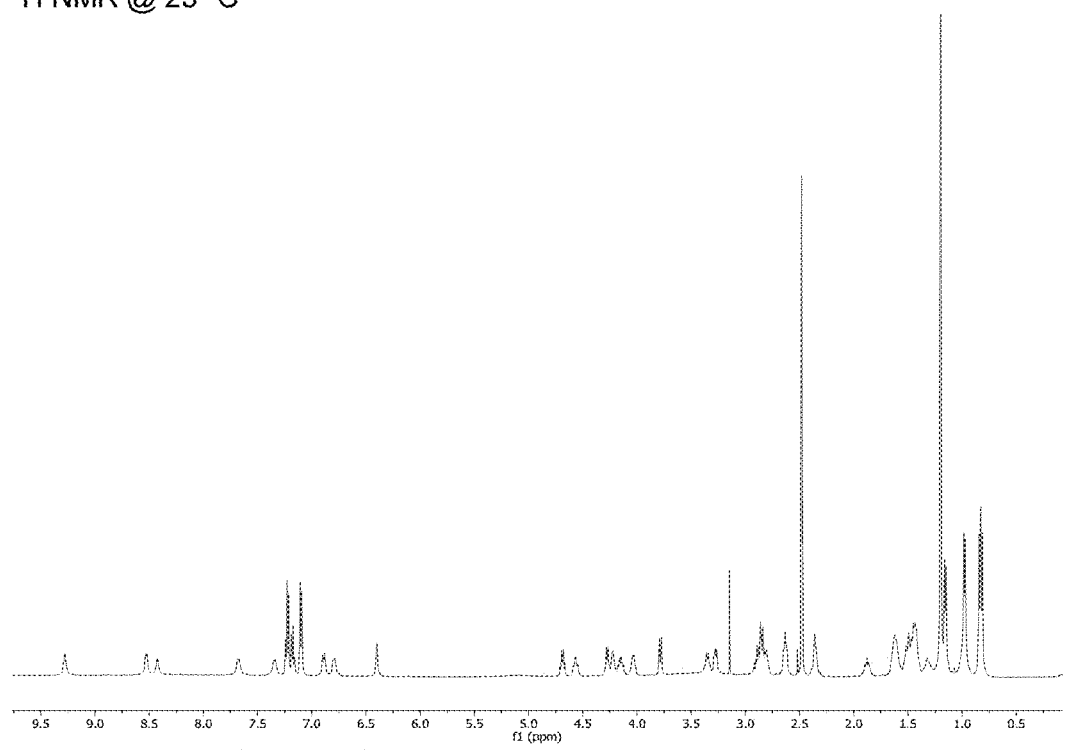
¹H-¹H TOCSY NMR @ 25 °C
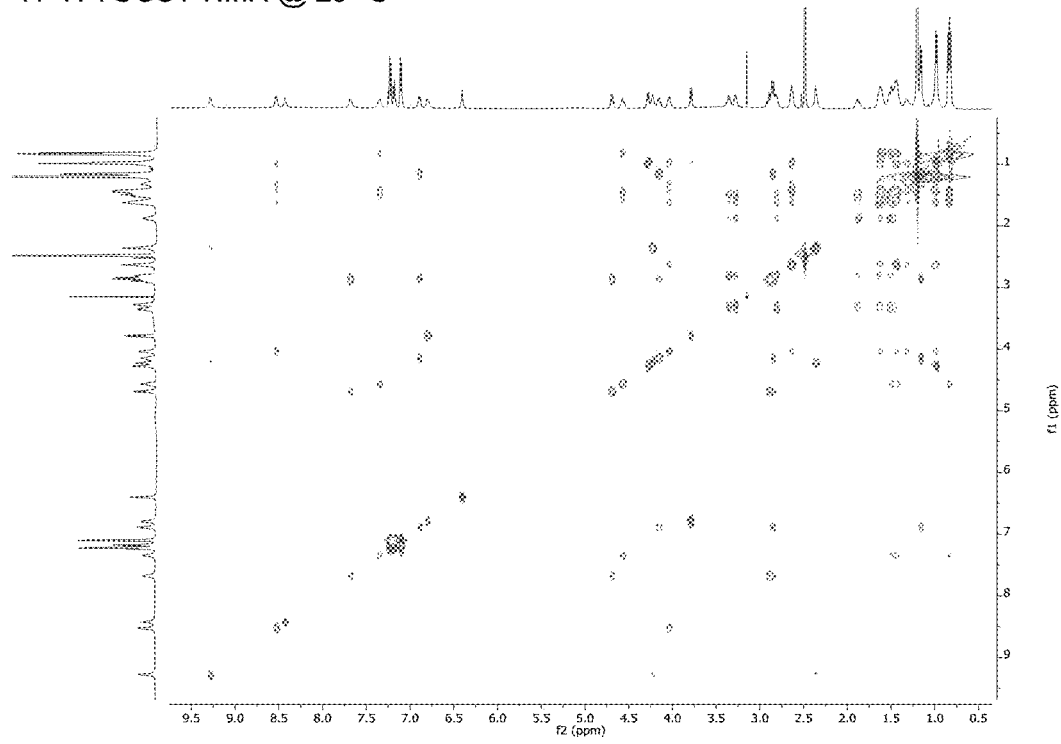

Figure 36
Compound No. 110
¹H NMR @ 25 °C
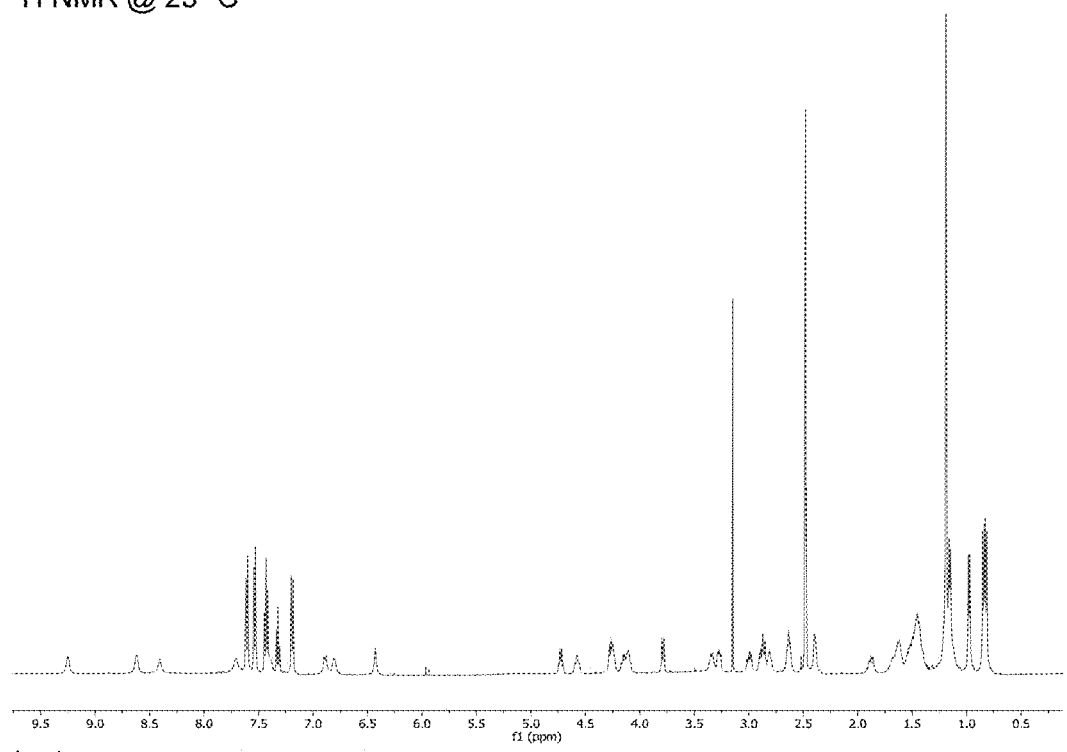
¹H-¹H TOCSY NMR @ 25 °C
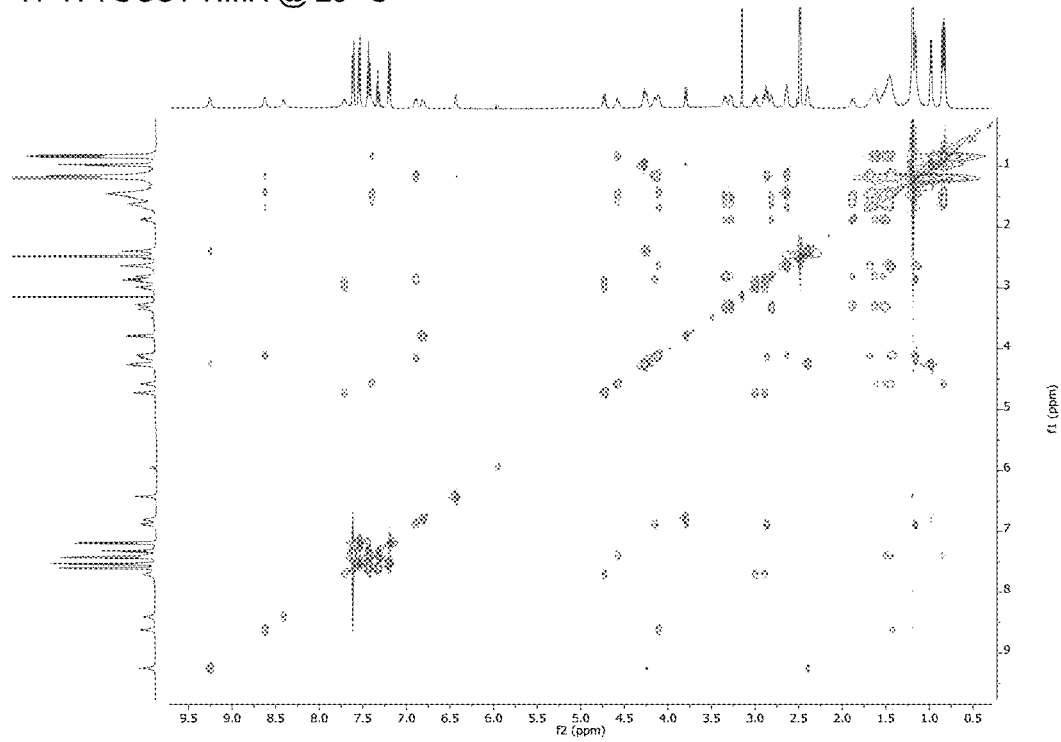

Figure 37
Compound No. 111
¹H NMR @ 25 °C
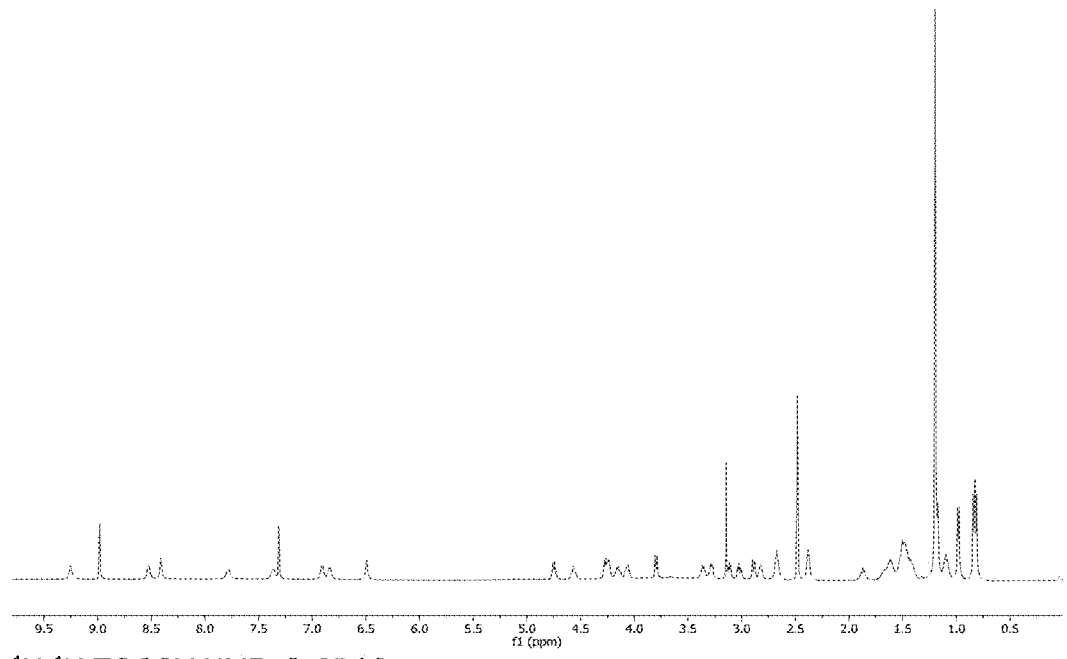
¹H-¹H TOCSY NMR @ 25 °C
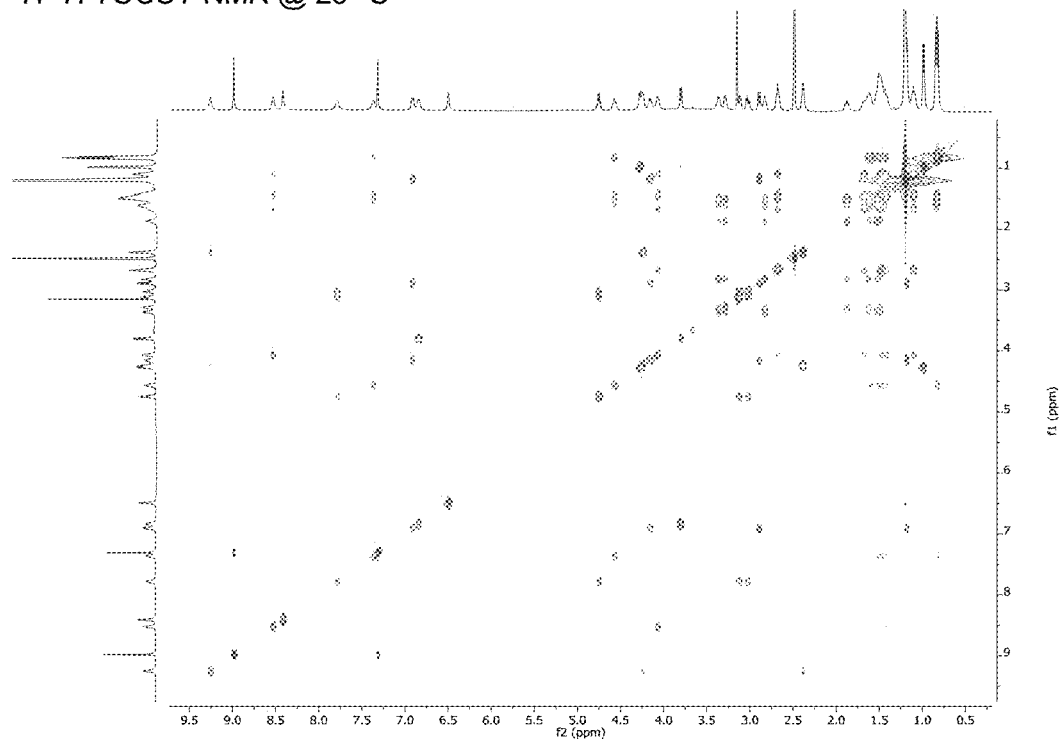

Figure 38
Compound No. 112
¹H NMR @ 25 °C
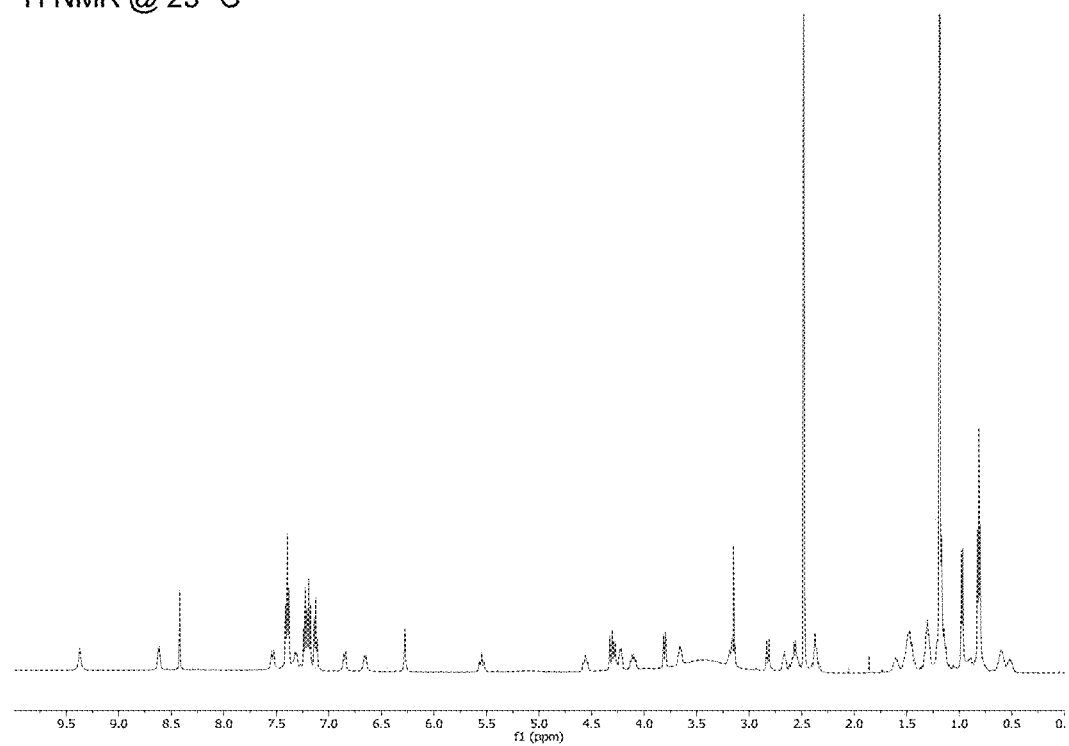
¹H-¹H TOCSY NMR @ 25 °C
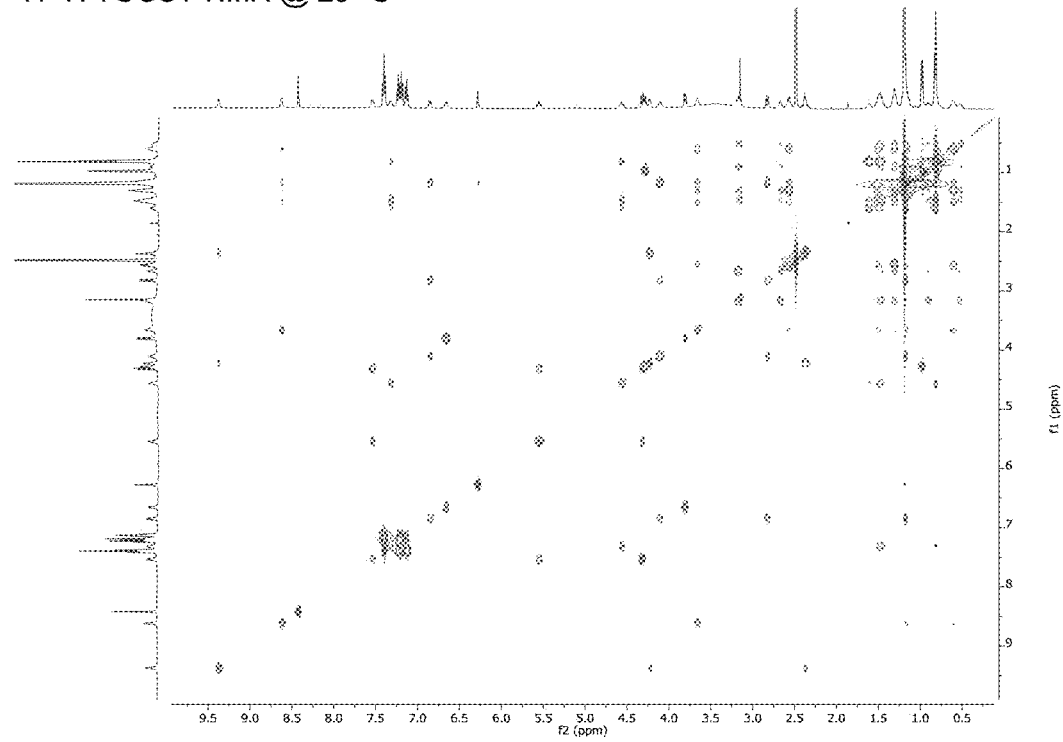

Figure 39
Compound No. 123
¹H NMR @ 25 °C
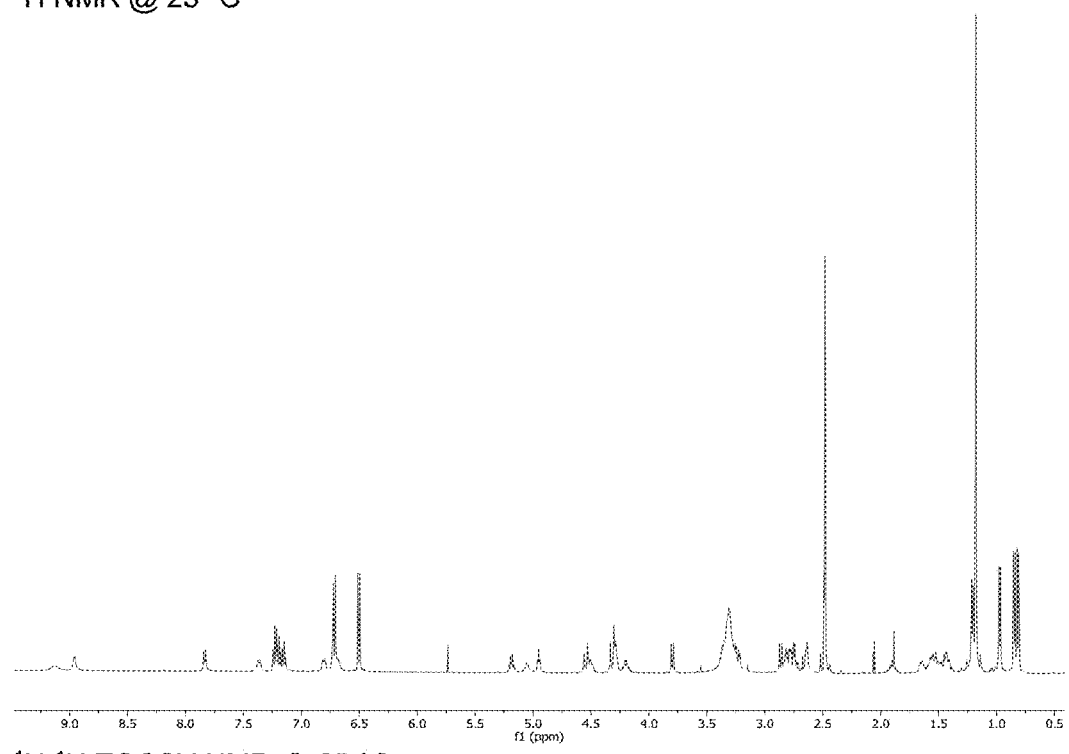
¹H-¹H TOCSY NMR @ 25 °C
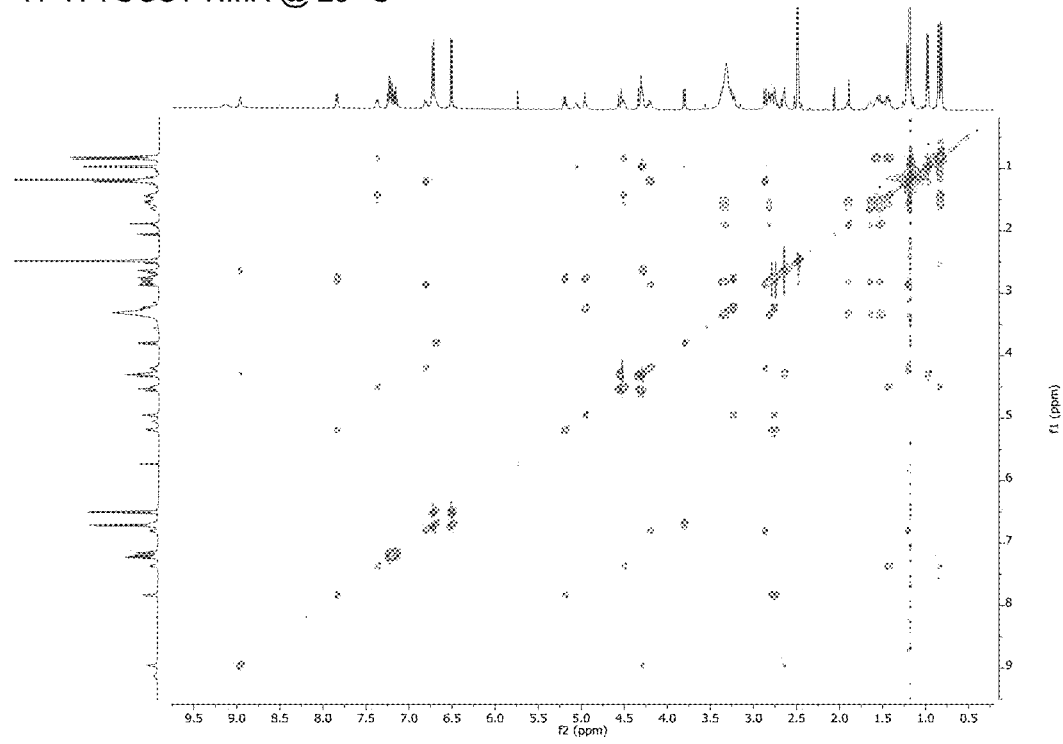

Figure 40
Compound No. 126
¹H NMR @ 25 °C
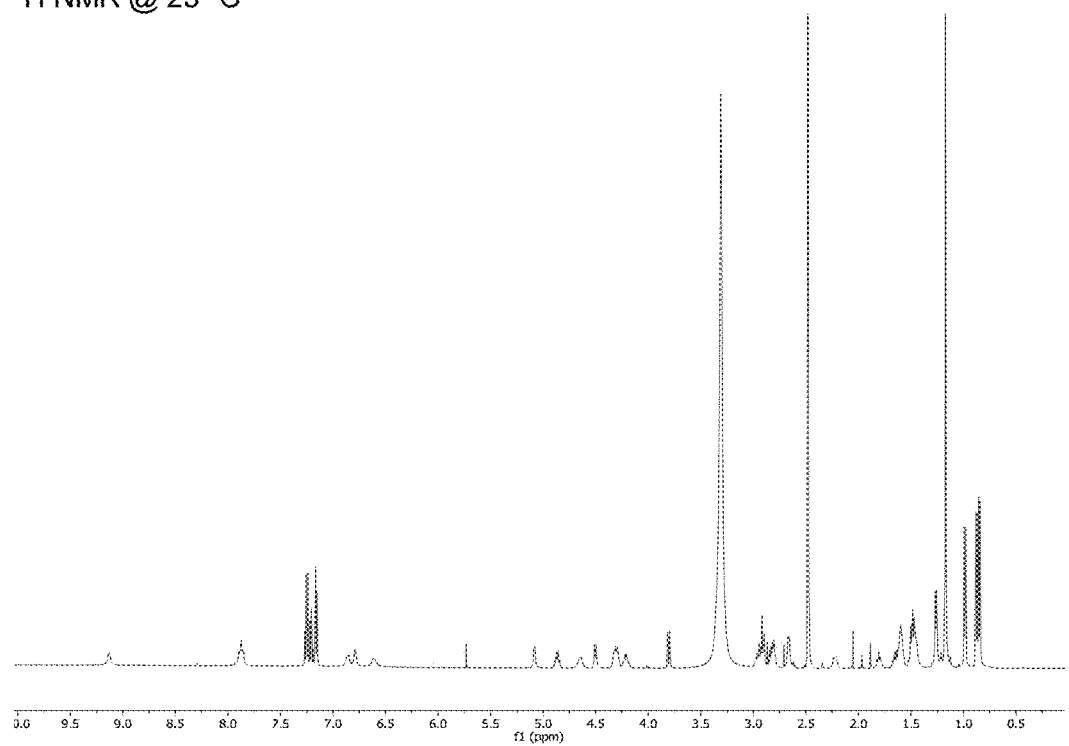
¹H-¹H TOCSY NMR @ 25 °C
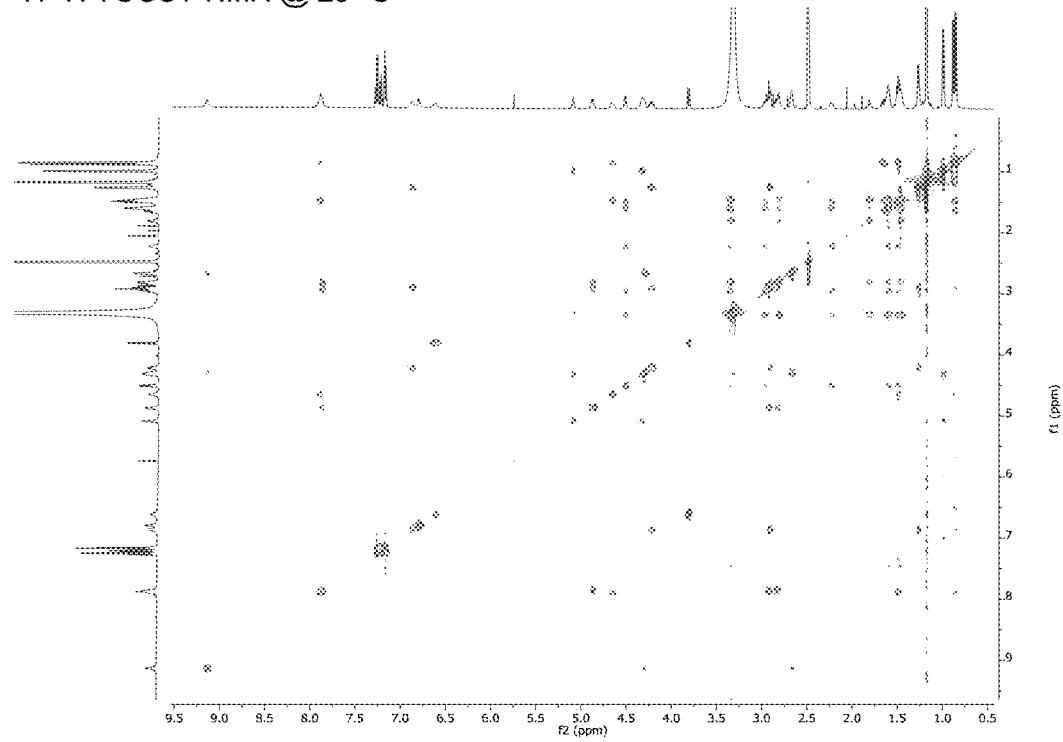

Figure 41
Compound No. 127
¹H NMR @ 25 °C
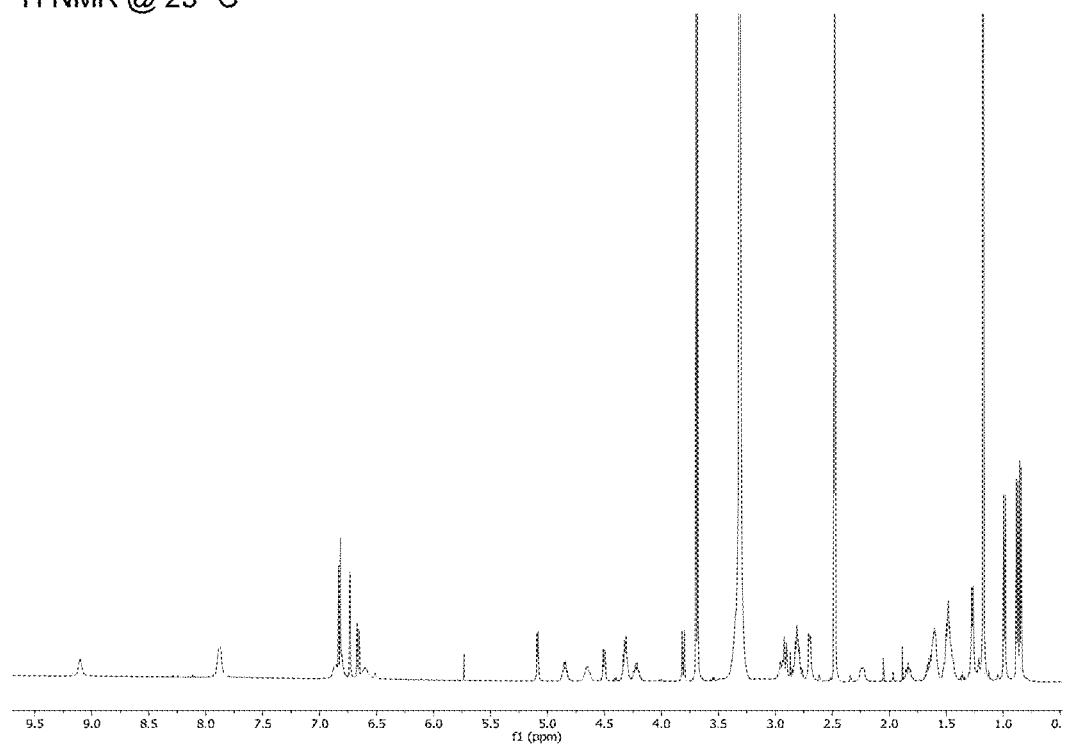
¹H-¹H TOCSY NMR @ 25 °C
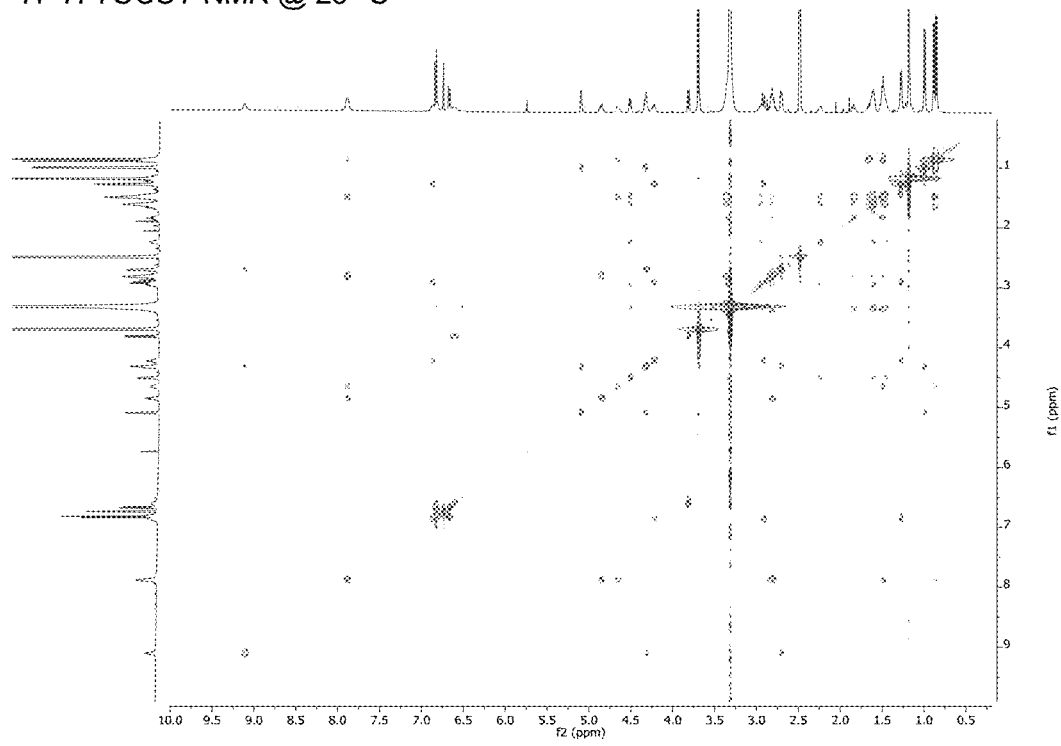

Figure 42
Compound No. 128
¹H NMR @ 25 °C
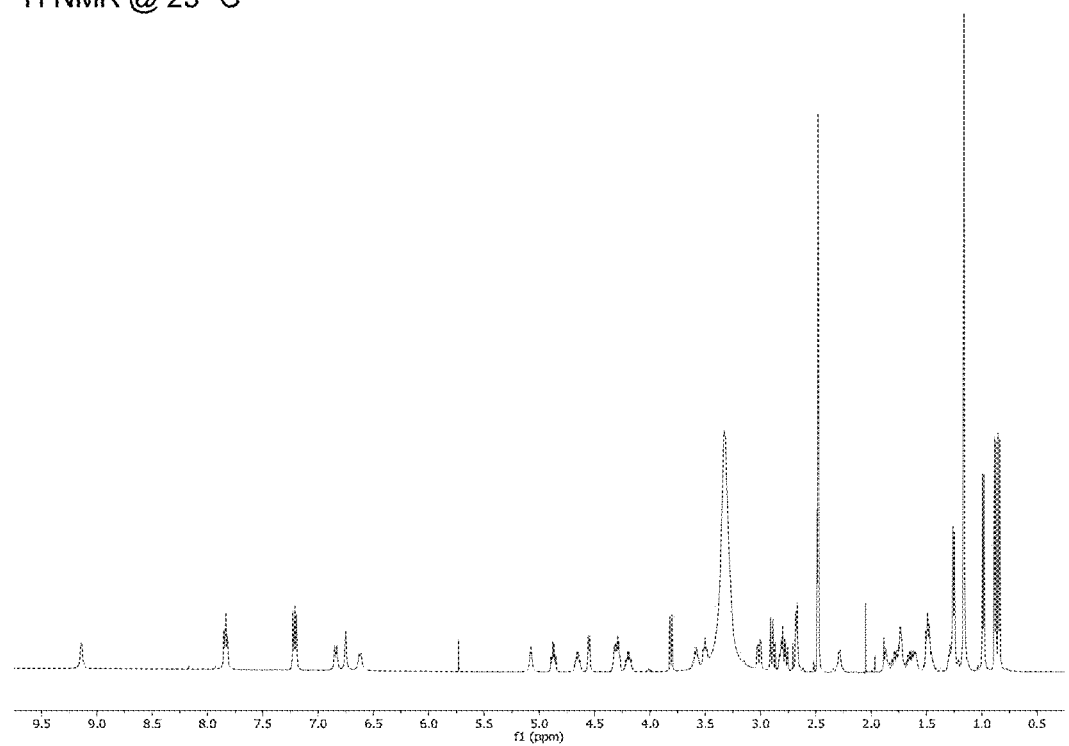
¹H-¹H TOCSY NMR @ 25 °C
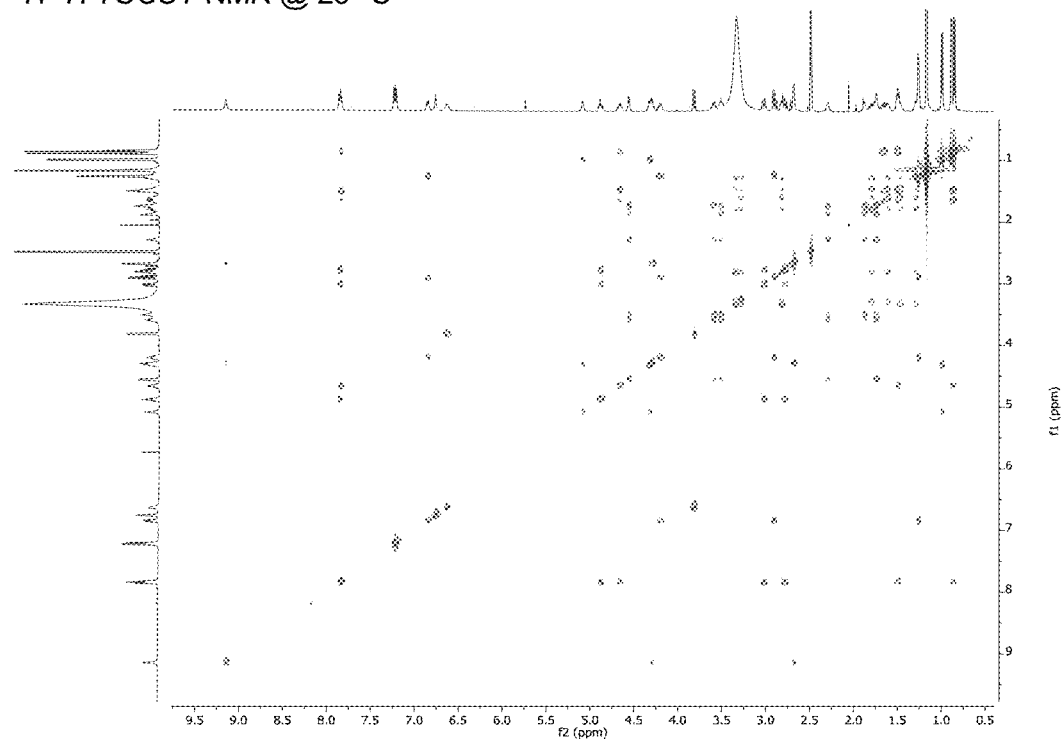

Figure 43
Compound No. 129
¹H NMR @ 25 °C
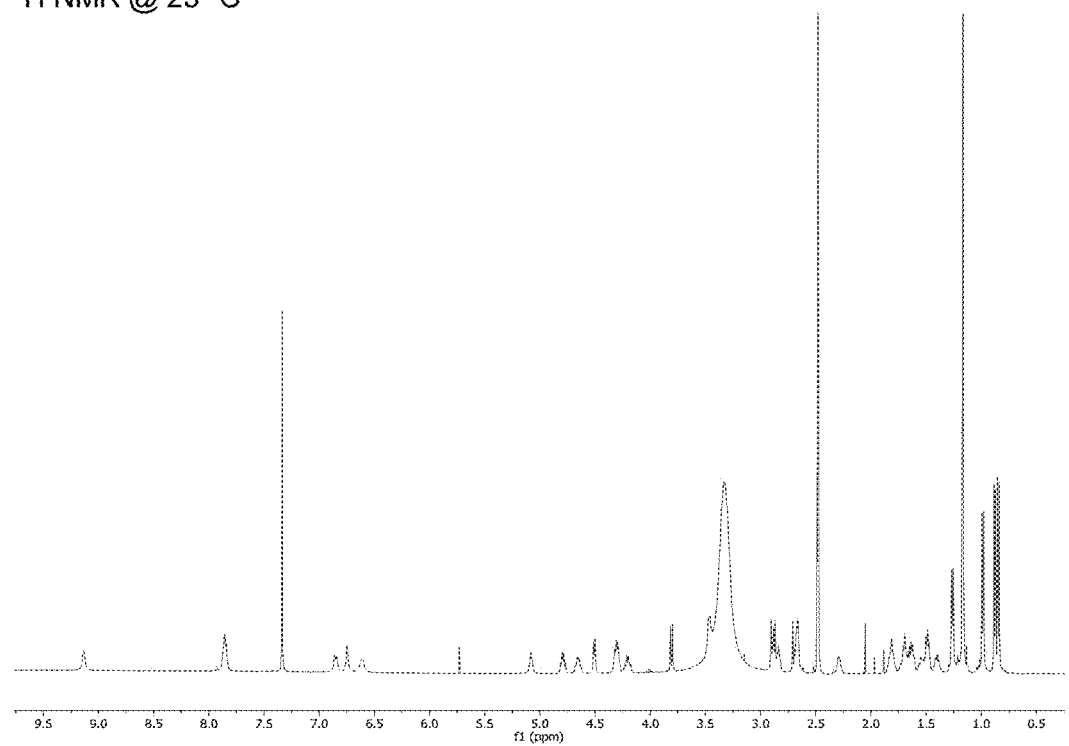
¹H-¹H TOCSY NMR @ 25 °C
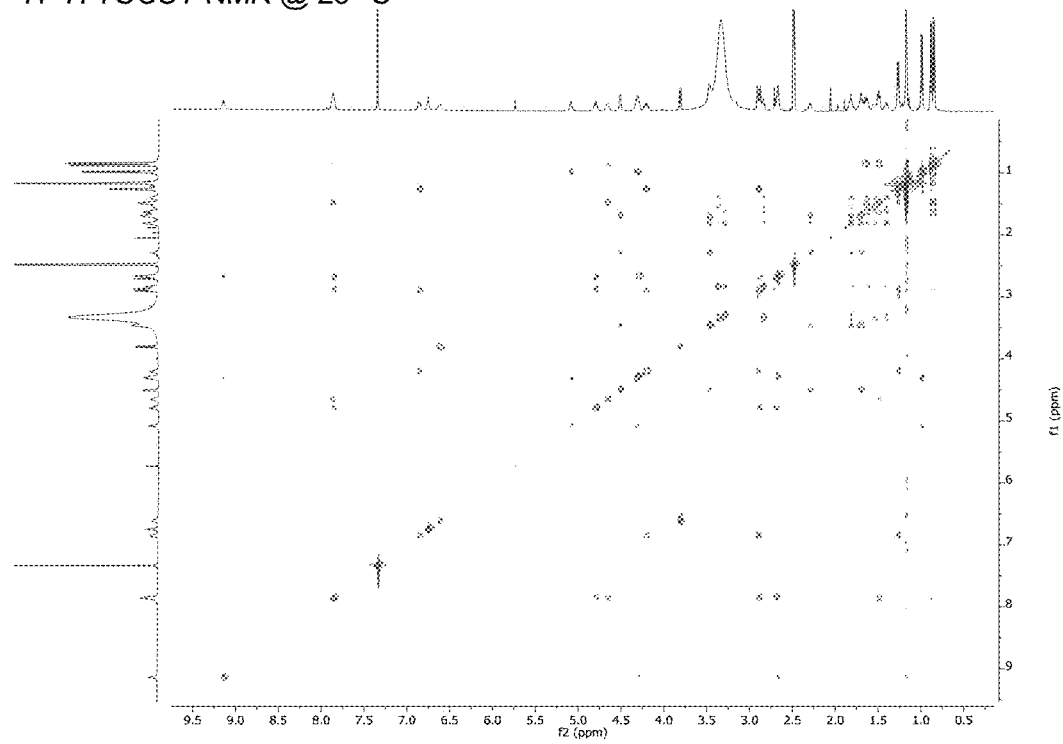

Figure 44
Compound No. 229
¹H NMR @ 25 °C
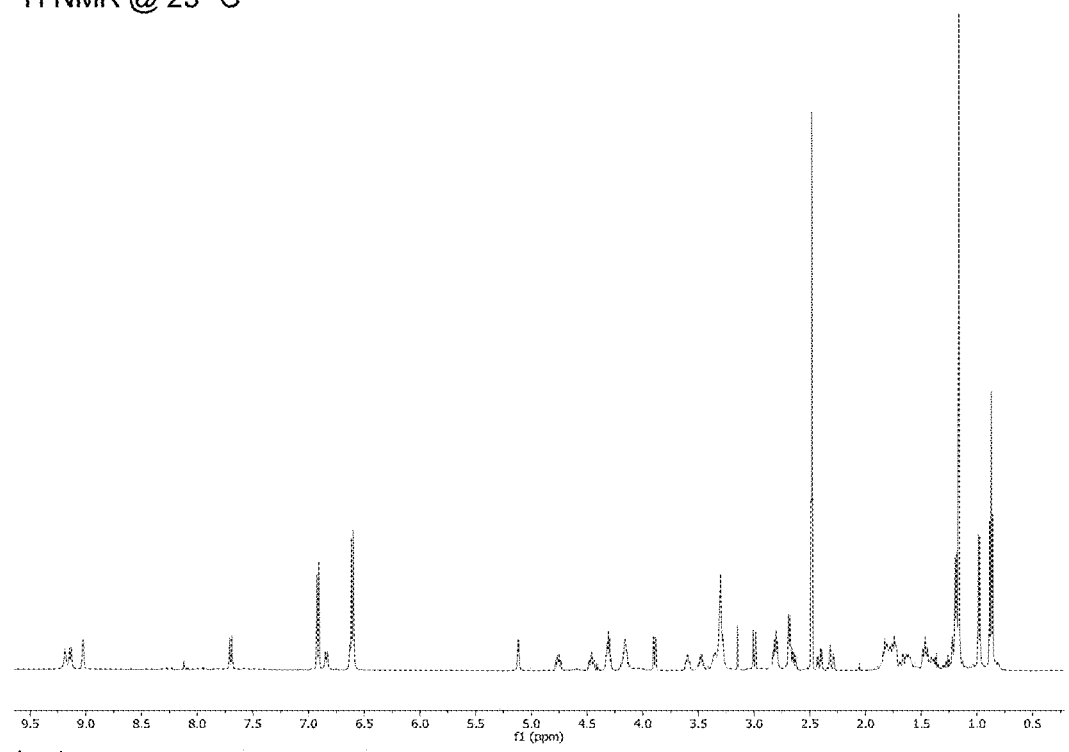
¹H-¹H TOCSY NMR @ 25 °C
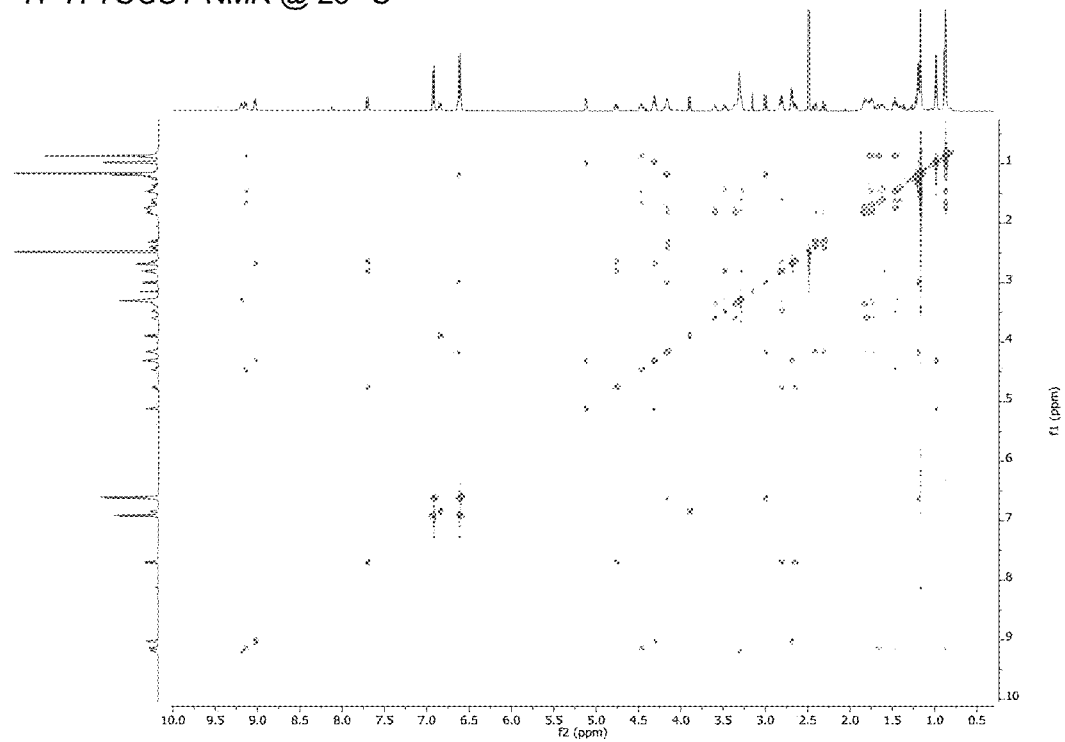

Figure 45
Compound No. 230
¹H NMR @ 25 °C
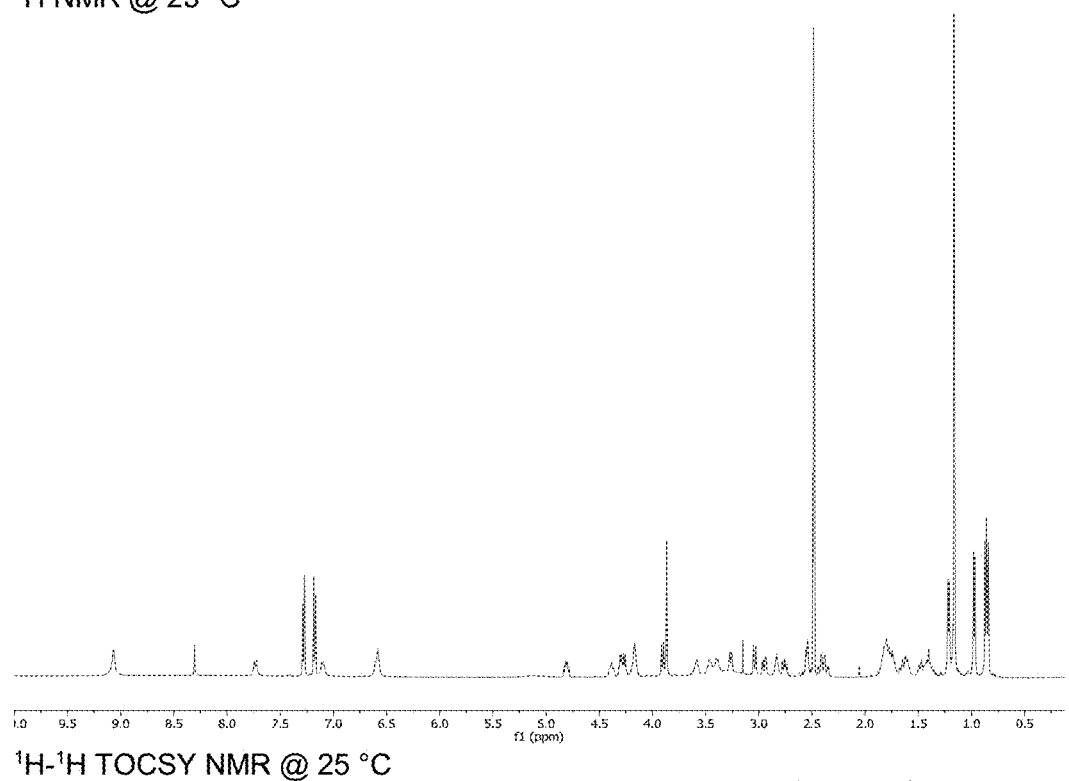
¹H-¹H TOCSY NMR @ 25 °C
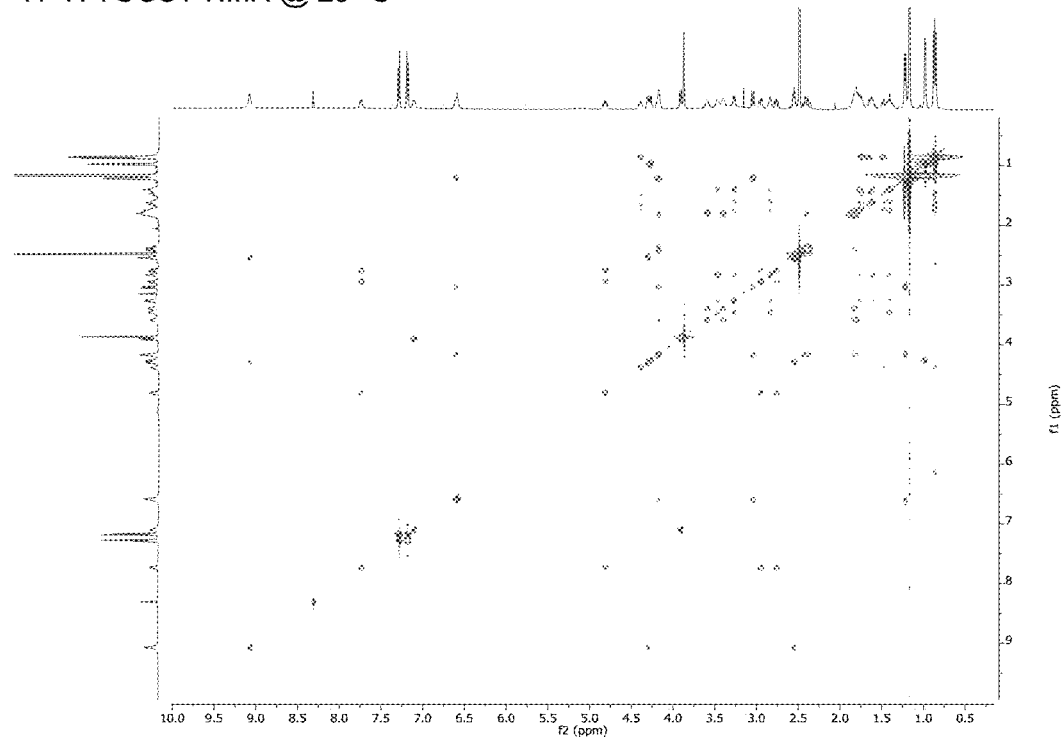

Figure 46
Compound No. 266
¹H NMR @ 25 °C
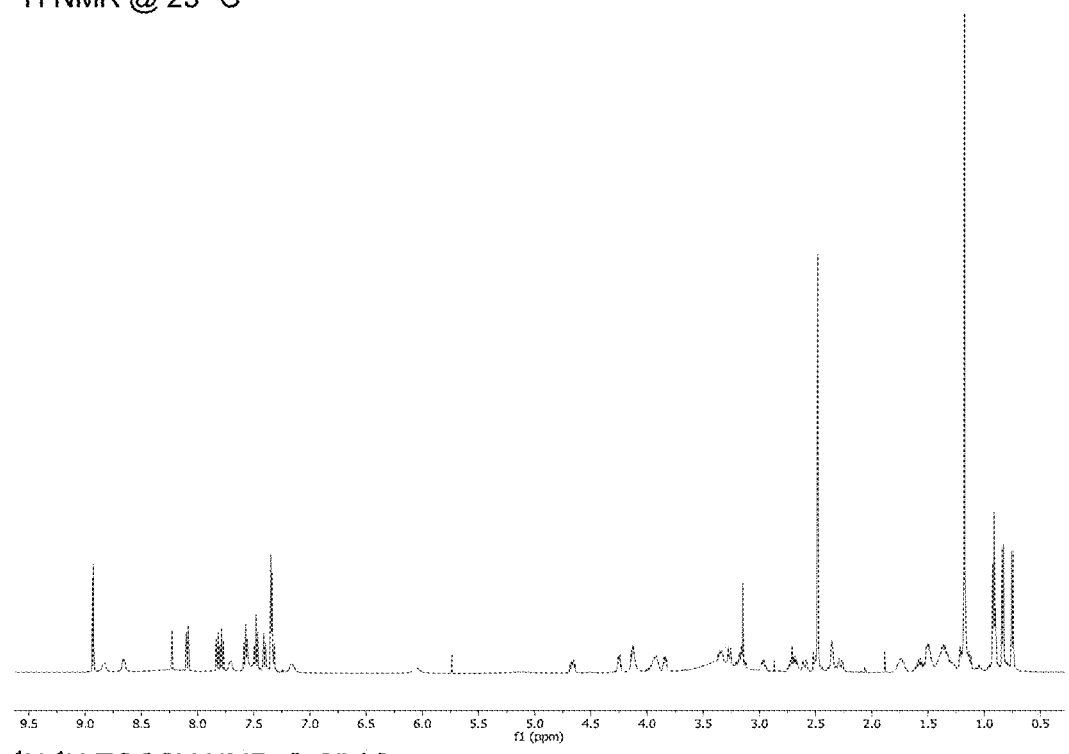
¹H-¹H TOCSY NMR @ 25 °C
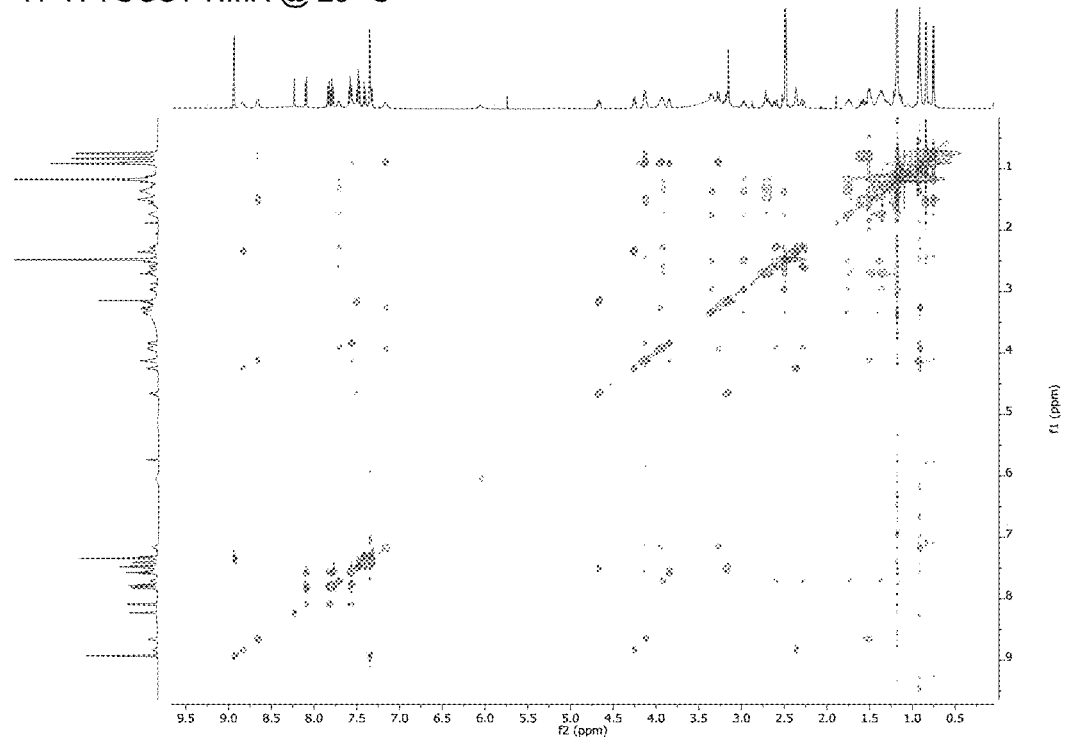

Figure 47
Compound No. 269
¹H NMR @ 25 °C
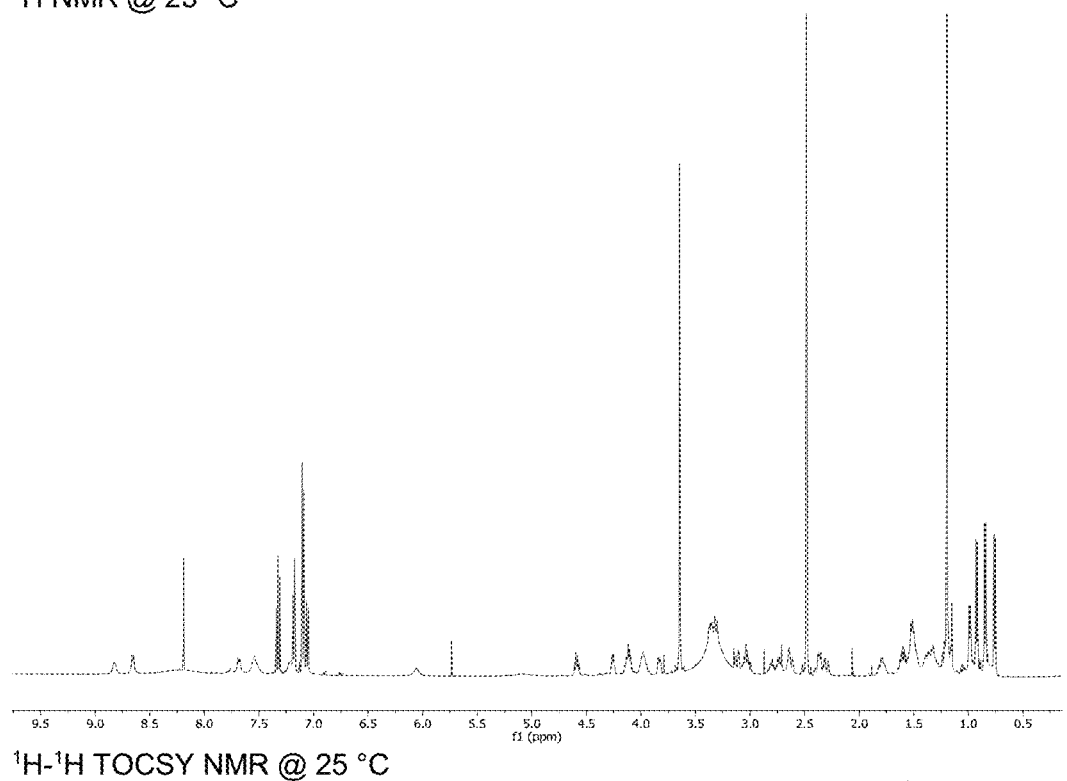
¹H-¹H TOCSY NMR @ 25 °C
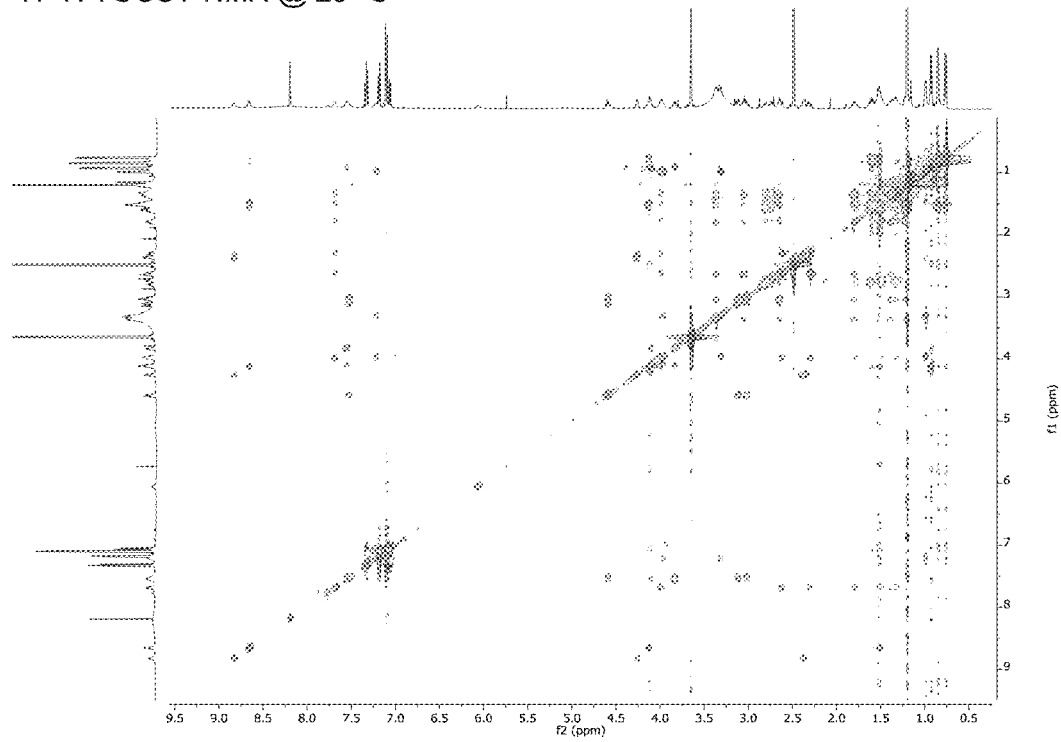

CYCLIC PEPTIDES TARGETING ALPHA-4-BETA-7 INTEGRIN

RELATED APPLICATIONS

This application is a national phase application under 35 U.S.C. & 371 of International Application No. PCT/CA2016/000274 filed Nov. 14, 2016, which claims priority from U.S. Provisional Application No. 62/254,003 filed on Nov. 11, 2015, both of which are incorporated herein by reference in their entirety.

FIELD OF THE INVENTION

The invention relates to antagonists of α4β7 integrin, and more particularly to cyclic peptide antagonists.

BACKGROUND OF THE INVENTION

Integrins are transmembrane receptors that are the bridges for cell-cell and cell-extracellular matrix (ECM) interactions. When triggered, integrins trigger chemical pathways to the interior (signal transduction), such as the chemical composition and mechanical status of the ECM.

Integrins are obligate heterodimers, having two different chains: the α (alpha) and β (beta) subunits.

The α4β7 integrin is expressed on lymphocytes and is responsible for T-cell homing into gut-associated lymphoid tissues through its binding to mucosal addressin cell adhesion molecule (MAdCAM), which is present on high endothelial venules of mucosal lymphoid organs.

Inhibitors of specific integrin-ligand interactions have been shown effective as anti-inflammatory agents for the treatment of various autoimmune diseases. For example, monoclonal antibodies displaying high binding affinity for α4β7 have displayed therapeutic benefits for gastrointestinal auto-inflammatory/autoimmune diseases, such as Crohn's disease, and ulcerative colitis.

There is a need to develop improved α4β7 antagonists to prevent or treat inflammatory conditions and/or autoimmune diseases.

Certain methods of making cyclic peptides (nacellins) are described in Applicant's PCT Publication No. WO 2010/105363.

SUMMARY OF THE INVENTION

In an aspect, there is provided, a compound of formula (I):

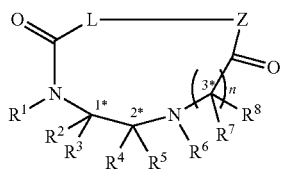

(I)

wherein
$R^1$ is H; lower alkyl; aryl; heteroaryl; alkenyl; or heterocycle; all of which are optionally substituted at one or more substitutable positions with one or more suitable substituents;

$R^2$ and $R^3$ are each independently an amino acid chain of a proteinogenic or a non-proteinogenic alpha-amino acid, provided that $R^2$ and $R^3$ may be covalently linked to each other to form a ring;

$R^4$ and $R^5$ are each independently H; lower alkyl; aryl; heteroaryl; alkenyl; heterocycle; acids of the formula —C(O)OH; esters of the formula —C(O)OR* wherein R* is selected from alkyl and aryl; amides of the formula —C(O)NRR*, wherein R and R* are independently selected from H, alkyl and aryl; —CH$_2$C(O)R, wherein R is selected from —OH, lower alkyl, aryl, -loweralkyl-aryl, or —NRaRb, where Ra and Rb are independently selected from H, lower alkyl, aryl or -loweralkyl-aryl; or —C(O)Rc, wherein Rc is selected from lower alkyl, aryl or -lower alkyl-aryl; or -lower alkyl-ORd, wherein Rd is a suitable protecting group or OH group; all of which are optionally substituted at one or more substitutable positions with one or more suitable substituents;

provided that $R^2$ or $R^3$ can be covalently linked to $R^1$ to form a cyclic secondary amine, and/or to $R^4$ or $R^5$ to form a ring, $R^4$ and $R^5$ may also be covalently linked to each other to form a ring;

$R^6$ is H, lower alkyl, benzyl, alkenyl, lower alkyloxy; aryl; heteroaryl; heterocycle; —C(O)R**, wherein R** is independently selected from alkyl, aryl, heteroaryl, amino, aminoalkyl, aminoaryl, aminoheteroaryl, alkoxy, aryloxy, heteroaryloxy; —CH$_2$C(O)R; or —C(O)Rc; all of which are optionally substituted at one or more substitutable positions with one or more suitable substituents, or along with $R^7$ or $R^8$, a cyclic side chain of a proteinogenic or a non-proteinogenic amino acid having, the N-terminus thereof being the N—$R^6$, wherein the proteinogenic or a non-proteinogenic amino acid can be substituted with a suitable substituent;

$R^7$ and $R^8$ are independently selected from the amino acid side chains of a proteinogenic or a non-proteinogenic alpha-amino acid having the N-terminus thereof being the N—$R^6$, or may form a cyclic side chain with $R^6$;

stereocentres 1*, 2* and 3* are each independently selected from R and S;

n is 1, 2, 3, or 4 and where n is 2-4, each $R^7$ and each $R^8$ are independent of each other; and wherein Z is an amino terminus of an amino acid; —C=O— adjacent L is the carboxy terminus of an amino acid; and L along with Z and —C=O— is a peptide having the following formula:

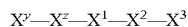

wherein $X^y$ and $X^z$ are each independently a proteinogenic or non-proteinogenic amino acid;

$X^1$ is Leucine or tert-butyl-Ala;

$X^2$ is Asp; and $X^3$ is any amino acid listed under column $X^3$ of Table 1B.

In an aspect, there is provided, a pharmaceutical composition comprising a compound described herein along with the pharmaceutically acceptable carrier. The pharmaceutical composition may be formulated for any one of oral delivery, topical delivery and parenteral delivery.

In an aspect, there is provided, a method of treating inflammation or an autoimmune disease in a patient, comprising administering to the patient a therapeutically effective amount of the compound described herein. Preferably the inflammation or an autoimmune disease is gastrointestinal.

In an aspect, there is provided, a method for treating a condition in a patient associated with a biological function of an α4β7 integrin, the method comprising administering to the patient a therapeutically effective amount of the compound described herein.

In an aspect, there is provided, a method for treating a disease or condition in a patient comprising administering to the patient a therapeutically effective amount of the compound described herein, wherein the disease or condition is a local or systemic infection of a virus or retrovirus.

In an aspect, there is provided, a method for treating a disease or condition in a patient comprising administering to the patient a therapeutically effective amount of the compound described herein, wherein the hepatitis A, B or C, hepatic encephalopathy, non-alcoholic steatohepatitis, cirrhosis, variceal bleeding, hemochromatosis, Wilson disease, tyrosinemia, alpha-1-antitrypsin deficiency, glycogen storage disease, hepatocellular carcinoma, liver cancer, primary biliary cholangitis, primary sclerosing cholangitis, primary biliary sclerosis, biliary tract disease, autoimmune hepatitis, or graft-versus-host disease.

BRIEF DESCRIPTION OF FIGURES AND TABLES

These and other features of the preferred embodiments of the invention will become more apparent in the following detailed description in which reference is made to the appended drawings and tables wherein:

FIG. 2 shows a representative 18-membered ring compound along with variations made at certain positions with corresponding α4β7 integrin ELISA 1050 binding values associated with those variations.

FIG. 14 is an $^1$H NMR at 25° C. and $^1$H-$^1$H TOCSY NMR at 25° C. of Compound No. 9.

FIG. 15 is an $^1$H NMR at 25° C. and $^1$H-$^1$H TOCSY NMR at 25° C. of Compound No. 10.

FIG. 16 is an $^1$H NMR at 25° C. and $^1$H-$^1$H TOCSY NMR at 25° C. of Compound No. 11.

FIG. 17 is an $^1$H NMR at 25° C. and $^1$H-$^1$H TOCSY NMR at 25° C. of Compound No. 12.

FIG. 18 is an $^1$H NMR at 25° C. and $^1$H-$^1$H TOCSY NMR at 25° C. of Compound No. 14.

FIG. 19 is an $^1$H NMR at 25° C. and $^1$H-$^1$H TOCSY NMR at 25° C. of Compound No. 15.

FIG. 20 is an $^1$H NMR at 25° C. and $^1$H-$^1$H TOCSY NMR at 25° C. of Compound No. 34.

FIG. 21 is an $^1$H NMR at 25° C. and $^1$H-$^1$H TOCSY NMR at 25° C. of Compound No. 40.

FIG. 22 is an $^1$H NMR at 25° C. and $^1$H-$^1$H TOCSY NMR at 25° C. of Compound No. 41.

FIG. 23 is an $^1$H NMR at 25° C. and $^1$H-$^1$H TOCSY NMR at 25° C. of Compound No. 42.

FIG. 24 is an $^1$H NMR at 25° C. and $^1$H-$^1$H TOCSY NMR at 25° C. of Compound No. 43.

FIG. 25 is an $^1$H NMR at 25° C. and $^1$H-$^1$H TOCSY NMR at 25° C. of Compound No. 45.

FIG. 26 is an $^1$H NMR at 25° C. and $^1$H-$^1$H TOCSY NMR at 25° C. of Compound No. 47.

FIG. 27 is an $^1$H NMR at 25° C. and $^1$H-$^1$H TOCSY NMR at 25° C. of Compound No. 50.

FIG. 28 is an $^1$H NMR at 25° C. and $^1$H-$^1$H TOCSY NMR at 25° C. of Compound No. 100.

FIG. 29 is an $^1$H NMR at 25° C. and $^1$H-$^1$H TOCSY NMR at 25° C. of Compound No. 101.

FIG. 30 is an $^1$H NMR at 25° C. and $^1$H-$^1$H TOCSY NMR at 25° C. of Compound No. 103

FIG. 31 is an $^1$H NMR at 25° C. and $^1$H-$^1$H TOCSY NMR at 25° C. of Compound No. 104.

FIG. 32 is an $^1$H NMR at 25° C. and $^1$H-$^1$H TOCSY NMR at 25° C. of Compound No. 106.

FIG. 33 is an $^1$H NMR at 25° C. and $^1$H-$^1$H TOCSY NMR at 25° C. of Compound No. 107.

FIG. 34 is an $^1$H NMR at 25° C. and $^1$H-$^1$H TOCSY NMR at 25° C. of Compound No. 108.

FIG. 35 is an $^1$H NMR at 25° C. and $^1$H-$^1$H TOCSY NMR at 25° C. of Compound No. 109.

FIG. 36 is an $^1$H NMR at 25° C. and $^1$H-$^1$H TOCSY NMR at 25° C. of Compound No. 110.

FIG. 37 is an $^1$H NMR at 25° C. and $^1$H-$^1$H TOCSY NMR at 25° C. of Compound No. 111.

FIG. 38 is an $^1$H NMR at 25° C. and $^1$H-$^1$H TOCSY NMR at 25° C. of Compound No. 112.

FIG. 39 is an $^1$H NMR at 25° C. and $^1$H-$^1$H TOCSY NMR at 25° C. of Compound No. 123.

FIG. 40 is an $^1$H NMR at 25° C. and $^1$H-$^1$H TOCSY NMR at 25° C. of Compound No. 126.

FIG. 41 is an $^1$H NMR at 25° C. and $^1$H-$^1$H TOCSY NMR at 25° C. of Compound No. 127.

FIG. 42 is an $^1$H NMR at 25° C. and $^1$H-$^1$H TOCSY NMR at 25° C. of Compound No. 128.

FIG. 43 is an $^1$H NMR at 25° C. and $^1$H-$^1$H TOCSY NMR at 25° C. of Compound No. 129.

FIG. 44 is an $^1$H NMR at 25° C. and $^1$H-$^1$H TOCSY NMR at 25° C. of Compound No. 229.

FIG. 45 is an $^1$H NMR at 25° C. and $^1$H-$^1$H TOCSY NMR at 25° C. of Compound No. 230.

FIG. 46 is an $^1$H NMR at 25° C. and $^1$H-$^1$H TOCSY NMR at 25° C. of Compound No. 266.

FIG. 47 is an $^1$H NMR at 25° C. and $^1$H-$^1$H TOCSY NMR at 25° C. of Compound No. 269.

Figure 1:
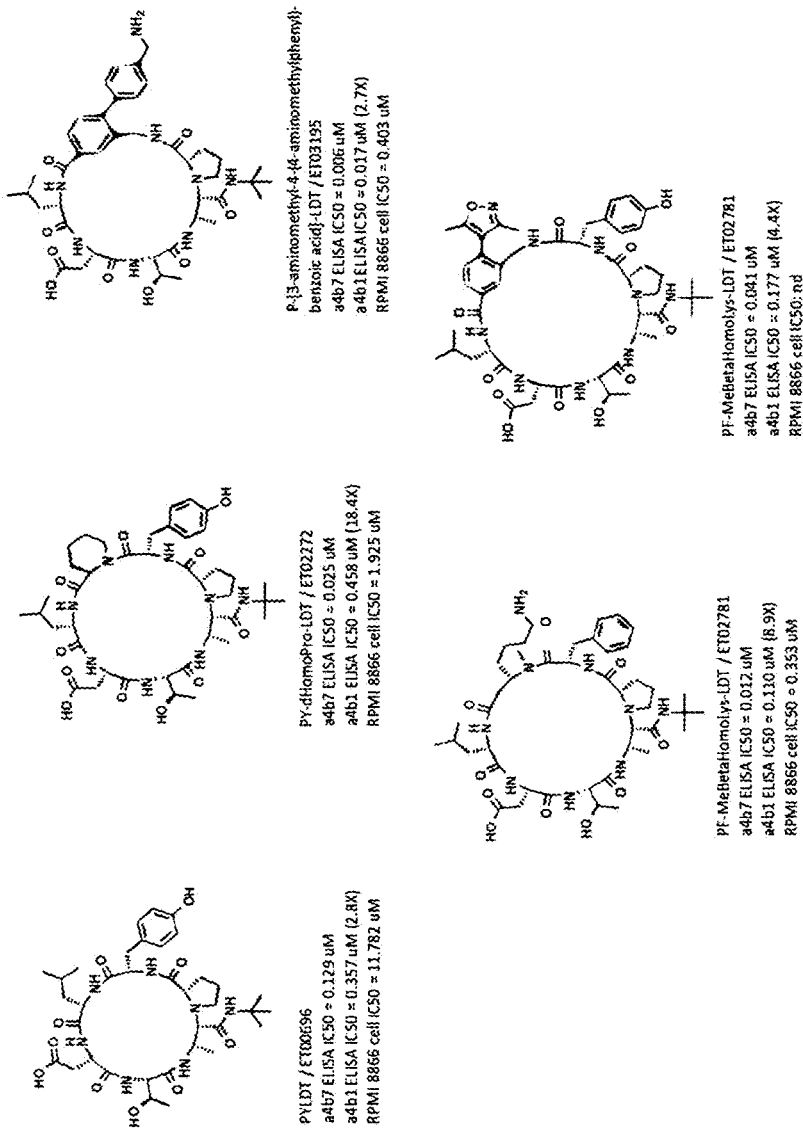
FIG. 1 shows representative compounds of the present application, namely from the following classes, 18-membered ring, 21-membered ring, 21-membered ring (non-canonical, i.e. having a delta amino acid), 22-membered ring, and 24-membered ring.
Figure 3:
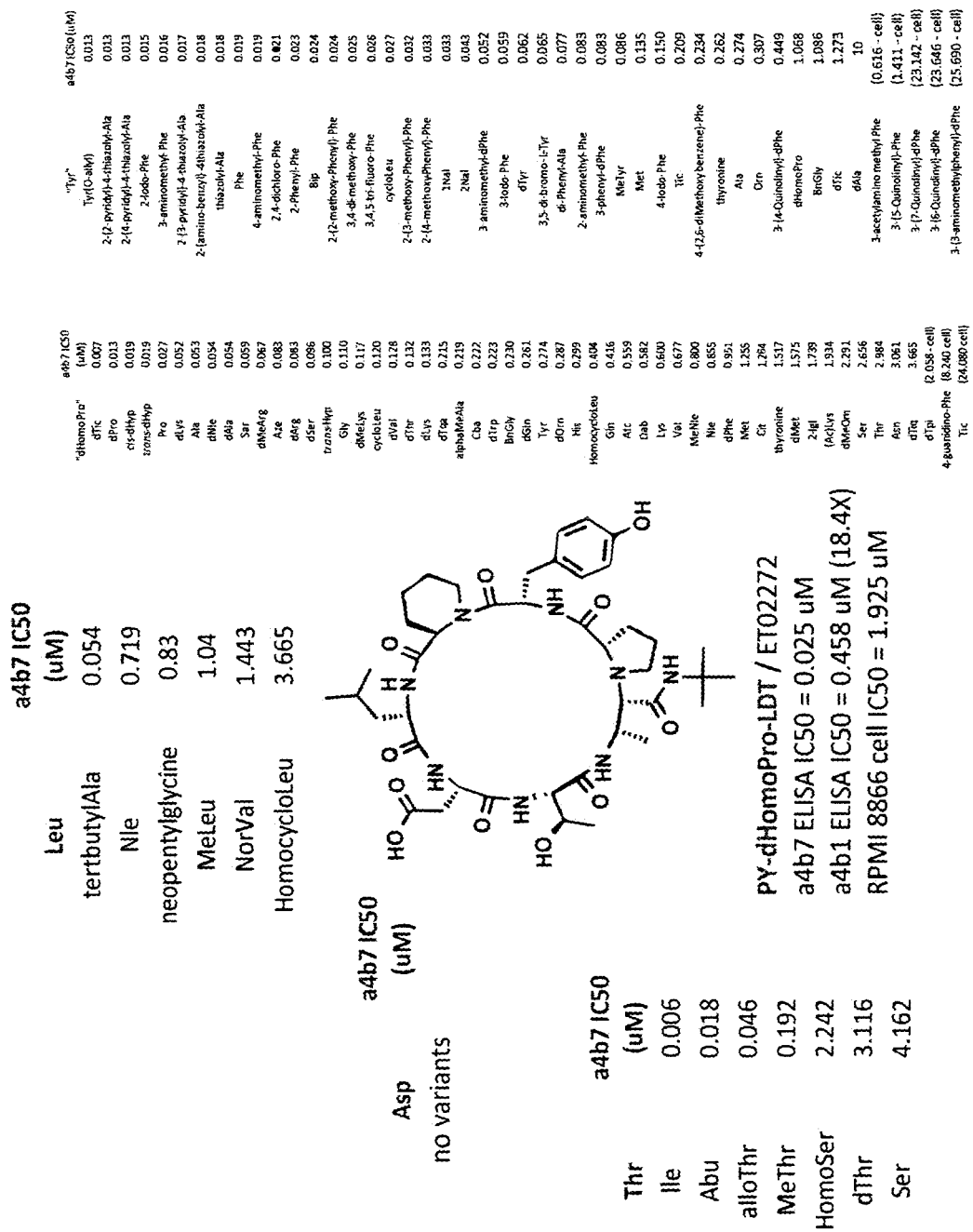
FIG. 3 shows a representative 21-membered ring compound along with variations made at certain positions with corresponding α4β7 integrin ELISA 1050 binding values associated with those variations.
Figure 4:
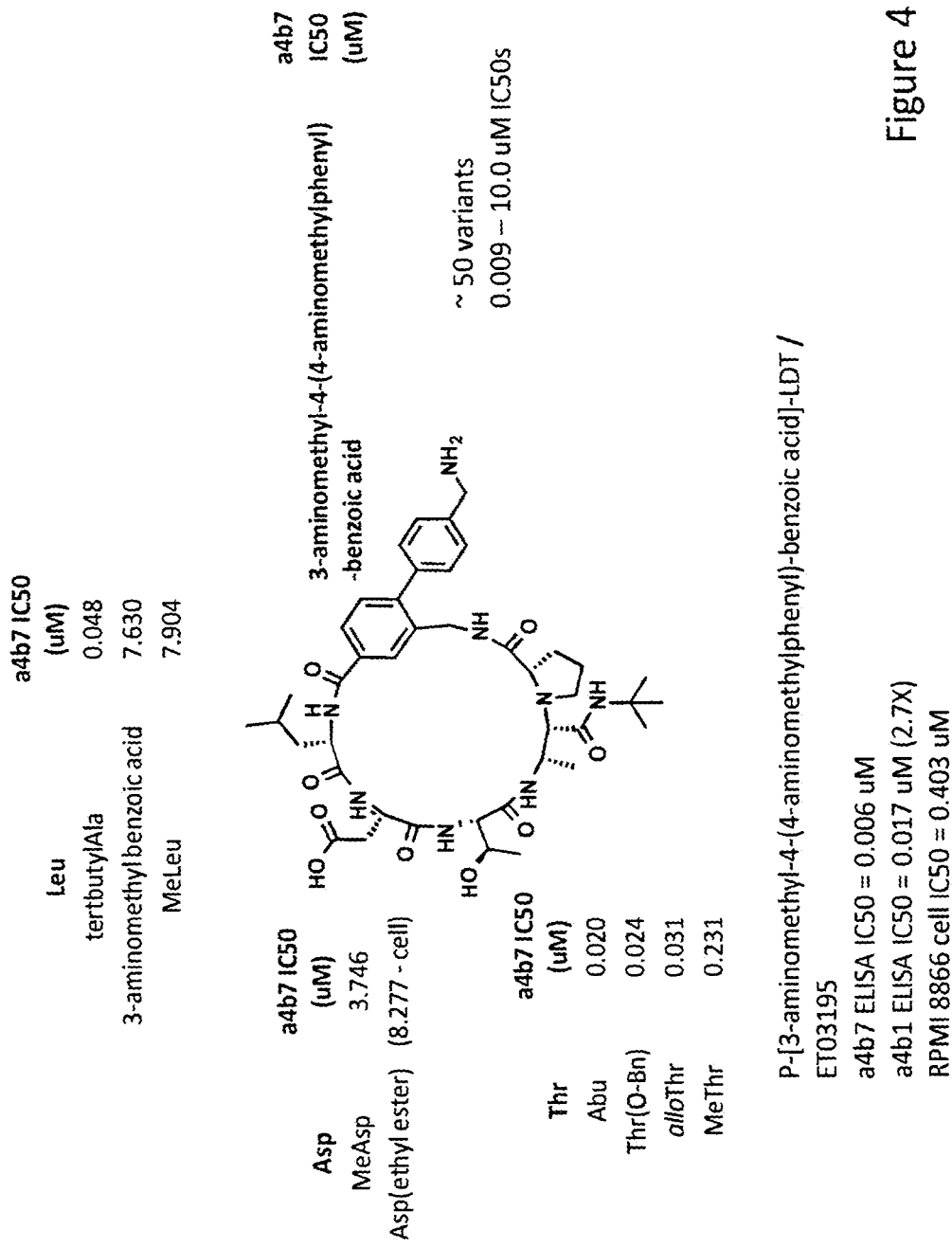
FIG. 4 shows a representative 21-membered ring (non-canonical, i.e. having a delta amino acid) compound along with variations made at certain positions with corresponding α4β7 integrin ELISA 1050 binding values associated with those variations.
Figure 5:
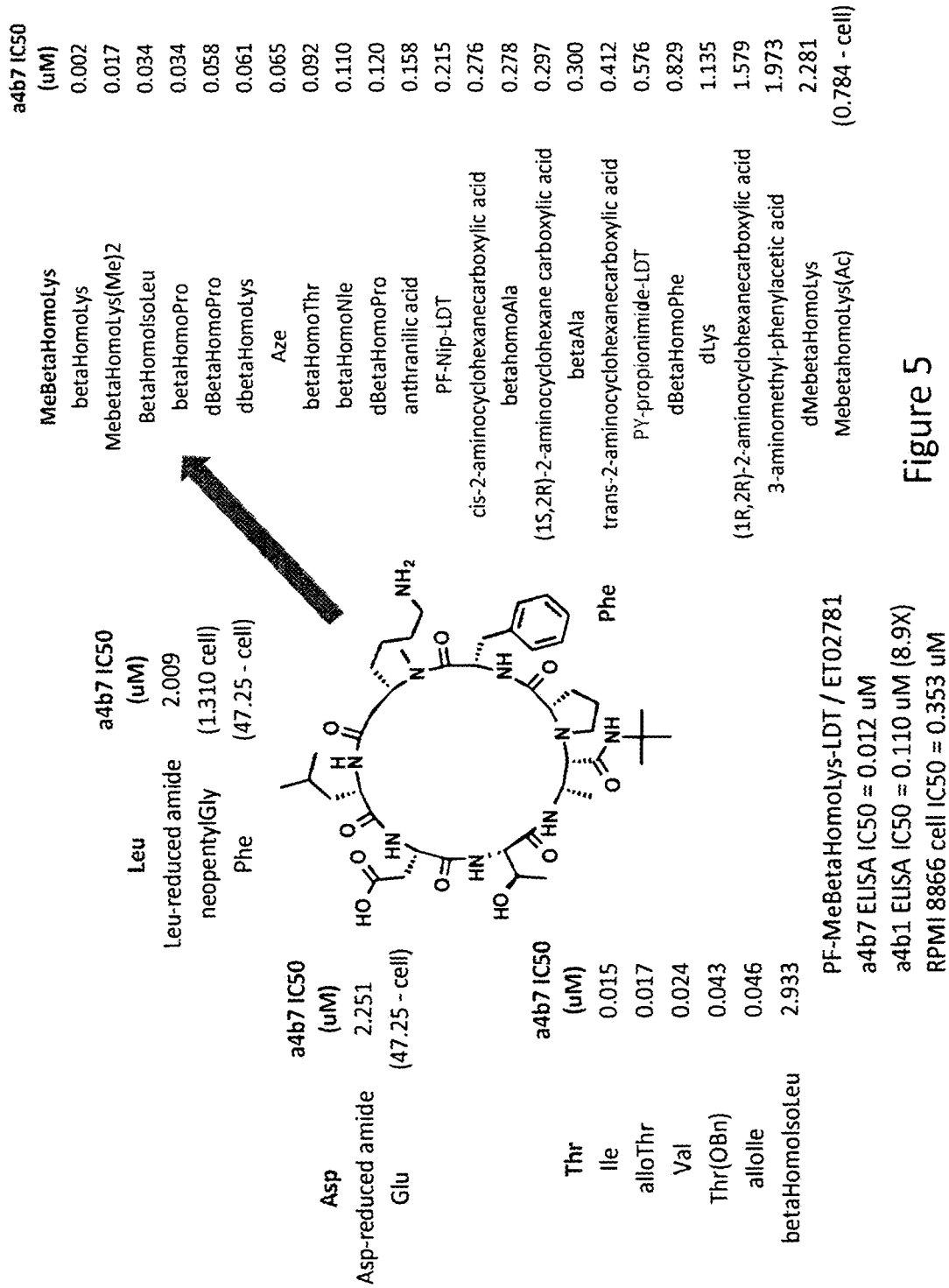
FIG. 5 shows a representative 22-membered ring compound along with variations made at certain positions with corresponding α4β7 integrin ELISA 1050 binding values associated with those variations.

Table 1 shows compounds exhibiting α4β7 integrin affinity, selectivity and/or activity; and specifically with respect to these compounds: (A) the structure of the linker portion; (B) the structure of the peptide portion; and (C) the affinity, selectivity and activity values.

To aid reading of the table, the following is noted:
Table 1A:
If R2 is H and R3 is CH3, the carbon atom bearing R2 and R3 has S-configuration.
If R2 is CH3 and R3 is H, the carbon atom bearing R2 and R3 has R-configuration.
If R2 is H and R3 is CH2-S-Ph, the carbon atom bearing R2 and R3 has S-configuration.
If R4 is H and R5 is C(O)—NH-tert-Butyl, the carbon atom bearing R4 and R5 has S-configuration.
If R4 is C(O)—NH-tert-Butyl and R5 is H, the carbon atom bearing R4 and R5 has R-configuration.
If R1 and R2 are both Pro-, the R1 and R2 substituents are covalently bound and form the pyrrolidine ring of Pro.
Table 1B
If R6 and R7 are both Pro, the R6 and R7 substituents are covalently bound and form the pyrrolidine ring of Pro.
If R6 and R8 are both dPro, the R6 and R8 substituents are covalently bound and form the pyrrolidine ring of dPro.
If R6 and R7 are both [(4S)-fluoro-Pro], the R6 and R7 substituents are covalently bound and form the pyrrolidine ring of [(4S)-fluoro-Pro].
If R7 is Nva and R8 is H, the carbon bearing R7 and R8 has S-configuration.
If R6 and R7 are both Hyp, the R6 and R7 substituents are covalently bound and form the pyrrolidine ring of Hyp.
If no entry exists under column Xz, the residue is absent.
Table 1C
If no entry exists under any of the columns, no data was collected.

Table 2 shows compounds exhibiting less α4β7 integrin affinity, selectivity and/or activity; and specifically with respect to these compounds: (A) the structure of the linker portion; (B) the structure of the peptide portion; and (C) the affinity, selectivity and activity values.

To aid reading of the table, the following is noted:
Table 2A
If R2 is H and R3 is CH3, the carbon atom bearing R2 and R3 has S-configuration.
If R2 is CH3 and R3 is H, the carbon atom bearing R2 and R3 has R-configuration.
If R4 is H and R5 is C(O)—NH-tert-Butyl, the carbon atom bearing R4 and R5 has S-configuration.
If R4 is C(O)—NH-tert-Butyl and R5 is H, the carbon atom bearing R4 and R5 has R-configuration.
If R1 and R2 are both Pro-, the R1 and R2 substituents are covalently bound and form the pyrrolidine ring of Pro.
Table 2B
If R6 and R7 are both Pro, the R6 and R7 substituents are covalently bound and form the pyrrolidine ring of Pro.
If R6 and R8 are both dPro, the R6 and R8 substituents are covalently bound and form the pyrrolidine ring of dPro.
If no entry exists under column Xz, the residue is absent.
Table 2C
If no entry exists under any of the columns, no data was collected.

Table S1 is a correspondence table linking the compounds described herein with the synthesis protocols outlined in the methods and materials.

DETAILED DESCRIPTION

In the following description, numerous specific details are set forth to provide a thorough understanding of the invention. However, it is understood that the invention may be practiced without these specific details.

In an aspect, there is provided, a compound of formula (I):

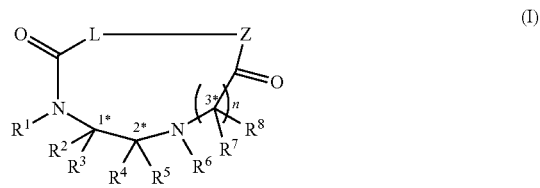

wherein
$R^1$ is H; lower alkyl; aryl; heteroaryl; alkenyl; or heterocycle; all of which are optionally substituted at one or more substitutable positions with one or more suitable substituents;

$R^2$ and $R^3$ are each independently an amino acid chain of a proteinogenic or a non-proteinogenic alpha-amino acid, provided that $R^2$ and $R^3$ may be covalently linked to each other to form a ring;

$R^4$ and $R^5$ are each independently H; lower alkyl; aryl; heteroaryl; alkenyl; heterocycle; acids of the formula —C(O)OH; esters of the formula —C(O)OR* wherein R* is selected from alkyl and aryl; amides of the formula —C(O)NRR*, wherein R and R* are independently selected from H, alkyl and aryl; —CH$_2$C(O)R, wherein R is selected from —OH, lower alkyl, aryl, -loweralkyl-aryl, or —NRaRb, where Ra and Rb are independently selected from H, lower alkyl, aryl or -loweralkyl-aryl; or —C(O)Rc, wherein Rc is selected from lower alkyl, aryl or -lower alkyl-aryl; or -lower alkyl-ORd, wherein Rd is a suitable protecting group or OH group; all of which are optionally substituted at one or more substitutable positions with one or more suitable substituents;

provided that $R^2$ or $R^3$ can be covalently linked to $R^1$ to form a cyclic secondary amine, and/or to $R^4$ or $R^5$ to form a ring, $R^4$ and $R^5$ may also be covalently linked to each other to form a ring;

$R^6$ is H, lower alkyl, benzyl, alkenyl, lower alkyloxy; aryl; heteroaryl; heterocycle; —C(O)R**, wherein R** is independently selected from alkyl, aryl, heteroaryl, amino, aminoalkyl, aminoaryl, aminoheteroaryl, alkoxy, aryloxy, heteroaryloxy; —CH$_2$C(O)R; or —C(O)Rc; all of which are optionally substituted at one or more substitutable positions with one or more suitable substituents, or along with $R^7$ or $R^8$, a cyclic side chain of a proteinogenic or a non-proteinogenic amino acid having, the N-terminus thereof being the N—$R^6$, wherein the proteinogenic or a non-proteinogenic amino acid can be substituted with a suitable substituent;

$R^7$ and $R^8$ are independently selected from the amino acid side chains of a proteinogenic or a non-proteinogenic alpha-amino acid having the N-terminus thereof being the N—$R^6$, or may form a cyclic side chain with $R^6$;

stereocentres 1*, 2* and 3* are each independently selected from R and S;

n is 1, 2, 3, or 4 and where n is 2-4, each $R^7$ and each $R^8$ are independent of each other; and wherein Z is an amino terminus of an amino acid; —C=O— adjacent L is the carboxy terminus of an amino acid; and L along with Z and —C=O— is a peptide having the following formula:

$$X^y\text{—}X^z\text{—}X^1\text{—}X^2\text{—}X^3$$

wherein $X^y$ and $X^z$ are each independently a proteinogenic or non-proteinogenic amino acid;
$X^1$ is Leucine or tert-butyl-Ala;
$X^2$ is Asp; and
$X^3$ is any amino acid listed under column $X^3$ of Table 1B.

The compounds shown in Tables 1A, 1B and 10 exhibit antagonistic activity against α4β7 integrin and having selectivity over α4β1 integrin. A person skilled in the art would expect that substituents $R^1$-$R^8$ and amino acids $X^y$, $X^z$, $X^1$, $X^2$, and $X^3$ outlined in—Tables 1A and 1B with respect to different compounds could be combined in any manner and would likely result in a compound that would exhibit α4β7 integrin activity and selectivity.

As used herein, the term "amino acid" refers to molecules containing an amine group, a carboxylic acid group and a side chain that varies. Amino acid is meant to include not only the twenty amino acids commonly found in proteins but also non-standard amino acids and unnatural amino acid derivatives known to those of skill in the art, and therefore includes, but is not limited to, alpha, beta and gamma amino acids. Peptides are polymers of at least two amino acids and may include standard, non-standard, and unnatural amino acids. A peptide is a polymer of two or more amino acids.

The following abbreviations are used herein:

| Abbreviation | Description |
| --- | --- |
| 1,2-cis-ACHC | cis-2-aminocyclohexanecarboxylic acid |
| 1,2-trans-ACHC | trans-2-aminocyclohexanecarboxylic acid |
| 1Nal | 1-napthylalanine |
| 2Abz | anthranilic acid, 2-aminobenzoic acid |
| 2Igl | 2-indanylglycine |
| 2Nal | 2-napthylalanine |
| Abu | 2-aminobutyric acid |
| Aic | aminoindan-2-carboxylic acid |
| alloIle | allo-sioleucine, (2S,3R)-2-amino-3-methylpentanoic acid |
| alloThr | allo-threonine, (2S,3S)-2-amino-3-hydroxybutyric acid |
| alphaMePhe | α-methyl-phenylalanine, (S)-(–)-2-amino-2-methyl-3-phenylpropionic acid |
| Asp(ethyl ester) | aspartic acid β-ethyl ester |
| Atc | 2-aminotetraline-2-carboxylic acid |
| Aze | azetidine-2-carboxylic acid |
| BHT | butylated hydroxytoluene |
| Bip | biphenylalanine |
| C10 | sebacic acid |
| C12 | dodecanedioic |
| C7 | pimelic acid |
| C8 | suberic acid |
| C9 | azelaic acid |
| Cha | β-cyclohexyl alanine, (S)-2-amino-3-cyclohexylpropionic acid |
| Chg | cyclohexyl glycine |
| cis-dhyp | cis-D-4-Hydroxyproline, (2R,4R)-4-Hydroxypyrrolidine-2-carboxylic acid |
| cycloLeu | cyclo leucine, 1-Aminocyclopentane-1-carboxylic acid |
| cyclopropylAla | β-cyclopropyl alanine, (S)-2-amino-3-cyclopropyl-propionic acid |
| d2Igl | 2-indanyl-D-glycine |
| Dap(Cbz) | Nβ-Z-2,3-diaminopropionic acid |
| DBU | 1,8-diazabicyclo[5.4.0]undec-7-ene |
| DEPBT | 3-(diethoxyphosphoryloxy)-1,2,3-benzotriazin-4(3H)-one |
| dHyp | trans-D-4-hydroxyproline, (2R,4S)-4-hydroxypyrrolidine-2-carboxylic acid |
| DIAD | diisopropyl azodicarboxylate |
| DIG | diglycolic acid |
| DIPEA | N,N-diisopropylethylamine |
| DMAP | 4-(Dimethylamino)pyridine |
| dMeArg | N-methyl-D-arginine |
| dMebetaHomoLys | N-methyl-D-β-homoLys |
| dMeLys | N-methyl-D-Lysine |
| DMF | N,N-dimethylformamide |
| DMSO | dimethyl sulfoxide |
| dNle | D-norleucine |
| dOrn | D-ornithine |
| dOrn(dimethyl) | Nδ-dimethyl-D-ornithine |
| dPip | D-pipecolic acid, D-homoPro |
| dSer(OBn) | O-benzyl-D-serine |
| dTic | (3R)-1,2,3,4-tetrahydroisoquinoline-3-carboxylic acid |
| dTiq | D-1,2,3,4-tetrahydroisoquinoline-1-carboxylic acid |
| dTyr(OAllyl) | O-allyl-D-tyrosine |
| dTyr(OBn) | O-benzyl-D-tyrosine |
| EDC | N-(3-Dimethylaminopropyl)-N'-ethylcarbodiimide hydrochloride |
| Fmoc | 9-fluorenylmethoxycarbonyl |
| HATU | O-(7-azabenzotriazol-1-yl)-N,N,N',N'-tetramethyluronium hexafluorophosphate |
| HCTU | 2-(6-chloro-1H-benzotriazole-1-yl)- 1,1,3,3-tetramethylaminium hexafluorophosphate |
| HFIP | 1,1,1,3,3,3-hexafluoro-2-propanol |
| His(Bn) | Nτ-benzyl-histidine |
| HomocycloLeu | homocyclo leucine, 1-Aminocyclohexanecarboxylic acid |
| Hyp | trans-4-hydroxyproline, (2S,4R)-4-hydroxypyrrolidine-2-carboxylic acid |
| Hyp(OBn) | O-benzyl-trans-4-hydroxyproline |

| Abbreviation | Description |
| --- | --- |
| MeAsp | N-methyl aspartic acid |
| MebetaHomoLys | N-methyl β-homoLysine |
| MebetaHomoLys(Me)2 | Nα-methyl-Nε-dimethyl-β-homoLysine |
| MeLeu | N-methyl leucine |
| MeMet | N-methyl methionine |
| MePhe | N-methyl phenylalanine |
| metaY(Opr) | metaTyrosine |
| MeThr | N-methyl threonine |
| MeTyr | N-methyl tyrosine |
| NMP | N-methylpyrrolidone |
| Nosyl chloride | 2-nitrobenzenesulfonyl chloride |
| Nva | norvaline |
| Orn(acetamide) | Nδ-acetamide-ornithine |
| Orn(benzamide) | Nδ-benzamide-ornithine |
| Orn(ethylcarbamate) | Nδ-ethylcarbamate-ornithine |
| Orn(methanesulfonamide) | Nδ-methanesulfonamide-ornithine |
| Orn(pentyl amide) | Nδ-pentyl amide-ornithine |
| PDA | 1,4-phenyldiacetic acid |
| Pen | penicillamine, β,β-dimethyl-cysteine |
| Pip | pipecolic acid, homoPro |
| Sar | sarcosine, N-methyl glycine |
| tertbutylAla | β-tert-butyl alanine, neopentylglycine |
| TFA | trifluoroacetic acid |
| TFE | 2,2,2-Trifluoroethanol |
| THF | tetrahydrofuran |
| Thr(OBn) | O-benzyl-threonine |
| Thr(OEt) | O-ethyl-threonine |
| Thr(OMe) | O-methyl-threonine |
| Tic | (3S)-1,2,3,4-tetrahydroisoquinoline-3-carboxylic acid |
| TIS | triisopropylsilane |
| Tyr(2-methoxy diaryl ether) | O-2-methoxy-phenyl-tyrosine |
| Tyr(2-tolyl diaryl ether) | O-2-methyl-phenyl-tyrosine |
| Tyr(3,4-difluoro diaryl ether) | O-3,4-difluoro-phenyl-tyrosine |
| Tyr(3,4-dimethyl diaryl ether) | O-3,4-dimethyl-phenyl-tyrosine |
| Tyr(3-CO2Me diaryl ether) | O-3-methylester-phenyl-tyrosine |
| Tyr(3-fluoro diaryl ether) | O-3-fluoro-phenyl-tyrosine |
| Tyr(3-methoxy diaryl ether) | O-3-methoxy-phenyl-tyrosine |
| Tyr(3-methyl diaryl ether) | O-3-methyl-phenyl-tyrosine |
| Tyr(4-CF3 diaryl ether) | O-4-trifluoromethyl-phenyl-tyrosine |
| Tyr(4-CO2H diaryl ether) | O-4-carboxylate-phenyl-tyrosine |
| Tyr(4-CO2Me diaryl ether) | O-4-methylester-phenyl-tyrosine |
| Tyr(4-fluoro diaryl ether) | O-4-fluoro-phenyl-tyrosine |
| Tyr(4-methoxy diaryl ether) | O-4-methoxy-phenyl-tyrosine |
| Tyr(OAllyl) | O-allyl-tyrosine |
| Tyr(OPh) | O-phenyl-tyrosine |
| vinyl-Br-Leu | 2-amino-4-bromo-4-pentenoic acid |

The term "suitable substituent" as used in the context of the present invention is meant to include independently H; hydroxyl; cyano; alkyl, such as lower alkyl, such as methyl, ethyl, propyl, n-butyl, t-butyl, hexyl and the like; alkoxy, such as lower alkoxy such as methoxy, ethoxy, and the like; aryloxy, such as phenoxy and the like; vinyl; alkenyl, such as hexenyl and the like; alkynyl; formyl; haloalkyl, such as lower haloalkyl which includes $CF_3$, $CCl_3$ and the like; halide; aryl, such as phenyl and napthyl; heteroaryl, such as thienyl and furanyl and the like; amide such as $C(O)NR_aR_b$, where $R_a$ and $R_b$ are independently selected from lower alkyl, aryl or benzyl, and the like; acyl, such as $C(O)$—$C_6H_5$, and the like; ester such as —$C(O)OCH_3$ the like; ethers and thioethers, such as O-Bn and the like; thioalkoxy; phosphino; and —$NR_aR_b$, where $R_a$ and $R_b$ are independently selected from lower alkyl, aryl or benzyl, and the like. It is to be understood that a suitable substituent as used in the context of the present invention is meant to denote a substituent that does not interfere with the formation of the desired product by the processes of the present invention.

As used in the context of the present invention, the term "lower alkyl" as used herein either alone or in combination with another substituent means acyclic, straight or branched chain alkyl substituent containing from one to six carbons and includes for example, methyl, ethyl, 1-methylethyl, 1-methylpropyl, 2-methylpropyl, and the like. A similar use of the term is to be understood for "lower alkoxy", "lower thioalkyl", "lower alkenyl" and the like in respect of the number of carbon atoms. For example, "lower alkoxy" as used herein includes methoxy, ethoxy, t-butoxy.

The term "alkyl" encompasses lower alkyl, and also includes alkyl groups having more than six carbon atoms, such as, for example, acyclic, straight or branched chain alkyl substituents having seven to ten carbon atoms.

The term "aryl" as used herein, either alone or in combination with another substituent, means an aromatic monocyclic system or an aromatic polycyclic system. For example, the term "aryl" includes a phenyl or a napthyl ring, and may also include larger aromatic polycyclic systems, such as fluorescent (eg. anthracene) or radioactive labels and their derivatives.

The term "heteroaryl" as used herein, either alone or in combination with another substituent means a 5, 6, or 7-membered unsaturated heterocycle containing from one to 4 heteroatoms selected from nitrogen, oxygen, and sulphur and which form an aromatic system. The term "heteroaryl" also includes a polycyclic aromatic system comprising a 5, 6, or 7-membered unsaturated heterocycle containing from one to 4 heteroatoms selected from nitrogen, oxygen, and sulphur.

The term "cycloalkyl" as used herein, either alone or in combination with another substituent, means a cycloalkyl substituent that includes for example, but is not limited to, cyclopropyl, cyclobutyl, cyclopentyl, cyclohexyl and cycloheptyl.

The term "cycloalkyl-alkyl-" as used herein means an alkyl radical to which a cycloalkyl radical is directly linked; and includes, but is not limited to, cyclopropylmethyl, cyclobutylmethyl, cyclopentylmethyl, 1-cyclopentylethyl, 2-cyclopentylethyl, cyclohexylmethyl, 1-cyclohexylethyl and 2-cyclohexylethyl. A similar use of the "alkyl" or "lower alkyl" terms is to be understood for aryl-alkyl-, aryl-lower-alkyl- (eg. benzyl), -lower alkyl-alkenyl (eg. allyl), heteroaryl-alkyl-, and the like as used herein. For example, the term "aryl-alkyl-" means an alkyl radical, to which an aryl is bonded. Examples of aryl-alkyl- include, but are not limited to, benzyl (phenylmethyl), 1-phenylethyl, 2-phenylethyl and phenylpropyl.

As used herein, the term "heterocycle", either alone or in combination with another radical, means a monovalent radical derived by removal of a hydrogen from a three- to seven-membered saturated or unsaturated (including aromatic) cyclic compound containing from one to four heteroatoms selected from nitrogen, oxygen and sulfur. Examples of such heterocycles include, but are not limited to, aziridine, epoxide, azetidine, pyrrolidine, tetrahydrofuran, thiazolidine, pyrrole, thiophene, hydantoin, diazepine, imidazole, isoxazole, thiazole, tetrazole, piperidine, piperazine, homopiperidine, homopiperazine, 1,4-dioxane, 4-morpholine, 4-thiomorpholine, pyridine, pyridine-N-oxide or pyrimidine, and the like.

The term "alkenyl", as used herein, either alone or in combination with another radical, is intended to mean an unsaturated, acyclic straight chain radical containing two or more carbon atoms, at least two of which are bonded to each other by a double bond. Examples of such radicals include, but are not limited to, ethenyl (vinyl), 1-propenyl, 2-propenyl, and 1-butenyl.

The term "alkynyl", as used herein is intended to mean an unsaturated, acyclic straight chain radical containing two or more carbon atoms, at least two of which are bonded to each other by a triple bond. Examples of such radicals include, but are not limited to, ethynyl, 1-propynyl, 2-propynyl, and 1-butynyl.

The term "alkoxy" as used herein, either alone or in combination with another radical, means the radical —O—($C_{1-n}$)alkyl wherein alkyl is as defined above containing 1 or more carbon atoms, and includes for example methoxy, ethoxy, propoxy, 1-methylethoxy, butoxy and 1,1-dimethylethoxy. Where n is 1 to 6, the term "lower alkoxy" applies, as noted above, whereas the term "alkoxy" encompasses "lower alkoxy" as well as alkoxy groups where n is greater than 6 (for example, n=7 to 10). The term "aryloxy" as used herein alone or in combination with another radical means —O-aryl, wherein aryl is defined as noted above.

A protecting group or protective group is a substituent introduced into a molecule to obtain chemoselectivity in a subsequent chemical reaction. Many protecting groups are known in the art and a skilled person would understand the kinds of protecting groups that would be incorporated and could be used in connection with the methods described herein. In "protecting group based peptide synthesis", typically solid phase peptide synthesis, the desired peptide is prepared by the step-wise addition of amino acid moieties to a building peptide chain. The two most widely used protocols, in solid-phase synthesis, employ tert-butyloxycarbonyl (Boc) or 9-fluorenylmethoxycarbonyl (Fmoc) as amino protecting groups. Amino protecting groups generally protect an amino group against undesirable reactions during synthetic procedures and which can later be removed to reveal the amine. Commonly used amino protecting groups are disclosed in Greene, T. W. et al., Protective Groups in Organic Synthesis, 3rd Edition, John Wiley & Sons (1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, .alpha.-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, .alpha.-,.alpha.-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

In some embodiments, $R^1$ is H.

In some embodiments, $R^2$ or $R^3$ is covalently linked to $R^1$ to form proline having NR' as the N-terminus.

In some embodiments, $R^2$ and $R^3$ are not both H.

In some embodiments, $R^2$ and $R^3$ are each independently selected from the group consisting of amino acid chains of a proteinogenic or a non-proteinogenic alpha-amino acids.

In some embodiments, $R^2$ and $R^3$ are H and $CH_3$ respectively or vice versa.

In some embodiments, $R^2$ or $R^3$ is —$CH_2$—S—$R^s$, wherein $R^s$ is selected from lower alkyl; lower amino alkyl; aryl; heteroaryl; alkenyl; or heterocycle; all of which are optionally substituted at one or more substitutable positions with one or more suitable substituents; preferably $R^s$ is phenyl or phenyl substituted with lower alkyl, halogen; or lower amino alkyl.

In some embodiments, $R^4$ and $R^5$ are not both H.

In some embodiments, R and R* are not both H.

In some embodiments, $R^4$ and $R^5$ are each independently H, or C(O)—NHR', wherein R' is H or a lower alkyl. Preferably, R' is tert-butyl or H.

In some embodiments, $R^6$ is H.

In some embodiments, $R^6$ and either $R^5$ or $R^9$ form a ring resulting in a proline residue having N—$R^6$ as its N-terminus.

In some embodiments, n is 1.

In some embodiments, Z along with L and —C=O is any one of SEQ ID NOs. 1-380.

In some embodiments, $X^1$ is Leu.

In some embodiments, $X^2$ is Asp.

In some embodiments, $X^3$ is Thr.

In some embodiments, $X^3$ is Val.

In some embodiments, $X^3$ is Ile.

In some embodiments, $X^y$ and $X^z$ are each independently a proteinogenic or non-proteinogenic alpha-amino acid.

In some embodiments, $X^z$ is a proteinogenic or non-proteinogenic beta-amino acid.

In some embodiments, $X^z$ is betaHomoLys or MethylbetaHomoLys.

In some embodiments, $X^y$ and $X^z$ are each a primary amino acid.

In some embodiments, $X^y$ and $X^z$ are each any amino acid listed under column $X^y$ and column $X^z$ respectively of Table 1B.

In various embodiments, the compound is any one of compounds 1-397.

In certain embodiments, there is provided pharmaceutically acceptable salts of the compounds described herein. The term "pharmaceutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by treatment of an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. In certain embodiments, any of the peptide compounds described herein are salt forms, e.g., acetate salts.

In an aspect, there is provided, a pharmaceutical composition comprising a compound described herein along with the pharmaceutically acceptable carrier. The pharmaceutical composition may be formulated for any one of oral delivery, topical delivery and parenteral delivery.

As used herein, "pharmaceutically acceptable carrier" means any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent.

In an aspect, there is provided, a method of treating inflammation or an autoimmune disease in a patient, comprising administering to the patient a therapeutically effective amount of the compound described herein. Preferably the inflammation or an autoimmune disease is gastrointestinal.

In an aspect, there is provided, a method for treating a condition in a patient associated with a biological function of an α4β7 integrin, the method comprising administering to the patient a therapeutically effective amount of the compound described herein.

In some embodiments, the condition or disease is Inflammatory Bowel Disease (IBD), ulcerative colitis, Crohn's disease, Celiac disease (nontropical Sprue), enteropathy associated with seronegative arthropathies, microscopic colitis, collagenous colitis, eosinophilic gastroenteritis, radiotherapy, chemotherapy, pouchitis resulting after proctocolectomy and ileoanal anastomosis, gastrointestinal cancer, pancreatitis, insulin-dependent diabetes mellitus, mastitis, cholecystitis, cholangitis, pericholangitis, chronic bronchitis, chronic sinusitis, asthma, primary sclerosing cholangitis, human immunodeficiency virus (HIV) infection in the GI tract, eosinophilic asthma, eosinophilic esophagitis, gastritis, colitis, microscopic colitis, graft versus host disease, colitis associated with radio- or chemo-therapy, colitis associated with disorders of innate immunity as in leukocyte adhesion deficiency-1, chronic granulomatous disease, glycogen storage disease type 1 b, Hermansky-Pudlak syndrome, Chediak-Higashi syndrome, and Wiskott-Aldrich Syndrome, or pouchitis resulting after proctocolectomy and ileoanal anastomosis and various forms of gastrointestinal cancer, osteoporosis, arthritis, multiple sclerosis, chronic pain, weight gain, and depression. In another embodiment, the condition is pancreatitis, insulin-dependent diabetes mellitus, mastitis, cholecystitis, cholangitis, pericholangitis, chronic bronchitis, chronic sinusitis, asthma or graft versus host disease.

In preferable embodiments, is an inflammatory bowel disease, such as ulcerative colitis or Crohn's disease.

In an aspect, there is provided, a method for treating a disease or condition in a patient comprising administering to the patient a therapeutically effective amount of the compound described herein, wherein the disease or condition is a local or systemic infection of a virus or retrovirus.

In some embodiments, the virus or retrovirus is echovirus 1 and 8, echovirus 9/Barty Strain, human papilloma viruses, hantaviruses, rotaviruses, adenoviruses, foot and mouth disease virus, coxsackievirus A9, human parechovirus 1 or human immunodeficiency virus type 1.

In an aspect, there is provided, a method for treating a disease or condition in a patient comprising administering to the patient a therapeutically effective amount of the compound described herein, wherein the hepatitis A, B or C, hepatic encephalopathy, non-alcoholic steatohepatitis, cirrhosis, variceal bleeding, hemochromatosis, Wilson disease, tyrosinemia, alpha-1-antitrypsin deficiency, glycogen storage disease, hepatocellular carcinoma, liver cancer, primary biliary cholangitis, primary sclerosing cholangitis, primary biliary sclerosis, biliary tract disease, autoimmune hepatitis, or graft-versus-host disease.

In some embodiments, the compound inhibits binding of α4β7 integrin to MAdCAM. Preferably, the compound selectively inhibits binding of α4β7 integrin to MAdCAM.

In any embodiment, the patient is preferably a human.

As used herein, the terms "disease", "disorder", and "condition" may be used interchangeably.

As used herein, "inhibition," "treatment," "treating," and "ameliorating" are used interchangeably and refer to, e.g., stasis of symptoms, prolongation of survival, partial or full amelioration of symptoms, and partial or full eradication of a condition, disease or disorder in a subject, e.g., a mammal.

As used herein, "prevent" or "prevention" includes (i) preventing or inhibiting the disease, injury, or condition from occurring in a subject, e.g., a mammal, in particular, when such subject is predisposed to the condition but has not yet been diagnosed as having it; or (ii) reducing the likelihood that the disease, injury, or condition will occur in the subject.

As used herein, "therapeutically effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

In some embodiments, the compound is administered by a form of administration selected from the group consisting of oral, intravenous, peritoneal, intradermal, subcutaneous, intramuscular, intrathecal, inhalation, vaporization, nebulization, sublingual, buccal, parenteral, rectal, vaginal, and topical.

In some embodiments, the compound is administered as an initial does followed by one or more subsequent doses and the minimum interval between any two doses is a period of less than 1 day, and wherein each of the doses comprises an effective amount of the compound.

In some embodiments, the effective amount of the compound is the amount sufficient to achieve at least one of the following selected from the group consisting of: a) about 50% or greater saturation of MAdCAM binding sites on α4β7 integrin molecules; b) about 50% or greater inhibition of α4β7 integrin expression on the cell surface; and c) about 50% or greater saturation of MAdCAM binding sites on α4β7 molecules and about 50% or greater inhibition of α4β7 integrin expression on the cell surface, wherein i) the saturation is maintained for a period consistent with a dosing frequency of no more than twice daily; ii) the inhibition is maintained for a period consistent with a dosing frequency of no more than twice daily; or iii) the saturation and the inhibition are each maintained for a period consistent with a dosing frequency of no more than twice daily.

In some embodiments, the compound is administered at an interval selected from the group consisting of around the clock, hourly, every four hours, once daily, twice daily, three times daily, four times daily, every other day, weekly, bi-weekly, and monthly.

The advantages of the present invention are further illustrated by the following examples. The examples and their particular details set forth herein are presented for illustration only and should not be construed as a limitation on the claims of the present invention.

Examples

Methods and Materials
Synthesis

Methods applicable for making the cyclic peptides described herein can be found generally in Applicant's PCT Publication No. WO 2010/105363 and in an application filed on the same day herewith titled "Fragment Synthesis of Cyclic Peptides" U.S. patent application Ser. No. 15/775, 319) and claiming common priority to U.S. Provisional Application No. 62/254,003 filed on Nov. 11, 2015.

More specifically, the below protocols were used to synthesize each of the compounds as indicated in Table 51.

Protocol A: General Nacellin Synthesis

1. Preparation of resin: Fmoc amino acid (1.1 eq. with respect to resin) was dissolved in $CH_2Cl_2$ (10 mL/g of resin). If the amino acid did not dissolve completely, DMF was added slowly dropwise until a homogeneous mixture persisted upon stirring/sonication. The 2-chlorotrityl resin was allowed to swell in $CH_2Cl_2$ (5 mL/g of resin) for 15 minutes. The $CH_2Cl_2$ was then drained and the Fmoc amino acid solution was added to the vessel containing the 2-Cl Trt resin. DIPEA was added (2 eq. with respect to the amino acid) and the vessel was agitated for five minutes. Another 2 eq. of DIPEA was then added and the vessel was left to agitate for an additional 60 minutes. The resin was then treated with methanol (1 mL/g of resin) to endcap any remaining reactive 2-Cl Trt groups. The solution was mixed for 15 minutes, drained and then rinsed with $CH_2Cl_2$ (×3), DMF (×3), $CH_2Cl_2$ (×2), and MeOH (×3). The resin was then dried under vacuum and weighed to determine the estimated loading of Fmoc amino acid.

2. Preparation of linear peptide sequence via manual or automated synthesis: Fully protected resin-bound peptides were synthesized via standard Fmoc solid-phase peptide chemistry manually or using an automated peptide synthesizer. All N-Fmoc amino acids were employed.

a. Fmoc deprotection: the resin was treated with 20% piperidine in NMP twice, for 5 and 10 minutes respectively, with consecutive DMF and NMP washes after each addition.

b. Fmoc amino acid coupling: the resin was treated with 3 eq. of Fmoc amino acid, 3 eq. of HATU and 6 eq. of DIPEA in NMP for 60 minutes. For difficult couplings, a second treatment with 3 eq. of Fmoc amino acid, 3 eq. of HATU and 6 eq. of DIPEA in NMP for 40 minutes was employed.

3. General cleavage with retention of protecting groups: Once the desired linear sequence was synthesized, the resin was treated with either 1.) 1:3, HFIP:$CH_2Cl_2$ or 2.) 5% TFA in $CH_2Cl_2$, twice for 30 minutes each, to afford cleavage from the solid support. The solvent was then removed, followed by trituration twice with chilled tert-butyl methyl ether (or diethyl ether/hexanes) to give the desired product. The purity was then analyzed by reverse-phase LCMS.

Protocol B: Preparation of N-Alkylated Fmoc Amino Acid Building Blocks

1. Resin prep: see protocol A, step 1
2. Fmoc deprotection: see protocol A, step 2a
3. Nosyl protection: The deprotected resin was stirred in $CH_2Cl_2$ (5 mL/mmol of resin) and DIPEA (6.5 eq.). A solution of Nosyl chloride (4.0 eq.) was added slowly, dropwise, over 30 minutes, to avoid a rapid exothermic reaction. After the addition was complete, stirring was continued at room temperature for three hours. The resulting nosyl-protected resin was filtered and washed with $CH_2Cl_2$, MeOH, $CH_2Cl_2$, and THF.

4. N-Methylation: To a suspension of resin in THF (10 mL/mmol of resin) was added a solution of triphenylphosphine (5 eq.) in THF (2 M) and MeOH (10 eq.). The stirring suspension was cooled in an ice bath. A solution of DIAD (5 eq.) in THF (1 M) was added dropwise, via addition funnel. After addition was complete the bath was removed and the reaction was stirred at room temperature for an additional 90 minutes. The resin was filtered, washed with THF (×4), $CH_2Cl_2$ (×3), and THF (×2).

5. Nosyl-deprotection: To a suspension of resin in NMP (10 mL/mmol of resin) was added 2-mercaptoethanol (10.1 eq.) and DBU (5.0 eq.). The solution became a dark green colour. After five minutes, the resin was filtered, washed with DMF until washes ran colourless. This procedure was repeated a second time, and the resin was then washed a final time with $CH_2Cl_2$.

6. Fmoc protection: To a suspension of resin in $CH_2Cl_2$ (7 mL/mmol of resin) was added a solution of Fmoc-Cl (4 eq.) in $CH_2Cl_2$ (7 mL), and DIPEA (6.1 eq.). The suspension was stirred at room temperature for four hours then filtered and washed with $CH_2Cl_2$ (×2), MeOH (×2), $CH_2Cl_2$ (×2), and $Et_2O$ (×2).

7. Cleavage from resin: see protocol A, step 3

Protocol C: Reductive Amination

1. Fmoc Weinreb amide formation: a mixture of Fmoc amino acid (1 mmol), N,O-dimethylhydroxylamine.HCl (1.2 eq.), and HCTU (1.2 eq.) in $CH_2Cl_2$ (6.5 mL), was cooled to 0° C. DIPEA (3 eq.) was then slowly added to the stirring mixture. The cooling bath was removed and the reaction was stirred at room temperature for 16 h. A 10% solution of HCl (4 mL) was added resulting in the formation of a precipitate, which was removed through filtration. The filtrate was washed with 10% HCl (3×4 mL) and brine (2×4 mL). The organic phase was then dried over $Na_2SO_4$. The solvent was removed under reduced pressure to give crude Fmoc Weinreb amide, which was used in the next reaction without purification.

2. Fmoc amino aldehyde formation: lithium aluminum hydride powder (3 eq.) was placed in a dry flask. THF (Sigma-Aldrich, 250 ppm of BHT, ACS reagent >99.0%, 6.5 mL) was added, and the resulting slurry was cooled to −78° C., with stirring. To the slurry was added a solution of the Fmoc Weinreb amide in THF (10 mL). The reaction vessel was transferred to an ice/water bath, and maintained at 0° C. for 1 h. To the reaction at 0° C., was added dropwise acetone (1.5 mL), then $H_2O$ (0.25 mL) and then the reaction was left to stir for an additional hour at room temperature. The mixture was filtered through Celite, washed with EtOAc (10 mL) and MeOH (10 mL), and the filtrate was concentrated. The crude material was dissolved in $CHCl_3$ (6.5 mL) and washed with brine (2×3 mL) and the organic phase was then dried over $Na_2SO_4$, filtered and concentrated to give the Fmoc amino aldehyde.

3. Reductive amination on-resin: the linear peptide on-resin was placed in a solid-phase peptide synthesis reaction vessel and diluted with DMF (22 mL/g of resin). The Fmoc aldehyde (4.0 eq.) was added and the reaction was left to shake overnight. The solution was then drained and the resin was washed with $CH_2Cl_2$ (×3) and DMF (×3). The resin was then diluted with a mixture of MeOH/$CH_2Cl_2$ (22 mL/g of resin, 1:3 ratio) and $NaBH_4$ (7 eq.) was subsequently added. The mixture was left to shake for four hours, then the solution was drained and the resin was washed with $CH_2Cl_2$ (×3) and DMF (×3).

Protocol D: Fragment-Based Macrocyclization

In a two-dram vial, 0.1 mmol of the linear peptide and DEPBT (1.5 eq.) were dissolved in 5 mL of freshly distilled THF (0.02 M). DIPEA (3 eq.) was then added and the reaction mixture was left to stir overnight at room temperature (16 h). Tetraalkylammonium carbonate resin (6 eq.) was then added to the reaction mixture and stirring was continued for an additional 24 h. The reaction was then filtered through a solid-phase extraction vessel and rinsed with $CH_2Cl_2$ (2 mL). The filtrate and washes were combined and the solvent was removed under reduced pressure.

Protocol E: Aziridine Aldehyde-Based Macrocyclization

The linear peptide was dissolved in TFE (if solubility problems were encountered, a 50:50 mixture of TFE:$CH_2Cl_2$ was used for the cyclization). Then 0.6 eq. of (S)-aziridine-2-carboxaldehyde dimer (prepared as per literature protocol: J. Am. Chem. Soc. 2006, 128 (46), 14772-14773 and Nat. Protoc. 2010, 5 (11), 1813-1822) as a TFE stock solution (0.2 M) was added, giving a final reaction mixture concentration of 0.1 M. tert-Butyl isocyanide (1.2 eq.) was then added and the reaction mixture was stirred for four hours. Progress was analyzed along the way via LC-MS.

Protocol F: Nucleophilic Ring-Opening of Acyl Aziridine, Post Macrocyclization a.) Thioacetic acid/thiobenzoic acid: thio acid (4 eq.) was added to the crude reaction mixture. Reaction progress was monitored by LC-MS, and was generally complete after 1-2 hours.

Or alternatively, b.) Thiophenol: thiophenol (4 eq.) and DIPEA (4 eq.) were added to the crude cyclization mixture. Reaction progress was monitored by LC-MS, and was generally complete after 1-2 hours. Solvent was removed under reduced pressure and dried under vacuum. Crude material was either triturated with $Et_2O$/hexanes or TBME, or alternatively, diluted with $H_2O$, frozen and lyophilized.

Protocol G: General Suzuki Coupling, Post Macrocyclization

An iodo-Phe-containing macrocycle (0.1 mmol), $Na_2CO_3$ (2 eq.), substituted boronic acid (1.1 eq.) and 4 mL of water:acetonitrile (1:1 ratio) were combined in a microwave vial. The mixture was degassed via $N_2$ flow for 10 minutes. While under $N_2$, silicon based Pd-catalyst (Siliacat-DPP Pd heterogenous catalyst, 0.05 eq.) was added. The reaction vial was sealed and placed in the microwave for 10 minutes at 150° C. Reaction progress was monitored by LCMS. Once complete, the reaction was filtered through a Celite plug and the solvent was removed under reduced pressure.

Protocol H: General Ulmann Coupling, Post Macrocyclization

Under inert atmosphere, the peptide macrocycle (0.018 mmol) was placed in a 2-dram vial containing 2 mL of dry $CH_2Cl_2$. $Cu(OAc)_2$ (1 eq.), benzene boronic acid (2 eq.) and 4 Å (oven-dried) molecular sieves were then added to the vial followed by DIPEA (4 eq.). The contents of the vial were stirred at room temperature overnight. The reaction progress was assessed by LCMS. Once the reaction was deemed complete, the mixture was filtered through a Celite plug and the solvent was removed under reduced pressure.

Protocol I: General Global Deprotection and Cleavage

Deprotection of the side chain protecting groups was achieved by dissolving the peptides in 2 mL of a cleavage cocktail consisting of TFA:$H_2O$:TIS (95:2.5:2.5) for two hours. Subsequently, the cleavage mixture was evaporated under reduced pressure and the peptides were precipitated twice from chilled diethyl ether/hexanes (or tert-butyl methyl ether).

Protocol J: General Cleavage of Reductively-Labile Protecting Groups a.) Pd/C and formic acid debenzylation: the benzyl protected macrocycle (0.35 mmol) was dissolved in MeOH (8 mL) with 10% formic acid, 50% wt. Pd/C (1 mg) and heated to 55° C. Once the reaction was deemed complete, the mixture was filtered through a Celite plug, washed with MeOH and the solvent was removed under reduced pressure.

Or alternatively, b.) Raney Ni desulfurization/debenzylation: Raney Ni slurry (1-2 mL) was added directly to the cyclization reaction mixture and stirred vigorously overnight. The vial was then centrifuged and the liquid was transferred using a pipette to a tared vial. MeOH was added to the vial containing Raney Ni. The vial was then sonicated, vortexed, and centrifuged. Again, the liquid was transferred to a tared vial. This process was repeated with EtOAc and then a final time with MeOH. The combined washes were then removed under reduced pressure and the residue dried under vacuum.

Protocol K: Amidation of Side Chain, Post Macrocyclization

Macrocycle (0.021 mmol) was dissolved in 1 mL of $CH_3CN$. $K_2CO_3$ (5 eq.) and acid chloride (2 eq.) were then added and the reaction mixture was left to stir at room temperature overnight. Reaction progress was checked by LC-MS in the morning. Upon completion, the solvent was removed by reduced pressure.

Protocol L: Fluorescent Dye Attachment

The macrocycle (4 μmol) was dissolved in DMSO (200 μL). DIPEA (5 eq.) was then added. In a separate vial, 5 mg of fluorescent dye as the NHS ester was dissolved in 200 μL of DMSO. The macrocycle solution was then added to the solution of the fluorescent label. The reaction mixture was stirred overnight. Reaction progress was checked by LC-MS in the morning and then the solvent was removed by lyophilization.

Protocol M: Purification Methods

All macrocycles were purified using reverse-phase flash column chromatography using a 30 g RediSep C18 Gold Column. The gradient consisted of eluents A (0.1% formic acid in double distilled water) and B (0.1% formic acid in HPLC-grade acetonitrile) at a flow rate of 35 mL/min.

Integrin α4β7—MAdCAM-1 Competition Assay

A 96-well Microlon 200 plate (Greiner, 655001) was coated with 100 μl per well of solution of 1 μg/ml recombinant integrin α4β1 (R&D Systems, 5397-A3-050) in carbonate buffer (50 mM, pH 9.6). The plate was incubated at 4° C. overnight. The solution was removed and 250 μl blocking buffer (50 mM Tris, 150 mM NaCl, 1 mM $MnCl_2$, 1% bovine serum albumin (BSA), 0.05% Tween) was added per well. The plate was then incubated for 1 hour at room temperature. The plate was washed three times with wash buffer (50 mM Tris, 100 mM NaCl, 1 mM $MnCl_2$, 0.05% Tween). To each well, 50 μl of compound diluted in assay buffer was added by transfer from a compound serial dilution plate. Fifty μl recombinant MAdCAM-FC (R&D systems, 6056-MC-050) at a concentration of 1 mg/ml in assay buffer (50 mM Tris, 150 mM NaCl, 1 mM $MnCl_2$, 0.1% BSA, 0.05% Tween) was added to each well. The plate was incubated at room temperature with shaking for 2 hours to reach binding equilibrium. Then the plate was washed three times in wash buffer and 100 μl anti-human IgG Fc specific-horseradish peroxidase (HRP) (Abcam, Ab97225) diluted at 1:2000 in assay buffer was added to each well. The plate was incubated at room temperature for 1 hour under agitation. The plates were then washed three times and 100 μl of 1,3',5,5'-tetramethylbenxidie (TMB) was then added to each well. The reaction was stopped after 2 minute-incubation by adding 50 μl of 1M $H_2SO_2$ and optical absorbance was read at 450 nM.

Integrin α4β1—VCAM-1 Competition Assay

A 96-well Microlon 200 plate (Greiner, 65001) was coated with 100 μl per well of a solution of 0.5 μg/ml recombinant integrin α4β1 (R&D Systems, 5397-A3-050) in carbonate buffer (50 mM, pH 9.6). The plate was incubated at 4° C. overnight. The solution was removed and 250 μl blocking buffer (50 mM Tris, 150 mM NaCl, 1 mM $MnCl_2$, 1% BSA, 0.05% Tween) was added per well. The plate was then incubated for 1 hour at room temperature. The plate was washed three times with wash buffer (50 mM Tris, 100 mM NaCl, 1 mM $MnCl_2$, 0.05% Tween). To each well, 50 μl of compound diluted in assay buffer was added by transfer from a compound serial dilution plate. Fifty μl recombinant VCAM-FC (R&D systems, 862-VC-100) at concentration of 1 mg/ml in assay buffer (50 mM Tris, 150 mM NaCl, 1 mM $MnCl_2$, 0.1% BSA, 0.05% Tween) was added to each well. The plate was incubated at room temperature with shaking for two hours to reach binding equilibrium. Then the plate was washed three times in wash buffer and 100 μl anti-human IgG Fc specific-HRP (Abcam, Ab97225) diluted at 1:2000 in assay buffer was added to each well. The plate was incubated at room temperature for 1 hour under agitation. The plates were then washed three times and 100 μl of 1,3',5,5'-TMB was then added to each well. The reaction was stopped after 2 minute-incubation by adding 50 μl of 1M $H_2SO_2$ and optical absorbance was read at 450 nM.

RPMI8866 Cell Adhesion Competition Assay

RPMI8866 human cells (Sigma #95041316) were cultured in RPMI 1640 medium (Wisent, 350-000-CL) supplemented with 10% Fetal Bovine Serum (FBS) (Wisent, 081-105) and 1% Penicillin-Streptomycin A MaxiSorp plate (Nunc, 442404) was coated with 100 ml/well of recombinant human MAdCAM-1 Fc Chimera (R&D Systems, 6056-MC-050) solution at 0.25 mg/mL in coating buffer (50 mM sodium carbonate, pH 9.6). The plate was incubated overnight at 4° C. and washed twice with 150 μl per well wash buffer (0.05% Tween 20 in phosphate buffered saline (PBS), blocked with 250 μl per well blocking buffer (1% non-fat dry milk in PBS), and incubated for 1 hour at room temperature. RPMI8866 cells were resuspended at 10 million cells/ml in PBS containing 5 mM calcein and incubated at 37° C. for 30 min in a 50 ml tube. PBS was added to fill the tube, cells were spun down and resuspended in RPMI 1640 medium to 2 million/ml. Compounds were diluted by serial dilution in binding buffer (1.5 mM $CaCl_2$), 0.5 mM $MnCl_2$, 50 mM Tris-HCl, pH 7.5) to a final volume of 50 μl per well at 2× concentration. The plate was washed once with 300 μl of PBS, 50 μl of compound and 50 μl of cells (100,000 cells) were transferred to each well and the plate was incubated in the dark at 37° C., 5% $CO_2$ for 45 min to allow cell adhesion. The plate was emptied by inverting and blotting on paper towels and washed manually twice with PBS. One hundred μl PBS was then added to each well. The plate was read on a Biotek Neo instrument using FITC 96 bottom read. To calculate the dose response, the fluorescence value of control wells not containing cells was subtracted from each test well.

Buffers

Coating Buffer (50 mM Carbonate)

Dissolve 420 mg sodium bicarbonate in 100 ml water (Soln 1). Dissolve 270 mb sodium carbonate in 50 ml water (Soln 2). Add Soln 2 to Soln 1 to a pH of 9.6

Wash Buffer 0.05% Tween 20 in PBS

Blocking buffer

1% Nonfat Dry Milk in PBS

Binding Buffer 1.5 mM $CaCl_2$)

0.5 mM $MnCl_2$ 50 mM Tris-HCl, pH to 7.5 with HCl

Plasma Protein Binding Determination

An equilibrium dialysis (HTDialysis) method was used employing 50% plasma collected from CD-1 mice or Sprague-Dawley rats and incubated with $K_2$EDTA. Test articles were assessed at 1 microM concentration in three replicates. Incubation time as 5 hours and plasma and buffer standards were assessed using LC/MS/MS. Percentage recovery was calculated as $(C_{buffer}+C_{plasma})$/[average] $C_{initial}$, [average]$C_{initial}$ being measured in triplicate from the test samples prior to dialysis. Percentage of compound unbound was calculated as $C_{buffer}/C_{plasma}$.

Aqueous Solubility Assay

Aqueous solubility was determined by using 1, 0.5 or 0.2 mM (maximum) of test compound in phosphate buffered saline with pH of 7.4. Solutions were incubated for four hours at room temperature and stirred at 600 rpm and run in triplicate. Centrifugation was performed for 15 minutes at 6000 rpm and solution concentration was determined using HPLC-UV (photodiode array detector acquiring between 220 nm, and 300 nm wavelengths).

Cytochrome P450 Inhibition Assay

Human liver microsomes (at 0.25 mg/ml, except for CYP1A2, where a concentration of 0.5 mg/ml was employed) were used to assess the $IC_{50}$ (in duplicate; concentration range of 0.25 nM to 15 microM) for test compounds on the activity four isoforms of cytochrome P450 ("CYP"): CYP2D6, CYP3A4, CYP2C9 and CYP1A2. The following substrates were employed: dextromethorphan (15 microM, CYP2D6), testosterone (50 microM, CYP3A4), diclofenac (10 microM, CYP2C9) and phenacetin (100 microM, CYP1A2). Control inhibitors were quinidine (0.03 nM to 1.5 microM, CYP2D6), ketoconazole (0.08 nM to 5 microM, CYP3A4), miconazole (0.25 nM to 15 microM, CYP2C9) and alpha-naphoflavone (0.03 nM to 1.5 microM, CYP1A2). Incubation time was 10-20 minutes and metabolites assessed were dextrorphan (CYP2D6), 6-beta-OH-testosterone (CYP3A4), 4'-OH-diclofenac (CYP2C9) and acetaminophen (CYP1A2). Internal standards were labetalol (CYP2D6), loratidine (CYP3A4), carbamazepine (CYP2C9) and metoprolol (CYP1A2). Analyses were performed using standard LC/MS/MS protocols.

In Vivo T Lymphocyte Trafficking Analyses

Animal care committee. The animal care facility employed is accredited by the Canadian Council on Animal Care (CCAC). This study was approved by a certified Animal Care Committee and complied with CACC standards and regulations governing the use of animals for research.

Animals. Female C57131/6 mice (Charles River, St-Constant, Qc), weighting 16-19 g at delivery were used for this study. Following arrival in the animal facility, all animals were subjected to a general health evaluation. An acclimation period of 7-14 days was allowed before the beginning of the study.

Housing environment. The animals were housed under standardized environmental conditions. The mice were housed in auto-ventilated cages, 2-3 per cage. Each cage was equipped with a manual water distribution system. A standard certified commercial rodent diet was provided ad libitum. Tap water was provided ad libitum at all times. It is considered that there are no known contaminants in the diet and water that would interfere with the objectives of the study. Each cage was identified for the corresponding group, indicating the treatment and the identity of the animals housed in the cage. Mice from different treatment groups were not mixed.

The animal room was maintained at a controlled temperature of 21.5±1° C. and a relative humidity of 40±10%. A controlled lighting system assured 12 hours light, 12 hours dark per day to the animals. Adequate ventilation of 8-10 air changes per hour was maintained.

Administration of DSS. Dextran sulfate sodium (DSS) was administered to C57Bl/6 mice through addition to their drinking water at 2-3%. Mice accessed the DSS-treated water ad libitum over a 5-day period. Body weight and disease activity index ("DAI") were measured on Day 5 in order to distribute DSS-treated animals in two uniform groups prior to dosing. Specific symptoms associated with colitis were scored based on the severity of each particular symptoms: 1—blood in stool (negative hemoccult, positive hemoccult, blood traces in stool visible, rectal bleeding); 2—stool consistency (normal, soft but still formed, very soft, diarrhea); 3—posture and fur (normal; ruffled fur; ruffled fur combined to slight hunched posture and slight dehydration; ruffled fur combined to hunched posture, dehydration and altered walking; moribund (euthanasia is mandatory before the animal reach this point). The overall DAI score was the sum of the three parameters (maximum score of 9). DAI assessment was performed on Day 5 only (prior to dosing).

Oral dosing of the test article and vehicle. On day 6, the test articles were administered in the morning, as a single slow bolus (over approximately 5 seconds) via oral route, according to the procedure of administration of solution by gavage: the animal was firmly restrained. A bulb-tipped gastric gavage needle of 22G was passed through the side of the mouth and was advanced towards the oesophagus. The test articles and the vehicle were dosed orally at 10 mL/kg. Dosing volume was individually adjusted according to the body weight of each animal to reach the target dose.

Intravenous dosing of the test article and the vehicle. On day 6, the test article, DATK32 antibody, and the vehicle were administered in the morning, as a single slow bolus injection (over approximately 5 seconds) via the tail vein, according to the procedure of administration of solution by intravenous administration: the animal was restrained and its tail was warmed prior to dosing. A needle of 30G was used to inject the test article, or the vehicle, through the median tail vein at a dosing volume of 5 mL/kg. Dosing volume was individually adjusted according to the body weight of each animal to reach the target dose of DATK32 control antibody.

Collection of samples. On Day 6, five hours after test article or vehicle dosing, the animals were euthanized by cardiac puncture under general anesthesia, according to the "Guide to the Care and Use of Experimental Animals" published by the CCAC. Blood was transferred in a Sarstedt tube containing EDTA. Mesenteric and peripheral (inguinal, auxiliary and brachial) lymph nodes were collected and transferred on ice to corresponding tubes containing cold PBS. Nodes were kept on ice until tissue preparation.

Cell population labeling. Blood was withdrawn by cardiac puncture and collected on EDTA-coated tubes. Mensenteric lymph nodes (MLN) and peripheral lymph nodes (PLN) were also collected. Mononuclear cells from the tissues were isolated using density gradient (Lympholyte) and they were stained with fluorescent antibodies. The cells (5×104) were first incubated 15 minutes with BD mouse FcBlock (Fcγ III/II Receptor) followed by a 30-minute incubation with specific antibodies. After washes, cells were fixed using BD Fix Solution.

Specific antibodies used:

| Antibodies | Company | Catalog # |
|---|---|---|
| CD3 FITC | BD Biosciences | 555274 |
| CD4 APC | BD Biosciences | 553051 |
| CD11a PE | BD Biosciences | 553121 |
| CD45 PE | BD Biosciences | 553081 |
| α4β7 PE | eBiosciences | 12-5887 |
| CD34 PE | BD Biosciences | 551387 |

Percentage of different subpopulations of T lymphocytes were then analyzed using FACS-Calibur cytometer.

In Vivo Pharmacokinetic Assessments in Rodents

Oral bioavailability of test compounds was conducted by assessing plasma exposure of following one or two oral doses in mice and, in some cases, comparing said plasma exposure with that following a single intravenous dose of the same compound.

More detail on experimental design follows:

| Group ID | Test article ID | Route | No. & sex of animals | Dosing Frequency | Dose (mg/kg) | Concentration (mg/mL) | Volume (mL-kg) | Sample Collection |
|---|---|---|---|---|---|---|---|---|
| 1 | | p.o. | 18 M | once | 40 | 4 | 10 | Terminal blood |
| 2 | | p.o. | 18 M | twice* | 40 | 4 | 10 | (3 mice/time-point) |

*Dosing will occur 8 hours apart.

In all cases, formulation of test compound was 30% Labrasol in PBS (v/v) for oral dosing and 25% PEG-400 in PBS (v/v) for intravenous dosing.

Collection of peripheral blood proceeded as follows:

| Group ID | Blood collection time (h) | Volume/animal/time-point |
|---|---|---|
| 1 &2* | 0.0833, 0.5, 1, 2, 3 & 5 | ~0.6 mL |

*For Group 2, sample collection will be conducted following the second dose.

In some cases, collections proceeded up to 24 hours. Also note that in a few studies, liver and colon were also collected from mice concomitantly with peripheral blood and on a terminal (and serial) basis.

Other study details include:

Animals: Male CD-1 mice (20-25 g) from Charles River Labs were acclimatized for a minimum of 5 days prior to dosing. Body weights were recorded on the day of dosing.

Food restriction: Animals dosed p.o. were deprived of food overnight and fed ~2 h following dosing.

Clinical observations: Animals were observed at the time of dosing and each sample collection. Any abnormalities were documented.

Dosing: The formulation containing the test compound were administered p.o. by gavage with disposable feeding needles.

Sample collection: Terminal blood and tissue samples were collected under O2/CO2 anesthesia by cardiac puncture. The colon samples (a 0.5 cm section, 2.5 cm distal to the cecum) will be excised, rinsed with ice cold PBS, blotted and weighed (as applicable). The livers will be blotted and weighed. Plasma, liver and colon samples will be stored frozen at −80 degrees centigrade until bioanalysis.

Sample processing/storage: All blood samples were transferred into K2EDTA tubes on wet ice and centrifuged within 5 min (3200×g for 5 min at 4° C.) to obtain plasma. Samples were stored frozen at −80° C. until bioanalysis.

Sample retention: Plasma samples were analyzed and any remaining samples were stored frozen at −80° C. until the study is completed. Remaining sample were discarded.

Bioanalytical Method Qualification and Sample Analysis:

Matrix: mouse plasma

Instrumentation: AB Sciex API 4000 Q-TRAP MS/MS system equipped with an Agilent LC system with a binary pump, a solvent degasser, a thermostatted column compartment, a CTC autosampler and a divert valve installed between the column and mass spectrometer inlet.

Method Qualification:

The determination of the quantification dynamic range using non-zero calibration standards (STDs) in singlet. The STDs will consist of a blank matrix sample (without IS), a zero sample (with IS), and at least 6 non-zero STDs covering the expected range and including the lower level of quantitation (LLOQ).

Three injections of a system suitability sample (neat solution containing the analytes and IS) bracketing the batch.

Method Acceptance Criteria:

At least 75% of non-zero STDs must be included in the calibration curve with all back-calculated concentrations within ±20% deviation from nominal concentrations (±25% for the lower level of quantification, LLOQ).

The correlation coefficient (r) of the calibration curve must be greater than or equal to 0.99.

The area ratio variation between the pre- and post-run injections of the system suitability samples is within ±25%.

Samples which are >1-fold the highest calibration standard, will be diluted and re-assayed along with a corresponding dilution quality control standard.

Sample Analysis Batch:

Three injections of a system suitability sample bracketing the batch

The STDs in ascending order bracketing the study samples and dosing solutions

1. The study samples
2. The dosing solutions diluted as 3 independent dilutions into blank matrix (mouse plasma)

8-Day Efficacy Study in DSS Model (Therapeutic) with ET02451-01 (Compound No. 340) and ET02452-01 (Compound No. 341)

Study Design

| Cohort | N | UC | Treatment | Dose | Volume |
|---|---|---|---|---|---|
| 1 | 5 | DSS | vehicle | 0 mg/kg | 5 mL/kg (p.o.) |
| 2 | 5 | DSS | ET02451-01 | 40 mg/kg | 5 mL/kg (p.o.) |
| 3 | 5 | DSS | ET02452-01 | 40 mg/kg | 5 mL/kg (p.o.) |
| 4 | 5 | DSS | ET02452-01 | 65 mg/kg | 5 mL/kg (i.p.) |
| 5 | 5 | DSS | DATK32 | 15 mg/kg | 6 mL/kg (i.p.) |

Description of Tested Compounds
Name: Vehicle Labrasol/PBS
Volume: 8.0 mL
Solution: Labrasol (30%)/PBS (70%)
Storage: 4° C.
Name: ET02451 (Compound No. 340)
Volume: 3.7 mL
Solution: 8 mg/mL in Labrasol (30%)/PBS (70%)
Storage: 4° C.
Name: ET02452 (Compound No. 341)
Volume: 3.45 mL
Solution: 8 mg/mL in Labrasol (30%)/PBS (70%)
Storage: 4° C.
Name: ET02452 (Compound No. 341)
Volume: 3.40 mL
Solution: 13 mg/mL in PEG400 (40%)/PBS (60%)
Storage: 4° C.
Name: DATK32 Antibody (eBiosciences #14-5887-85, lot #4282190)
Volume: 5 mL
Solution: 0.5 mg/mL concentrated to 2.5 mg/mL following concentration step
Storage: 4° C.
Name: Vehicle PEG/PBS
Volume: 8.0 mL
Solution: PEG400 (40%)/PBS (60%)
Storage: 4° C.

Animal care committee. The animal care facility employed is accredited by the Canadian Council on Animal Care (CCAC). This study was approved by a certified Animal Care Committee and complied with CACC standards and regulations governing the use of animals for research.

Animals. Female C57Bl/6 mice (Charles River, St-Constant, Qc), weighting 16-19 g at delivery were used for this study. Following arrival in the animal facility, all animals were subjected to a general health evaluation. An acclimation period of 7-14 days was allowed before the beginning of the study.

Housing environment. The animals were housed under standardized environmental conditions. The mice were housed in auto-ventilated cages, 2-3 per cage. Each cage was equipped with a manual water distribution system. A standard certified commercial rodent diet was provided ad libitum. Tap water was provided ad libitum at all times. It is considered that there are no known contaminants in the diet and water that would interfere with the objectives of the study. Each cage was identified for the corresponding group, indicating the treatment and the identity of the animals housed in the cage. Mice from different treatment groups were not mixed.

The animal room was maintained at a controlled temperature of 21.5±1° C. and a relative humidity of 40±10%. A controlled lighting system assured 12 hours light, 12 hours dark per day to the animals. Adequate ventilation of 8-10 air changes per hour was maintained.

Oral dosing of the test article and the vehicle. From Day 5 to Day 8, nacellins and the vehicle were administered as a single slow bolus (over approximately 5 seconds) via oral route (p.o.), according to the procedure of administration of solution by gavage: the animal was firmly restrained. A bulb-tipped gastric gavage needle of 22G was passed through the side of the mouth and was advanced towards the oesophagus. The test articles and the vehicle were dosed orally at 5 mL/kg. Dosing volume was individually adjusted according to the body weight of each animal to reach the target dose of ET02451 and ET02452 (40 mg/kg).

Intraperitoneal dosing of the test articles and the vehicle. On day 5, DATK32 antibody was administered in only on Day 5, as a single slow bolus (over approximately 5 seconds) via the i.p. route. ET02452 prepared in PEG400 (40%)/PBS (60%) and the i.p. vehicle (PEG400 (40%)/PBS (60%)) were administered from Day 5 to Day 8. Intraperitoneal administration was performed accordingly to the following procedure: the mouse was restrained manually and held with the head and body tilted downward. The tip of the needle (27 G) was inserted through the skin and just past the abdominal wall. A short pull back of the plunger of the syringe was done prior to administration of the solution to make sure that the syringe was not inserted in any abdominal organ (fluid would be pulled back into the syringe in this case). Dosing volume was individually adjusted according to the body weight of each animal to reach the target dose of DATK32 antibody (15 mg/kg) and of ET02452 (65 mg/kg).

Inflammation Score. Once the mouse was euthanized, the colon was collected and its length was measured. Lesion length was also measured. Colon inflammation was scored based on severity of oedema and ulceration.

Disease Activity Index (DAI) assessment. Body weight and DAI were measured on Day 5 in order to distribute DSS-treated animals in two uniform groups prior dosing. Specific symptoms associated to UC were scored based on the severity of each particular symptoms: 1—blood in stool (negative hemoccult, positive hemoccult, blood traces in stool visible, rectal bleeding); 2—stool consistency (normal, soft but still formed, very soft, diarrhea); 3—posture and fur (normal; ruffled fur; ruffled fur combined to slight hunched posture and slight dehydration; ruffled fur combined to hunched posture, dehydration and altered walking; moribund (euthanasia is mandatory before the animal reach this point). The overall DAI score was the sum of the three parameters (maximum score 9). Body weight measurement and DAI assessment were performed also on Day 8 to evaluate the effect of the treatments.

Collection of samples. On Day 8, five hours after ET02451-01, ET02452-01 and vehicle dosing, the animals were euthanized by cardiac puncture under general anesthesia, according to the "Guide to the Care and Use of Experimental Animals" published by the CCAC. Blood was transferred in a Sarstedt tube containing EDTA. Mesenteric and peripheral (inguinal, auxiliary and brachial) lymph nodes were collected and transferred on ice in corresponding tubes containing cold PBS. Nodes were kept on ice until tissue preparation.

ranged from an 9.5% to 76.9% (mean of 42.6%), whereas in mouse plasma, free fraction ranged from 15.7% to 79.9% (mean of 47.8%). Plasma protein binding for the small molecule positive control, propranolol, was in the normal range of ~21% (free fraction) in mouse plasma and ~15% (free fraction) in rat plasma. The compounds assessed include:

ET01792 (Compound No. 5)

ET00762 (an analog of Compound No. 5, in which the phenylalanine residue has been replaced by a tryptophan residue)

ET01813 (Compound No. 12)

ET01827 (Compound No. 15)

| List of compounds | % unbound ($C_{buffer}/C_{plasma}$) Mouse plasma | | | | | | | Control buffer/ Buffer at 0.1 uM | |
|---|---|---|---|---|---|---|---|---|---|
| | 1 | 2 | 3 | Average | sd | % RSD | % recovery | Recovery | Cdonor/Creceiver |
| ET01792 | 64.8 | 52.9 | 67.9 | 61.9 | 7.9 | 13% | 130% | 108% | 80% |
| ET00762 | 80.6 | 74.4 | 75.7 | 76.9 | 3.3 | 4% | 150% | 99% | 79% |
| E101813 | 24.7 | 22.2 | 18.8 | 21.9 | 3.0 | 14% | 113% | 128% | 94% |
| ET01827 | 10.0 | 9.3 | 9.3 | 9.5 | 0.4 | 4% | 103% | 70% | 86% |
| Propranolol | 22.9 | 20.1 | 20.1 | 21.0 | 1.6 | 7% | 93% | | |

| List of compounds | % unbound (Cbuffer/Cplasma) Rat plasma | | | | | | |
|---|---|---|---|---|---|---|---|
| | 1 | 2 | 3 | Average | sd | % RSD | % recovery |
| E101792 | 82.9 | 77.3 | 79.5 | 79.9 | 2.8 | 4% | 97% |
| ET00762 | 83.3 | 76.1 | 70.2 | 76.5 | 6.6 | 9% | 94% |
| E101813 | 15.8 | 20.1 | 21.7 | 19.2 | 3.1 | 16% | 89% |
| E101827 | 16.2 | 17.4 | 13.6 | 15.7 | 1.9 | 12% | 143% |
| Propranolol | 14.6 | 14.7 | 14.7 | 14.7 | 0.1 | 0% | 79% |

Cell population labeling. Blood was withdrawn by cardiac puncture and collected on EDTA-coated tubes. Mensenteric lymph nodes (MLN) and peripheral lymph nodes (PLN) were also collected. Mononuclear cells from the tissues will be isolated using density gradient (Lympholyte) and they were stained with fluorescent antibodies. The cells ($5 \times 10^4$) were first incubated 15 minutes with BD mouse FcBlock (Fcγ III/II Receptor) followed by a 30-minute incubation with specific antibodies. After washes, cells were fixed using BD Fix Solution. Percentage of different subpopulations of T lymphocytes were then analysed using FACSCalibur cytometer. Antibodies employed were the same as listed for the single-dose PD studies above.

Results and Discussion

Compounds were synthesized in accordance with the above-noted methods. A selection of compounds were characterized using NMR (not all data shown). A subset of NMR data is provided for select compounds in FIGS. 14-47.

Plasma Protein Binding Determination

The sequestration of nacellins by plasma proteins was relatively low. In rat plasma, free fraction (% unbound)

Aqueous Solubility Assay

As shown in the table below, the aqueous solubility of integrin alpha-4-beta-7-inhibiting nacellins was relatively high, with a mean solubility of 715 microM. The range of solubilities measured in triplicate for 15 distinct compounds was 183 microM to greater than 1000 microM. Note that the maximum concentration evaluated was different for different test articles based on the presumed aqueous solubility. The compounds assessed include:

UM0131995-05 (Compound No. 4)

UM0132366-01 (Compound No. 87)

UM0132368-01 (Compound No. 88)

UM0132369-01 (Compound No. 89)

UM0132370-01 (Compound No. 52)

UM0132371-01 (Compound No. 90)

UM0132374-01 (Compound No. 65)

UM0132375-02 (Compound No. 42)

UM0132376-01 (Compound No. 92)

UM0132377-01 (an analog of Compound No. 92, in which the lysine residue has been replaced by an ornithine residue)

UM0134839-01 (an analog of Compound No. 455, in which the phenylalanine and betaHomoLys residues have been replaced by a tyrosine residue)

UM0134690-01 (Compound No. 358)

UM0134830-01 (an analog of Compound No. 159, in which the tyrosine and alanine residues have been exchanged with respect to position within the sequence)

UM0134677-01 (Compound No. 158)
UM0134700-01 (Compound No. 62)

| List of compounds | Maximal solubility evaluated (μM) | Determined concentration (μM) Rep 1 | Rep 2 | Rep 3 | Mean | SD | RSD (%) |
|---|---|---|---|---|---|---|---|
| UM0331995-05 | 1000 | 883.9 | 897.3 | 914.7 | 898.5 | 15.4 | 1.7 |
| UM0132365-01 | 500 | 474.2 | 477.4 | 451.9 | 467.8 | 13.9 | 3.0 |
| UM0132368-01 | 1000 | 926.3 | 917.9 | 934.3 | 926.3 | 8.4 | 0.9 |
| UM0138369-01 | 1000 | 874.4 | 885.9 | 887.3 | 882.5 | 7.1 | 0.8 |
| UM0132370-01 | 200 | 187.0 | 182.4 | 180.2 | 183.2 | 3.5 | 1.9 |
| UM0132371-01 | 1000 | 786.7 | 837.3 | 879.6 | 834.5 | 46.6 | 5.6 |
| UM0132374-01 | 200 | 179.4 | 184.0 | 185.9 | 183.1 | 3.3 | 1.8 |
| UM0132375-02 | 1000 | 966.6 | 960.0 | 936.8 | 954.5 | 15.6 | 1.6 |
| UM0132376-01 | 1000 | 990.7 | 958.6 | 939.5 | 962.9 | 25.9 | 2.7 |
| UM0132377-01 | 200 | 225.7 | 218.9 | 211.2 | 218.6 | 7.3 | 3.3 |
| UM0134839-01 | 1000 | 1038.0 | 1000.1 | 1004.0 | 1014.0 | 20.8 | 2.1 |
| UM0134690-01 | 1000 | 957.3 | 950.5 | 920.8 | 942.9 | 19.4 | 2.1 |
| UM0134830-01 | 1000 | 1012.0 | 1016.4 | 971.7 | 1000.0 | 24.7 | 2.5 |
| UM0134677-01 | 200 | 225.4 | 230.6 | 217.8 | 224.6 | 6.4 | 2.9 |
| UM0134700-01 | 1000 | 1044.8 | 933.2 | 950.6 | 994.5 | 47.4 | 4.8 |

Cytochrome P450 Inhibition Assay

The inhibitory activity of various nacellins against four isoforms of cytochrome P450 was assessed using human liver microsomes. The four isoforms evaluated were: CYP2D5, CYP3A4, CYP2C9, and CYP1A2. As shown below, for the seven nacellins evaluated in this experiment, 85% of the results of the assays showed an $IC_{50}$>15 microM (above the limit of detection). However, $IC_{50}$s of <10 microM, and in one case, <1 microM, were recorded for a few compounds. These compounds were subjected to a structural analysis so as to understand the functional groups contributing to this mild CYP450-inhibiting activity. The compounds assessed include:

ET01792 (Compound No. 5)

ET00762-02 (an analog of Compound No. 5, in which the phenylalanine residue has been replaced by a tryptophan residue)

ET01813 (Compound No. 12)

ET00328-01 (an analog of Compound No. 4, in which the tyrosine, leucine, aspartic acid and threonine residues have been replaced by threonine, methyl leucine, valine and phenylalanine residues)

ET01827 (Compound No. 15)

ET01842-01 (Compound No. 413)

| | IC50 (mM) | | | |
|---|---|---|---|---|
| List of compounds | CYP2D6 | CYP3A4 | CYP2C9 | CYP1A2 |
| ET01792-01 | >15 | >15 | >15 | >15 |
| ET00762-02 | >15 | >15 | >15 | >15 |
| ET01813-01 | >15 | >15 | >15 | >15 |
| ET00328-01 | >15 | 9.7 | >15 | >15 |
| ET01827-01 | >15 | >15 | >15 | >15 |
| ET01838-01 | 11 | 3.7 | >15 | >15 |
| ET01842-01 | >15 | 0.89* | >15 | >15 |
| Quinidine | 0.17 | — | — | — |
| Ketoconazole | — | 0.023 | — | — |
| Miconazole | — | — | 0.32 | — |
| α-naphthoflavone | — | — | — | 0.05 |

In Vivo T Lymphocyte Trafficking Analyses

Figure 6:
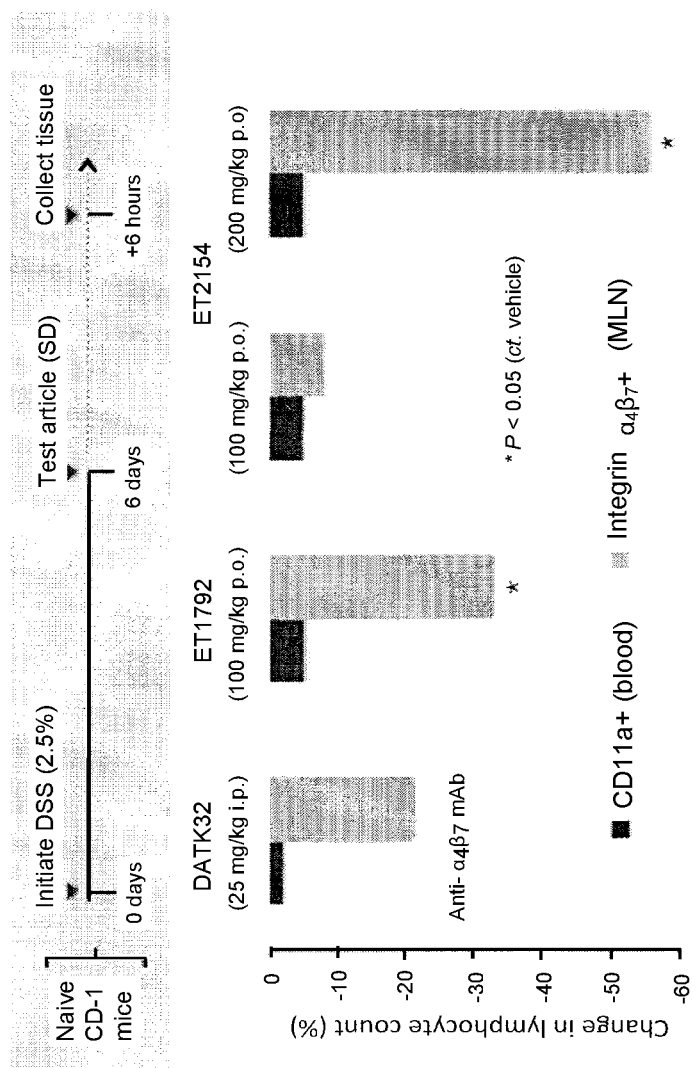
FIG. 6 shows results of T lymphocyte trafficking studies (from peripheral blood to mesenteric lymph nodes) following single doses of various compounds.

The ability of several integrin alpha-4-beta-7-inhibiting nacellins to attenuate the trafficking of integrin alpha-4-beta-7-expressing T lymphocytes was demonstrated in in vivo pharmacodynamics studies in DSS-treated mice. As shown in FIG. 6, this study was conducted in mice exposed for 5 days to dextran sulfate in their drinking water. On day 6, single doses of test articles were administered and, 5-6 hours later, peripheral blood, mesenteric lymph nodes and other tissues were collected and assessed.

As shown, the murine anti-alpha-4-beta-7 monoclonal antibody (DATK32; 25 mg/kg) substantially reduces homing of integrin a4b7+ T lymphocytes to the mesenteric lymph nodes ("MLN"), but did not affect the counts of CD11a+ T lymphocytes in the peripheral blood. As for the nacellins, at 100 mg/kg, the high oral bioavailability nacellin, ET1792 (Compound No. 5), but not the low oral bioavailability nacellin, ET2154 (Compound No. 105), evoked a significant reduction of homing to the MLN following oral dosing. When the dose of ET2154 was increased to 200 mg/kg, it evoked a significant and robust attenuation of homing to the MLN. These results demonstrate the importance of oral bioavailability (and the concomitant systemic exposure) to attenuate trafficking of T lymphocytes via an integrin alpha-4-beta-7—MAdCAM facilitated extravasation event from high endothelial venules in gut-associated lymphoid tissues. Under no circumstances did test nacellins produce a significant change in the content of CD11a+ T cells in peripheral blood (similarly, no changes in the CD34 and CD45 T lymphocyte content in peripheral blood was recorded for any nacellin; data not shown).

In Vivo Pharmacokinetic Assessments in Rodents

We assessed the pharmacokinetic profile of several integrin alpha-4-beta-7-inhibiting nacellins following oral doses, and in some cases, intravenous doses for naïve mice.

Figure 7:
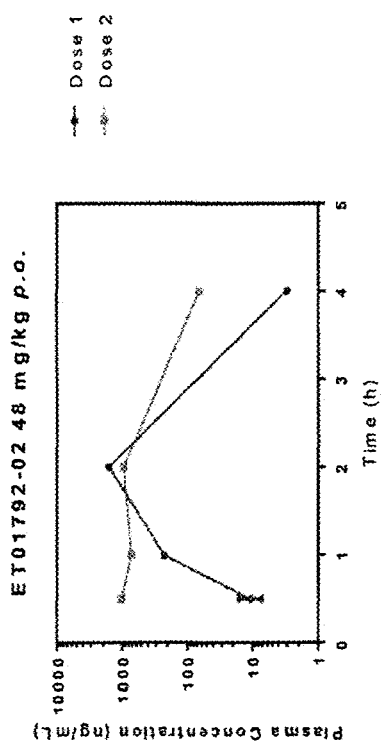
FIG. 7 shows the pharmacokinetic profile for a test article (ET1792) via one and two oral doses in naïve mice.

As shown in the FIG. 7 below, one and two oral doses of ET1792 (Compound No. 5) at 48 mg/kg to naïve mice produced significant absorption and systemic exposure. The exposure (AUC-0-tlast) following the first dose was 1,475 h*ng/ml, whereas following the second dose, the exposure was 2,188 h*ng/ml. The maximum plasma concentration recorded after the first dose was nearly 1,600 ng/ml.

Figure 8:
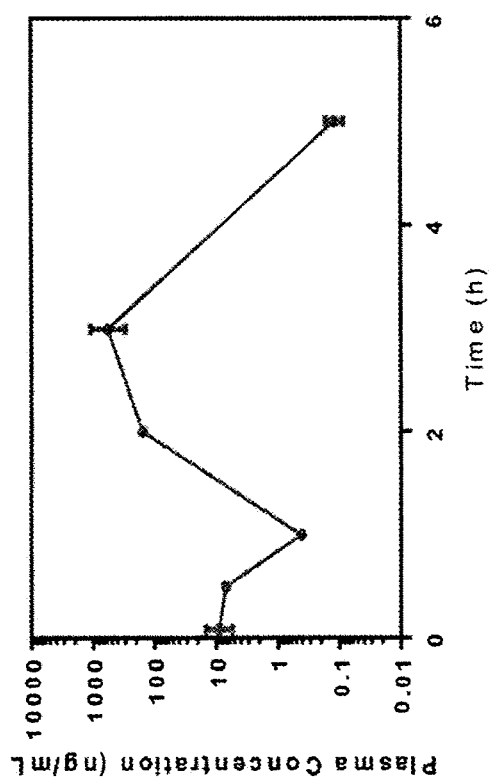
FIG. 8 shows the pharmacokinetic profile for a test article (ET1792) after a single oral dose.

Referring to FIG. 8, in a second study of orally administered ET1792 (at 40 mg/kg), a similar profile was recorded, with an exposure (AUC0-tlast) of 589 h*ng/ml. The biphasic absorption and delayed Tmax is likely indicative of an initial transcellular perfusion of enterocytes followed by a more prolonged transcellular perfusion.

In a subsequent study of ET1813 (Compound No. 12), single doses were administered via oral gavage (40 mg/kg) and intravenous injection (5 mg/kg). The absorption of this compound was less than that of ET1792, with a calculated oral bioavailability of ~1%, despite a significant terminal half-life of nearly 2 hours.

| PK parameter summary for i.v. dosing. | | | | | |
|---|---|---|---|---|---|
| | Parameter estimate for each animal | | | | |
| Parameter | R01 | R02 | R03$^a$ | Mean (n = 2) | SD |
| $C_0$ (ng/mL) | 6330 | 7590 | 9980 | 6960 | n/a |
| Apparent $t_{1/2}$ (h) | 1.45 | 2.79 | 0.225 | 2.12 | n/a |
| $AUC_{0-inf}$ (h*ng/mL) | 741 | 711 | 1290 | 726 | n/a |
| $CL_s$ (mL/h/kg) | 6740 | 7030 | 3880 | 6885 | n/a |
| $MRT_{0-inf}$ (h) | 0.253 | 0.136 | 0.166 | 0.195 | n/a |
| $V_{ss}$ (mL/kg) | 1700 | 957 | 645 | 1329 | n/a |

| PK parameter summary for p.o. dosing | | | | | |
|---|---|---|---|---|---|
| | Parameter estimate for each animal | | | | |
| Parameter | R04 | R05 | R06 | Mean | SD |
| $t_{max}$ (h) | 0.0833 | 0.0833 | 0.0833 | 0.0833 | 0.000 |
| $C_{max}$ (ng/mL) | 387 | 28.0 | 22.9 | 146 | 209 |
| Apparent $t_{1/2}$ (h) | 4.47 | 0.638 | 0.466 | 1.86 | 2.26 |
| $AUC_{0-inf}$ (h*ng/mL) | 166 | 3.77 | 3.74 | 57.8 | 93.7 |
| $MRT_{0-inf}$ (h) | 1.48 | 0.449 | 0.409 | 0.779 | 0.607 |
| F (%) | 2.86 | 0.0649 | 0.0644 | 0.996 | 1.61 |

Figure 9:
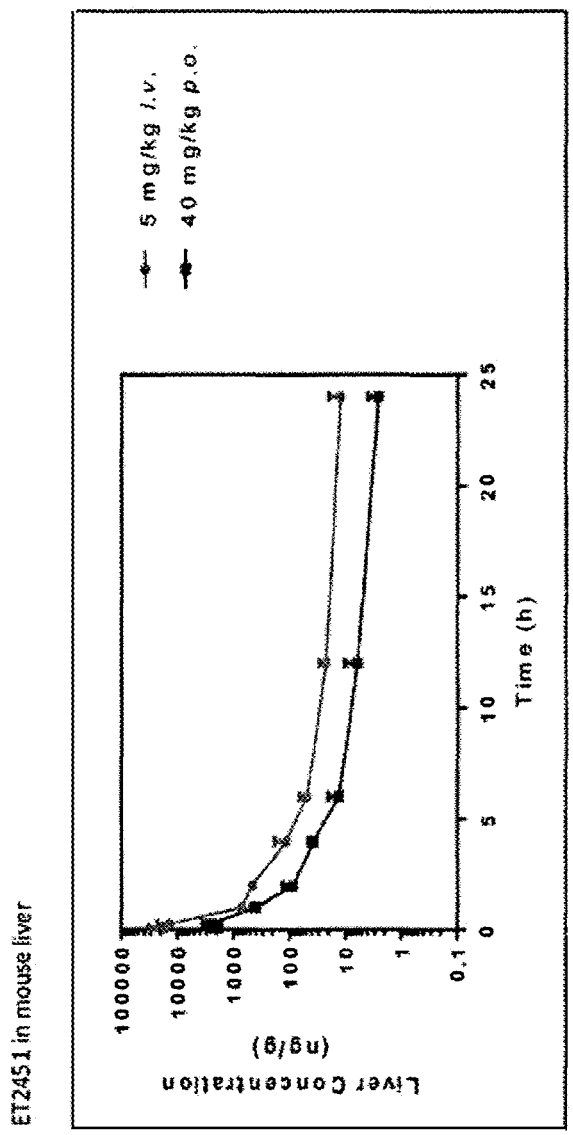
FIG. 9 shows the exposure of ET2451 in the liver of naïve mice that have received the test compound as a single oral or intravenous dose.

Another set of pharmacokinetic studies were performed on ET2451 (Compound No. 340) in naïve mice. In this study, compound exposure in plasma, colon and liver were measured following both single oral doses (40 mg/kg) and single intravenous doses (5 mg/kg). As illustrated in the FIG. 9 and in the tables below, ET2451 was found to have an oral bioavailability of approximately 11% in plasma, and closer to 100% in colon. Also noteworthy is the difference in elimination half-life: in plasma the half-life was found to be ~30 minutes following oral dosing, whereas the half-life in colon was greater than 21 hours. We also assessed bioavailability in the liver (figure below), which was similar to that measured in the plasma (~8%) but half-life was significantly longer at ~8 hours following oral dosing. It is clear from this study and others that the main route of elimination of ET2451 and other nacellins is through hepatobiliary clearance.

| Summary of Plasma PK Parameters for ET02451 | | | |
|---|---|---|---|
| | | Estimate | |
| Parameter | Unit | i.v. | p.o. |
| $C_0$ | ng/mL | 1408 | n/a |
| $t_{max}$ | h | 0.083 | 0.0833 |
| $C_{max}$ | ng/mL | 1326 | 4638 |
| Apparent $t_{1/2}$ | h | 2.00 | 0.537 |
| $AUC_{0-tlast}$ | h*ng/mL | 778 | 686 |
| $AUC_{0-inf}$ | h*ng/mL | 778 | 690 |
| CL | mL/kg/h | 6426 | n/a |
| $MRT_{0-inf}$ | h | 0.698 | 0.689 |
| $V_{ss}$ | mL/kg | 4487 | n/a |
| F | % | 100 | 11.0 | n/a denotes not applicable.

| Summary of Colon PK Parameters for ET02451 | | | |
|---|---|---|---|
| | | Estimate | |
| Parameter | Unit | i.v. | p.o. |
| $t_{max}$ | h | 2.00 | 2.00 |
| $C_{max}$ | ng/mL | 8210 | 49115 |
| Apparent $t_{1/2}$ | h | 3.40 | 21.5 |
| $AUC_{0-tlast}$ | h*ng/mL | 17109 | 130746 |
| $AUC_{0-inf}$ | h*ng/mL | 17140 | 145327 |
| $MRT_{0-inf}$ | h | 3.43 | 4.59 |
| AUC Ratio (Colon/Plasma) | | 22.0 | 211 |

| Summary of Liver PK Parameters for ET02451 | | | |
|---|---|---|---|
| | | Estimate | |
| Parameter | Unit | i.v. | p.o. |
| $t_{max}$ | h | 0.0833 | 2.00 |
| $C_{max}$ | ng/mL | 16613 | 4792 |
| Apparent $t_{1/2}$ | h | 9.60 | 7.94 |
| $AUC_{0-tlast}$ | h*ng/mL | 8289 | 6024 |
| $AUC_{0-inf}$ | h*ng/mL | 8460 | 6054 |
| $MRT_{0-inf}$ | h | 2.00 | 2.11 |
| AUC Ratio (Liver/Plasma) | | 10.9 | 8.78 |

$C_0$ concentration extrapolated to time zero following an i.v. dose
$t_{max}$ time as which maximum concentration is observed
$C_{max}$ maximum observed concentration
Apparent $t_{1/2}$ apparent terminal half-life
$AUC_{0-tlast}$ area under the concentration vs time curve from time 0 to the time of the last measurable concentration
$AUC_{0-inf}$ area under the concentration vs time curve from time 0 to infinity
CL systemic clearance
$MRT_{0-inf}$ mean residence time from time zero vs the time of the last measurable concentration
$V_{ss}$ steady-state-volume of distribution
F oral bioavailability + $(Dose^{IV} \cdot AUC^{PO})/(Dose^{PO} \cdot AUC^{iv}) \cdot 100$ 8-Day Efficacy Study in DSS Model (Therapeutic)

We assessed the efficacy of two distinct nacellins in the DSS experimental model of ulcerative colitis: ET2451 (Compound No. 340) and ET2452 (Compound No. 341). As shown above, ET2451 demonstrates significant absorption from the gut and systemic exposure following oral dosing, whereas ET2452 is a low oral bioavailability entity. Both test compounds were administered b.i.d. to mice over the course of three days—following an initial 5-days exposure to DSS (2-3%) in their drinking water. The efficacy and pharmacodynamics effect of the nacellins was compared to the mouse anti-integrin alpha-4-beta-7 mAb, DATK32. ET2452 was administered both orally and, to another group, via i.p. injection. The objective of this experimental design was to demonstrate that, although it may not be efficacious when administered orally, it produced substantial efficacy with i.p. dosing.

Figure 10:
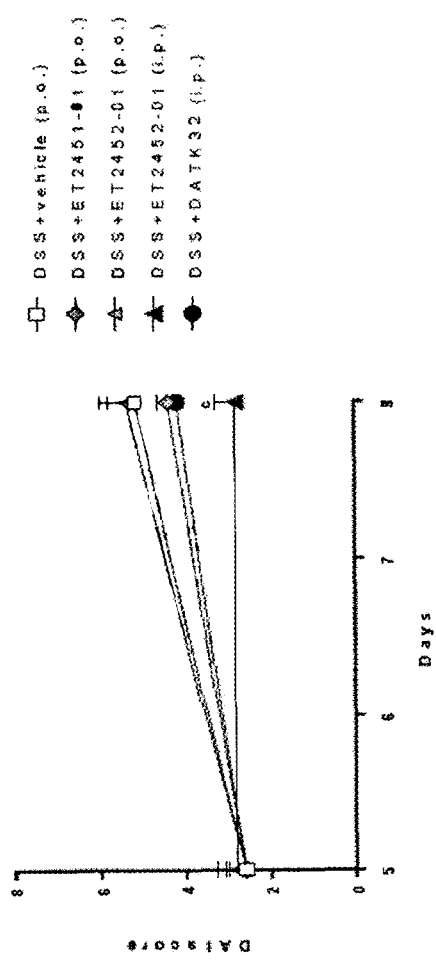
FIG. 10 shows the disease activity index score for the various treatment groups at day 5 and day 8 following the initiation of dextran sulfate sodium treatment in mice.

Disease activity index ("DAI") score was assessed individually based on the severity of three specific symptoms: blood in stool, stool consistency and general health assessment (posture, fur and dehydration), on Day 5 and 8. As shown in FIG. 10, DAI score increased significantly from Day 5 to Day 8 in DSS+vehicle control group. Oral administration of ET02451-01 and i.p. administration of DATK32 led to a reduction of 15% and 19% respectively, but only the ET02451-01-evoked effect proved statistically significant. Oral administration of ET02452-01 did not have any beneficial effect on DAI. In contrast, intraperitoneal ET02452-01 treatment led to a significant reduction of DAI score on Day 8, by 46%, in comparison to DSS+vehicle control group (p<0.05). In fact, ET02452-01 i.p. treatment prevented the increased severity of UC symptoms observed in the control vehicle-treated group, from day 5 to day 8.

Figure 11:
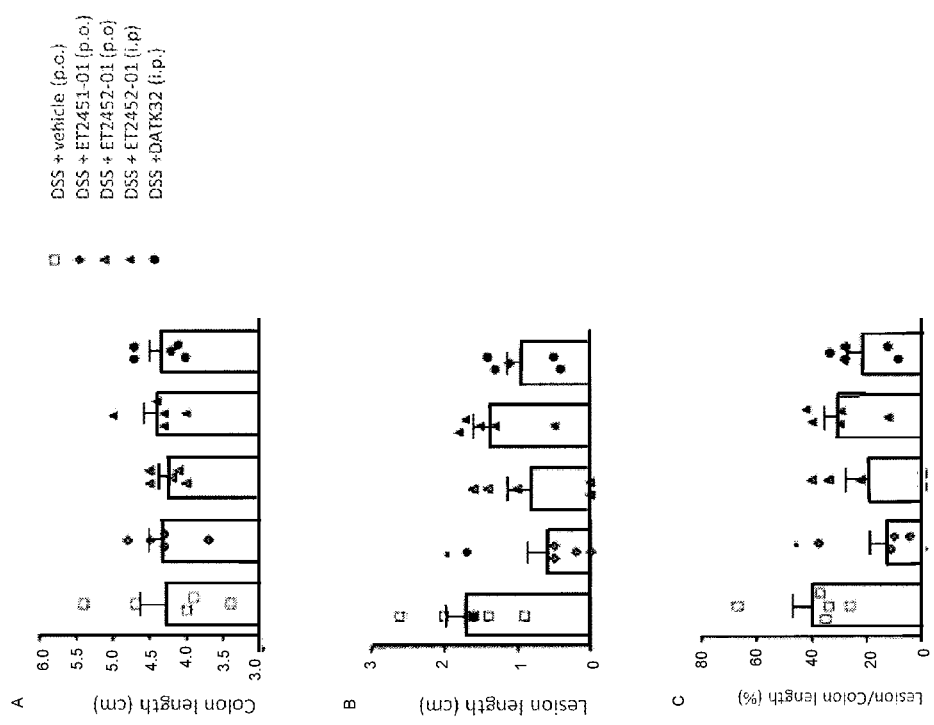
FIG. 11 shows data from ex vivo assessments of the colon taken from mice exposed to DSS and treated with various test compounds.

Ulcerative colitis is associated with inflammatory changes of the intestinal tract with reduction of the length of the mice colon (raw data in Annex IV). DSS+vehicle control group showed a mean colon length of 4.3±0.3 cm and a lesion length of 1.7±0.3 cm corresponding to a lesion/colon length of 40% (FIG. 11). Treatments did not have any effect on colon length (FIG. 11). However, ET02451-01 significantly reduced the lesion length of this group (p<0.05), leading to a significant improvement of the lesion/colon length ratio, by reaching a value of lesion/colon length of 12% (p<0.05). Oral and i.p. administration of ET02452-01 led to a reduction of lesion length by 53% and 20% respectively, in comparison to the control vehicle treated-group, but these reductions were not statistically significant (FIG. 11B). Beside, DATK32, administered on Day 5 by i.p. route, led to a reduction, not statistically significant, of 45% in comparison to the control vehicle treated-group.

Whether treatments would have been compared in separate experiments, a Student t-test would have been used for statistical comparison of each test article treated-group with the control vehicle treated-group. In that case, by a separated Student t-test, a statistical significant effect by oral ET02452-01 and i.p. DATK32 would have been obtained on lesion length and lesion/colon length.

Figure 12:
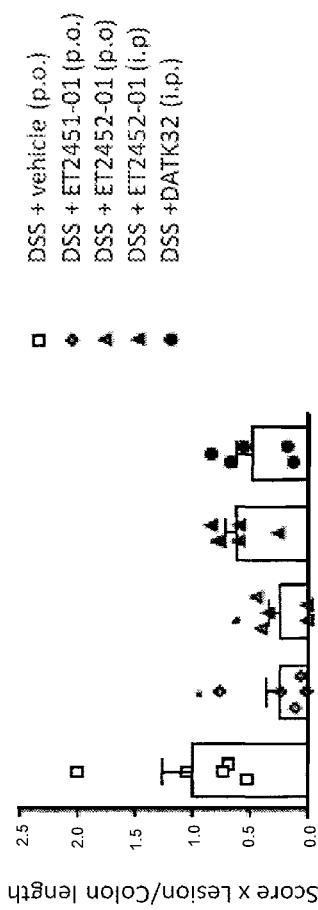
FIG. 12 shows further detail on the colon injury following DSS exposure and test nacellin treatment in mice.

The final score of colon inflammation was calculated by multiplying macroscopic score×lesion/colon length ratio for each mouse. Referring to FIG. 12, the measurement of this parameter shows a significant reduction of lesion inflammation by the oral administration of ET02451-01 (by 77%) and ET02452-01 (by 76%) in comparison to the control vehicle-treated group. Intraperitoneal administration of ET02452-01 and DATK32 led to a reduction of 39% and 53% respectively, but this effect was not statistically significant.

Cell Populations

Figure 13:
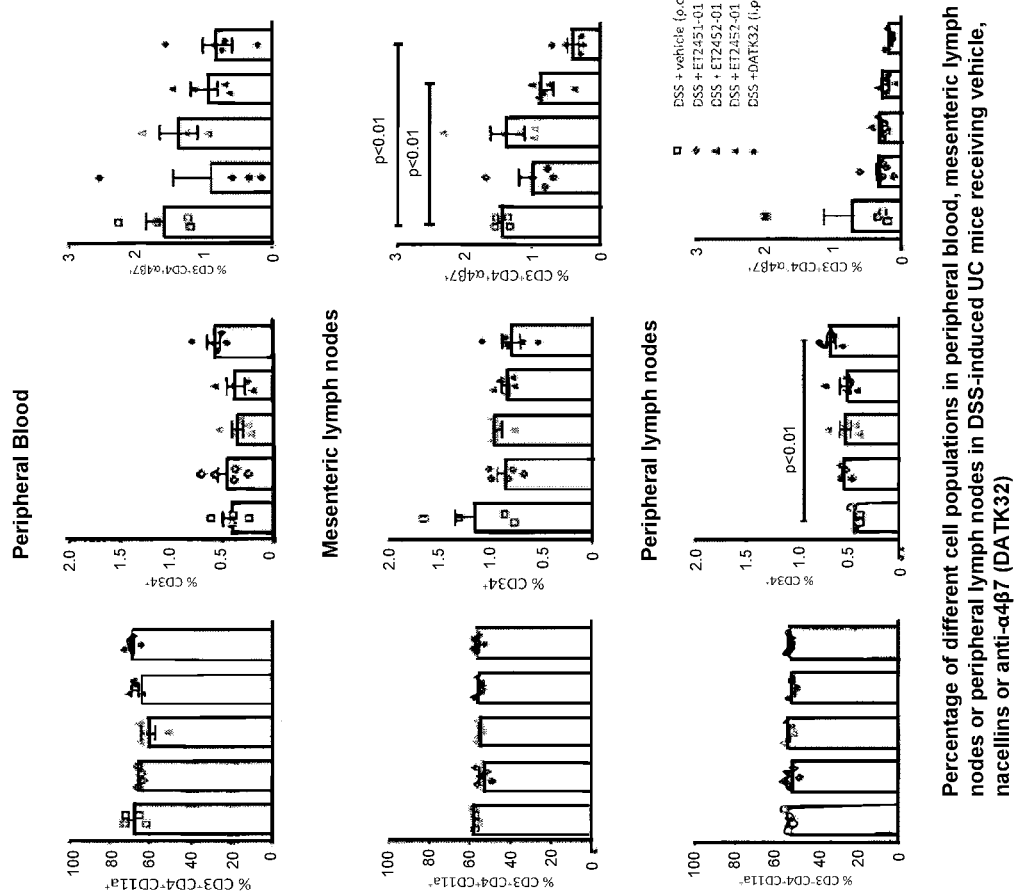
FIG. 13 shows the outcome of FACS analyses of T lymphocyte content in peripheral lymph nodes, mesenteric lymph nodes and peripheral blood taken from mice exposed to DSS irritant and treated for three days with various test nacellins or control.

There are no statistical differences between the percentage of CD3+CD4+CD11a+ T cell populations in vehicle mice and compound-treated ones in the three tissues tested (see FIG. 13). In all tissues, the population of CD34+ cells is the same in vehicle- and -nacellin-treated mice. However, a significant increase (p<0.01) of CD34+ cells is observed in the mice receiving the anti-α4β7 antibody (DATK32). For the CD3+CD4+α4β7+ cell population, no difference was observed in blood neither in peripheral lymph nodes. However, a significant decrease of this population was observed in mesenteric lymph nodes in mice receiving ET02452 (Compound No. 341) i.p. or ET02451 (Compound No. 340) p.o. Intraperitoneal administration of DATK32 also significantly decreased the percentage of CD3+CD4+α4β7+ T lymphocytes.

It is of note that over 600 macrocycles were made that exhibited less activity than those summarized in Tables 1A, 1B and 1C. A selection of the macrocycles with less or little activity are summarized in Tables 2A, 2B and 2C.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

TABLE 1A

| Compound No. | $R^1$ | $R^2$ | $R^3$ | $R^4$ | $R^5$ |
|---|---|---|---|---|---|
| 1 | H | H | CH2—S—Ph | H | C(O)—NH-tert-Butyl |
| 2 | H | H | CH2—S—Ph | H | C(O)—NH-tert-Butyl |
| 3 | H | H | CH2—S—Ph | H | C(O)—NH-tert-Butyl |
| 4 | H | H | $CH_3$ | H | C(O)—NH-tert-Butyl |
| 5 | H | H | $CH_3$ | H | C(O)—NH-tert-Butyl |
| 6 | H | H | $CH_3$ | H | C(O)—NH-tert-Butyl |
| 7 | H | H | $CH_3$ | H | C(O)—NH-tert-Butyl |
| 8 | H | H | $CH_3$ | H | C(O)—NH-tert-Butyl |
| 9 | H | H | $CH_3$ | H | C(O)—NH-tert-Butyl |
| 10 | H | H | $CH_3$ | H | C(O)—NH-tert-Butyl |
| 11 | H | H | $CH_3$ | H | C(O)—NH-tert-Butyl |
| 12 | H | H | $CH_3$ | H | C(O)—NH-tert-Butyl |
| 13 | H | H | $CH_3$ | H | C(O)—NH-tert-Butyl |
| 14 | H | H | $CH_3$ | H | C(O)—NH-tert-Butyl |
| 15 | H | H | $CH_3$ | H | C(O)—NH-tert-Butyl |
| 16 | H | H | $CH_3$ | H | C(O)—NH-tert-Butyl |
| 17 | H | H | $CH_3$ | H | C(O)—NH-tert-Butyl |
| 18 | H | H | $CH_3$ | H | C(O)—NH-tert-Butyl |
| 19 | H | H | $CH_3$ | H | C(O)—NH-tert-Butyl |
| 20 | H | H | $CH_3$ | H | C(O)—NH-tert-Butyl |
| 21 | H | H | $CH_3$ | H | C(O)—NH-tert-Butyl |
| 22 | H | H | $CH_3$ | H | C(O)—NH-tert-Butyl |
| 23 | H | H | $CH_3$ | H | C(O)—NH-tert-Butyl |
| 24 | H | H | $CH_3$ | H | C(O)—NH-tert-Butyl |
| 25 | H | H | $CH_3$ | H | C(O)—NH-tert-Butyl |
| 26 | H | H | $CH_3$ | H | C(O)—NH-tert-Butyl |
| 27 | H | H | $CH_3$ | H | C(O)—NH-tert-Butyl |
| 28 | H | H | $CH_3$ | H | C(O)—NH-tert-Butyl |
| 29 | H | H | $CH_3$ | H | C(O)—NH-tert-Butyl |
| 30 | H | H | $CH_3$ | H | C(O)—NH-tert-Butyl |
| 31 | H | H | $CH_3$ | H | C(O)—NH-tert-Butyl |
| 32 | H | H | $CH_3$ | H | C(O)—NH-tert-Butyl |
| 33 | H | H | $CH_3$ | H | C(O)—NH-tert-Butyl |
| 34 | H | H | $CH_3$ | H | C(O)—NH-tert-Butyl |
| 35 | H | H | $CH_3$ | H | C(O)—NH-tert-Butyl |
| 36 | H | H | $CH_3$ | H | C(O)—NH-tert-Butyl |

TABLE 1A-continued

| Compound No. | R¹ | R² | R³ | R⁴ | R⁵ |
|---|---|---|---|---|---|
| 37 | H | H | CH₃ | H | C(O)—NH-tert-Butyl |
| 38 | H | H | CH₃ | H | C(O)—NH-tert-Butyl |
| 39 | H | H | CH₃ | H | C(O)—NH-tert-Butyl |
| 40 | H | H | CH₃ | H | C(O)—NH-tert-Butyl |
| 41 | H | H | CH₃ | H | C(O)—NH-tert-Butyl |
| 42 | H | H | CH₃ | H | C(O)—NH-tert-Butyl |
| 43 | H | CH₃ | H | H | C(O)—NH-tert-Butyl |
| 44 | H | H | CH₃ | H | C(O)—NH-tert-Butyl |
| 45 | H | H | CH₃ | H | C(O)—NH-tert-Butyl |
| 46 | H | H | CH₃ | H | C(O)—NH-tert-Butyl |
| 47 | H | H | CH₃ | H | C(O)—NH-tert-Butyl |
| 48 | H | H | CH₃ | H | C(O)—NH-tert-Butyl |
| 49 | H | H | CH₃ | H | C(O)—NH-tert-Butyl |
| 50 | H | H | CH₃ | H | C(O)—NH-tert-Butyl |
| 51 | H | H | CH₃ | H | C(O)—NH-tert-Butyl |
| 52 | H | H | CH₃ | H | C(O)—NH-tert-Butyl |
| 53 | H | H | CH₃ | H | C(O)—NH-tert-Butyl |
| 54 | H | H | CH₃ | H | C(O)—NH-tert-Butyl |
| 55 | H | H | CH₃ | H | C(O)—NH-tert-Butyl |
| 56 | H | H | CH3 | H | C(O)—NH-tert-Butyl |
| 57 | H | H | CH₃ | H | C(O)—NH-tert-Butyl |
| 58 | H | H | CH₃ | H | C(O)—NH-tert-Butyl |
| 59 | H | H | CH₃ | H | C(O)—NH-tert-Butyl |
| 60 | H | H | CH₃ | H | C(O)—NH-tert-Butyl |
| 61 | H | H | CH₃ | H | C(O)—NH-tert-Butyl |
| 52 | H | H | CH₃ | H | C(O)—NH-tert-Butyl |
| 53 | H | H | CH₃ | H | C(O)—NH-tert-Butyl |
| 54 | H | H | CH₃ | H | C(O)—NH-tert-Butyl |
| 65 | H | H | CH₃ | H | C(O)—NH-tert-Butyl |
| 66 | H | H | CH₃ | H | C(O)—NH-tert-Butyl |
| 67 | H | H | CH₃ | H | C(O)—NH-tert-Butyl |
| 68 | H | H | CH₃ | H | C(O)—NH-tert-Butyl |
| 69 | H | H | CH₃ | H | C(O)—NH-tert-Butyl |
| 70 | H | H | CH₃ | H | C(O)—NH-tert-Butyl |
| 71 | H | H | CH₃ | H | C(O)—NH-tert-Butyl |
| 72 | H | H | CH₃ | H | C(O)—NH-tert-Butyl |
| 73 | H | H | CH₃ | H | C(O)—NH-tert-Butyl |
| 74 | H | H | CH₃ | H | C(O)—NH-tert-Butyl |
| 75 | H | H | CH₃ | H | C(O)—NH-tert-Butyl |
| 76 | H | H | CH₃ | H | C(O)—NH-tert-Butyl |
| 77 | H | H | CH₃ | H | C(O)—NH-tert-Butyl |
| 78 | H | H | CH₃ | H | C(O)—NH-tert-Butyl |
| 79 | H | H | CH₃ | H | C(O)—NH-tert-Butyl |
| 80 | H | H | CH₃ | H | C(O)—NH-tert-Butyl |
| 81 | H | H | CH₃ | H | C(O)—NH-tert-Butyl |
| 82 | H | H | CH₃ | H | C(O)—NH-tert-Butyl |
| 83 | H | H | CH₃ | H | C(O)—NH-tert-Butyl |
| 84 | H | H | CH₃ | H | C(O)—NH-tert-Butyl |
| 85 | H | H | CH₃ | H | C(O)—NH-tert-Butyl |
| 86 | H | H | CH₃ | H | C(O)—NH-tert-Butyl |
| 87 | H | H | CH₃ | H | C(O)—NH-tert-Butyl |
| 88 | H | H | CH₃ | H | C(O)—NH-tert-Butyl |
| 89 | H | H | CH₃ | H | C(O)—NH-tert-Butyl |
| 90 | H | H | CH₃ | H | C(O)—NH-tert-Butyl |
| 91 | H | H | CH₃ | H | C(O)—NH-tert-Butyl |
| 92 | H | H | CH₃ | H | C(O)—NH-tert-Butyl |
| 93 | H | H | CH₃ | H | C(O)—NH-tert-Butyl |
| 94 | H | H | CH₃ | H | C(O)—NH-tert-Butyl |
| 95 | H | H | CH₃ | H | C(O)—NH-tert-Butyl |
| 96 | H | H | CH₃ | H | C(O)—NH-tert-Butyl |
| 97 | H | H | CH₃ | H | C(O)—NH-tert-Butyl |
| 98 | H | H | CH₃ | H | C(O)—NH-tert-Butyl |
| 99 | H | H | CH₃ | H | C(O)—NH-tert-Butyl |
| 100 | H | H | CH₃ | H | C(O)—NH-tert-Butyl |
| 101 | H | H | CH₃ | H | C(O)—NH-tert-Butyl |
| 102 | H | H | CH₃ | H | C(O)—NH-tert-Butyl |
| 103 | H | CH₃ | H | H | C(O)—NH-tert-Butyl |
| 104 | H | H | CH₃ | H | C(O)—NH-tert-Butyl |
| 105 | H | H | CH₃ | H | C(O)—NH-tert-Butyl |
| 106 | H | H | CH₃ | H | C(O)—NH-tert-Butyl |
| 107 | H | H | CH₃ | H | C(O)—NH-tert-Butyl |
| 108 | H | H | CH₃ | H | C(O)—NH-tert-Butyl |
| 109 | H | H | CH₃ | H | C(O)—NH-tert-Butyl |
| 110 | H | H | CH₃ | H | C(O)—NH-tert-Butyl |
| 111 | H | H | CH₃ | H | C(O)—NH-tert-Butyl |
| 112 | H | H | CH₃ | H | C(O)—NH-tert-Butyl |
| 113 | H | H | CH₃ | H | C(O)—NH-tert-Butyl |

TABLE 1A-continued

| Compound No. | R¹ | R² | R³ | R⁴ | R⁵ |
|---|---|---|---|---|---|
| 114 | H | H | CH₃ | H | C(O)—NH-tert-Butyl |
| 115 | H | H | CH₃ | H | C(O)—NH-tert-Butyl |
| 116 | H | H | CH₃ | H | C(O)—NH-tert-Butyl |
| 117 | H | H | CH₃ | H | C(O)—NH-tert-Butyl |
| 118 | H | H | CH₃ | H | C(O)—NH-tert-Butyl |
| 119 | H | H | CH₃ | H | C(O)—NH-tert-Butyl |
| 120 | H | H | CH₃ | H | C(O)—NH-tert-Butyl |
| 121 | H | H | CH₃ | H | C(O)—NH-tert-Butyl |
| 122 | H | H | CH₃ | H | C(O)—NH-tert-Butyl |
| 123 | H | H | CH₃ | H | C(O)—NH-tert-Butyl |
| 124 | H | CH₃ | H | H | C(O)—NH-tert-Butyl |
| 125 | H | H | CH₃ | H | C(O)—NH-tert-Butyl |
| 126 | H | H | CH₃ | H | C(O)—NH-tert-Butyl |
| 127 | H | H | CH₃ | H | C(O)—NH-tert-Butyl |
| 128 | H | H | CH₃ | H | C(O)—NH-tert-Butyl |
| 129 | H | H | CH₃ | H | C(O)—NH-tert-Butyl |
| 130 | H | H | CH₃ | H | C(O)—NH-tert-Butyl |
| 131 | H | H | CH₃ | H | C(O)—NH-tert-Butyl |
| 132 | H | H | CH₃ | H | C(O)—NH-tert-Butyl |
| 133 | H | H | CH₃ | H | C(O)—NH-tert-Butyl |
| 134 | H | H | CH₃ | H | C(O)—NH-tert-Butyl |
| 135 | H | H | CH₃ | H | C(O)—NH-tert-Butyl |
| 136 | H | H | CH₃ | H | C(O)—NH-tert-Butyl |
| 137 | H | H | CH₃ | H | C(O)—NH-tert-Butyl |
| 138 | H | H | CH₃ | H | C(O)—NH-tert-Butyl |
| 139 | H | H | CH₃ | H | C(O)—NH-tert-Butyl |
| 140 | H | H | CH₃ | H | C(O)—NH-tert-Butyl |
| 141 | H | H | CH₃ | H | C(O)—NH-tert-Butyl |
| 142 | H | CH₃ | H | C(O)—NH-tert-Butyl | H |
| 143 | H | H | CH₃ | H | C(O)—NH-tert-Butyl |
| 144 | H | H | CH₃ | H | C(O)—NH-tert-Butyl |
| 145 | H | H | CH₃ | H | C(O)—NH-tert-Butyl |
| 146 | H | H | CH₃ | H | C(O)—NH-tert-Butyl |
| 147 | H | H | CH₃ | H | C(O)—NH-tert-Butyl |
| 148 | H | H | CH₃ | H | C(O)—NH-tert-Butyl |
| 149 | H | H | CH₃ | H | C(O)—NH-tert-Butyl |
| 150 | H | H | CH₃ | H | C(O)—NH-tert-Butyl |
| 151 | H | H | CH₃ | H | C(O)—NH-tert-Butyl |
| 152 | H | H | CH₃ | H | C(O)—NH-tert-Butyl |
| 153 | H | H | CH₃ | H | C(O)—NH-tert-Butyl |
| 154 | H | H | CH₃ | H | C(O)—NH-tert-Butyl |
| 155 | H | H | CH₃ | H | C(O)—NH-tert-Butyl |
| 156 | H | H | CH₃ | H | C(O)—NH-tert-Butyl |
| 157 | H | H | CH₃ | H | C(O)—NH-tert-Butyl |
| 158 | H | H | CH₃ | H | C(O)—NH-tert-Butyl |
| 159 | H | H | CH₃ | H | C(O)—NH-tert-Butyl |
| 160 | H | H | CH₃ | H | C(O)—NH-tert-Butyl |
| 161 | H | H | CH₃ | H | C(O)—NH-tert-Butyl |
| 162 | H | H | CH₃ | H | C(O)—NH-tert-Butyl |
| 163 | H | H | CH₃ | H | C(O)—NH-tert-Butyl |
| 164 | H | H | CH₃ | H | C(O)—NH-tert-Butyl |
| 165 | H | H | CH₃ | H | C(O)—NH-tert-Butyl |
| 166 | H | H | CH₃ | H | C(O)—NH-tert-Butyl |
| 167 | H | H | CH₃ | H | C(O)—NH-tert-Butyl |
| 168 | H | H | CH₃ | H | C(O)—NH-tert-Butyl |
| 169 | H | H | CH₃ | H | C(O)—NH-tert-Butyl |
| 170 | H | H | CH₃ | H | C(O)—NH-tert-Butyl |
| 171 | H | H | CH₃ | H | C(O)—NH-tert-Butyl |
| 172 | H | H | CH₃ | H | C(O)—NH-tert-Butyl |
| 173 | H | H | CH₃ | H | C(O)—NH-tert-Butyl |
| 174 | H | H | CH₃ | H | C(O)—NH-tert-Butyl |
| 175 | H | H | CH₃ | H | C(O)—NH-tert-Butyl |
| 176 | H | H | CH₃ | H | C(O)—NH-tert-Butyl |
| 177 | H | H | CH₃ | H | C(O)—NH-tert-Butyl |
| 178 | H | H | CH₃ | H | C(O)—NH-tert-Butyl |
| 179 | H | H | CH₃ | H | C(O)—NH-tert-Butyl |
| 180 | H | H | CH₃ | H | C(O)—NH-tert-Butyl |
| 181 | H | H | CH₃ | H | C(O)—NH-tert-Butyl |
| 182 | H | H | CH₃ | H | C(O)—NH-tert-Butyl |
| 183 | H | H | CH₃ | H | C(O)—NH-tert-Butyl |
| 184 | H | H | CH₃ | H | C(O)—NH-tert-Butyl |
| 185 | H | H | CH₃ | H | C(O)—NH-tert-Butyl |
| 186 | H | H | CH₃ | H | C(O)—NH-tert-Butyl |
| 187 | H | H | CH₃ | H | C(O)—NH-tert-Butyl |
| 188 | H | H | CH₃ | H | C(O)—NH-tert-Butyl |
| 189 | H | H | CH₃ | H | C(O)—NH-tert-Butyl |
| 190 | H | H | CH₃ | H | C(O)—NH-tert-Butyl |

TABLE 1A-continued

| Compound No. | R¹ | R² | R³ | R⁴ | R⁵ |
|---|---|---|---|---|---|
| 191 | H | H | CH₃ | H | C(O)—NH-tert-Butyl |
| 192 | H | H | CH₃ | H | C(O)—NH-tert-Butyl |
| 193 | H | H | CH₃ | H | C(O)—NH-tert-Butyl |
| 194 | H | H | CH₃ | H | C(O)—NH-tert-Butyl |
| 195 | H | H | CH₃ | H | C(O)—NH-tert-Butyl |
| 196 | H | H | CH₃ | H | C(O)—NH-tert-Butyl |
| 197 | H | H | CH₃ | H | C(O)—NH-tert-Butyl |
| 198 | H | H | CH₃ | H | C(O)—NH-tert-Butyl |
| 199 | H | H | CH₃ | H | C(O)—NH-tert-Butyl |
| 200 | H | H | CH₃ | H | C(O)—NH-tert-Butyl |
| 201 | H | H | CH₃ | H | C(O)—NH-tert-Butyl |
| 202 | H | H | CH₃ | H | C(O)—NH-tert-Butyl |
| 203 | H | H | CH₃ | H | C(O)—NH-tert-Butyl |
| 204 | H | H | CH₃ | H | C(O)—NH-tert-Butyl |
| 205 | H | H | CH₃ | H | C(O)—NH-tert-Butyl |
| 206 | H | H | CH₃ | H | C(O)—NH-tert-Butyl |
| 207 | H | H | CH₃ | H | C(O)—NH-tert-Butyl |
| 208 | H | H | CH₃ | H | C(O)—NH-tert-Butyl |
| 209 | H | H | CH₃ | H | C(O)—NH-tert-Butyl |
| 210 | H | H | CH₃ | H | C(O)—NH-tert-Butyl |
| 211 | H | H | CH₃ | H | C(O)—NH-tert-Butyl |
| 212 | H | H | CH₃ | H | C(O)—NH-tert-Butyl |
| 213 | H | H | CH₃ | H | C(O)—NH-tert-Butyl |
| 214 | H | H | CH₃ | H | C(O)—NH-tert-Butyl |
| 215 | H | H | CH₃ | H | C(O)—NH-tert-Butyl |
| 216 | H | H | CH₃ | H | C(O)—NH-tert-Butyl |
| 217 | H | H | CH₃ | H | C(O)—NH-tert-Butyl |
| 218 | H | H | CH₃ | H | C(O)—NH-tert-Butyl |
| 219 | H | H | CH₃ | H | C(O)—NH-tert-Butyl |
| 220 | H | H | CH₃ | H | C(O)—NH-tert-Butyl |
| 221 | H | H | CH₃ | H | C(O)—NH-tert-Butyl |
| 222 | H | H | CH₃ | H | C(O)—NH-tert-Butyl |
| 223 | H | H | CH₃ | H | C(O)—NH-tert-Butyl |
| 224 | H | H | CH₃ | H | C(O)—NH-tert-Butyl |
| 225 | H | H | CH₃ | H | C(O)—NH-tert-Butyl |
| 226 | H | H | CH₃ | H | C(O)—NH-tert-Butyl |
| 227 | H | H | CH₃ | H | C(O)—NH-tert-Butyl |
| 228 | H | H | CH₃ | H | C(O)—NH-tert-Butyl |
| 229 | H | H | CH₃ | H | C(O)—NH-tert-Butyl |
| 230 | H | H | CH₃ | H | C(O)—NH-tert-Butyl |
| 231 | H | H | CH₃ | H | C(O)—NH-tert-Buty) |
| 232 | H | H | CH₃ | H | C(O)—NH-tert-Butyl |
| 233 | H | H | CH₃ | H | C(O)—NH-tert-Butyl |
| 234 | H | H | CH₃ | H | C(O)—NH-tert-Butyl |
| 235 | H | H | CH₃ | H | C(O)—NH-tert-Butyl |
| 236 | H | H | CH₃ | H | C(O)—NH-tert-Butyl |
| 237 | H | H | CH₃ | H | C(O)—NH-tert-Butyl |
| 238 | H | H | CH₃ | H | C(O)—NH-tert-Butyl |
| 239 | H | H | CH₃ | H | C(O)—NH-tert-Butyl |
| 240 | H | H | CH₃ | H | C(O)—NH-tert-Butyl |
| 241 | H | H | CH₃ | H | C(O)—NH-tert-Butyl |
| 242 | H | H | CH₃ | H | C(O)—NH-tert-Butyl |
| 243 | H | H | CH₃ | H | C(O)—NH-tert-Butyl |
| 244 | H | H | CH₃ | H | C(O)—NH-tert-Butyl |
| 245 | H | H | CH₃ | H | C(O)—NH-tert-Butyl |
| 246 | H | H | CH₃ | H | C(O)—NH-tert-Butyl |
| 247 | H | H | CH₃ | H | C(O)—NH-tert-Butyl |
| 248 | H | H | CH₃ | H | C(O)—NH-tert-Butyl |
| 249 | H | H | CH₃ | H | C(O)—NH-tert-Butyl |
| 250 | H | H | CH₃ | H | C(O)—NH-tert-Butyl |
| 251 | H | H | CH₃ | H | C(O)—NH-tert-Butyl |
| 252 | H | H | CH₃ | H | C(O)—NH-tert-Butyl |
| 253 | H | H | CH₃ | H | C(O)—NH-tert-Butyl |
| 254 | H | H | CH₃ | H | C(O)—NH-tert-Butyl |
| 255 | H | H | CH₃ | H | C(O)—NH-tert-Butyl |
| 256 | H | H | CH₃ | H | C(O)—NH-tert-Butyl |
| 257 | H | H | CH₃ | H | C(O)—NH-tert-Butyl |
| 258 | H | H | CH₃ | H | C(O)—NH-tert-Butyl |
| 259 | H | H | CH₃ | H | C(O)—NH-tert-Butyl |
| 260 | H | H | CH₃ | H | C(O)—NH-tert-Butyl |
| 251 | H | H | CH₃ | H | C(O)—NH-tert-Butyl |
| 262 | H | H | CH₃ | H | C(O)—NH-tert-Butyl |
| 263 | H | H | CH₃ | H | C(O)—NH-tert-Butyl |
| 264 | H | H | CH₃ | H | C(O)—NH-tert-Butyl |
| 265 | H | H | CH₃ | H | C(O)—NH-tert-Butyl |
| 266 | H | H | CH₃ | H | C(O)—NH-tert-Butyl |
| 267 | H | H | CH₃ | H | C(O)—NH-tert-Butyl |

TABLE 1A-continued

| Compound No. | R¹ | R² | R³ | R⁴ | R⁵ |
|---|---|---|---|---|---|
| 268 | H | H | CH₃ | H | C(O)—NH-tert-Butyl |
| 269 | H | H | CH₃ | H | C(O)—NH-tert-Butyl |
| 270 | H | H | CH₃ | H | C(O)—NH-tert-Butyl |
| 271 | H | H | CH₃ | H | C(O)—NH-tert-Butyl |
| 272 | H | H | CH₃ | H | C(O)—NH-tert-Butyl |
| 273 | H | H | CH₃ | H | C(O)—NH-tert-Butyl |
| 274 | H | H | CH₃ | H | C(O)—NH-tert-Butyl |
| 275 | H | H | CH₃ | H | C(O)—NH-tert-Butyl |
| 275 | H | H | CH₃ | H | C(O)—NH-tert-Butyl |
| 277 | H | H | CH₃ | H | C(O)—NH-tert-Butyl |
| 278 | H | H | CH₃ | H | C(O)—NH-tert-Butyl |
| 279 | H | H | CH₃ | H | C(O)—NH-tert-Butyl |
| 280 | H | H | CH₃ | H | C(O)—NH-tert-Butyl |
| 281 | H | H | CH₃ | H | C(O)—NH-tert-Butyl |
| 282 | H | H | CH₃ | H | C(O)—NH-tert-Butyl |
| 283 | H | H | CH₃ | H | C(O)—NH-tert-Butyl |
| 284 | H | H | CH₃ | H | C(O)—NH-tert-Butyl |
| 285 | H | H | CH₃ | H | C(O)—NH-tert-Butyl |
| 286 | H | H | CH₃ | H | C(O)—NH-tert-Butyl |
| 287 | H | H | CH₃ | H | C(O)—NH-tert-Butyl |
| 288 | H | H | CH₃ | H | C(O)—NH-tert-Butyl |
| 289 | H | H | CH₃ | H | C(O)—NH-tert-Butyl |
| 290 | H | H | CH₃ | H | C(O)—NH-tert-Butyl |
| 291 | H | H | CH₃ | H | C(O)—NH-tert-Butyl |
| 292 | H | H | CH₃ | H | C(O)—NH-tert-Butyl |
| 293 | H | H | CH₃ | H | C(O)—NH-tert-Butyl |
| 294 | H | H | CH₃ | H | C(O)—NH-tert-Butyl |
| 295 | PRO-FI | PRO-H | H | H | C(O)—NH-tert-Butyl |
| 296 | H | H | CH₃ | H | C(O)—NH-tert-Butyl |
| 297 | H | H | CH₃ | H | C(O)—NH-tert-Butyl |
| 298 | H | H | CH₃ | H | C(O)—NH-tert-Butyl |
| 299 | H | H | CH₃ | H | C(O)—NH-tert-Butyl |
| 300 | H | H | CH₃ | H | C(O)—NH-tert-Butyl |
| 301 | H | H | CH₃ | H | C(O)—NH-tert-Butyl |
| 302 | H | H | CH₃ | H | C(O)—NH-tert-Butyl |
| 303 | H | H | CH₃ | H | C(O)—NH-tert-Butyl |
| 304 | H | H | CH₃ | H | C(O)—NH-tert-Butyl |
| 305 | H | H | CH₃ | H | C(O)—NH-tert-Butyl |
| 306 | H | H | CH₃ | H | C(O)—NH-tert-Butyl |
| 307 | H | H | CH₃ | H | C(O)—NH-tert-Butyl |
| 308 | H | H | CH₃ | H | C(O)—NH-tert-Butyl |
| 309 | H | H | CH₃ | H | C(O)—NH-tert-Butyl |
| 310 | H | H | CH₃ | H | C(O)—NH-tert-Butyl |
| 311 | H | H | CH₃ | H | C(O)—NH-tert-Butyl |
| 312 | H | H | CH₃ | H | C(O)—NH-tert-Butyl |
| 313 | H | H | CH₃ | H | C(O)—NH-tert-Butyl |
| 314 | H | H | CH₃ | H | C(O)—NH-tert-Butyl |
| 315 | H | H | CH₃ | H | C(O)—NH-tert-Butyl |
| 316 | H | H | CH₃ | H | C(O)—NH-tert-Butyl |
| 317 | H | H | CH₃ | H | C(O)—NH-tert-Butyl |
| 318 | H | H | CH₃ | H | C(O)—NH-tert-Butyl |
| 319 | H | H | CH₃ | H | C(O)—NH-tert-Butyl |
| 320 | H | H | CH₃ | H | C(O)—NH-tert-Butyl |
| 321 | H | H | CH₃ | H | C(O)—NH-tert-Butyl |
| 322 | H | H | CH₃ | H | C(O)—NH-tert-Butyl |
| 323 | H | H | CH₃ | H | C(O)—NH-tert-Butyl |
| 324 | H | H | CH₃ | H | C(O)—NH-tert-Butyl |
| 325 | H | H | CH₃ | H | C(O)—NH-tert-Butyl |
| 326 | H | H | CH₃ | H | C(O)—NH-tert-Butyl |
| 327 | H | H | CH₃ | H | C(O)—NH-tert-Butyl |
| 328 | H | H | CH₃ | H | C(O)—NH-tert-Butyl |
| 329 | H | H | CH₃ | H | C(O)—NH-tert-Butyl |
| 330 | H | H | CH₃ | H | C(O)—NH-tert-Butyl |
| 331 | H | H | CH₃ | H | C(O)—NH-tert-Butyl |
| 332 | H | H | CH₃ | H | C(O)—NH-tert-Butyl |
| 333 | H | H | CH₃ | H | C(O)—NH-tert-Butyl |
| 334 | H | H | CH₃ | H | C(O)—NH-tert-Butyl |
| 335 | H | H | CH₃ | H | C(O)—NH-tert-Butyl |
| 335 | H | H | CH₃ | H | C(O)—NH-tert-Butyl |
| 337 | H | H | CH₃ | H | C(O)—NH-tert-Butyl |
| 338 | H | H | CH₃ | H | C(O)—NH-tert-Butyl |
| 339 | H | H | CH₃ | H | C(O)—NH-tert-Butyl |
| 340 | H | H | CH₃ | H | C(O)—NH-tert-Butyl |
| 341 | H | H | CH₃ | H | C(O)—NH-tert-Butyl |
| 342 | H | H | CH₃ | H | C(O)—NH-tert-Butyl |
| 343 | H | H | CH₃ | H | C(O)—NH-tert-Butyl |
| 344 | H | CH₃ | H | C(O)—NH-tert-Butyl | H |

TABLE 1A-continued

| Compound No. | R¹ | R² | R³ | R⁴ | R⁵ |
|---|---|---|---|---|---|
| 345 | H | H | $CH_3$ | H | C(O)—NH-tert-Butyl |
| 346 | H | H | $CH_3$ | H | C(O)—NH-tert-Butyl |
| 347 | H | H | $CH_3$ | H | C(O)—NH-tert-Butyl |
| 348 | H | H | $CH_3$ | H | C(O)—NH-tert-Butyl |
| 349 | H | H | $CH_3$ | H | C(O)—NH-tert-Butyl |
| 350 | H | H | $CH_3$ | H | C(O)—NH-tert-Butyl |
| 351 | H | H | $CH_3$ | C(O)—NH-tert-Butyl | H |
| 352 | H | H | $CH_3$ | H | C(O)—NH-tert-Butyl |
| 353 | H | H | $CH_3$ | H | C(O)—NH-tert-Butyl |
| 354 | H | H | $CH_3$ | H | C(O)—NH-tert-Butyl |
| 355 | H | H | $CH_3$ | H | C(O)—NH-tert-Butyl |
| 356 | H | H | $CH_3$ | H | C(O)—NH-tert-Butyl |
| 357 | H | H | $CH_3$ | H | C(O)—NH-tert-Butyl |
| 358 | H | H | $CH_3$ | H | C(O)—NH-tert-Butyl |
| 359 | H | H | $CH_3$ | H | C(O)—NH-tert-Butyl |
| 360 | H | H | $CH_3$ | H | C(O)—NH-tert-Butyl |
| 361 | H | H | $CH_3$ | H | C(O)—NH-tert-Butyl |
| 362 | H | H | $CH_3$ | H | C(O)—NH-tert-Butyl |
| 363 | H | H | $CH_3$ | H | C(O)—NH-tert-Butyl |
| 364 | H | H | $CH_3$ | H | C(O)—NH-tert-Butyl |
| 365 | H | H | $CH_3$ | H | C(O)—NH-tert-Butyl |
| 366 | H | H | $CH_3$ | H | C(O)—NH-tert-Butyl |
| 367 | H | H | $CH_3$ | H | C(O)—NH-tert-Butyl |
| 368 | H | H | $CH_3$ | H | C(O)—NH-tert-Butyl |
| 369 | H | H | $CH_3$ | H | C(O)—NH-tert-Butyl |
| 370 | H | H | $CH_3$ | H | C(O)—NH-tert-Butyl |
| 371 | H | H | $CH_3$ | H | C(O)—NH-tert-Butyl |
| 372 | H | H | $CH_3$ | H | C(O)—NH-tert-Butyl |
| 373 | H | H | $CH_3$ | H | C(O)—NH-tert-Butyl |
| 374 | H | H | $CH_3$ | H | C(O)—NH-tert-Butyl |
| 375 | H | H | $CH_3$ | H | C(O)—NH-tert-Butyl |
| 376 | H | H | $CH_3$ | H | C(O)—NH-tert-Butyl |
| 377 | H | H | $CH_3$ | H | C(O)—NH-tert-Butyl |
| 378 | H | H | $CH_3$ | H | C(O)—NH-tert-Butyl |
| 379 | H | H | $CH_3$ | H | C(O)—NH-tert-Butyl |
| 380 | H | H | $CH_3$ | H | C(O)—NH-tert-Butyl |
| 381 | H | H | $CH_3$ | H | C(O)—NH-tert-Butyl |
| 382 | H | H | $CH_3$ | H | C(O)—NH-tert-Butyl |
| 383 | H | H | $CH_3$ | H | C(O)—NH-tert-Butyl |
| 384 | H | H | $CH_3$ | H | C(O)—NH-tert-Butyl |
| 385 | H | H | $CH_3$ | H | C(O)—NH-tert-Butyl |
| 386 | H | H | $CH_3$ | H | C(O)—NH-tert-Butyl |
| 387 | H | H | $CH_3$ | H | C(O)—NH-tert-Butyl |
| 388 | H | H | $CH_3$ | H | C(O)—NH-tert-Butyl |
| 389 | H | H | $CH_3$ | H | C(O)—NH-tert-Butyl |
| 390 | H | H | $CH_3$ | H | C(O)—NH-tert-Butyl |
| 391 | H | H | $CH_3$ | H | C(O)—NH-tert-Butyl |
| 392 | H | H | $CH_3$ | H | C(O)—NH-tert-Butyl |
| 393 | H | H | $CH_3$ | H | C(O)—NH-tert-Butyl |
| 394 | H | H | $CH_3$ | H | C(O)—NH-tert-Butyl |
| 395 | H | H | $CH_3$ | H | C(O)—NH-tert-Butyl |
| 395 | H | H | $CH_3$ | H | C(O)—NH-tert-Butyl |
| 397 | H | H | $CH_3$ | H | C(O)—NH-tert-Butyl |

TABLE 1B

| Compound No. | Seq. ID. No. | R⁵ | R⁷ | R⁸ | $X^Y$ | $X^Z$ | $X^1$ | $X^2$ | $X^3$ |
|---|---|---|---|---|---|---|---|---|---|
| 1 | 1 | PRO | PRO | H | Y | | L | D | V |
| 2 | 2 | PRO | PRO | H | H | | L | D | V |
| 3 | 3 | PRO | PRO | H | Y | | L | D | T |
| 4 | 3 | PRO | PRO | H | Y | | L | D | T |
| 5 | 4 | PRO | PRO | H | F | | L | D | T |
| 6 | 5 | PRO | PRO | H | HomoPhe | | L | D | T |
| 7 | 6 | PRO | PRO | H | Cha | | L | D | T |
| 8 | 7 | PRO | PRO | H | W | | L | D | I |
| 9 | 8 | PRO | PRO | H | 1Nal | | L | D | T |
| 10 | 9 | PRO | PRO | H | 2Nal | | L | D | T |
| 11 | 10 | PRO | PRO | H | W | | L | D | Thr(OBn) |
| 12 | 11 | PRO | PRO | H | Bip | | L | D | T |
| 13 | 12 | PRO | PRO | H | Tyr(OPh) | | L | D | T |
| 14 | 13 | PRO | PRO | H | 1Nal | | L | D | I |
| 15 | 14 | PRO | PRO | H | 2Nal | | L | D | I |

TABLE 1B-continued

| Compound No. | Seq. ID. No. | R5 | R7 | R8 | X^Y | X^z | X^1 | X^2 | X^3 |
|---|---|---|---|---|---|---|---|---|---|
| 16 | 15 | PRO | PRO | H | 2Nal | | L | D | Thr(OBn) |
| 17 | 16 | [(4S)-fluoro-Pro] | [(4S)-fluoro-Pro] | H | W | | L | D | T |
| 18 | 17 | PRO | PRO | H | Bip | | L | D | Thr(OBn) |
| 19 | 18 | PRO | PRO | H | Tyr(2-tolyl diaryl ether) | | L | D | T |
| 20 | 19 | PRO | PRO | H | Tyr(4-CF3 diaryl ether) | | L | D | T |
| 21 | 20 | PRO | PRO | H | Tyr(4-methoxy diaryl ether) | | L | D | T |
| 22 | 21 | PRO | PRO | H | Tyr(4-fluoro diaryl ether) | | L | D | T |
| 23 | 22 | PRO | PRO | H | Tyr(2-methoxy diaryl ether) | | L | D | T |
| 24 | 23 | PRO | PRO | H | Tyr(3-methoxy diaryl ether) | | L | D | T |
| 25 | 24 | PRO | PRO | H | Tyr(3-fluoro diaryl ether) | | L | D | T |
| 26 | 25 | PRO | PRO | H | Tyr(3,4-difluoro diaryl ether) | | L | D | T |
| 27 | 26 | PRO | PRO | H | Tyr(3-methyl diaryl ether) | | L | D | T |
| 28 | 27 | PRO | PRO | H | Tyr(3,4-dimethyl diaryl ether) | | L | D | T |
| 29 | 28 | PRO | PRO | H | Tyr(4-CO2Me diaryl ether) | | L | D | T |
| 30 | 29 | PRO | PRO | H | Tyr(3-CO2Me diaryl ether) | | L | D | T |
| 31 | 30 | PRO | PRO | H | Tyr(4-CO2H diaryl ether) | | L | D | T |
| 32 | 31 | HYP | HYP | H | F | | L | D | T |
| 33 | 32 | PRO | PRO | H | metaY(Opr) | | L | D | T |
| 34 | 33 | PRO | PRO | H | Orn(benzamide) | | L | D | Thr(OBn) |
| 35 | 34 | PRO | PRO | H | Orn(acetamide) | | L | D | Thr(OBn) |
| 36 | 35 | PRO | PRO | H | Orn(methanesulfonamide) | | L | D | Thr(OBn) |
| 37 | 36 | PRO | PRO | H | Orn(ethylcarbamate) | | L | D | Thr(OBn) |
| 38 | 37 | PRO | PRO | H | Orn(pentyl amide) | | I. | D | Thr(OBn) |
| 39 | 38 | PRO | PRO | H | R | | L | D | T |
| 40 | 39 | PRO | PRO | H | F | | L | D | Thr(OMe) |
| 41 | 40 | PRO | PRO | H | F | | L | D | Thr(OEt) |
| 42 | 41 | PRO | PRO | H | dTyr | | L | D | T |
| 43 | 42 | PRO | PRO | H | dTic | | L | D | T |
| 44 | 43 | HYP | HYP | H | [3-(3'-pyridyl)-Ala] | | L | D | T |
| 45 | 44 | [(4R)-fluoro-Pro] | [(4R)-fluoro-Pro] | H | F | | L | D | T |
| 46 | 45 | [(4R)-fluoro-Pro] | [(4R)-fluoro-Pro] | H | Bip | | L | D | T |
| 47 | 46 | [(4R)-fluoro-Pro] | [(4R)-fluoro-Pro] | H | [3-(3'-pyridyl)-Ala] | | L | D | T |
| 48 | 47 | [(4R)-fluoro-Pro] | [(4R)-fluoro-Pro] | H | Y | | L | D | T |
| 49 | 48 | [(4S)-fluoro-Pro] | [(4S)-fluoro-Pro] | H | Y | | L | D | T |
| 50 | 49 | PRO | PRO | H | dArg | | L | D | T |
| 51 | 50 | PRO | PRO | H | dPip | | L | D | T |
| 52 | 51 | PRO | PRO | H | [3-(4-thiazolyl)-Ala] | | L | D | T |
| 53 | 52 | PRO | PRO | H | Y | | L | D | I |
| 54 | 53 | PRO | PRO | H | (4-aza-Phe) | | L | D | T |
| 55 | 54 | PRO | PRO | H | Y | | L | D | Pen |
| 56 | 55 | PRO | PRO | H | (vinyl-Br-Leu) | | L | D | T |
| 57 | 56 | PRO | PRO | H | Hyp(OBn) | | L | D | T |
| 58 | 56 | PRO | PRO | H | Hyp(OBn) | | L | D | T |
| 59 | 57 | PRO | PRO | H | Dap(Cbz) | | L | D | T |
| 60 | 58 | PRO | PRO | H | His(Bn) | | L | D | T |
| 61 | 59 | PRO | PRO | H | (4-amino-Phe) | | L | D | T |
| 62 | 60 | PRO | PRO | H | (4-aza-dPhe) | | L | D | T |
| 63 | 61 | PRO | PRO | H | Hyp | | L | D | T |
| 64 | 62 | PRO | PRO | H | dTrp | | L | D | T |
| 65 | 63 | PRO | PRO | H | M | | L | D | T |
| 66 | 64 | PRO | PRO | H | dMet | | L | D | T |
| 67 | 65 | PRO | PRO | H | (4-guanidino-Phe) | | L | D | T |
| 68 | 66 | PRO | PRO | H | (3-aza-Phe) | | L | D | T |
| 69 | 42 | PRO | PRO | H | dTic | | L | D | T |
| 70 | 67 | PRO | PRO | H | (3-aza-dPhe) | | L | D | T |
| 71 | 68 | PRO | PRO | H | Nva | | L | D | T |
| 72 | 69 | PRO | PRO | H | dNle | | L | D | T |
| 73 | 70 | PRO | PRO | H | dLys | | L | D | T |
| 74 | 71 | PRO | PRO | H | dPro | | L | D | T |
| 75 | 72 | PRO | PRO | H | dOrn | | L | D | T |
| 76 | 73 | PRO | PRO | H | (3-benzothienyl-Ala) | | L | D | T |
| 77 | 74 | PRO | PRO | H | dTyr(OAllyl) | | L | D | T |
| 78 | 75 | PRO | PRO | H | dSer(OBn) | | L | D | T |
| 79 | 76 | PRO | PRO | H | [3-(4-thiazolyl)-dAla] | | L | D | T |
| 80 | 77 | PRO | PRO | H | (3-benzothienyl-dAla) | | L | D | T |
| 81 | 78 | PRO | PRO | H | [3-(2-thienyl)-dAla] | | L | D | T |
| 82 | 79 | PRO | PRO | H | (4-aminomethyl-Phe) | | L | D | T |
| 83 | 80 | PRO | PRO | H | dOrn(dimethyl) | | L | D | T |
| 84 | 81 | PRO | PRO | H | (4-arnino-dPhe) | | L | D | T |
| 85 | 82 | PRO | PRO | H | (4-aminomethyl-dPhe) | | L | D | T |
| 86 | 83 | PRO | PRO | H | dTyr(OBn) | | L | D | T |

TABLE 1B-continued

| Compound No. | Seq. ID. No. | R5 | R7 | R8 | XY | XZ | X1 | X2 | X3 |
|---|---|---|---|---|---|---|---|---|---|
| 87 | 84 | PRO | PRO | H | P | | L | D | T |
| 88 | 85 | PRO | PRO | H | cycloLeu | | L | D | T |
| 89 | 86 | PRO | PRO | H | Aic | | L | D | T |
| 90 | 87 | PRO | PRO | H | Tyr(OAllyl) | | L | D | T |
| 91 | 88 | PRO | PRO | H | Chg | | L | D | T |
| 92 | 89 | PRO | PRO | H | K | | L | D | T |
| 93 | 90 | PRO | PRO | H | (2-aza-dPhe) | | L | D | T |
| 94 | 91 | PRO | PRO | H | (2-aza-Phe) | | L | D | T |
| 95 | 92 | PRO | PRO | H | [2-(2-pyridyl)-4-thiazolyl-Ala] | | L | D | T |
| 96 | 93 | PRO | PRO | H | [2-(3-pyridyl)-4-thiazolyl-Ala] | | L | D | T |
| 97 | 94 | PRO | PRO | H | [2-(4-pyridyl)-4-thiazolyl-Ala] | | L | D | T |
| 98 | 95 | PRO | PRO | H | dTiq | | L | D | T |
| 99 | 96 | PRO | PRO | H | [1-(5)-isoindoline-carboxylic acid] | | L | D | T |
| 100 | 97 | PRO | PRO | H | Y | dThr | L | D | T |
| 101 | 98 | PRO | PRO | H | Y | P | L | D | T |
| 102 | 99 | PRO | PRO | H | Y | dPro | L | D | T |
| 103 | 100 | PRO | PRO | H | Y | Sar | L | D | T |
| 104 | 101 | PRO | PRO | H | Y | cycloLeu | L | D | T |
| 105 | 100 | PRO | PRO | H | Y | Sar | L | D | T |
| 106 | 102 | PRO | PRO | H | (3-iodo-Phe) | Sar | L | D | T |
| 107 | 103 | PRO | PRO | H | (4-iodo-Phe) | Sar | L | D | T |
| 108 | 104 | PRO | PRO | H | (3,3-diphenyl-Ala) | Sar | L | D | T |
| 109 | 105 | PRO | PRO | H | F | dLys | L | D | T |
| 110 | 106 | PRO | PRO | H | Bip | dLys | L | D | T |
| 111 | 107 | PRO | PRO | H | [3-(4-thiazolyl)-Ala] | dLys | L | D | T |
| 112 | 108 | PRO | PRO | H | (3,3-diphenyl-Ala) | dLys | L | D | T |
| 113 | 109 | PRO | PRO | H | Y | dLys | L | D | I |
| 114 | 110 | PRO | PRO | H | Y | dArg | L | D | T |
| 115 | 111 | PRO | PRO | H | 1' | dSer | L | D | T |
| 116 | 112. | PRO | PRO | H | Bip | Sar | L | D | T |
| 117 | 113 | PRO | PRO | H | 1Nal | Sar | L | D | T |
| 118 | 114 | PRO | PRO | H | Y | Pip | L | D | T |
| 119 | 115 | PRO | PRO | H | (2-iodo-Phe) | Sar | L | D | T |
| 120 | 116 | PRO | PRO | H | 1Nal | dLys | L | D | T |
| 121 | 117 | PRO | PRO | H | Y | dLys | L | D | MeThr |
| 122 | 118 | PRO | PRO | H | F | Sar | L | D | T |
| 123 | 119 | PRO | PRO | H | Y | dTic | L | D | T |
| 124 | 99 | PRO | PRO | H | Y | dPro | L | D | T |
| 125 | 120 | PRO | PRO | H | Y | dPip | L | D | T |
| 126 | 121 | PRO | PRO | H | F | dPro | L | D | T |
| 127 | 122 | PRO | PRO | H | (3,4-dimethoxy-Phe) | dPro | L | D | T |
| 128 | 123 | PRO | PRO | H | (3,4,5-trifluoro-Phe) | dPro | L | D | T |
| 129 | 124 | PRO | PRO | H | (3,5-dibromo-Tyr) | dPro | L | D | T |
| 130 | 125 | PRO | PRO | H | F | dPip | L | D | T |
| 131 | 126 | PRO | PRO | H | [3-(4-thiazolyl)-Ala] | dPip | L | D | T |
| 132 | 127 | PRO | PRO | H | (4-aminomethyl-Phe) | dPip | L | D | T |
| 133 | 128 | PRO | PRO | H | [2-iodo-Phe] | dPip | L | D | T |
| 134 | 129 | PRO | PRO | H | (2-phenyl-Phe) | dPip | L | D | T |
| 135 | 130 | PRO | PRO | H | [2-(2-methoxy-phenyl)-Phe] | dPip | L | D | T |
| 136 | 131 | PRO | PRO | H | [2-(3-methoxy-phenyl)-Phe] | dPip | L | D | T |
| 137 | 132 | PRO | PRO | H | [2-(4-methoxy-phenyl)-Phe] | dPip | L | D | T |
| 138 | 133 | PRO | PRO | H | Bip | dPip | L | D | T |
| 139 | 134 | PRO | PRO | H | Y | Hyp | L | D | T |
| 140 | 135 | PRO | PRO | H | Y | dHyp | L | D | T |
| 141 | 136 | PRO | PRO | H | Y | (cis-dHyp) | L | D | T |
| 142 | 137 | dPRO | H | dPRO | dTyr | dPip | L | D | T |
| 143 | 138 | PRO | PRO | H | 1Nal | dPip | L | D | T |
| 144 | 139 | PRO | PRO | H | 2Nal | dPip | L | D | T |
| 145 | 140 | PRO | PRO | H | (4-aminomethyl-Phe) | dTic | L | D | T |
| 146 | 141 | PRO | PRO | H | (3-aminomethyl-Phe) | dTic | L | D | T |
| 147 | 142 | PRO | PRO | H | (3-aminomethyl-dPhe) | dTic | L | D | T |
| 148 | 143 | PRO | PRO | H | MeTyr | dPip | L | D | 1 |
| 149 | 144 | PRO | PRO | H | Y | dPip | L | D | alloThr |
| 150 | 145 | PRO | PRO | H | Y | dPip | tertbutylAla | D | T |
| 151 | 146 | PRO | PRO | H | [3-(4-thiazolyl)-Ala] | dHyp | L | D | T |
| 152 | 147 | PRO | PRO | H | (4-a rninomethyl-Phe) | dHyp | L | D | T |
| 153 | 148 | PRO | PRO | H | Y | dPip | L | D | I |
| 154 | 149 | PRO | PRO | H | Y | dMeLys | L | D | I |
| 155 | 150 | PRO | PRO | H | Y | dNle | L | D | T |
| 156 | 151 | PRO | PRO | H | F | dHyp | L | D | T |
| 157 | 152 | PRO | PRO | H | Y | dMeArg | L | D | T |
| 158 | 153 | PRO | PRO | H | Y | G | L | D | T |
| 159 | 154 | PRO | PRO | H | Y | A | L | D | T |
| 160 | 155 | PRO | PRO | H | Y | dAla | L | D | T |
| 161 | 156 | PRO | PRO | H | M | G | L | D | T |
| 162 | 157 | PRO | PRO | H | Tyr(OAllyl) | Sar | L | D | T |

TABLE 1B-continued

| Compound No. | Seq. ID. No. | R⁵ | R⁷ | R⁸ | X^Y | X^Z | X¹ | X² | X³ |
|---|---|---|---|---|---|---|---|---|---|
| 163 | 158 | PRO | PRO | H | Tyr(OAllyl) | G | L | D | T |
| 164 | 159 | PRO | PRO | H | [3-(4-thiazol)-Aa] | Sar | L | D | T |
| 165 | 160 | PRO | PRO | H | (4-aminomethyl-Phe) | G | L | D | T |
| 166 | 161 | PRO | PRO | H | Tyr(OAllyl) | dVal | L | D | T |
| 167 | 162 | PRO | PRO | H | Tyr(OAllyl) | cSer | L | D | T |
| 168 | 163 | PRO | PRO | H | Tyr(OAllyl) | dAla | L | D | T |
| 169 | 164 | PRO | PRO | H | Tyr(OAllyl) | P | L | D | T |
| 170 | 165 | PRO | PRO | H | Tyr(OAllyl) | dPro | L | D | T |
| 171 | 166 | PRO | PRO | H | [3-(4-thiazolyl)-Ala] | dVal | L | D | T |
| 172 | 167 | PRO | PRO | H | [3-(4-thiazolyl)-Ala] | dSer | L | D | T |
| 173 | 168 | PRO | PRO | H | [3-(4-thiazolyl)-Ala] | dAla | L | D | T |
| 174 | 169 | PRO | PRO | H | [3-(4-thiazolyl)-Ala] | P | L | D | T |
| 175 | 170 | PRO | PRO | H | [3-(4-thiazolyl)-Ala] | dPro | L | D | T |
| 176 | 171 | PRO | PRO | H | (4-aminornethyl-Phe) | P | L | D | T |
| 177 | 172 | PRO | PRO | H | (4-aminomethyl-Phe) | dPro | L | D | T |
| 178 | 173 | PRO | PRO | H | cycloLeu | P | L | D | T |
| 179 | 174 | PRO | PRO | H | [2-(2-pyridyl)-4-thiazolyl-Ala] | Sar | L | D | T |
| 180 | 175 | PRO | PRO | H | [2-(2-pyridyl)-4-thiazolyl-Ala] | dPro | L | D | T |
| 181 | 176 | PRO | PRO | H | [2-(3-pyridyl)-4-thiazolyl-Ala] | Sar | L | D | T |
| 182 | 177 | PRO | PRO | H | [2-(3-pyridyl)-4-thiazolyl-Ala] | dPro | L | D | T |
| 183 | 178 | PRO | PRO | H | [2-(4-pyridyl)-4-thiazolyl-Ala] | dPro | L | D | T |
| 184 | 179 | PRO | PRO | H | [3-(2-aminobenzyl-4-thiazolyl)-Ala] | Sar | L | D | T |
| 185 | 180 | PRO | PRO | H | [2-(amino-benzyl)-4-thiazolyl-Ala] | dPro | L | D | T |
| 186 | 181 | PRO | PRO | H | dTyr | dPip | L | D | I |
| 187 | 182 | PRO | PRO | H | (2-aminomethyl-Phe) | Aze | L | D | T |
| 188 | 183 | PRO | PRO | H | Y | dPip | L | D | Abu |
| 189 | 184 | PRO | PRO | H | (3-aminomethyl-Phe) | dTic | L | D | Abu |
| 190 | 185 | PRO | PRO | H | (2,4-dichloro-Phe) | dPip | L | D | T |
| 191 | 186 | PRO | PRO | H | (3-phenyl-dPhe) | dPip | L | D | T |
| 192 | 187 | PRO | PRO | H | (3-(5-quinolinyl)-dPhe) | dPip | L | D | T |
| 193 | 188 | PRO | PRO | H | Y | betaHomoLys | L | D | T |
| 194 | 189 | PRO | PRO | H | Y | betaHomoPro | L | D | T |
| 195 | 190 | PRO | PRO | H | Y | betaHomoLys | L | D | T |
| 196 | 191 | PRO | PRO | H | Y | 2Abz | L | D | T |
| 197 | 192 | PRO | PRO | H | F | betaHomoLys | L | D | T |
| 198 | 193 | PRO | PRO | H | [3-(4-thiazolyl)-Ala] | betaHomoLys | L | D | T |
| 199 | 194 | PRO | PRO | H | (4-aminomethyl-Phe) | betaHomoLys | L | D | T |
| 200 | 195 | PRO | PRO | H | Y | betaHomoLys | L | D | Thr(OBn) |
| 201 | 196 | PRO | PRO | H | MeTyr | dbetaHomoLys | L | D | T |
| 202 | 197 | PRO | PRO | H | 1Nal | betaHomoLys | L | D | T |
| 203 | 198 | PRO | PRO | H | 2Nal | betaHomoLys | L | D | T |
| 204 | 199 | PRO | PRO | H | Bip | betaHomoLys | L | D | T |
| 205 | 200 | PRO | PRO | H | (2-iodo-Phe) | betaHomoLys | L | D | T |
| 206 | 201 | PRO | PRO | H | [2-(2,5-dimethyl-isoxazole)-Phe] | betaHomoLys | L | D | T |
| 707 | 202 | PRO | PRO | H | (2-phenyl-Phe) | betaHomoLys | L | D | T |
| 208 | 202 | PRO | PRO | H | (2-phenyl-Phe) | betaHomoLys | L | D | T |
| 209 | 203 | PRO | PRO | H | [(2-piperazinyl-2-Phenyl)-Phe] | betaHomoLys | L | D | T |
| 210 | 204 | PRO | PRO | H | Cha | betaHomoLys | L | D | T |
| 211 | 205 | PRO | PRO | H | W | betaHomoLys | L | D | T |
| 212 | 206 | PRO | PRO | H | dTrp | betaHomoLys | L | D | T |
| 213 | 207 | PRO | PRO | H | (3-aminomethyl-Phe) | betaHomoLys | L | D | T |
| 214 | 208 | PRO | PRO | H | (4-aminomethyl-dPhe) | betaHomoLys | L | D | T |
| 215 | 209 | PRO | PRO | H | (4-aminomethyl-Phe) | betaHomoLys | L | D | I |
| 216 | 210 | PRO | PRO | H | Y | dbetaHomoLys | L | D | I |
| 217 | 211 | PRO | PRO | H | dArg | betaHomoLys | L | D | T |
| 218 | 212 | PRO | PRO | H | (4-aminomethyl-Phe)-reduced | betaHomoLys | L | D | T |
| 219 | 213 | PRO | PRO | H | [3-(4-thiazolyI)-Ala] | dbetaHomoLys | L | D | I |
| 220 | 214 | PRO | PRO | H | F | dbetaHomoLys | L | D | I |
| 221 | 215 | PRO | PRO | H | [3-(4-thiazolyl)-Ala] | MebetaHomoLys | L | D | T |
| 222 | 216 | PRO | PRO | H | (4-aminomethyl-Phe) | MebetaHomoLys | L | D | T |
| 223 | 217 | PRO | PRO | H | [3-(4-thiazolyl)-Ala] | betaHomoLys | L | D | I |
| 224 | 218 | PRO | PRO | H | Tic | betaHomoLys | L | D | T |
| 225 | 219 | PRO | PRO | H | dTic | betaHomoLys | L | D | T |
| 226 | 220 | PRO | PRO | H | dTic | dbetaHomoLys | L | D | T |
| 227 | 221 | PRO | PRO | H | y | betaHomoIle | L | D | T |
| 228 | 222 | PRO | PRO | H | (4-aminomethyl-Phe) | betaHomoPro | L | D | T |
| 229 | 223 | PRO | PRO | H | Y | dbetaHomoPro | L | D | T |
| 230 | 224 | PRO | PRO | H | (4-aminomethyl-Phe) | dbetaHomoPro | L | D | T |
| 231 | 225 | PRO | PRO | H | R | betaHomoLys | L | D | T |
| 232 | 226 | PRO | PRO | H | F | MebetaHomoLys | L | D | T |
| 233 | 227 | PRO | PRO | H | Phe-reduced | betaHomoLys | L | D | T |
| 234 | 228 | PRO | PRO | H | (3-aminomethyl-dPhe) | betaHomoLys | L | D | T |
| 235 | 229 | PRO | PRO | H | -[3-3-(1-piperazinyl)phenyl]-Phe)-betaHomoI | betaHomoLys | L | D | T |
| 236 | 230 | PRO | PRO | H | [3-(4-thiazoyl)-dAla] | betaHomoLys | L | D | T |

TABLE 1B-continued

| Compound No. | Seq. ID. No. | R⁵ | R⁷ | R⁸ | X^Y | X^z | X¹ | X² | X³ |
|---|---|---|---|---|---|---|---|---|---|
| 237 | 231 | PRO | PRO | H | (2-bromo-Phe) | betaHomoLys | L | D | T |
| 238 | 232 | PRO | PRO | H | (2-chloro-Phe) | betaHomoLys | L | D | T |
| 239 | 233 | PRO | PRO | H | (2-fluoro-Phe) | betaHomoLys | L | D | T |
| 240 | 234 | PRO | PRO | H | (2-CF3-Phe) | betaHomoLys | L | D | T |
| 241 | 235 | PRO | PRO | H | (2,4-dichloro-Phe) | betaHomoLys | L | D | T |
| 242 | 236 | PRO | PRO | H | (2-aminomethyl-Phe) | betaHomoLys | L | D | T |
| 243 | 237 | PRO | PRO | H | [2-(4-quinolinyl)-Phe] | betaHomoLys | L | D | T |
| 244 | 238 | PRO | PRO | H | [2-(5-quinolinyl)-Phe] | betaHomoLys | L | D | T |
| 245 | 239 | PRO | PRO | H | [2-(3-quinolinyl)-Phe] | betaHomoLys | L | D | T |
| 246 | 240 | PRO | PRO | H | dhomoPhe | betaHomoLys | L | D | T |
| 247 | 241 | PRO | PRO | H | (2-iodo-dPbe) | betaHomoLys | L | D | T |
| 248 | 242 | PRO | PRO | H | (2-phenyl-dPhe) | betaHomoLys | L | D | T |
| 249 | 243 | PRO | PRO | H | [(2-piperazinyl-2-Phenyl)-dPhe] | betaHomoLys | L | D | T |
| 250 | 244 | PRO | PRO | H | Y | betaHomoLys | L | D | I |
| 251 | 245 | PRO | PRO | H | Y | betaHomoLys | L | D | V |
| 252 | 246 | PRO | PRO | H | dTyr | betaHomoLys | L | D | I |
| 253 | 247 | PRO | PRO | H | (4-aminomethyl-dPhe) | betaHomoLys | L | D | I |
| 254 | 248 | PRO | PRO | H | (4-aminomethyl-Phe) | betaHomoLys | L | D | V |
| 255 | 249 | PRO | PRO | H | (3-iodo-Phe) | betaHomoLys | L | D | T |
| 256 | 250 | PRO | PRO | H | (3-phenyl-Phe) | betaHomolys | L | D | T |
| 257 | 251 | PRO | PRO | H | [3-(2-methoxy-phenyl)-Phe] | betaHomoLys | L | D | T |
| 258 | 252 | PRO | PRO | H | [3-(2,6-dimethoxy-phenyl)-Phe] | betaHomoLys | L | D | T |
| 259 | 253 | PRO | PRO | H | [3-(2-trifluoromethoxy-phenyl)-Phe] | betaHomoLys | L | D | T |
| 260 | 254 | PRO | PRO | H | (4-iodo-Phe) | betaHomoLys | L | D | T |
| 261 | 255 | PRO | PRO | H | [4-2-methoxy-phenyl)-Phe] | betaHomoLys | L | D | T |
| 262 | 256 | PRO | PRO | H | [4-(2-trifluoromethoxy-phenyl)-Phe] | betaHomoLys | L | D | T |
| 263 | 257 | PRO | PRO | H | alphaMePhe | betaHomoLys | L | D | T |
| 264 | 258 | PRO | PRO | H | MePhe | betaHomoLys | L | D | T |
| 265 | 259 | PRO | PRO | H | (3-2,6-dimethyl-phenyl)-Phe) | betaHomoLys | L | D | T |
| 266 | 260 | PRO | PRO | H | (3-(quinolin-4-yl)-Phe) | betaHomoLys | L | D | T |
| 267 | 261 | PRO | PRO | H | [3-(3,4-difluoro-phenyl)-Phe] | betaHomoLys | L | D | T |
| 268 | 262 | PRO | PRO | H | [4-(2,6-dimethyl-phenyl)-Phe] | betaHomoLys | L | D | T |
| 269 | 263 | PRO | PRO | H | [4-(2-chloro-6-methoxy-phenyl)-Phe] | betaHomoLys | L | D | T |
| 270 | 264 | PRO | PRO | H | [3-(4-thiazolyl)-Ala(-reduced | betaHomoLys | L | D | T |
| 271 | 265 | PRO | PRO | H | [2-4-(1-piperazinyl)phenyl]-Phe] | betaHomoLys | L | D | T |
| 272 | 266 | PRO | PRO | H | [2-(2,6-dimethylphenyl)-Phe] | betaHomoLys | L | D | T |
| 273 | 267 | PRO | PRO | H | [2-(benzothiazol-5-yl)-Phe] | betaHomoLys | L | D | T |
| 274 | 268 | PRO | PRO | H | HomoPhe | betaHomoLys | L | D | T |
| 275 | 269 | PRO | PRO | H | (piperidine-4-amino-4-carboxylic acid) | betaHomoLys | L | D | T |
| 276 | 270 | PRO | PRO | H | [2-(2,5-dimethyl-isoxazole)-dPhe] | betaHomoLys | L | D | T |
| 277 | 271 | PRO | PRO | H | dTyr | betaHomoLys | L | D | V |
| 278 | 272 | PRO | PRO | H | (4-aminomethyl-dPhe) | betaHomoLys | L | D | T |
| 279 | 273 | PRO | PRO | H | [2-(2-chloro-6-methoxyphenyl)-Phe] | betaHomoLys | L | D | T |
| 280 | 274 | PRO | PRO | H | 2lgl | betaHomoLys | L | D | T |
| 281 | 275 | PRO | PRO | H | d2lgl | betaHomoLys | L | D | T |
| 282 | 276 | PRO | PRO | H | Atc | betaHomoLys | L | D | T |
| 283 | 277 | PRO | PRO | H | Y | betaHomoLys | L | D | alloIle |
| 284 | 278 | PRO | PRO | H | dTyr | betaHomoLys | L | D | alloIle |
| 285 | 279 | PRO | PRO | H | (4-aminomethyl-Phe) | betaHomoLys | L | D | alloIle |
| 286 | 280 | PRO | PRO | H | [2-[2,5-Bis(trifluoromethyl) phenyl]-Phe] | betaHomoLys | L | D | T |
| 287 | 281 | PRO | PRO | H | [2-[2,5-Bis(trifluoromethyl) phenyl]-Phe] | betaHomoLys | L | D | T |
| 288 | 282 | PRO | PRO | H | Aic | betaHomoLys | L | D | r |
| 289 | 283 | PRO | PRO | H | P | betaHomoLys | L | D | T |
| 290 | 284 | PRO | PRO | H | dPro | betaHomoLys | L | D | T |
| 291 | 285 | PRO | PRO | H | Pip | betaHomoLys | L | D | T |
| 292 | 286 | PRO | PRO | H | [2-(3-Pyridyl)-Phe] | betaHomoLys | L | D | T |
| 293 | 287 | PRO | PRO | H | [2-(4-Pyridyl)-Phe] | betaHomoLys | L | D | T |
| 294 | 288 | PRO | PRO | H | [2-(3-bromo-2-Pyridyl)-Phe] | betaHomoLys | L | D | T |
| 295 | 289 | PRO | PRO | H | Y | dbetaHomoLys | L | D | T |
| 296 | 290 | PRO | PRO | H | (N-benzyl-Gly) | betaHomoLys | L | D | T |
| 297 | 291 | PRO | PRO | H | [2-(2-bromo-3-Pyridyl)-Phe] | betaHomoLys | L | D | T |
| 298 | 292 | PRO | PRO | H | [3-(2-chloro-6-methoxy-phenyl)-Phe] | betaHomoLys | L | D | T |
| 299 | 293 | PRO | PRO | H | [3-(benzothiazol-5-yl)-Phe] | betaHomoLys | L | D | T |
| 300 | 294 | PRO | PRO | H | (2-aminomethyl-Phe) | MebetaHomoLys | L | D | T |
| 301 | 295 | PRO | PRO | H | (2-aminomethyl-dPhe) | MebetaHomoLys | L | D | T |

TABLE 1B-continued

| Compound No. | Seq. ID. No. | R5 | R7 | R8 | XY | XZ | X1 | X2 | X3 |
|---|---|---|---|---|---|---|---|---|---|
| 302 | 296 | PRO | PRO | H | [3-(4-thiazolyl)-dAla] | MebetaHomoLys | L | D | T |
| 303 | 297 | PRO | PRO | H | [2-(2-trifluoromethoxy-phenyl)-dPhe] | MebetaHomoLys | L | D | T |
| 304 | 298 | PRO | PRO | H | Tic | MebetaHomoLys | L | D | T |
| 305 | 299 | PRO | PRO | H | dTic | MebetaHomoLys | L | D | T |
| 306 | 300 | PRO | PRO | H | [2-(5-quinolinyl)-dPhe] | betaHomoLys | L | D | alloThr |
| 307 | 301 | PRO | PRO | H | Y | betaHomoLys | L | D | alloThr |
| 308 | 302 | PRO | PRO | H | Y | MebetaHomoLys | L | D | alloThr |
| 309 | 303 | PRO | PRO | H | MeTyr | MebetaHomoLys | L | D | T |
| 310 | 304 | PRO | PRO | H | MeTyr | MebetaHomoLys | L | D | alloThr |
| 311 | 305 | PRO | PRO | H | MePhe | MebetaHomoLys | L | D | T |
| 312 | 306 | PRO | PRO | H | (2-fluoro-Phe) | MebetaHomoLys | L | D | T |
| 313 | 307 | PRO | PRO | H | (2-fluoro-MePhe) | MebetaHomoLys | L | D | T |
| 314 | 308 | PRO | PRO | H | (2,4-dichloro-Phe) | MebetaHomoLys | L | D | T |
| 315 | 309 | PRO | PRO | H | (2,4-dichloro-MePhe) | MebetaHomoLys | L | D | T |
| 316 | 310 | PRO | PRO | H | (2-aminomethyl-MePhe) | MebetaHomoLys | L | D | T |
| 317 | 311 | PRO | PRO | H | [3-(2,6-dimethoxy-phenyl)-dPhe] | betaHomoLys | L | D | T |
| 318 | 312 | PRO | PRO | H | [3-(4-Quinolinyl)-dPhe] | betaHomoLys | L | D | T |
| 319 | 313 | PRO | PRO | H | betaHomoLys | Aze | L | D | T |
| 320 | 314 | PRO | PRO | H | (3-phenyl-dPhe) | betaHomoLys | L | D | T |
| 321 | 315 | PRO | PRO | H | [3-(2-trifluoromethoxy-phenyl)-dPhe] | betaHomoLys | L | D | T |
| 322 | 316 | PRO | PRO | H | [3-(2-methoxy-phenyl)-dPhe] | betaHomoLys | L | D | T |
| 323 | 317 | PRO | PRO | H | [2-(5-quinolinyl)-MePhe] | MebetaHomoLys | L | D | T |
| 324 | 318 | PRO | PRO | H | F | betaHomoNle | L | D | T |
| 325 | 319 | PRO | PRO | H | F | MebetaHomoLys(Me)2 | L | D | T |
| 326 | 320 | PRO | PRO | H | MePhe | MebetaHomoLys(Me)2 | L | D | T |
| 327 | 321 | PRO | PRO | H | M | MebetaHomoLys | L | D | T |
| 328 | 322 | PRO | PRO | H | Igl | MebetaHomoLys | L | D | T |
| 329 | 323 | PRO | PRO | H | HomoPhe | MebetaHomoLys | L | D | T |
| 330 | 324 | PRO | PRO | H | Hyp(OBn) | MebetaHomoLys | L | D | T |
| 331 | 325 | PRO | PRO | H | (1,2-cis-ACHC) | MebetaHomoLys | L | D | T |
| 332 | 326 | PRO | PRO | H | MeMet | MebetaHomoLys | L | D | T |
| 333 | 327 | PRO | PRO | H | betaHomoLys | betaHomoLys | L | D | T |
| 334 | 328 | PRO | PRO | H | BetaHomoPhe | MebetaHomoLys | L | D | T |
| 335 | 329 | PRO | PRO | H | betahomoMet | MebetaHomoLys | L | D | T |
| 336 | 330 | PRO | PRO | H | Y | (3-aminomethyl-4-bromo-benzoic acid) | L | D | T |
| 337 | 331 | PRO | PRO | H | Y | [3-aminomethyl-4-(4-aza-phenyl)-benzoic acid] | L | D | T |
| 338 | 332 | PRO | PRO | H | Y | [3-aminomethyl-4-(2,5-dimethyl-isoxazole)-benzoic acid] | L | D | T |
| 339 | 333 | PRO | PRO | H | Y | [3-aminomethyl-4-(3-aminomethyl-phenyl)-benzoic acid] | L | D | T |
| 340 | 334 | PRO | PRO | H | [3-aminomethyl-4-(1-piperazinyl-phenyl)-benzoic acid] | | L | D | T |
| 341 | 335 | PRO | PRO | H | [3-aminomethyl-4-(4-quinolinyl)-benzoic acid] | | L | D | T |
| 342 | 336 | PRO | PRO | H | (3-aminomethyl-4-bromo-benzoic acid) | | L | D | T |
| 343 | 337 | PRO | PRO | H | [3-aminomethyl-4-(2,5-dimethyl-isozazole)-benzoic acid] | | L | D | T |
| 344 | 338 | dPRO | H | dPRO | [3-aminomethyl-4-(4-pyridyl)-benzoic acid] | | L | D | T |
| 345 | 339 | PRO | PRO | H | [3-aminomethyl-(4-methylpyrazole-3-yl)-benzoic acid] | | L | D | T |
| 346 | 340 | PRO | PRO | H | [3-aminomethyl-4-(3-quinolinyl)-benzoic acid] | | L | D | T |
| 347 | 341 | PRO | PRO | H | [3-aminomethyl-4-(5-quinolinyl)-benzoic acid] | | L | D | T |
| 348 | 342 | PRO | PRO | H | [3-aminomethyl-4-[2-(1-piperazinyl)phenyl]-benzoic acid] | | L | D | T |
| 349 | 343 | PRO | PRO | H | [3-aminomethyl-4-[3-(1-piperazinyl)phenyl]-benzoic acid] | | L | D | T |
| 350 | 344 | PRO | PRO | H | [3-aminomethyl-4-2-[3-(piperidin-4-ylmethoxy)phenyl]-benzoic acid] | | L | D | T |
| 351 | 345 | PRO | PRO | H | [3-aminomethyl-4-(4-pyridyl)-acid] | | L | D | T |
| 352 | 346 | PRO | PRO | H | (3-aminomethyl-4-(4-pyriclyl)-benzoic acid) | | L | D | Thr(OBn) |
| 353 | 347 | PRO | PRO | H | [3-aminomethyl-4-(4-quinolinyl)-benzoic acid] | | L | D | alloThr |

TABLE 1B-continued

| Compound No. | Seq. ID. No. | R⁵ | R⁷ | R⁸ | X^Y | X^Z | X¹ | X² | X³ |
|---|---|---|---|---|---|---|---|---|---|
| 354 | 348 | PRO | PRO | H | [3-aminomethyl-4-[4-(1-piperazinyl) phenyl]-benzoic acid] | | L | D | T |
| 355 | 349 | PRO | PRO | H | [3-aminomethyl-4-(4-quinolinyl)]-benzoic acid | | tertbutylAla | D | T |
| 356 | 334 | PRO | PRO | H | [3-aminomethyl-4-[4-(1-piperazinyl-4-FITC)phenyl]-benzoic acid] | | L | D | T |
| 357 | 350 | PRO | PRO | H | (N-benzyl-3-aminomethyl-benzoic acid) | | L | D | T |
| 358 | 351 | PRO | PRO | H | (3-aminomethyl-benzoic acid | | L | D | T |
| 359 | 352 | PRO | PRO | H | (3-aminomethyl-5-bromo-benzoic acid) | | L | D | T |
| 360 | 353 | PRO | PRO | H | (3-aminomethyl-6-bromo-benzoic acid) | | L | D | T |
| 361 | 336 | PRO | PRO | H | (3-aminomethyl-4-bromo-benzoic acid) | | L | D | T |
| 362 | 354 | PRO | PRO | H | [3-aminomethyl-5-(4-aza-phenyl)-benzoic acid] | | L | D | T |
| 363 | 355 | PRO | PRO | H | [3-aminomethyl-4-(3-thiophenyl)-benzoic acid] | | L | D | T |
| 364 | 356 | PRO | PRO | H | [3-aminomethyl-4-(4-N,N-dimethyl-carboxamide-phenyl)-benzoic acid] | | L | D | T |
| 365 | 357 | PRO | PRO | H | [3-aminomethyl-4-[4-aza-phenyl]-benzoic acid] | | L | D | T |
| 366 | 358 | PRO | PRO | H | [3-aminomethyl-4-(3-aza-phenyl)-benzoic add] | | L | D | T |
| 367 | 359 | PRO | PRO | H | [3-aminomethyl-4-(4-hydroxy-phenyl)-benzoic acid] | | L | D | T |
| 368 | 360 | PRO | PRO | H | [3-aminomethyl-4-[5-(2,4-dimethyl) thiazole]-benzoic acid] | | L | D | T |
| 369 | 361 | PRO | PRO | H | [3-aminomethyl-4(3-N,N-dimethylaniline)-benzoic acid] | | L | D | T |
| 370 | 362 | PRO | PRO | H | [3-aminomethyl-4-(2-fluoro-pyridyl)-benzoic acid] | | L | D | T |
| 371 | 363 | PRO | PRO | H | [3-aminomethyl-4-(5-pyrimidinyl)-benzoic acid] | | L | D | T |
| 372 | 364 | PRO | PRO | H | [3-aminomethyl-4-(3-N,N-dimethyl-diaryl ether)-benzoic acid] | | L | D | T |
| 373 | 365 | PRO | PRO | H | [3-aminomethyl-4-(3-CF3-phenyl)-benzoic acid] | | L | D | T |
| 374 | 366 | PRO | PRO | H | [3-aminomethyl-4-(2,5-dimethoxy-phenyl)-benzoic acid] | | L | D | T |
| 375 | 367 | PRO | PRO | H | [3-aminomethyl-4-[(2,3,4-tri-methoxy)-phenyl]-benzoic acid] | | L | D | T |
| 376 | 368 | PRO | PRO | H | [3-aminomethyl-4-(4-carboxy)-phenyl)-benzoic acid] | | L | D | T |
| 377 | 369 | PRO | PRO | H | [3-aminomethyl-4-(piperonyl)-benzoic acid] | | L | D | T |
| 378 | 370 | PRO | PRO | H | (3-aminomethyl-4-piperidinyl-benzoic acid) | | L | D | T |
| 379 | 371 | PRO | PRO | H | (3-aminomethyl-4-morpholinyl-benzoic acid) | | L | D | T |
| 380 | 372 | PRO | PRO | H | [3--aminomethyl-4-(N,N-dimethyl)-benzoic acid] | | L | D | T |
| 381 | 373 | PRO | PRO | H | [3-aminomethyl-4-(2-aminomethylphenyl)-benzoic acid] | | L | D | T |
| 382 | 374 | PRO | PRO | H | [3-aminomethyl-4-(3-aminomethylphenyl)-benzoic acid] | | L | D | T |
| 383 | 375 | PRO | PRO | H | [3-aminomethyl-4-(4-aminomethylphenyl)-benzoic acid] | | L | D | T |
| 384 | 376 | PRO | PRO | H | [3-aminomethyl-4-(4-quinolinyl)-benzoic acid] | | L | D | Abu |
| 385 | 377 | H | Nva | H | [3-aminomethyl-4-(4-quinolinyl)-benzoic acid] | | L | D | T |
| 386 | 334 | PRO | PRO | H | [3-aminomethyl-4-[4-(1-piperazinyl-4-AlexaFluor 647)phenyl]-benzoic acid] | | L | D | T |
| 387 | 378 | PRO | PRO | H | (N-methyl-3-aminomethyl-benzoic acid) | | L | D | T |
| 388 | 379 | PRO | PRO | H | [N-methyl-3-aminomethyl-4-(4-quinolinyl)-benzoic acid] | | L | D | T |
| 389 | 380 | PRO | PRO | H | [2-(5-quinolinyl)-Phe]-reduced | betaHomoLys | L | D | T |
| 390 | 334 | PRO | PRO | H | [3-aminomethyl-4-[4-(1-piperazinyl)-phenyl]-benzoic acid] | | L | D | T |

TABLE 1B-continued

| Compound No. | Seq. ID. No. | R⁵ | R⁷ | R⁸ | X^Y | X^z | X¹ | X² | X³ |
|---|---|---|---|---|---|---|---|---|---|
| 391 | 334 | PRO | PRO | H | [3-aminomethyl-4-[4-(1-piperazinyl)-phenyl]-benzoic acid] | | L | D | T |
| 392 | 334 | PRO | PRO | H | [3-aminomethyl-4-[4-(1-piperazinyl)-phenyl]-benzoic acid] | | L | D | T |
| 393 | 31 | HYP | HYP | H | F | | L | D | T |
| 394 | 31 | HYP | HYP | H | F | | L | D | T |
| 395 | 31 | HYP | HYP | H | F | | L | D | T |
| 396 | 31 | HYP | HYP | H | F | | L | D | T |
| 397 | 31 | HYP | HYP | H | F | | L | D | T |

TABLE 1C

| Compound No. | a4b7 ELISA IC$_{50}$ (mM) | a4b1 ELISA IC$_{50}$ (mM) | Selectivity ELISA | RPMI 8866 cell IC$_{50}$ (mM) |
|---|---|---|---|---|
| 1 | 0.164 | 0.162 | 0.988 | |
| 2 | 0.109 | 0.185 | 1.697 | |
| 3 | 0.192 | 0.475 | 2.474 | 25.000 |
| 4 | 0.129 | 0.357 | 2.8 | 11.782 |
| 5 | 0.087 | 0.062 | 0.7 | 7.916 |
| 6 | 0.103 | 0.200 | 1.9 | |
| 7 | 0.117 | 0.190 | 1.6 | 23.000 |
| 8 | 0.103 | 0.096 | 0.9 | |
| 9 | 0.061 | 0.106 | 1.7 | |
| 10 | 0.052 | 0.070 | 1.3 | |
| 11 | 0.051 | 0.094 | 1.8 | 3.602 |
| 12 | 0.063 | 0.113 | 1.8 | 8.885 |
| 13 | 0.097 | 0.171 | 1.8 | 19.520 |
| 14 | 0.026 | 0.025 | 1.0 | 2.664 |
| 15 | 0.040 | 0.026 | 0.7 | 3.071 |
| 16 | 0.086 | 0.053 | 0.6 | 1.624 |
| 17 | 0.173 | | | 26.923 |
| 18 | 0.120 | | | |
| 19 | 0.114 | | | 15.044 |
| 20 | 0.146 | | | 8.716 |
| 21 | 0.092 | | | 9.466 |
| 22 | 0.100 | | | 11.556 |
| 23 | 0.176 | 0.458 | 2.6 | 18.880 |
| 24 | 0.087 | 0.192 | 2.2 | 7.632 |
| 25 | 0.096 | 0.209 | 2.2 | 12.431 |
| 26 | 0.088 | 0.236 | 2.7 | 14.070 |
| 27 | 0.067 | 0.161 | 2.4 | 10.478 |
| 28 | 0.117 | 0.264 | 2.3 | 12.562 |
| 29 | 0.073 | 0.167 | 2.3 | 8.133 |
| 30 | 0.058 | 0.162 | 2.8 | 9.277 |
| 31 | 0.057 | 0.215 | 3.7 | 7.950 |
| 32 | 0.100 | 0.311 | 3.1 | 11.161 |
| 33 | 0.090 | 0.324 | 3.6 | 13.059 |
| 34 | 0.043 | 0.083 | 1.9 | 1.153 |
| 35 | 0.039 | 0.096 | 2.5 | 1.230 |
| 36 | 0.112 | 0.215 | 1.9 | 2.392 |
| 37 | 0.036 | 0.063 | 1.8 | 0.856 |
| 38 | 0.065 | 0.120 | 1.9 | 1.899 |
| 39 | 0.152 | 0.595 | 3.9 | 7.576 |
| 40 | 0.063 | 0.119 | 1.9 | |
| 41 | 0.042 | 0.106 | 2.5 | |
| 42 | 0.079 | 0.232 | 2.9 | |
| 43 | 0.026 | 0.072 | 2.8 | |
| 44 | 0.083 | 0.188 | 2.3 | |
| 45 | 0.074 | 0.238 | 3.2 | |
| 46 | 0.106 | 0.258 | 2.4 | |
| 47 | 0.061 | 0.135 | 2.2 | 6.777 |
| 48 | 0.094 | 0.332 | 3.5 | 20.686 |
| 49 | 0.137 | 0.326 | 2.4 | 17.374 |
| 50 | 0.023 | 0.290 | 12.6 | 3.709 |
| 51 | 0.031 | 0.102 | 3.3 | |
| 52 | 0.075 | 0.367 | 4.9 | 14.719 |
| 53 | 0.182 | | | 21.956 |
| 54 | 0.190 | | | 23.916 |
| 55 | 0.113 | 0.119 | 1.1 | |
| 56 | 0.058 | 0.200 | 3.5 | 4.203 |
| 57 | 0.059 | 0.148 | 2.5 | |
| 58 | 0.156 | 0.445 | 2.9 | |
| 59 | 0.197 | 0.610 | 3.1 | |
| 60 | 0.066 | 0.214 | 3.3 | 6.554 |
| 61 | 0.063 | 0.223 | 3.6 | |
| 52 | 0.027 | 0.115 | 4.3 | 2.548 |
| 63 | 0.107 | 0.251 | 2.3 | |
| 64 | 0.046 | 0.268 | 5.8 | 5.367 |
| 65 | 0.005 | 0.095 | 18.1 | 1.033 |
| 66 | 0.093 | 0.326 | 3.5 | 6.348 |
| 67 | 0.075 | 0.341 | 4.5 | 5.093 |
| 68 | 0.067 | 0.280 | 4.2 | 4.158 |
| 69 | 0.022 | 0.060 | 2.7 | 2.646 |
| 70 | 0.035 | 0.099 | 2.9 | 1.163 |
| 71 | 0.184 | 0.816 | 4.4 | |
| 72 | 0.151 | 0.409 | 2.7 | 7.284 |
| 73 | 0.144 | 1.247 | 8.6 | 17.304 |
| 74 | 0.100 | 0.763 | 7.6 | 15.503 |
| 75 | 0.171 | 1.209 | 7.1 | 13.166 |
| 76 | 0.114 | 0.466 | 4.1 | 6.267 |
| 77 | 0.036 | 0.185 | 5.1 | 5.633 |
| 78 | 0.069 | 0.272 | 3.9 | 6.479 |
| 79 | 0.110 | 0.552 | 5.0 | 13.217 |
| 80 | 0.053 | 0.556 | 10.6 | 3.599 |
| 81 | 0.054 | 0.241 | 4.5 | 5.405 |
| 82 | 0.073 | 0.213 | 2.9 | 5.716 |
| 83 | 0.179 | 1.226 | 6.9 | 32.316 |
| 84 | 0.035 | 0.218 | 6.2 | 6.143 |
| 85 | 0.052 | 0.206 | 3.9 | 4.229 |
| 86 | 0.050 | 0.167 | 3.3 | 4.074 |
| 87 | 0.019 | 0.269 | 14.1 | |
| 88 | 0.011 | 0.166 | 14.9 | |
| 89 | 0.016 | 0.232 | 14.4 | |
| 90 | 0.009 | 0.317 | 35.0 | |
| 91 | 0.126 | 1.824 | 14.5 | |
| 92 | 0.053 | 1.063 | 19.9 | |
| 93 | 0.078 | 0.311 | 4.0 | 6.009 |
| 94 | 0.080 | 0.250 | 3.1 | 9.484 |
| 95 | 0.125 | 0.303 | 2.4 | |
| 96 | 0.138 | 0.321 | 2.3 | |
| 97 | 0.124 | 0.311 | 2.5 | |
| 98 | 0.021 | 0.058 | 2.7 | |
| 99 | 0.057 | 0.154 | 2.7 | |
| 100 | 0.132 | 0.453 | 3.4 | 4.446 |
| 101 | 0.129 | 0.609 | 4.7 | 16.092 |
| 102 | 0.021 | 0.136 | 6.6 | 1.464 |
| 103 | 0.108 | 1.531 | 15.1 | |
| 104 | 0.120 | 0.506 | 4.2 | |
| 105 | 0.110 | 1.734 | 15.8 | 9.731 |
| 106 | 0.059 | 1.109 | 18.7 | |
| 107 | 0.150 | 2.390 | 16.0 | |
| 108 | 0.077 | 0.814 | 10.5 | 13.867 |
| 109 | 0.133 | 3.312 | 24.9 | 15.287 |
| 110 | 0.185 | 3.923 | 21.3 | 21.753 |
| 111 | 0.100 | 3.923 | 39.3 | 12.926 |
| 112 | 0.138 | 3.008 | 21.7 | 17.420 |
| 113 | 0.052 | 0.709 | 13.7 | 7.634 |
| 114 | 0.083 | 1.889 | 22.8 | 6.865 |
| 115 | 0.125 | 1.121 | 9.0 | 15.436 |
| 116 | 0.156 | 1.385 | 8.4 | |
| 117 | 0.158 | 1.381 | 8.7 | |
| 118 | 0.112 | 0.132 | 1.2 | 14.202 |

TABLE 1C-continued

| Compound No. | a4b7 ELISA IC$_{50}$ (mM) | a4b1 ELISA IC$_{50}$ (mM) | Selectivity ELISA | RPMI 8866 cell IC$_{50}$ (mM) |
|---|---|---|---|---|
| 119 | 0.079 | 1.688 | 21.5 | 14.057 |
| 120 | 0.157 | 3.000 | 19.1 | |
| 121 | 0.192 | 2.187 | 11.4 | |
| 122 | 0.090 | 1.666 | 18.6 | 16.615 |
| 123 | 0.007 | 0.019 | 2.5 | 1.138 |
| 124 | 0.013 | 0.104 | 8.3 | 1.172 |
| 125 | 0.025 | 0.458 | 18.4 | 1.925 |
| 126 | 0.024 | 0.135 | 5.6 | 1.232 |
| 127 | 0.025 | 0.196 | 7.8 | |
| 128 | 0.026 | 0.296 | 11.4 | |
| 129 | 0.065 | 0.636 | 9.7 | |
| 130 | 0.022 | 0.125 | 5.6 | 1.327 |
| 131 | 0.026 | 0.080 | 3.1 | |
| 132 | 0.029 | 0.309 | 10.8 | 3.626 |
| 133 | 0.015 | 0.080 | 5.3 | |
| 134 | 0.023 | 0.178 | 7.6 | |
| 135 | 0.024 | 0.119 | 4.9 | |
| 136 | 0.032 | 0.209 | 6.6 | |
| 137 | 0.033 | 0.254 | 7.8 | |
| 138 | 0.024 | 0.118 | 5.0 | |
| 139 | 0.100 | 0.073 | 0.7 | |
| 140 | 0.053 | 0.512 | 9.6 | |
| 141 | 0.019 | 0.036 | 2.0 | |
| 142 | 0.164 | 0.084 | 0.5 | |
| 143 | 0.033 | 0.068 | 2.1 | |
| 144 | 0.043 | 0.027 | 0.6 | 6.083 |
| 145 | 0.023 | 0.045 | 2.0 | 3.268 |
| 146 | 0.016 | 0.012 | 0.7 | 0.672 |
| 147 | 0.052 | 0.039 | 0.8 | |
| 148 | 0.085 | 0.105 | 1.2 | |
| 149 | 0.046 | 0.546 | 12.0 | 12.600 |
| 150 | 0.054 | 0.447 | 8.2 | |
| 151 | 0.053 | 0.218 | 4.1 | |
| 152 | 0.102 | 1.347 | 13.2 | |
| 153 | 0.006 | 0.017 | 2.8 | 0.125 |
| 154 | 0.117 | 2.664 | 22.8 | |
| 155 | 0.054 | 1.085 | 20.3 | |
| 156 | 0.019 | 0.258 | 13.3 | 1.412 |
| 157 | 0.067 | 3.707 | 55.3 | |
| 158 | 0.110 | 1.537 | 14.0 | 15.746 |
| 159 | 0.053 | 0.467 | 8.9 | 41.275 |
| 160 | 0.141 | 1.349 | 9.5 | 8.794 |
| 161 | 0.135 | 2.035 | 15.1 | 6.662 |
| 162 | 0.107 | 1.875 | 17.5 | 16.696 |
| 163 | 0.126 | 1.389 | 11.0 | 22.489 |
| 164 | 0.127 | 3.288 | 25.8 | 30.192 |
| 165 | 0.128 | 2.918 | 22.8 | 30.337 |
| 166 | 0.179 | 1.382 | 7.7 | |
| 167 | 0.147 | 1.997 | 13.6 | |
| 168 | 0.077 | 1.051 | 13.6 | 17.847 |
| 169 | 0.176 | 0.488 | 2.8 | |
| 170 | 0.013 | 0.104 | 8.0 | 1.033 |
| 171 | 0.128 | 0.658 | 5.1 | 14.357 |
| 172 | 0.096 | 1.030 | 10.7 | 9.922 |
| 173 | 0.054 | 0.719 | 13.4 | 12.042 |
| 174 | 0.160 | 0.619 | 3.9 | |
| 175 | 0.018 | 0.130 | 7.2 | 0.986 |
| 176 | 0.189 | 1.202 | 6.3 | |
| 177 | 0.019 | 0.463 | 24.0 | 2.853 |
| 178 | 0.027 | 0.113 | 4.1 | 2.710 |
| 179 | 0.174 | 2.655 | 15.2 | |
| 180 | 0.013 | 0.068 | 5.1 | 0.841 |
| 181 | 0.180 | 2.272 | 12.6 | |
| 182 | 0.017 | 0.083 | 5.0 | 1.128 |
| 183 | 0.014 | 0.105 | 7.5 | 1.070 |
| 184 | 0.099 | 0.953 | 9.6 | |
| 185 | 0.018 | 0.095 | 5.4 | 0.662 |
| 186 | 0.062 | 0.027 | 0.4 | |
| 187 | 0.083 | 0.404 | 4.9 | |
| 188 | 0.027 | 0.189 | 7.0 | 7.308 |
| 189 | 0.018 | 0.019 | 1.0 | 2.251 |
| 190 | 0.021 | 0.145 | 7.0 | 2.470 |
| 191 | 0.083 | 4.020 | 48.4 | |
| 192 | 0.118 | 6.823 | 57.8 | 37.800 |
| 193 | 0.092 | 0.303 | 3.3 | 5.621 |
| 194 | 0.038 | 0.207 | 5.4 | 4.617 |
| 195 | 0.049 | 1.917 | 38.9 | 7.931 |
| 196 | 0.158 | 0.275 | 1.7 | |
| 197 | 0.044 | 1.327 | 30.2 | 7.441 |
| 198 | 0.041 | 1.223 | 29.9 | 5.089 |
| 199 | 0.069 | 3.138 | 45.2 | 19.350 |
| 200 | 0.134 | 0.352 | 2.6 | |
| 201 | 0.061 | 0.695 | 11.4 | |
| 202 | 0.086 | 0.680 | 8.0 | |
| 203 | 0.055 | 0.534 | 9.8 | |
| 204 | 0.063 | 0.429 | 6.8 | |
| 205 | 0.047 | 1.517 | 32.2 | 2.231 |
| 206 | 0.046 | 2.890 | 63.0 | 27.621 |
| 207 | 0.025 | 0.460 | 18.5 | |
| 208 | 0.019 | 0.522 | 28.1 | 4.679 |
| 209 | 0.035 | 1.977 | 56.9 | 16.508 |
| 210 | 0.072 | 1.148 | 16.0 | |
| 211 | 0.060 | 2.511 | 42.2 | 8.101 |
| 212 | 0.068 | 2.190 | 32.1 | |
| 213 | 0.055 | 2.247 | 41.2 | 10.605 |
| 214 | 0.069 | 4.222 | 60.8 | 72.055 |
| 215 | 0.033 | 0.413 | 12.4 | |
| 216 | 0.123 | 2.509 | 20.4 | |
| 217 | 0.034 | 1.088 | 31.8 | |
| 218 | 0.190 | 3.135 | 16.5 | |
| 219 | 0.147 | 3.253 | 22.1 | |
| 220 | 0.096 | 1.740 | 18.2 | |
| 221 | 0.015 | 0.165 | 11.1 | 0.248 |
| 222 | 0.013 | 0.212 | 16.1 | 0.325 |
| 223 | 0.015 | 0.122 | 8.2 | 0.549 |
| 224 | 0.055 | 2.978 | 53.9 | 10.962 |
| 225 | 0.099 | 4.523 | 45.6 | 18.130 |
| 226 | 0.094 | 10.797 | 115.0 | 4.076 |
| 227 | 0.034 | 0.047 | 1.4 | 1.491 |
| 228 | 0.034 | 0.503 | 14.7 | |
| 229 | 0.058 | 0.075 | 1.3 | |
| 230 | 0.120 | 0.131 | 1.1 | |
| 231 | 0.031 | 0.993 | 32.0 | |
| 232 | 0.012 | 0.110 | 8.9 | 0.353 |
| 233 | 0.094 | 3.861 | 41.0 | 19.372 |
| 234 | 0.099 | 3.203 | 32.3 | |
| 235 | 0.025 | 1.553 | 62.6 | 4.614 |
| 235 | 0.060 | 6.203 | 104.2 | 7.320 |
| 237 | 0.020 | 0.870 | 43.9 | 5.131 |
| 238 | 0.025 | 1.049 | 42.3 | 8.425 |
| 239 | 0.020 | 0.641 | 32.3 | 4.407 |
| 240 | 0.027 | 0.905 | 33.2 | 12.040 |
| 241 | 0.031 | 3.207 | 103.4 | 6.006 |
| 242 | 0.067 | 5.307 | 79.0 | 8.335 |
| 243 | 0.026 | 0.767 | 29.4 | 2.007 |
| 244 | 0.016 | 0.753 | 46.7 | 0.719 |
| 245 | 0.024 | 0.414 | 17.5 | 3.067 |
| 246 | 0.120 | 17.702 | 147.1 | |
| 247 | 0.035 | 4.514 | 132.8 | 15.134 |
| 248 | 0.045 | 3.088 | 69.2 | 16.371 |
| 249 | 0.045 | 4.233 | 94.8 | 23.107 |
| 250 | 0.017 | 0.150 | 8.7 | 0.401 |
| 251 | 0.024 | 0.349 | 14.8 | 1.386 |
| 252 | 0.032 | 0.390 | 12.1 | 2.408 |
| 253 | 0.069 | 1.087 | 15.6 | |
| 254 | 0.055 | 1.803 | 33.0 | |
| 255 | 0.043 | 3.024 | 69.7 | |
| 256 | 0.072 | 3.246 | 45.1 | 9.562 |
| 257 | 0.058 | 1.604 | 27.5 | |
| 258 | 0.056 | 1.584 | 28.4 | |
| 259 | 0.058 | 5.995 | 102.8 | 4.279 |
| 260 | 0.155 | 9.562 | 58.1 | |
| 261 | 0.096 | 23.155 | 241.0 | 16.926 |
| 262 | 0.080 | 3.740 | 47.0 | |
| 263 | 0.102 | 2.345 | 23.1 | |
| 264 | 0.117 | 5.560 | 47.5 | |
| 265 | 0.039 | 1.818 | 46.2 | |
| 266 | 0.037 | 1.206 | 33.0 | 11.641 |
| 267 | 0.044 | 1.936 | 44.1 | 20.440 |
| 268 | 0.076 | 1.868 | 24.6 | |
| 269 | 0.056 | 1.764 | 31.6 | |
| 270 | 0.160 | 17.562 | 109.8 | 18.900 |
| 271 | 0.033 | 1.151 | 34.6 | |
| 272 | 0.041 | 2.383 | 58.1 | |

TABLE 1C-continued

| Compound No. | a4b7 ELISA IC$_{50}$ (mM) | a4b1 ELISA IC$_{50}$ (mM) | Selectivity ELISA | RPMI 8866 cell IC$_{50}$ (mM) |
|---|---|---|---|---|
| 273 | 0.012 | 0.303 | 24.6 | 1.730 |
| 274 | 0.026 | 0.454 | 17.5 | 7.938 |
| 275 | 0.101 | 0.779 | 7.7 | |
| 276 | 0.134 | 14.235 | 106.2 | |
| 277 | 0.052 | 0.357 | 6.9 | |
| 278 | 0.104 | 1.062 | 10.2 | |
| 279 | 0.100 | 5.847 | 58.2 | |
| 280 | 0.010 | 0.400 | 39.7 | 2.150 |
| 281 | 0.144 | 3.161 | 21.9 | |
| 282 | 0.119 | 0.626 | 5.2 | |
| 283 | 0.128 | 1.495 | 11.7 | |
| 284 | 0.046 | 0.228 | 5.0 | |
| 285 | 0.089 | 0.553 | 6.2 | |
| 286 | 0.064 | 5.236 | 81.9 | |
| 287 | 0.084 | 3.553 | 42.1 | |
| 288 | 0.136 | 1.664 | 12.2 | |
| 289 | 0.038 | 0.349 | 9.3 | 1.242 |
| 290 | 0.067 | 1.894 | 28.4 | |
| 291 | 0.035 | 0.777 | 22.4 | 8.742 |
| 292 | 0.030 | 0.374 | 12.4 | |
| 293 | 0.019 | 0.198 | 10.6 | 4.008 |
| 294 | 0.045 | 0.937 | 20.7 | |
| 295 | 0.094 | 20.950 | 222.7 | 18.900 |
| 296 | 0.155 | 14.698 | 94.8 | |
| 297 | 0.037 | 0.786 | 21.3 | |
| 298 | 0.076 | 4.349 | 57.2 | |
| 299 | 0.002 | 0.090 | 41.5 | 0.556 |
| 300 | 0.022 | 0.225 | 10.4 | 0.672 |
| 301 | 0.018 | 0.846 | 47.6 | 1.020 |
| 302 | 0.012 | 0.598 | 51.6 | 1.764 |
| 303 | 0.020 | 0.497 | 24.8 | 1.662 |
| 304 | 0.015 | 0.293 | 19.0 | 0.191 |
| 305 | 0.008 | 0.221 | 26.6 | 3.533 |
| 306 | 0.104 | 2.763 | 26.5 | |
| 307 | 0.091 | 4.343 | 47.8 | |
| 308 | 0.039 | 0.480 | 12.3 | 1.982 |
| 309 | 0.008 | 0.023 | 3.0 | 0.126 |
| 310 | 0.017 | 0.300 | 17.6 | 0.434 |
| 311 | 0.007 | 0.198 | 27.6 | 0.158 |
| 312 | 0.011 | 0.145 | 13.4 | 0.273 |
| 313 | 0.011 | 0.206 | 19.2 | 0.210 |
| 314 | 0.011 | 0.138 | 12.8 | 0.305 |
| 315 | 0.013 | 0.312 | 24.9 | 0.431 |
| 316 | 0.022 | 0.349 | 16.2 | 0.690 |
| 317 | 0.047 | 0.685 | 14.5 | 9.408 |
| 318 | 0.091 | 1.513 | 16.6 | |
| 319 | 0.065 | 0.309 | 4.8 | |
| 320 | 0.163 | 0.127 | 0.8 | |
| 321 | 0.101 | 7.368 | 72.7 | |
| 322 | 0.093 | 4.166 | 44.7 | |
| 323 | 0.025 | 0.297 | 11.8 | 1.056 |
| 324 | 0.110 | 1.058 | 9.6 | 11.844 |
| 325 | 0.020 | 0.170 | 8.6 | 0.714 |
| 326 | 0.017 | 0.476 | 28.4 | 0.280 |
| 327 | 0.010 | 0.128 | 13.2 | 0.308 |
| 328 | 0.010 | 0.234 | 24.1 | 0.368 |
| 329 | 0.005 | 0.050 | 10.6 | 0.326 |
| 330 | 0.005 | 0.179 | 32.9 | 0.185 |
| 331 | 0.016 | 0.093 | 6.0 | 0.399 |
| 332 | 0.010 | 0.120 | 12.5 | 0.140 |
| 333 | 0.046 | 0.757 | 16.5 | 12.922 |
| 334 | | | | 5.061 |
| 335 | | | | 4.956 |
| 336 | 0.162 | 0.917 | 5.6 | |
| 337 | 0.061 | 0.177 | 2.9 | |
| 338 | 0.041 | 0.177 | 4.4 | |
| 339 | 0.051 | 0.299 | 5.8 | |
| 340 | 0.019 | 0.048 | 2.5 | 0.263 |
| 341 | 0.012 | 0.026 | 2.1 | 0.306 |
| 342 | 0.041 | 0.139 | 3.4 | |
| 343 | 0.018 | 0.029 | 1.6 | 0.269 |
| 344 | 0.052 | 0.107 | 2.1 | |
| 345 | 0.039 | 0.052 | 1.3 | |
| 346 | 0.028 | 0.011 | 0.4 | 0.580 |
| 347 | 0.023 | 0.030 | 1.3 | |
| 348 | 0.027 | 0.041 | 1.5 | |
| 349 | 0.023 | 0.043 | 1.9 | 0.479 |
| 350 | 0.027 | 0.055 | 2.0 | |
| 351 | 0.160 | 0.184 | 1.2 | |
| 352 | 0.024 | 0.005 | 0.2 | 0.070 |
| 353 | 0.031 | 0.103 | 3.3 | |
| 354 | 0.050 | 0.175 | 3.5 | |
| 355 | 0.048 | 0.069 | 1.4 | |
| 356 | 0.017 | 0.027 | 1.6 | |
| 357 | 0.102 | 0.406 | 4.0 | |
| 358 | 0.127 | 1.108 | 8.7 | 34.923 |
| 359 | 0.053 | 0.450 | 8.5 | 7.880 |
| 360 | 0.125 | 0.779 | 6.2 | 18.937 |
| 361 | 0.049 | 0.288 | 5.9 | 2.843 |
| 362 | 0.043 | 0.238 | 5.6 | |
| 363 | 0.022 | 0.105 | 4.8 | 1.571 |
| 364 | 0.018 | 0.074 | 4.0 | 0.602 |
| 365 | 0.017 | 0.064 | 3.7 | 0.638 |
| 366 | 0.023 | 0.059 | 2.6 | 0.384 |
| 367 | 0.018 | 0.053 | 3.0 | 0.535 |
| 368 | 0.010 | 0.024 | 2.4 | 0.342 |
| 369 | 0.024 | 0.069 | 2.9 | 0.974 |
| 370 | 0.015 | 0.047 | 3.1 | 0.661 |
| 371 | 0.016 | 0.055 | 3.4 | 0.482 |
| 372 | 0.024 | 0.104 | 4.3 | 2.133 |
| 373 | 0.018 | 0.074 | 4.1 | 0.879 |
| 374 | 0.018 | 0.081 | 4.5 | 1.246 |
| 375 | 0.015 | 0.067 | 4.5 | 1.164 |
| 376 | 0.019 | 0.078 | 4.1 | 1.135 |
| 377 | 0.013 | 0.045 | 3.6 | 0.839 |
| 378 | 0.042 | 0.182 | 4.3 | |
| 379 | 0.033 | 0.161 | 4.9 | |
| 380 | 0.041 | 0.217 | 5.3 | |
| 381 | 0.010 | 0.010 | 1.1 | 0.323 |
| 382 | 0.012 | 0.025 | 2.0 | |
| 383 | 0.006 | 0.017 | 2.7 | 0.403 |
| 384 | 0.020 | 0.049 | 2.5 | 2.260 |
| 385 | 0.039 | 0.023 | 0.6 | 1.548 |
| 385 | 0.044 | 0.034 | 2.5 | 2.604 |
| 387 | 0.063 | 6.133 | 96.7 | 16.142 |
| 388 | 0.009 | 0.102 | 12.0 | 0.336 |
| 389 | 0.042 | 0.234 | 5.535 | 6.664 |
| 390 | 0.010 | 0.017 | 1.749 | 0.019 |
| 391 | 0.011 | 0.025 | 2.138 | 0.022 |
| 392 | 0.011 | 0.062 | 5.427 | 0.056 |
| 393 | 0.035 | 0.109 | 3.137 | 0.635 |
| 394 | 0.039 | 0.133 | 3.429 | 0.860 |
| 395 | 0.042 | 0.126 | 2.998 | 1.521 |
| 396 | 0.044 | 0.063 | 1.424 | 1.953 |
| 397 | 0.079 | 0.158 | 1.987 | 2.061 |

TABLE 2A

| Compound No. | R$^1$ | R$^2$ | R$^3$ | R$^4$ | R$^5$ |
|---|---|---|---|---|---|
| 5 | H | H | CH$_3$ | H | C(O)—NH-tert-Butyl |
| 398 | H | H | H | H | H |
| 399 | H | H | CH$_3$ | H | C(O)—NH2 |
| 4 | H | H | CH$_3$ | H | C(O)—NH-tert-Butyl |
| 400 | H | H | H | C(O)—NH-tert-Butyl | H |
| 401 | H | H | H | H | C(O)—NH-tert-Butyl |
| 402 | H | H | CH$_3$ | H | H |

TABLE 2A-continued

| Compound No. | R¹ | R² | R³ | R⁴ | R⁵ |
|---|---|---|---|---|---|
| 403 | H | H | CH₃ | C(O)—NH-tert-Butyl | H |
| 404 | H | CH₃ | H | C(O)—NH-tert-Butyl | H |
| 405 | H | H | CH₃ | H | C(O)—NH-tert-Butyl |
| 406 | H | H | CH₃ | H | C(O)—NH-tert-Butyl |
| 407 | H | H | CH₃ | H | C(O)—NH-tert-Butyl |
| 408 | H | H | CH₃ | H | C(O)—NH-tert-Butyl |
| 409 | H | H | CH₃ | H | C(O)—NH-tert-Butyl |
| 410 | H | H | CH₃ | H | C(O)—NH-tert-Butyl |
| 411 | H | H | CH₃ | H | C(O)—NH-tert-Butyl |
| 412 | H | H | CH₃ | H | C(O)—NH-tert-Butyl |
| 413 | H | H | CH₃ | H | C(O)—NH-tert-Butyl |
| 414 | H | H | CH₃ | H | C(O)—NH-tert-Butyl |
| 415 | H | H | CH₃ | H | C(O)—NH-tert-Butyl |
| 416 | H | H | CH₃ | H | C(O)—NH-tert-Butyl |
| 417 | H | H | CH₃ | H | C(O)—NH-tert-Butyl |
| 418 | H | CH₃ | H | C(O)—NH-tert-Butyl | H |
| 419 | H | CH₃ | H | C(O)—NH-tert-Butyl | H |
| 420 | H | H | CH₃ | H | C(O)—NH-tert-Butyl |
| 125 | H | H | CH₃ | H | C(O)—NH-tert-Butyl |
| 421 | H | CH₃ | H | C(O)—NH-tert-Butyl | H |
| 422 | H | H | CH₃ | H | C(O)—NH-tert-Butyl |
| 423 | H | H | CH₃ | H | C(O)—NH-tert-Butyl |
| 424 | H | H | CH₃ | H | C(O)—NH-tert-Butyl |
| 425 | H | H | CH₃ | H | C(O)—NH-tert-Butyl |
| 426 | H | H | CH₃ | H | C(O)—NH-tert-Butyl |
| 427 | H | H | CH₃ | H | C(O)—NH-tert-Butyl |
| 428 | H | H | CH₃ | H | C(O)—NH-tert-Butyl |
| 429 | H | H | CH₃ | H | C(O)—NH-tert-Butyl |
| 430 | H | H | CH₃ | H | C(O)—NH-tert-Butyl |
| 431 | H | H | CH₃ | H | C(O)—NH-tert-Butyl |
| 432 | PRO- | PRO- | H | H | C(O)—NH-tert-Butyl |
| 341 | H | H | CH₃ | H | C(O)—NH-tert-Butyl |
| 433 | H | H | CH₃ | H | C(O)—NH-tert-Butyl |
| 434 | H | H | CH₃ | H | C(O)—NH-tert-Butyl |
| 435 | H | H | CH₃ | H | C(O)—NH-tert-Butyl |
| 436 | PRO- | PRO- | H | C(O)—NH-tert-Butyl | H |
| 437 | H | H | CH₃ | H | C(O)—NH-tert-Butyl |
| 232 | H | H | CH₃ | H | C(O)—NH-tert-Butyl |
| 438 | H | H | CH₃ | H | C(O)—NH-tert-Butyl |
| 439 | H | H | CH₃ | H | C(O)—NH-tert-Butyl |
| 440 | H | H | CH₃ | H | C(O)—NH-tert-Butyl |
| 441 | H | H | CH₃ | H | C(O)—NH-tert-Butyl |
| 442 | H | H | CH₃ | H | C(O)—NH-tert-Butyl |
| 443 | H | H | CH₃ | C(O)—NH-tert-Butyl | H |
| 444 | H | CH₃ | H | C(O)—NH-tert-Butyl | H |
| 445 | PRO- | PRO- | H | C(O)—NH-tert-Butyl | H |
| 445 | PRO- | PRO- | H | H | C(O)—NH-tert-Butyl |
| 447 | H | H | CH₃ | H | C(O)—NH-tert-Butyl |
| 448 | H | H | CH₃ | H | C(O)—NH-tert-Butyl |
| 449 | H | H | CH₃ | H | C(O)—NH-tert-Butyl |
| 450 | H | H | CH₃ | H | C(O)—NH-tert-Butyl |
| 270 | H | H | CH₃ | H | C(O)—NH-tert-Butyl |
| 451 | H | H | CH₃ | H | C(O)—NH-tert-Butyl |
| 452 | H | H | CH₃ | H | C(O)—NH-tert-Butyl |
| 453 | H | H | CH₃ | H | C(O)—NH-tert-Butyl |
| 454 | H | H | CH₃ | H | C(O)—NH-tert-Butyl |
| 455 | H | H | CH₃ | H | C(O)—NH-tert-Butyl |

TABLE 2B

| Compound No. | Seq. ID. No. | R⁶ | R⁷ | R⁸ | Xʸ | Xᶻ | X¹ | X² | X³ |
|---|---|---|---|---|---|---|---|---|---|
| 5 | 4 | PRO | PRO | H | F | | L | D | T |
| 398 | 4 | PRO | PRO | H | F | | L | D | T |
| 399 | 4 | PRO | PRO | H | F | | L | D | T |
| 4 | 3 | PRO | PRO | H | Y | | L | D | T |
| 400 | 3 | PRO | PRO | H | Y | | L | D | T |
| 401 | 3 | PRO | PRO | H | Y | | L | D | T |
| 402 | 3 | PRO | PRO | H | Y | | L | D | T |
| 403 | 3 | PRO | PRO | H | Y | | L | D | T |
| 404 | 3 | PRO | PRO | H | Y | | L | D | T |
| 405 | 381 | PRO | PRO | H | L | | D | T | Y |
| 406 | 382 | PRO | PRO | H | D | | L | D | T |

TABLE 2B-continued

| Compound No. | Seq. ID. No. | R⁶ | R⁷ | R⁸ | X^Y | X^z | X¹ | X² | X³ |
|---|---|---|---|---|---|---|---|---|---|
| 407 | 383 | PRO | PRO | H | 1-(R)-isoindoline-carboxylic acid | | L | D | T |
| 408 | 384 | PRO | PRO | H | betaHomolys | | L | D | T |
| 409 | 385 | PRO | PRO | H | Y | | cyclopropylAla | D | T |
| 410 | 386 | PRO | PRO | H | Y | | betaHomoLeu | D | T |
| 411 | 387 | PRO | PRO | H | Y | | W | D | T |
| 412 | 388 | PRO | PRO | H | Y | | L | betaHomoAsp | T |
| 413 | 389 | PRO | PRO | H | 2Nal | | L | HomoSer | I |
| 414 | 390 | PRO | PRO | H | 2Nal | | L | Asp(ethyl ester) | I |
| 415 | 391 | PRO | PRO | H | Y | | L | D | H |
| 416 | 392 | PRO | PRO | H | Y | | L | D | (2-aza-Phe) |
| 417 | 393 | PRO | PRO | H | Y | | L | D | betaHomoThr |
| 418 | 394 | dPro | H | dPro | dTyr | | dLeu | dAsp | dThr |
| 419 | 395 | dPro | H | dPro | dThr | | dAsp | dLeu | dTyr |
| 420 | 396 | PRO | PRO | H | dThr | | dAsp | dLeu | dTyr |
| 125 | 120 | PRO | PRO | H | Y | dPip | L | D | T |
| 421 | 397 | dPro | H | dPro | V | dPip | L | D | T |
| 422 | 398 | PRO | PRO | H | dTic | G | L | D | T |
| 423 | 399 | PRO | PRO | H | dAla | Y | L | D | T |
| 424 | 400 | PRO | PRO | H | (2-aminomethyl-phenylacetic acid) | | L | D | r |
| 425 | 401 | PRO | PRO | H | Y | dMet | L | D | T |
| 426 | 402 | PRO | PRO | H | Y | dTiq | L | D | T |
| 427 | 403 | PRO | PRO | H | Y | dPip | MeLeu | D | 1 |
| 428 | 404 | PRO | PRO | H | Y | Sar | HomocycloLeu | D | T |
| 429 | 405 | PRO | PRO | H | Y | dlys | L | D | dThr |
| 430 | 406 | PRO | PRO | H | Y | dPip | L | D | betaHomoIle |
| 431 | 407 | PRO | PRO | H | Y | L | D | T | dAla |
| 432 | 120 | PRO | PRO | H | Y | dPip | L | D | T |
| 341 | 335 | PRO | PRO | H | [3-aminomethyl-4-(4-quinolinyl)-benzoic acid] | | L | D | T |
| 433 | 408 | PRO | PRO | H | [3-aminomethyl-4-(4-quinolinyl)-benzoic acid] | | MeLeu | D | T |
| 434 | 409 | PRO | PRO | H | [3-aminomethyl-4-(4-quinolinyl)-benzoic acid] | | L | MeAsp | T |
| 435 | 410 | PRO | PRO | H | [3-aminomethyl-4-(4-quinolinyl)-benzoic acid] | | L | D | MeThr |
| 436 | 335 | PRO | PRO | H | [3-aminomethyl-4-(4-quinolinyl)-benzoic acid] | | L | D | T |
| 437 | 411 | PRO | PRO | H | [3-aminomethyl-4-(4-quinolinyl)-benzoic acid] | K | L | D | T |
| 232 | 226 | PRO | PRO | H | F | MebetaHomoLys | L | D | T |
| 438 | 412 | PRO | PRO | H | [4-(2,6-dimethoxy-phenyl)-Phe] | betaHomoLys | L | D | T |
| 439 | 413 | PRO | PRO | H | Y | 1,2-trans-ACHC | L | D | T |
| 440 | 414 | PRO | PRO | H | Y | betaAla | L | D | T |
| 441 | 415 | PRO | PRO | H | Y | (2-aminobenzoic acid) | L | D | T |
| 442 | 416 | PRO | PRO | H | [3-(4-thiazolyl)-Ala] | dMebetaHomoLys | L | D | T |
| 443 | 190 | PRO | PRO | H | Y | betaHomoLys | L | D | T |
| 444 | 417 | dPro | H | dPro | Y | betaHomoLys | L | D | T |
| 445 | 190 | PRO | PRO | H | Y | betaHomoLys | L | D | T |
| 446 | 190 | PRO | PRO | H | Y | betaHomoLys | L | D | T |
| 447 | 418 | PRO | PRO | H | L | D | T | F | betaHomoLys |
| 448 | 419 | PRO | PRO | H | Y | L | G | D | T |
| 449 | 420 | PRO | PRO | H | L | D | T | A | P |
| 450 | 421 | PRO | PRO | H | Y | L | D | T | A |
| 270 | 264 | PRO | PRO | H | [3-(4-thiazolyl)-Ala]-reduced | betaHomoLys | L | D | T |
| 451 | 422 | PRO | PRO | H | [3(4-thiazoiyl)-Ala] | betaHomoLys-reduced | L | D | 7 |
| 452 | 423 | PRO | PRO | H | [3-(4-thiazolyl)-Ala] | betaHomoLys | Leu-reduced | D | T |
| 453 | 424 | PRO | PRO | H | [3-(4-thiazolyl)-Ala] | betaHomoLys | L | Asp-reduced | T |
| 454 | 425 | PRO | PRO | H | [3-(4-thiazolyl)-Ala] | betaHomoLys | L | D | Th-reduced |
| 455 | 426 | PRO | PRO | H | F | betaHomoLys-reduced | L | D | T |

TABLE 2C

| Compound No. | a4b7 ELISA IC₅₀ (mM) | a4b1 ELISA IC₅₀ (mM) | Selectivity ELISA | RPMI 8866 cell ELISA IC₅₀ (mM) |
|---|---|---|---|---|
| 5 | 0.087 | 0.062 | 0.7 | 7.916 |
| 398 | 39.605 | 38.21.1 | | |
| 399 | | | | 47 |
| 4 | 0.129 | 0.357 | 2.8 | 11.782 |
| 400 | 7.348 | 4.904 | | |
| 401 | 1.27 | 3.843 | | |
| 402 | 6.45 | 2.842 | | |
| 403 | 6.45 | 2.842 | | |
| 404 | 6.45 | 2.842 | | |
| 405 | 40.313 | | | |
| 406 | 3.832 | | | |
| 407 | 3.664 | 3.727 | | |

TABLE 2C-continued

| Compound No. | a4b7 ELISA IC$_{50}$ (mM) | a4b1 ELISA IC$_{50}$ (mM) | Selectivity ELISA | RPMI 8866 cell IC$_{50}$ (mM) |
|---|---|---|---|---|
| 408 | 3.22 | 19.216 | | |
| 409 | 3.025 | | | |
| 410 | 3.817 | | | |
| 411 | 40 | | | |
| 412 | 7.633 | | | |
| 413 | 27.725 | | | 26.923 |
| 414 | 50 | | | 26.923 |
| 415 | 45.263 | | | |
| 416 | 56.579 | 49.128 | | |
| 417 | 6.515 | | | |
| 418 | 15.5 | 28.42 | | |
| 419 | 15.5 | 28.42 | | |
| 420 | 3.116 | 3 | | |
| 125 | 0.025 | 0.458 | 18.4 | 1.925 |
| 421 | 0.462 | 0.726 | | |
| 422 | 1.273 | 2.122 | | |
| 423 | 10 | | | |
| 424 | 1.0 | | | |
| 425 | 1.575 | 3.717 | | |
| 426 | 3.665 | 3.727 | | |
| 427 | 1.04 | 1.2 | | |
| 428 | 3.665 | 1.012 | | |
| 429 | 3.116 | 3.00 | | |
| 430 | 2.933 | 8.69 | | |
| 431 | 10 | | | |
| 432 | 4.33 | 2.905 | | |
| 341 | 0.012 | 0.026 | 2.1 | 0.306 |
| 433 | 7.904 | 37.5 | | |
| 434 | 3.746 | 29.919 | | |
| 435 | 0.231 | 0.342 | | |
| 436 | 4.82 | 13.377 | | |
| 437 | 5.305 | 7.302 | | |
| 232 | 0.012 | 0110 | 8.9 | 0.353 |
| 438 | 0.941 | 21.709 | | |
| 439 | 1.579 | 1.902 | | |
| 440 | 1.833 | 9.679 | | |
| 441 | 0.994 | 4.095 | | |
| 442 | 2.281 | 4.701 | | |
| 443 | 7.442 | 28.424 | | |
| 444 | 7.566 | 28.424 | | |
| 445 | 10.492 | 1.123 | | |
| 446 | 10.541 | 26.869 | | |
| 447 | 8.109 | 8.859 | | |
| 448 | 50 | | | |
| 449 | 6.494 | 4.658 | | |
| 450 | 0.400 | 2.007 | | |
| 270 | 0.160 | 17.562 | 109.8 | 18.900 |
| 451 | 41.17 | 86.84 | | |
| 452 | 2.009 | 110 | | |
| 453 | 2.251 | 36.125 | | |
| 454 | 8.274 | 43.01 | | |
| 455 | 20.512 | 96.78 | | |

TABLE S1

| Compound No. | LC-MS (m/z) | Experimental Protocol |
|---|---|---|
| 1 | | A, E, Fb, I, M |
| 2 | | A, E, Fb, I, M |
| 3 | | A, E, Fb, I, M |
| 4 | | A, E, Fa, Jb, I, M |
| 5 | | A, E, Fa, Jb, I, M |
| 6 | | A, E, Fa, Jb, I, M |
| 7 | | A, E, Fa, Jb, I, M |
| 8 | | A, E, Fa, Jb, I, M |
| 9 | 780.4 | A, E, Fa, Jb, I, M |
| 10 | 780.4 | A, E, Fa, Jb, I, M |
| 11 | 859.4 | A, E, Fa, Jb, I, M |
| 12 | 806.4 | A, E, Fa, Jb, I, M |
| 13 | | A, E, Fa, Jb, H, I, M |
| 14 | 792.4 | A, E, Fa, Jb, I, M |
| 15 | 792.4 | A, E, Fa, Jb, I, M |
| 16 | | A, E, Fa, Jb, I, M |
| 17 | | A, E, Fa, Jb, I, M |
| 18 | | A, E, Fa, Jb, I, M |
| 19 | | A, E, Fa, Jb, H, I, M |
| 20 | | A, E, Fa, Jb, H, I, M |
| 21 | | A, E, Fa, Jb, H, I, M |
| 22 | | A, E, Fa, Jb, H, I, M |
| 23 | | A, E, Fa, Jb, H, I, M |
| 24 | | A, E, Fa, Jb, H, I, M |
| 25 | | A, E, Fa, Jb, H, I, M |
| 26 | | A, E, Fa, Jb, H, I, M |
| 27 | 836.4 | A, E, Fa, Jb, H, I, M |
| 28 | | A, E, Fa, Jb, H, I, M |
| 29 | 880.4 | A, E, Fa, Jb, H, I, M |
| 30 | 880.4 | A, E, Fa, Jb, H, I, M |
| 31 | 866.4 | A, E, Fa, Jb, H, I, M |
| 32 | | A, E, Fa, Jb, I, M |
| 33 | | A, E, Fa, Jb, H, I, M |
| 34 | 891.4 | A, E, Fa, Jb, K, I, M |
| 35 | 829.4 | A, E, Fa, Jb, K, I, M |
| 36 | | A, E, Fa, Jb, K, I, M |
| 37 | 859.4 | A, E, Fa, Jb, K, I, M |
| 38 | 871.4 | A, E, Fa, Jb, K, I, M |
| 39 | | A, E, Fa, Jb, I, M |
| 40 | 744.4 | A, E, Fa, Jb, I, M |
| 41 | 758.4 | A, E, Fa, Jb, I, M |
| 42 | 746.4 | A, D, I, M |
| 43 | 742.4 | A, D, I, M |
| 44 | | A, E, Fa, Jb, I, M |
| 45 | 748.4 | A, E, Fa, Jb, I, M |
| 46 | | A, E, Fa, Jb, I, M |
| 47 | 749.3 | A, E, Fa, Jb, I, M |
| 48 | | A, E, Fa, Jb, I, M |
| 49 | | A, E, Fa, Jb, I, M |
| 50 | 739.4 | A, D, I, M |
| 51 | | A, D, I, M |
| 52 | | A, D, I, M |
| 53 | | A, D, I, M |
| 54 | | A, D, I, M |
| 55 | | A, D, I, M |
| 56 | | A, D, I, M |
| 57 | | A, D, I, M |
| 58 | | A, D, I, M |
| 59 | | A, D, I, M |
| 60 | | A, D, I, M |
| 61 | | A, D, I, M |
| 62 | | A, D, I, M |
| 63 | | A, D, I, M |
| 64 | | A, D, I, M |
| 65 | | A, D, I, M |
| 66 | | A, D, I, M |
| 67 | | A, D, I, M |
| 68 | | A, D, I, M |
| 69 | | A, D, I, M |
| 70 | | A, D, I, M |
| 71 | | A, D, I, M |
| 72 | | A, D, I, M |
| 73 | | A, D, I, M |
| 74 | | A, D, I, M |
| 75 | | A, D, I, M |
| 76 | | A, D, I, M |
| 77 | | A, D, I, M |
| 78 | | A, D, I, M |
| 79 | | A, D, I, M |
| 80 | | A, D, I, M |
| 81 | | A, D, I, M |
| 82 | | A, D, I, M |
| 83 | | A, D, I, M |
| 84 | | A, D, I, M |
| 85 | | A, D, I, M |
| 86 | | A, D, I, M |
| 87 | | A, D, I, M |
| 88 | | A, D, I, M |
| 89 | | A, D, I, M |
| 90 | | A, D, I, M |
| 91 | | A, D, I, M |
| 92 | | A, D, I, M |
| 93 | | A, D, I, M |
| 94 | | A, D, I, M |
| 95 | | A, D, G, I, M |

TABLE S1-continued

| Compound No. | LC-MS (m/z) | Experimental Protocol |
|---|---|---|
| 96 |  | A, D, G, I, M |
| 97 |  | A, D, G, I, M |
| 98 |  | A, D, I, M |
| 99 |  | A, D, I, M |
| 100 | 847.4 | A, D, I, M |
| 101 | 843.6 | A, D, I, M |
| 102 | 843.6 | A, D, I, M |
| 103 | 817.4 | A, D, I, M |
| 104 | 857.4 | A, D, I, M |
| 105 | 817.4 | A, D, I, M |
| 106 | 927.2 | A, D, I, M |
| 107 | 927.2 | A, D, I, M |
| 108 | 877.4 | A, D, I, M |
| 109 | 858.4 | A, D, I, M |
| 110 | 934.4 | A, D, I, M |
| 111 | 865.4 | A, D, I, M |
| 112 | 934.4 | A, D, I, M |
| 113 | 886.4 | A, D, I, M |
| 114 | 902.4 | A, D, I, M |
| 115 | 833.4 | A, D, I, M |
| 116 | 877.4 | A, D, I, M |
| 117 | 851.4 | A, D, I, M |
| 118 | 857.4 | A, D, I, M |
| 119 | 927.2 | A, D, I, M |
| 120 | 908.4 | A, D, I, M |
| 121 | 888.4 | A, D, I, M |
| 122 | 801.4 | A, D, I, M |
| 123 | 905.4 | A, D, I, M |
| 124 | 843.4 | A, D, I, M |
| 125 | 857.4 | A, D, I, M |
| 126 | 827.4 | A, D, I, M |
| 127 | 887.4 | A, D, I, M |
| 128 | 881.4 | A, D, I, M |
| 129 | 1001.2 | A, D, I, M |
| 130 |  | A, D, I, M |
| 131 |  | A, D, I, M |
| 132 |  | A, D, I, M |
| 133 |  | A, D, I, M |
| 134 |  | A, D, G, I, M |
| 135 |  | A, D, G, I, M |
| 136 |  | A, D, G, I, M |
| 137 |  | A, D, G, I, M |
| 138 |  | A, D, I, M |
| 139 |  | A, D, I, M |
| 140 |  | A, D, I, M |
| 141 |  | A, D, I, M |
| 142 |  | A, D, I, M |
| 143 | 891.1 | A, D, I, M |
| 144 | 891.1 | A, D, I, M |
| 145 | 918.1 | A, D, I, M |
| 146 | 918.1 | A, D, I, M |
| 147 | 918.1 | A, D, I, M |
| 148 | 871.1 | A, D, I, M |
| 149 | 857.1 | A, D, I, M |
| 150 | 871.1 | A, D, I, M |
| 151 | 850.0 | A, D, I, M |
| 152 | 872.1 | A, D, I, M |
| 153 | 869.2 | A, D, I, M |
| 154 | 900.2 | A, D, I, M |
| 155 | 859.4 | A, D, I, M |
| 156 | 843.4 | A, D, I, M |
| 157 | 916.2 | A, D, I, M |
| 158 |  | A, D, I, M |
| 159 |  | A, D, I, M |
| 160 |  | A, D, I, M |
| 161 |  | A, D, I, M |
| 162 |  | A, D, I, M |
| 163 |  | A, D, I, M |
| 164 |  | A, D, I, M |
| 165 |  | A, D, I, M |
| 166 |  | A, D, I, M |
| 167 |  | A, D, I, M |
| 168 |  | A, D, I, M |
| 169 |  | A, D, I, M |
| 170 |  | A, D, I, M |
| 171 |  | A, D, I, M |
| 172 |  | A, D, I, M |
| 173 |  | A, D, I, M |
| 174 |  | A, D, I, M |
| 175 |  | A, D, I, M |
| 176 |  | A, D, I, M |
| 177 |  | A, D, I, M |
| 178 |  | A, D, I, M |
| 179 |  | A, D, G, I, M |
| 180 |  | A, D, G, I, M |
| 181 |  | A, D, G, I, M |
| 182 |  | A, D, G, I, M |
| 183 |  | A, D, G, I, M |
| 184 |  | A, D, G, I, M |
| 185 |  | A, D, G, I, M |
| 186 | 869.3 | A, D, I, M |
| 187 | 842.4 | A, D, I, M |
| 188 | 842.1 | A, D, I, M |
| 189 | 902.1 | A, D, I, M |
| 190 | 909.1 | A, D, I, M |
| 191 | 948.4 | A, D, G, I, M |
| 192 | 968.4 | A, D, G, I, M |
| 193 | 861.4 | A, D, I, M |
| 194 | 857.4 | A, D, I, M |
| 195 | 888.4 | A, D, I, M |
| 196 | 702.4 | A, D, I, M |
| 197 |  | A, D, I, M |
| 198 |  | A, D, I, M |
| 199 |  | A, D, I, M |
| 200 |  | A, D, I, M |
| 201 |  | A, D, I, M |
| 202 |  | A, D, I, M |
| 203 |  | A, D, I, M |
| 204 |  | A, D, I, M |
| 205 |  | A, D, I, M |
| 206 | 967.2 | A, D, G, I, M |
| 207 | 948.2 | A, D, G, I, M |
| 208 | 948.2 | A, D, G, I, M |
| 209 |  | A, D, G, I, M |
| 210 |  | A, D, I, M |
| 211 |  | A, D, I, M |
| 212 |  | A, D, I, M |
| 213 |  | A, D, I, M |
| 214 |  | A, D, I, M |
| 215 |  | A, D, I, M |
| 216 | 900.4 | A, D, I, M |
| 217 |  | A, D, I, M |
| 218 |  | A, C, D, I, M |
| 219 |  | A, D, I, M |
| 220 |  | A, D, I, M |
| 221 | 893.1 | A, B, D, I, M |
| 222 | 915.2 | A, B, D, I, M |
| 223 | 891.1 | A, D, I, M |
| 224 |  | A, D, I, M |
| 225 |  | A, D, I, M |
| 226 |  | A, D, I, M |
| 227 |  | A, D, I, M |
| 228 |  | A, D, I, M |
| 229 | 857.4 | A, D, I, M |
| 230 | 870.4 | A, D, I, M |
| 231 |  | A, D, I, M |
| 232 | 886.2 | A, B, D, I, M |
| 233 |  | A, C, D, I, M |
| 234 |  | A, D, I, M |
| 235 |  | A, D, G, I, M |
| 236 |  | A, D, I, M |
| 237 | 952.0 | A, D, I, M |
| 238 |  | A, D, I, M |
| 239 | 890.2 | A, D, I, M |
| 240 |  | A, D, I, M |
| 241 |  | A, D, I, M |
| 242 |  | A, D, I, M |
| 243 |  | A, D, G, I, M |
| 244 | 999.3 | A, D, G, I, M |
| 245 |  | A, D, G, I, M |
| 246 |  | A, D, I, M |
| 247 |  | A, D, I, M |
| 248 |  | A, D, G, I, M |
| 249 |  | A, D, G, I, M |
| 250 | 900.2 | A, D, I, M |
| 251 | 886.1 | A, D, I, M |

TABLE S1-continued

| Compound No. | LC-MS (m/z) | Experimental Protocol |
|---|---|---|
| 252 | | A, D, I, M |
| 253 | | A, D, I, M |
| 254 | | A, D, I, M |
| 255 | 998.4 | A, D, I, M |
| 256 | 948.6 | A, D, G, I, M |
| 257 | 978.6 | A, D, G, I, M |
| 258 | 1008.6 | A, D, G, I, M |
| 259 | 1032.6 | A, D, G, I, M |
| 260 | 998.4 | A, D, I, M |
| 261 | 978.4 | A, D, G, I, M |
| 262 | 1032.4 | A, D, G, I, M |
| 263 | 886.6 | A, D, I, M |
| 264 | 886.6 | A, D, I, M |
| 265 | 976.6 | A, D, G, I, M |
| 266 | 1000.6 | A, D, G, I, M |
| 267 | 984.5 | A, D, G, I, M |
| 268 | 976.6 | A, D, G, I, M |
| 269 | 1012.6 | A, D, G, I, M |
| 270 | | A, C, D, J, M |
| 271 | | A, D, G, I, M |
| 272 | | A, D, G, I, M |
| 273 | 1005.3 | A, D, G, I, M |
| 274 | | A, D, I, M |
| 275 | | A, D, I, M |
| 276 | | A, D, G, I, M |
| 277 | | A, D, I, M |
| 278 | | A, D, I, M |
| 279 | | A, D, I, M |
| 280 | 898.1 | A, D, I, M |
| 281 | | A, D, I, M |
| 282 | | A, D, I, M |
| 283 | | A, D, I, M |
| 284 | | A, D, I, M |
| 285 | | A, D, I, M |
| 286 | | A, D, G, I, M |
| 287 | | A, D, G, I, M |
| 288 | | A, D, I, M |
| 289 | | A, D, I, M |
| 290 | | A, D, I, M |
| 291 | | A, D, I, M |
| 292 | | A, D, G, I, M |
| 293 | 949.2 | A, D, G, I, M |
| 294 | | A, D, G, I, M |
| 295 | | A, D, I, M |
| 296 | | A, D, I, M |
| 297 | | A, D, G, I, M |
| 298 | 1012.6 | A, D, G, I, M |
| 299 | 1005.4 | A, D, G, I, M |
| 300 | 915.2 | A, B, D, I, M |
| 301 | 915.2 | A, B, D, I, M |
| 302 | 893.2 | A, B, D, I, M |
| 303 | 1047.3 | A, B, D, I, M |
| 304 | 898.2 | A, B, D, I, M |
| 305 | 898.2 | A, B, D, I, M |
| 306 | | A, D, G, I, M |
| 307 | | A, D, I, M |
| 308 | | A, B, D, I, M |
| 309 | 916.2 | A, B, D, I, M |
| 310 | 916.2 | A, B, D, I, M |
| 311 | 900.2 | A, B, D, I, M |
| 312 | 904.2 | A, B, D, I, M |
| 313 | 918.2 | A, B, D, I, M |
| 314 | 954.1 | A, B, D, I, M |
| 315 | 968.1 | A, B, D, I, M |
| 316 | 929.2 | A, B, D, I, M |
| 317 | | A, D, G, I, M |
| 318 | 999.4 | A, D, G, I, M |
| 319 | 808.6 | A, D, I, M |
| 320 | 917.4 | A, D, G, I, M |
| 321 | 1032.4 | A, D, G, I, M |
| 322 | 978.5 | A, D, G, I, M |
| 323 | | A, B, D, G, I, M |
| 324 | | A, D, I, M |
| 325 | 914.3 | A, B, D, I, M |
| 326 | 928.2 | A, B, D, I, M |
| 327 | 870.2 | A, B, D, I, M |
| 328 | 912.2 | A, B, D, I, M |
| 329 | 900.4 | A, B, D, I, M |
| 330 | 942.5 | A, B, D, I, M |
| 331 | 852.5 | A, B, D, I, M |
| 332 | 884.6 | A, B, D, I, M |
| 333 | 867.2 | A, D, I, M |
| 334 | 900.4 | A, B, D, I, M |
| 335 | 884.5 | A, B, D, I, M |
| 336 | | A, D, I, M |
| 337 | | A, D, G, I, M |
| 338 | | A, D, G, I, M |
| 339 | | A, D, G, I, M |
| 340 | | A, D, G, I, M |
| 341 | | A, D, G, I, M |
| 342 | | A, D, I, M |
| 343 | | A, D, G, I, M |
| 344 | | A, D, G, I, M |
| 345 | | A, D, G, I, M |
| 346 | | A, D, G, I, M |
| 347 | | A, D, G, I, M |
| 348 | | A, D, G, I, M |
| 349 | | A, D, G, I, M |
| 350 | | A, D, G, I, M |
| 351 | | A, D, G, I, M |
| 352 | | A, D, G, I, M |
| 353 | | A, D, G, I, M |
| 354 | | A, D, G, I, M |
| 355 | | A, D, G, I, M |
| 356 | | A, D, G, I, M, L, M |
| 357 | | A, D, I, M |
| 358 | | A, D, I, M |
| 359 | | A, D, I, M |
| 360 | | A, D, I, M |
| 361 | | A, D, I, M |
| 362 | | A, D, G, I, M |
| 363 | | A, D, G, I, M |
| 364 | | A, D, G, I, M |
| 365 | | A, D, G, I, M |
| 366 | | A, D, G, I, M |
| 367 | | A, D, G, I, M |
| 368 | | A, D, G, I, M |
| 369 | | A, D, G, I, M |
| 370 | | A, D, G, I, M |
| 371 | | A, D, G, I, M |
| 372 | | A, D, G, I, M |
| 373 | | A, D, G, I, M |
| 374 | | A, D, G, I, M |
| 375 | | A, D, G, I, M |
| 376 | | A, D, G, I, M |
| 377 | | A, D, G, I, M |
| 378 | | A, D, G, I, M |
| 379 | | A, D, G, I, M |
| 380 | | A, D, G, I, M |
| 381 | | A, D, G, I, M |
| 382 | | A, D, G, I, M |
| 383 | | A, D, G, I, M |
| 384 | | A, D, G, I, M |
| 385 | | A, D, G, I, M |
| 386 | | A, D, G, I, M |
| 387 | | A, B, D, I, M |
| 388 | | A, B, D, G, I, M |
| 389 | 985.2 | A, C, D, G, I, M |
| 398 | | A, D, I, M |
| 399 | | A, D, I, M |
| 400 | | A, D, I, M |
| 401 | | A, D, I, M |
| 402 | | A, D, I, M |
| 403 | | A, D, I, M |
| 404 | | A, D, I, M |
| 405 | | A, E, Fa, Jb, I, M |
| 406 | | A, E, Fa, Jb, I, M |
| 407 | | A, D, I, M |
| 408 | | A, D, I, M |
| 409 | | A, D, I, M |
| 410 | | A, D, I, M |
| 411 | | A, E, Fa, Jb, I, M |
| 412 | | A, D, I, M |
| 413 | | A, E, Fa, Jb, I, M |
| 414 | | A, E, Fa, Jb, I, M |
| 415 | | A, D, I, M |

TABLE S1-continued

| Compound No. | LC-MS (m/z) | Experimental Protocol |
|---|---|---|
| 416 | | A, D, I, M |
| 417 | | A, D, I, M |
| 418 | | A, D, I, M |
| 419 | | A, D, I, M |
| 420 | | A, D, I, M |
| 421 | | A, D, I, M |
| 422 | | A, D, I, M |
| 423 | | A, D, I, M |
| 424 | | A, D, I, M |
| 425 | | A, D, I, M |
| 426 | | A, D, I, M |
| 427 | | A, D, I, M |
| 428 | | A, D, I, M |
| 429 | | A, D, I, M |
| 430 | | A, D, I, M |
| 431 | | A, D, I, M |
| 432 | | A, D, I, M |
| 433 | | A, D, G, I, M |
| 434 | | A, D, G, I, M |
| 435 | | A, D, G, I, M |
| 436 | | A, D, G, I, M |
| 437 | | A, D, G, I, M |
| 438 | | A, D, G, I, M |
| 439 | | A, D, I, M |
| 440 | | A, D, I, M |
| 441 | | A, D, I, M |
| 442 | | A, B, D, I, M |
| 443 | | A, D, I, M |
| 444 | | A, D, I, M |
| 445 | | A, D, I, M |
| 446 | | A, D, I, M |
| 447 | | A, D, I, M |
| 448 | | A, D, I, M |
| 449 | | A, D, I, M |
| 450 | | A, D, I, M |
| 451 | | A, C, D, I, M |
| 452 | | A, C, D, I, M |
| 453 | | A, C, D, I, M |
| 454 | | A, C, D, I, M |
| 455 | | A, C, D, I, M |

The invention claimed is:

1. A compound of formula (I):

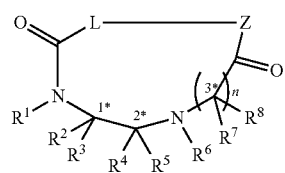

wherein $R^1$ is H; $C_1$-$C_6$ alkyl; aryl; heteroaryl; alkenyl; or heterocycle; all of which are optionally substituted with one or more substituents selected from the group consisting of hydroxyl, cyano, alkyl, alkoxy, vinyl, alkenyl, alkynyl, formyl, haloalkyl, halide, aryl, heteroaryl, amide, acyl, ester, ether, thioether, thioalkoxy, phosphino, and —$NR_aR_b$, wherein $R_a$ and $R_b$ are independently selected from $C_1$-$C_6$ alkyl, aryl or benzyl;

and where the one or more substituents is not alkyl when $R^1$ is $C_1$-$C_6$ alkyl;

$R^2$ and $R^3$ are each independently an amino acid side chain of a proteinogenic or a non-proteinogenic alpha-amino acid, or $R^2$ and $R^3$ are covalently linked to each other to form a ring;

$R^4$ and $R^5$ are each independently H; $C_1$-$C_6$ alkyl; aryl; heteroaryl; alkenyl; heterocycle; acids of the formula —C(O)OH; esters of the formula —C(O)OR* wherein R* is selected from alkyl and aryl; amides of the formula —C(O)NRR*, wherein R and R* are independently selected from H, alkyl and aryl; —CH$_2$C(O)R, wherein R is selected from —OH, $C_1$-$C_6$ alkyl, aryl, —$C_1$-$C_6$ alkyl-aryl, or NR$_a$R$_b$, where R$_a$ and R$_b$ are independently selected from $C_1$-$C_6$ alkyl, aryl or benzyl; or —C(O)R$_c$, wherein R$_c$ is selected from $C_1$-$C_6$ alkyl, aryl or —$C_1$-$C_6$ alkyl-aryl; or —$C_1$-$C_6$ alkyl-OR$_d$, wherein R$_d$ is an OH group or a protecting group selected from the group consisting of formyl, acetyl, propionyl, pivaloyl, t-butylacetyl, 2-chloro-acetyl, 2-bromoacetyl, trifluoroacetyl, trichloroacetyl, o-nitrophenoxyacetyl, alpha.-chlorobutyryl, benzoyl, 4-chlorobenzoyl, 4-bromobenzoyl, 4-nitrobenzoyl, benzenesulfonyl, p-toluenesulfonyl, benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, alpha.-, alpha.-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl, benzyl, triphenylmethyl, benzyloxymethyl, and trimethylsilyl; all of which are optionally substituted with one or more substituents selected from the group consisting of hydroxyl, cyano, alkyl, alkoxy, vinyl, alkenyl, alkynyl, formyl, haloalkyl, halide, aryl, heteroaryl, amide, acyl, ester, ether, thioether, thioalkoxy, phosphino, and —NR$_a$R$_b$, wherein R$_a$ and R$_b$ are independently selected from $C_1$-$C_6$alkyl, aryl or benzyl; and where, when $R^4$, $R^5$, R, R$_a$, R$_b$ or R$_c$ is $C_1$-$C_6$ alkyl, the one or more substituents is not alkyl at that position; and wherein the one or more substituents is not —NR$_a$R$_b$ when R is —NR$_a$R$_b$;

or $R^2$ or $R^3$ are covalently linked to $R^1$ to form a cyclic secondary amine, and/or to $R^4$ or $R^5$ to form a ring, or $R^4$ and $R^5$ are covalently linked to each other to form a ring;

$R^6$ is H, $C_1$-$C_6$ alkyl, benzyl, alkenyl, $C_1$-$C_6$ alkyloxy; aryl; heteroaryl; heterocycle; —C(O)R**, wherein R** is independently selected from alkyl, aryl, heteroaryl, amino, aminoalkyl, aminoaryl, aminoheteroaryl, alkoxy, aryloxy, heteroaryloxy; —CH$_2$C(O)R; or —C(O)R$_c$; all of which are optionally substituted with one or more substituents selected from the group consisting of hydroxyl, cyano, alkyl, alkoxy, vinyl, alkenyl, alkynyl, formyl, haloalkyl, halide, aryl, heteroaryl, amide, acyl, ester, ether, thioether, thioalkoxy, phosphino, and —NR$_a$R$_b$, wherein R$_a$ and R$_b$ are independently selected from $C_1$-$C_6$ alkyl, aryl or benzyl, and where the one or more substituents is not alkyl when $R^6$ is $C_1$-$C_6$ alkyl, or $R^6$ forms, along with $R^7$ or $R^8$, a cyclic side chain of a proteinogenic or a non-proteinogenic amino acid having, the N-terminus thereof being the N—$R^6$, wherein the proteinogenic or a non-proteinogenic amino acid is optionally substituted with a substituent selected from the group consisting of hydroxyl, cyano, alkyl, alkoxy, vinyl, alkenyl, alkynyl, formyl, haloalkyl, halide, aryl, heteroaryl, amide, acyl, ester, ether, thioether, thioalkoxy, phosphino, and —NR$_a$R$_b$, wherein R$_a$ and R$_b$ are independently selected from $C_1$-$C_6$ alkyl, aryl or benzyl;

$R^7$ and $R^8$ are independently selected from the amino acid side chains of a proteinogenic or a non-proteinogenic alpha-amino acid having the N-terminus thereof being the N—$R^6$, or $R^7$ or $R^8$ forms a cyclic side chain with $R^6$;

stereocenters 1*, 2* and 3*, where present, are each independently selected from R and S;

n is 1, 2, 3, or 4 and where n is 2-4, each $R^7$ and each $R^8$ are independent of each other; and wherein Z is an amino terminus of an amino acid; —C=O— adjacent L is the carboxy terminus of an amino acid; and L along with Z and —C=O— is a peptide having the following formula:

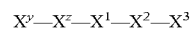

wherein $X^y$ and $X^z$ are each independently a proteinogenic or non-proteinogenic amino acid, or $X^z$ is absent;

$X^1$ is Leucine or tert-butyl-Ala;

$X^2$ is Asp; and $X^3$ is an amino acid selected from the group consisting of Thr, Thr(OBn), Thr(OEt), Pen, MeThr, alloThr, Abu, Val, Ile and AlloIle, or a pharmaceutically acceptable salt thereof.

2. The compound of claim 1 or a pharmaceutically acceptable salt thereof, wherein $R^1$ is H.

3. The compound of claim 1 or a pharmaceutically acceptable salt thereof, wherein $R^2$ or $R^3$ is covalently linked to $R^1$ to form proline having NR$^1$ as the N-terminus.

4. The compound of claim 1 or a pharmaceutically acceptable salt thereof, wherein $R^2$ and $R^3$ are not both H.

5. The compound of claim 1 or a pharmaceutically acceptable salt thereof, wherein $R^2$ and $R^3$ are each independently selected from the group consisting of amino acid side chains of a proteinogenic or a non-proteinogenic alpha-amino acids.

6. The compound of claim 1 or a pharmaceutically acceptable salt thereof, wherein $R^2$ and $R^3$ are H and CH$_3$ respectively or vice versa.

7. The compound of claim 1 or a pharmaceutically acceptable salt thereof, wherein $R^2$ or $R^3$ is —CH$_2$—S—$R^5$, wherein $R^5$ is selected from $C_1$-$C_6$ alkyl; $C_1$-$C_6$ amino alkyl; aryl; heteroaryl; alkenyl; or heterocycle; all of which are optionally substituted with one or more substituents selected from the group consisting of hydroxyl, cyano, alkyl, alkoxy, vinyl, alkenyl, alkynyl, formyl, haloalkyl, halide, aryl, heteroaryl, amide, acyl, ester, ether, thioether, thioalkoxy, phosphino, and —NR$_a$R$_b$, wherein R$_a$ and R$_b$ are independently selected from $C_1$-$C_6$ alkyl, aryl or benzyl; wherein the one or more substituents is not alkyl when $R^5$ is $C_1$-$C_6$ alkyl; preferably $R^5$ is phenyl or phenyl substituted with $C_1$-$C_6$ alkyl, halogen; or $C_1$-$C_6$ amino alkyl.

8. The compound of claim 1 or a pharmaceutically acceptable salt thereof, wherein $R^4$ and $R^5$ are not both H.

9. The compound of claim 1 or a pharmaceutically acceptable salt thereof, wherein R and R* are not both H.

10. The compound of claim 1 or a pharmaceutically acceptable salt thereof, wherein $R^4$ and $R^5$ are each independently H, or C(O)—$NHR^1$, wherein $R^1$ is H or a $C_1$-$C_6$ alkyl.

11. The compound of claim 10 or a pharmaceutically acceptable salt thereof, wherein $R^1$ is tert-butyl.

12. The compound of claim 10 or a pharmaceutically acceptable salt thereof wherein $R^1$ is H.

13. The compound of claim 1 or a pharmaceutically acceptable salt thereof, wherein $R^6$ is H.

14. The compound of claim 1 or a pharmaceutically acceptable salt thereof, wherein $R^6$ and either $R^7$ or $R^8$ form a ring resulting in a proline residue having N—$R^6$ as its N-terminus.

15. The compound of claim 1 or a pharmaceutically acceptable salt thereof, wherein n is 1.

16. The compound of claim 1 or a pharmaceutically acceptable salt thereof, wherein Z along with L and —C=O is any one of SEQ ID NOs. 1-380.

17. The compound of claim 1 or a pharmaceutically acceptable salt thereof, wherein $X^1$ is Leu.

18. The compound of claim 1 or a pharmaceutically acceptable salt thereof, wherein $X^2$ is Asp.

19. The compound of claim 1 or a pharmaceutically acceptable salt thereof, wherein $X^3$ is Thr.

20. The compound of claim 1 or a pharmaceutically acceptable salt thereof, wherein $X^3$ is Val.

21. The compound of claim 1 or a pharmaceutically acceptable salt thereof, wherein $X^3$ is Ile.

22. The compound of claim 1 or a pharmaceutically acceptable salt thereof, wherein $X^y$ and $X^z$ are each independently a proteinogenic or non-proteinogenic alpha-amino acid.

23. The compound of claim 1 or a pharmaceutically acceptable salt thereof, wherein $X^z$ is a proteinogenic or non-proteinogenic beta-amino acid.

24. The compound of claim 1 or a pharmaceutically acceptable salt thereof, wherein $X^z$ is betaHomoLys or MethylbetaHomoLys.

25. The compound of claim 1 or a pharmaceutically acceptable salt thereof, wherein $X^y$ and $X^z$ are each a primary amino acid.

26. The compound of claim 1 or a pharmaceutically acceptable salt thereof, wherein $X^y$ and $X^z$ are selected from the group consisting of:

| $X^y$ | $X^z$ |
|---|---|
| Y | absent |
| H | absent |
| Y | absent |
| Y | absent |
| F | absent |
| HomoPhe | absent |
| Cha | absent |
| W | absent |
| 1Nal | absent |
| 2Nal | absent |
| W | absent |
| Bip | absent |
| Tyr(OPh) | absent |
| 1Nal | absent |
| 2Nal | absent |
| 2Nal | absent |
| W | absent |
| Bip | absent |
| Tyr(2-tolyl diaryl ether) | absent |
| Tyr(4-CF3 diaryl ether) | absent |
| Tyr(4-methoxy diaryl ether) | absent |
| Tyr(4-fluoro diaryl ether) | absent |
| Tyr(2-methoxy diaryl ether) | absent |
| Tyr(3-methoxy diaryl ether) | absent |
| Tyr(3-fluoro diaryl ether) | absent |
| Tyr(3,4-difluoro diaryl ether) | absent |
| Tyr(3-methyl diaryl ether) | absent |
| Tyr(3,4-dimethyl diaryl ether) | absent |
| Tyr(4-CO2Me diaryl ether) | absent |
| Tyr(3-CO2Me diaryl ether) | absent |
| Tyr(4-CO2H diaryl ether) | absent |
| F | absent |
| metaY(Opr) | absent |
| Orn(benzamide) | absent |
| Orn(acetamide) | absent |
| Orn(methanesulfonamide) | absent |
| Orn(ethylcarbamate) | absent |
| Orn(pentyl amide) | absent |
| R | absent |
| F | absent |
| F | absent |
| dTyr | absent |
| dTic | absent |
| [3-(3'-pyridyl)-Ala] | absent |
| F | absent |
| Bip | absent |
| [3-(3'-pyridyl)-Ala] | absent |
| Y | absent |
| Y | absent |
| dArg | absent |
| dPip | absent |
| [3-(4-thiazolyl)-Ala] | absent |
| Y | absent |
| (4-aza-Phe) | absent |
| Y | absent |
| (vinyl-Br-Leu) | absent |
| Hyp(OBn) | absent |
| Hyp(OBn) | absent |
| Dap(Cbz) | absent |
| His(Bn) | absent |
| (4-amino-Phe) | absent |
| (4-aza-dPhe) | absent |
| Hyp | absent |
| dTrp | absent |
| M | absent |
| dMet | absent |
| (4-guanidino-Phe) | absent |
| (3-aza-Phe) | absent |
| dTic | absent |
| (3-aza-dPhe) | absent |
| Nva | absent |
| dNle | absent |
| dLys | absent |
| dPro | absent |
| dOrn | absent |
| (3-benzothienyl-Ala) | absent |
| dTyr(OAllyl) | absent |
| dSer(OBn) | absent |
| [3-(4-thiazolyl)-dAla] | absent |
| (3-benzothienyl-dAla) | absent |
| [3-(2-thienyl)-dAla] | absent |
| (4-aminomethyl-Phe) | absent |
| dOrn(dimethyl) | absent |
| (4-amino-dPhe) | absent |
| (4-aminomethyl-dPhe) | absent |
| dTyr(OBn) | absent |
| P | absent |
| cycloLeu | absent |
| Aic | absent |
| Tyr(OAllyl) | absent |

-continued

| X^y | X^z |
|---|---|
| Chg | absent |
| K | absent |
| (2-aza-dPhe) | absent |
| (2-aza-Phe) | absent |
| [2-(2-pyridyl)-4-thiazolyl-Ala] | absent |
| [2-(3-pyridyl)-4-thiazolyl-Ala] | absent |
| [2-(4-pyridyl)-4-thiazolyl-Ala] | absent |
| dTiq | absent |
| [1-(S)-isoindoline-carboxylic acid] | absent |
| Y | dThr |
| Y | P |
| Y | dPro |
| Y | Sar |
| Y | cycloLeu |
| Y | Sar |
| (3-iodo-Phe) | Sar |
| (4-iodo-Phe) | Sar |
| (3,3-diphenyl-Ala) | Sar |
| F | dLys |
| Bip | dLys |
| [3-(4-thiazolyl)-Ala] | dLys |
| (3,3-diphenyl-Ala) | dLys |
| Y | dLys |
| Y | dArg |
| Y | dSer |
| Bip | Sar |
| 1Nal | Sar |
| Y | Pip |
| (2-iodo-Phe) | Sar |
| 1Nal | dLys |
| Y | dLys |
| F | Sar |
| Y | dTic |
| Y | dPro |
| Y | dPip |
| F | dPro |
| (3,4-dimethoxy-Phe) | dPro |
| (3,4,5-trifluoro-Phe) | dPro |
| (3,5-dibromo-Tyr) | dPro |
| F | dPip |
| [3-(4-thiazolyl)-Ala] | dPip |
| (4-aminomethyl-Phe) | dPip |
| [2-iodo-Phe] | dPip |
| (2-phenyl-Phe) | dPip |
| [2-(2-methoxy-phenyl)-Phe] | dPip |
| [2-(3-methoxy-phenyl)-Phe] | dPip |
| [2-(4-methoxy-phenyl)-Phe] | dPip |
| Bip | dPip |
| Y | Hyp |
| Y | dHyp |
| Y | (cis-dHyp) |
| dTyr | dPip |
| 1Nal | dPip |
| 2Nal | dPip |
| (4-aminomethyl-Phe) | dTic |
| (3-aminomethyl-Phe) | dTic |
| (3-aminomethyl-dPhe) | dTic |
| MeTyr | dPip |
| Y | dPip |
| Y | dPip |
| [3-(4-thiazolyl)-Ala] | dHyp |
| (4-aminomethyl-Phe) | dHyp |
| Y | dPip |
| Y | dMeLys |
| Y | dNle |
| F | dHyp |
| Y | dMeArg |
| Y | G |
| Y | A |
| Y | dAla |
| M | G |
| Tyr(OAllyl) | Sar |
| Tyr(OAllyl) | G |
| [3-(4-thiazolyl)-Ala] | Sar |
| (4-aminomethyl-Phe) | G |
| Tyr(OAllyl) | dVal |
| Tyr(OAllyl) | dSer |
| Tyr(OAllyl) | dAla |
| Tyr(OAllyl) | P |
| Tyr(OAllyl) | dPro |
| [3-(4-thiazolyl)-Ala] | dVal |
| [3-(4-thiazolyl)-Ala] | dSer |
| [3-(4-thiazolyl)-Ala] | dAla |
| [3-(4-thiazolyl)-Ala] | P |
| [3-(4-thiazolyl)-Ala] | dPro |
| (4-aminomethyl-Phe) | P |
| (4-aminomethyl-Phe) | dPro |
| cycloLeu | P |
| [2-(2-pyridyl)-4-thiazolyl-Ala] | Sar |
| [2-(2-pyridyl)-4-thiazolyl-Ala] | dPro |
| [2-(3-pyridyl)-4-thiazolyl-Ala] | Sar |
| [2-(3-pyridyl)-4-thiazolyl-Ala] | dPro |
| [2-(4-pyridyl)-4-thiazolyl-Ala] | dPro |
| [3-(2-aminobenzyl-4-thiazolyl)-Ala] | Sar |
| [2-(amino-benzyl)-4-thiazolyl-Ala] | dPro |
| dTyr | dPip |
| (2-aminomethyl-Phe) | Aze |
| Y | dPip |
| (3-aminomethyl-Phe) | dTic |
| (2,4-dichloro-Phe) | dPip |
| (3-phenyl-dPhe) | dPip |
| [3-(5-quinolinyl)-dPhe] | dPip |
| Y | betaHomoLys |
| Y | betaHomoPro |
| Y | betaHomoLys |
| Y | 2Abz |
| F | betaHomoLys |
| [3-(4-thiazolyl)-Ala] | betaHomoLys |
| (4-aminomethyl-Phe) | betaHomoLys |
| Y | betaHomoLys |
| MeTyr | dbetaHomoLys |
| 1Nal | betaHomoLys |
| 2Nal | betaHomoLys |
| Bip | betaHomoLys |
| (2-iodo-Phe) | betaHomoLys |
| [2-(2,5-dimethyl-isoxazole)-Phe] | betaHomoLys |
| (2-phenyl-Phe) | betaHomoLys |
| (2-phenyl-Phe) | betaHomoLys |
| [(2-piperazinyl-2-Phenyl)-Phe] | betaHomoLys |
| Cha | betaHomoLys |
| W | betaHomoLys |
| dTrp | betaHomoLys |
| (3-aminomethyl-Phe) | betaHomoLys |
| (4-aminomethyl-dPhe) | betaHomoLys |
| (4-aminomethyl-Phe) | betaHomoLys |
| Y | dbetaHomoLys |
| dArg | betaHomoLys |
| (4-aminomethyl-Phe)-reduced | betaHomoLys |
| [3-(4-thiazolyl)-Ala] | dbetaHomoLys |
| F | dbetaHomoLys |
| [3-(4-thiazolyl)-Ala] | MebetaHomoLys |
| (4-aminomethyl-Phe) | MebetaHomoLys |
| [3-(4-thiazolyl)-Ala] | betaHomoLys |
| Tic | betaHomoLys |
| dTic | betaHomoLys |
| dTic | dbetaHomoLys |
| Y | betaHomoIle |
| (4-aminomethyl-Phe) | betaHomoPro |
| Y | dbetaHomoPro |
| (4-aminomethyl-Phe) | dbetaHomoPro |
| R | betaHomoLys |
| F | MebetaHomoLys |
| Phe-reduced | betaHomoLys |
| (3-aminomethyl-dPhe) | betaHomoLys |
| [2-[3-(1-piperazinyl)phenyl]-Phe]-betaHomoLys | |
| [3-(4-thiazolyl)-dAla] | betaHomoLys |
| (2-bromo-Phe) | betaHomoLys |
| (2-chloro-Phe) | betaHomoLys |
| (2-fluoro-Phe) | betaHomoLys |
| (2-CF3-Phe) | betaHomoLys |
| (2,4-dichloro-Phe) | betaHomoLys |
| (2-aminomethyl-Phe) | betaHomoLys |
| [2-(4-quinolinyl)-Phe] | betaHomoLys |

| X^y | X^z |
|---|---|
| [2-(5-quinolinyl)-Phe] | betaHomoLys |
| [2-(3-quinolinyl)-Phe] | betaHomoLys |
| dhomoPhe | betaHomoLys |
| (2-iodo-dPhe) | betaHomoLys |
| (2-phenyl-dPhe) | betaHomoLys |
| [(2-piperazinyl-2-Phenyl)-dPhe] | betaHomoLys |
| Y | betaHomoLys |
| Y | betaHomoLys |
| dTyr | betaHomoLys |
| (4-aminomethyl-dPhe) | betaHomoLys |
| (4-aminomethyl-Phe) | betaHomoLys |
| (3-iodo-Phe) | betaHomoLys |
| (3-phenyl-Phe) | betaHomoLys |
| [3-(2-methoxy-phenyl)-Phe] | betaHomoLys |
| [3-(2,6-dimethoxy-phenyl)-Phe] | betaHomoLys |
| [3-(2-trifluoromethoxy-phenyl)-Phe] | betaHomoLys |
| (4-iodo-Phe) | betaHomoLys |
| [4-(2-methoxy-phenyl)-Phe] | betaHomoLys |
| [4-(2-trifluoromethoxy-phenyl)-Phe] | betaHomoLys |
| alphaMePhe | betaHomoLys |
| MePhe | betaHomoLys |
| [3-(2,6-dimethyl-phenyl)-Phe] | betaHomoLys |
| [3-(quinolin-4-yl)-Phe] | betaHomoLys |
| [3-(3,4-difluoro-phenyl)-Phe] | betaHomoLys |
| [4-(2,6-dimethyl-phenyl)-Phe] | betaHomoLys |
| [4-(2-chloro-6-methoxy-phenyl)-Phe] | betaHomoLys |
| [3-(4-thiazolyl)-Ala]-reduced | betaHomoLys |
| [2-[4-(1-piperazinyl)phenyl]-Phe] | betaHomoLys |
| [2-(2,6-dimethylphenyl)-Phe] | betaHomoLys |
| [2-(benzothiazol-5-yl)-Phe] | betaHomoLys |
| HomoPhe | betaHomoLys |
| (piperidine-4-amino-4-carboxylic acid) | betaHomoLys |
| [2-(2,5-dimethyl-isoxazole)-dPhe] | betaHomoLys |
| dTyr | betaHomoLys |
| (4-aminomethyl-dPhe) | betaHomoLys |
| [2-(2-chloro-6-methoxyphenyl)-Phe] | betaHomoLys |
| 2Igl | betaHomoLys |
| d2Igl | betaHomoLys |
| Atc | betaHomoLys |
| Y | betaHomoLys |
| dTyr | betaHomoLys |
| (4-aminomethyl-Phe) | betaHomoLys |
| [2-[2,5-Bis(trifluoromethyl)phenyl]-Phe] | betaHomoLys |
| [2-[2,5-Bis(trifluoromethyl)phenyl]-Phe] | betaHomoLys |
| Aic | betaHomoLys |
| P | betaHomoLys |
| dPro | betaHomoLys |
| Pip | betaHomoLys |
| [2-(3-Pyridyl)-Phe] | betaHomoLys |
| [2-(4-Pyridyl)-Phe] | betaHomoLys |
| [2-(3-bromo-2-Pyridyl)-Phe] | betaHomoLys |
| Y | dbetaHomoLys |
| (N-benzyl-Gly) | betaHomoLys |
| [2-(2-bromo-3-Pyridyl)-Phe] | betaHomoLys |
| [3-(2-chloro-6-methoxy-phenyl)-Phe] | betaHomoLys |
| [3-(benzothiazol-5-yl)-Phe] | betaHomoLys |
| (2-aminomethyl-Phe) | MebetaHomoLys |
| (2-aminomethyl-dPhe) | MebetaHomoLys |
| [3-(4-thiazolyl)-dAla] | MebetaHomoLys |
| [2-(2-trifluoromethoxy-phenyl)-dPhe] | MebetaHomoLys |
| Tic | MebetaHomoLys |
| dTic | MebetaHomoLys |
| [2-(5-quinolinyl)-dPhe] | betaHomoLys |
| Y | betaHomoLys |
| Y | MebetaHomoLys |
| MeTyr | MebetaHomoLys |
| MeTyr | MebetaHomoLys |
| MePhe | MebetaHomoLys |
| (2-fluoro-Phe) | MebetaHomoLys |
| (2-fluoro-MePhe) | MebetaHomoLys |
| (2,4-dichloro-Phe) | MebetaHomoLys |
| (2,4-dichloro-MePhe) | MebetaHomoLys |
| (2-aminomethyl-MePhe) | MebetaHomoLys |
| [3-(2,6-dimethoxy-phenyl)-dPhe] | betaHomoLys |
| [3-(4-Quinolinyl)-dPhe] | betaHomoLys |
| betaHomoLys | Aze |
| (3-phenyl-dPhe) | betaHomoLys |
| [3-(2-trifluoromethoxy-phenyl)-dPhe] | betaHomoLys |
| [3-(2-methoxy-phenyl)-dPhe] | betaHomoLys |
| [2-(5-quinolinyl)-MePhe] | MebetaHomoLys |
| F | betaHomoNle |
| F | MebetaHomoLys(Me)2 |
| MePhe | MebetaHomoLys(Me)2 |
| M | MebetaHomoLys |
| Igl | MebetaHomoLys |
| HomoPhe | MebetaHomoLys |
| Hyp(OBn) | MebetaHomoLys |
| (1,2-cis-ACHC) | MebetaHomoLys |
| MeMet | MebetaHomoLys |
| betaHomoLys | betaHomoLys |
| BetaHomoPhe | MebetaHomoLys |
| betahomoMet | MebetaHomoLys |
| Y | (3-aminomethyl-4-bromo-benzoic acid) |
| Y | [3-aminomethyl-4-(4-aza-phenyl)-benzoic acid] |
| Y | [3-aminomethyl-4-(2,5-dimethyl-isoxazole)-benzoic acid] |
| Y | [3-aminomethyl-4-(3-aminomethyl-phenyl)-benzoic acid] |
| [3-aminomethyl-4-[4-(1-piperazinyl)-phenyl]-benzoic acid] | absent |
| [3-aminomethyl-4-(4-quinolinyl)-benzoic acid] | absent |
| (3-aminomethyl-4-bromo-benzoic acid) | absent |
| [3-aminomethyl-4-(2,5-dimethyl-isoxazole)-benzoic acid] | absent |
| [3-aminomethyl-4-(4-pyridyl)-benzoic acid] | absent |
| [3-aminomethyl-(4-methylpyrazole-3-yl)-benzoic acid] | absent |
| [3-aminomethyl-4-(3-quinolinyl)-benzoic acid] | absent |
| [3-aminomethyl-4-(5-quinolinyl)-benzoic acid] | absent |
| [3-aminomethyl-4-[2-(1-piperazinyl)phenyl]-benzoic acid] | absent |
| [3-aminomethyl-4-[3-(1-piperazinyl)phenyl]-benzoic acid] | absent |
| [3-aminomethyl-4-[2-(3-(piperidin-4-ylmethoxy)phenyl]-benzoic acid] | absent |
| [3-aminomethyl-4-(4-pyridyl)-benzoic acid] | absent |
| [3-aminomethyl-4-(4-quinolinyl)-benzoic acid] | absent |
| [3-aminomethyl-4-[4-(1-piperazinyl)phenyl]-benzoic acid] | absent |
| [3-aminomethyl-4-(4-quinolinyl)]-benzoic acid | absent |
| [3-aminomethyl-4-[4-(1-piperazinyl-4-FITC)phenyl]-benzoic acid] | absent |
| (N-benzyl-3-aminomethyl-benzoic acid) | absent |
| (3-aminomethyl-benzoic acid) | absent |
| (3-aminomethyl-5-bromo-benzoic acid) | absent |
| (3-aminomethyl-6-bromo-benzoic acid) | absent |
| (3-aminomethyl-benzoic acid) | absent |
| [3-aminomethyl-5-(4-aza-phenyl)-benzoic acid] | absent |
| [3-aminomethyl-4-(3-thiophenyl)-benzoic acid] | absent |
| [3-aminomethyl-4-(4-N,N-dimethyl-carboxamide-phenyl)-benzoic acid] | absent |
| [3-aminomethyl-4-(4-aza-phenyl)-benzoic acid] | absent |
| [3-aminomethyl-4-(3-aza-phenyl)-benzoic acid] | absent |
| [3-aminomethyl-4-(4-hydroxy-phenyl)-benzoic acid] | absent |
| [3-aminomethyl-4-[5-(2,4-dimethyl)thiazole]-benzoic acid] | absent |
| [3-aminomethyl-4-(3-N,N-dimethylaniline)-benzoic acid] | absent |
| [3-aminomethyl-4-(2-fluoro-pyridyl)-benzoic acid] | absent |
| [3-aminomethyl-4-(5-pyrimidinyl)-benzoic acid] | absent |
| [3-aminomethyl-4-(3-N,N-dimethyl-diaryl ether)-benzoic acid] | |

-continued

| X^y | X^z |
|---|---|
| [3-aminomethyl-4-(3-CF3-phenyl)-benzoic acid] | absent |
| [3-aminomethyl-4-(2,5-dimethoxy-phenyl)-benzoic acid] | absent |
| [3-aminomethyl-4-[(2,3,4-tri-methoxy)-phenyl]-benzoic acid] | absent |
| [3-aminomethyl-4-(4-carboxy)-phenyl)-benzoic acid] | absent |
| [3-aminomethyl-4-(piperonyl)-benzoic acid] | absent |
| (3-aminomethyl-4-piperidinyl-benzoic acid) | absent |
| (3-aminomethyl-4-morpholinyl-benzoic acid) | absent |
| [3-aminomethyl-4-(N,N-dimethyl)-benzoic acid] | absent |
| [3-aminomethyl-4-(2-aminomethylphenyl)-benzoic acid] | absent |
| [3-aminomethyl-4-(3-aminomethylphenyl)-benzoic acid] | absent |
| [3-aminomethyl-4-(4-aminomethylphenyl)-benzoic acid] | absent |
| [3-aminomethyl-4-(4-quinolinyl)-benzoic acid] | absent |
| [3-aminomethyl-4-(4-quinolinyl)-benzoic acid] | absent |
| [3-aminomethyl-4-[4-(1-piperazinyl-4-AlexaFluor 647)phenyl]-benzoic acid] | absent |
| (N-methyl-3-aminomethyl-benzoic acid) | absent |
| [N-methyl-3-aminomethyl-4-(4-quinolinyl)-benzoic acid] | absent |
| [2-(5-quinolinyl)-Phe]-reduced | betaHomoLys |
| [3-aminomethyl-4-[4-(1-piperazinyl)-phenyl]-benzoic acid] | absent |
| [3-aminomethyl-4-[4-(1-piperazinyl)-phenyl]-benzoic acid] | absent |
| [3-aminomethyl-4-[4-(1-piperazinyl)-phenyl]-benzoic acid] | absent |
| F | absent |
| F | absent |
| F | absent |
| F | absent |
| F | absent. |

27. The compound of claim 1, being any one of compounds 1-397, or a pharmaceutically acceptable salt thereof.

28. A pharmaceutical composition comprising the compound of claim 1 or a pharmaceutically acceptable salt thereof, along with the pharmaceutically acceptable carrier.

29. The pharmaceutical composition of claim 28, formulated for oral delivery.

30. The pharmaceutical composition of claim 28, formulated for topical delivery.

31. The pharmaceutical composition of claim 28, formulated for parenteral delivery.

32. A method of treating inflammation or an autoimmune disease in a patient, comprising administering to the patient a therapeutically effective amount of the compound of claim 1.

33. The method of claim 32, wherein the inflammation or an autoimmune disease is gastrointestinal.

34. The method of claim 32, wherein the condition or disease is Inflammatory Bowel Disease (IBD); ulcerative Crohn's disease; Celiac disease; enteropathy associated with seronegative arthropathies microscopic colitis; collagenous colitis; eosinophilic gastroenteritis; radiotherapy; chemotherapy; pouchitis resulting after proctocolectomy and ileoanal anastomosis; gastrointestinal cancer; pancreatitis; insulin-dependent diabetes mellitus; mastitis; cholecystitis; cholangitis; pericholangitis; chronic bronchitis; chronic sinusitis; asthma; primary sclerosing cholangitis; human immunodeficiency virus (HIV) infection in the GI tract; eosinophilic asthma; eosinophilic esophagitis; gastritis; colitis; microscopic colitis; graft versus host disease; colitis associated with radio- or chemo-therapy; colitis associated with disorders of innate immunity; leukocyte adhesion deficiency-1; chronic granulomatous disease; glycogen storage disease type 1; Hermansky-Pudlak syndrome; Chediak-Higashi syndrome; and Wiskott-Aldrich Syndrome; osteoporosis; arthritis; multiple sclerosis; chronic pain; weight gain; or depression.

35. The method of claim 34, wherein the condition is an inflammatory bowel disease.

36. The method of claim 35, wherein the inflammatory bowel disease is ulcerative colitis.

37. The method of claim 35, wherein the inflammatory bowel disease is Crohn's disease.

38. The method of claim 32, wherein the compound inhibits binding of α4β7 integrin to MAdCAM.

39. The method of claim 32, wherein the patient is a human.

40. The compound of claim 1 or a pharmaceutically acceptable salt thereof, being selected from the group consisting of compounds 340, 348, 349, and 358.

* * * * *

SEQUENCE LISTING

<160> NUMBER OF SEQ ID NOS: 380

<210> SEQ ID NO 1
<211> LENGTH: 5
<212> TYPE: PRT
<213> ORGANISM: Artificial Sequence
<220> FEATURE:
<223> OTHER INFORMATION: peptide motif

<400> SEQUENCE: 1

Pro Tyr Leu Asp Val
1               5

<210> SEQ ID NO 2
<211> LENGTH: 5
<212> TYPE: PRT
<213> ORGANISM: Artificial Sequence
<220> FEATURE:
<223> OTHER INFORMATION: peptide motif

<400> SEQUENCE: 2

Pro His Leu Asp Val
1               5

<210> SEQ ID NO 3
<211> LENGTH: 5
<212> TYPE: PRT
<213> ORGANISM: Artificial Sequence
<220> FEATURE:
<223> OTHER INFORMATION: peptide motif

<400> SEQUENCE: 3

Pro Tyr Leu Asp Thr
1               5

<210> SEQ ID NO 4
<211> LENGTH: 5
<212> TYPE: PRT
<213> ORGANISM: Artificial Sequence
<220> FEATURE:
<223> OTHER INFORMATION: peptide motif

<400> SEQUENCE: 4

```
Pro Phe Leu Asp Thr
1               5

<210> SEQ ID NO 5
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is homophe

<400> SEQUENCE: 5

Pro Xaa Leu Asp Thr
1               5

<210> SEQ ID NO 6
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is beta-cyclohexyl alanine, (S)-2-amino-3-
      cyclohexylpropionic acid

<400> SEQUENCE: 6

Pro Xaa Leu Asp Thr
1               5

<210> SEQ ID NO 7
<211> LENGTH: 5
<212> TYPE: PRT
<213> ORGANISM: Artificial Sequence
<220> FEATURE:
<223> OTHER INFORMATION: peptide motif

<400> SEQUENCE: 7

Pro Trp Leu Asp Ile
1               5

<210> SEQ ID NO 8
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 1-napthylalanine

<400> SEQUENCE: 8

Pro Xaa Leu Asp Thr
1               5

<210> SEQ ID NO 9
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-napthylalanine
```

```
<400> SEQUENCE: 9

Pro Xaa Leu Asp Thr
1               5

<210> SEQ ID NO 10
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (5)..(5)
<223> OTHER INFORMATION: X is O-benzyl-threonine

<400> SEQUENCE: 10

Pro Trp Leu Asp Xaa
1               5

<210> SEQ ID NO 11
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is biphenylalanine

<400> SEQUENCE: 11

Pro Xaa Leu Asp Thr
1               5

<210> SEQ ID NO 12
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-phenyl-tyrosine

<400> SEQUENCE: 12

Pro Xaa Leu Asp Thr
1               5

<210> SEQ ID NO 13
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 1-napthylalanine

<400> SEQUENCE: 13

Pro Xaa Leu Asp Ile
1               5

<210> SEQ ID NO 14
<211> LENGTH: 5
<212> TYPE: PRT
<213> ORGANISM: Artificial Sequence
```

```
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-napthylalanine

<400> SEQUENCE: 14

Pro Xaa Leu Asp Ile
1               5

<210> SEQ ID NO 15
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-napthylalanine
<220> FEATURE:
<221> NAME/KEY: MISC_FEATURE
<222> LOCATION: (5)..(5)
<223> OTHER INFORMATION: X is O-benzyl-threonine

<400> SEQUENCE: 15

Pro Xaa Leu Asp Xaa
1               5

<210> SEQ ID NO 16
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (1)..(1)
<223> OTHER INFORMATION: X is (4S)-fluoro-proline

<400> SEQUENCE: 16

Xaa Trp Leu Asp Thr
1               5

<210> SEQ ID NO 17
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is biphenylalanine
<220> FEATURE:
<221> NAME/KEY: MISC_FEATURE
<222> LOCATION: (5)..(5)
<223> OTHER INFORMATION: X is O-benzyl-threonine

<400> SEQUENCE: 17

Pro Xaa Leu Asp Xaa
1               5

<210> SEQ ID NO 18
<211> LENGTH: 5
<212> TYPE: PRT
<213> ORGANISM: Artificial Sequence
<220> FEATURE:
<223> OTHER INFORMATION: peptide motif
<220> FEATURE:
```

```
<221> NAME/KEY: MISC_FEATURE
<222> LOCATION: (2)..(2)
<223> OTHER INFORMATION: X is O-2-methyl-phenyl-tyrosine

<400> SEQUENCE: 18

Pro Xaa Leu Asp Thr
1               5

<210> SEQ ID NO 19
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-4-trifluoromethyl-phenyl-tyrosine

<400> SEQUENCE: 19

Pro Xaa Leu Asp Thr
1               5

<210> SEQ ID NO 20
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-4-methoxy-phenyl-tyrosine

<400> SEQUENCE: 20

Pro Xaa Leu Asp Thr
1               5

<210> SEQ ID NO 21
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-4-fluoro-phenyl-tyrosine

<400> SEQUENCE: 21

Pro Xaa Leu Asp Thr
1               5

<210> SEQ ID NO 22
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-2-methoxy-phenyl-tyrosine

<400> SEQUENCE: 22

Pro Xaa Leu Asp Thr
1               5

<210> SEQ ID NO 23
```

```
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-3-methoxy-phenyl-tyrosine

<400> SEQUENCE: 23

Pro Xaa Leu Asp Thr
1               5

<210> SEQ ID NO 24
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-3-fluoro-phenyl-tyrosine

<400> SEQUENCE: 24

Pro Xaa Leu Asp Thr
1               5

<210> SEQ ID NO 25
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-3,4-difluoro-phenyl-tyrosine

<400> SEQUENCE: 25

Pro Xaa Leu Asp Thr
1               5

<210> SEQ ID NO 26
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-3-methyl-phenyl-tyrosine

<400> SEQUENCE: 26

Pro Xaa Leu Asp Thr
1               5

<210> SEQ ID NO 27
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-3,4-dimethyl-phenyl-tyrosine

<400> SEQUENCE: 27
```

```
Pro Xaa Leu Asp Thr
1               5

<210> SEQ ID NO 28
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-4-methylester-phenyl-tyrosine

<400> SEQUENCE: 28

Pro Xaa Leu Asp Thr
1               5

<210> SEQ ID NO 29
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-3-methylester-phenyl-tyrosine

<400> SEQUENCE: 29

Pro Xaa Leu Asp Thr
1               5

<210> SEQ ID NO 30
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-4-carboxylate-phenyl-tyrosine

<400> SEQUENCE: 30

Pro Xaa Leu Asp Thr
1               5

<210> SEQ ID NO 31
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (1)..(1)
<223> OTHER INFORMATION: X is trans-4-hydroxyproline,
      (2S,4R)-4-hydroxypyrrolidine-2-carboxylic acid

<400> SEQUENCE: 31

Xaa Phe Leu Asp Thr
1               5

<210> SEQ ID NO 32
<211> LENGTH: 5
<212> TYPE: PRT
<213> ORGANISM: Artificial Sequence
<220> FEATURE:
```

```
<223> OTHER INFORMATION: peptide motif
<220> FEATURE:
<221> NAME/KEY: MISC_FEATURE
<222> LOCATION: (2)..(2)
<223> OTHER INFORMATION: X is metaTyrosine

<400> SEQUENCE: 32

Pro Xaa Leu Asp Thr
1               5

<210> SEQ ID NO 33
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is Ndelta-benzamide-ornithine
<220> FEATURE:
<221> NAME/KEY: MISC_FEATURE
<222> LOCATION: (5)..(5)
<223> OTHER INFORMATION: X is O-benzyl-threonine

<400> SEQUENCE: 33

Pro Xaa Leu Asp Xaa
1               5

<210> SEQ ID NO 34
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is Ndelta-acetamide-ornithine
<220> FEATURE:
<221> NAME/KEY: MISC_FEATURE
<222> LOCATION: (5)..(5)
<223> OTHER INFORMATION: X is O-benzyl-threonine

<400> SEQUENCE: 34

Pro Xaa Leu Asp Xaa
1               5

<210> SEQ ID NO 35
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is Ndelta-methanesulfonamide-ornithine
<220> FEATURE:
<221> NAME/KEY: MISC_FEATURE
<222> LOCATION: (5)..(5)
<223> OTHER INFORMATION: X is O-benzyl-threonine

<400> SEQUENCE: 35

Pro Xaa Leu Asp Xaa
1               5

<210> SEQ ID NO 36
<211> LENGTH: 5
<212> TYPE: PRT
<213> ORGANISM: Artificial Sequence
```

```
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is Ndelta-ethylcarbamate-ornithine
<220> FEATURE:
<221> NAME/KEY: MISC_FEATURE
<222> LOCATION: (5)..(5)
<223> OTHER INFORMATION: X is O-benzyl-threonine

<400> SEQUENCE: 36

Pro Xaa Leu Asp Xaa
1               5

<210> SEQ ID NO 37
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is Ndelta-pentyl amide-ornithine
<220> FEATURE:
<221> NAME/KEY: MISC_FEATURE
<222> LOCATION: (5)..(5)
<223> OTHER INFORMATION: X is O-benzyl-threonine

<400> SEQUENCE: 37

Pro Xaa Leu Asp Xaa
1               5

<210> SEQ ID NO 38
<211> LENGTH: 5
<212> TYPE: PRT
<213> ORGANISM: Artificial Sequence
<220> FEATURE:
<223> OTHER INFORMATION: peptide motif

<400> SEQUENCE: 38

Pro Arg Leu Asp Thr
1               5

<210> SEQ ID NO 39
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (5)..(5)
<223> OTHER INFORMATION: X is O-methyl-threonine

<400> SEQUENCE: 39

Pro Phe Leu Asp Xaa
1               5

<210> SEQ ID NO 40
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (5)..(5)
<223> OTHER INFORMATION: X is O-ethyl-threonine
```

```
<400> SEQUENCE: 40

Pro Phe Leu Asp Xaa
1               5

<210> SEQ ID NO 41
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-tyrosine

<400> SEQUENCE: 41

Pro Xaa Leu Asp Thr
1               5

<210> SEQ ID NO 42
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is (3R)-1,2,3,4-tetrahydroisoquinoline-3-
      carboxylic acid

<400> SEQUENCE: 42

Pro Xaa Leu Asp Thr
1               5

<210> SEQ ID NO 43
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (1)..(1)
<223> OTHER INFORMATION: X is trans-4-hydroxyproline,
      (2S,4R)-4-hydroxypyrrolidine-2-carboxylic acid
<220> FEATURE:
<221> NAME/KEY: MISC_FEATURE
<222> LOCATION: (2)..(2)
<223> OTHER INFORMATION: X is [3-(3'-pyridyl)-alanine]

<400> SEQUENCE: 43

Xaa Xaa Leu Asp Thr
1               5

<210> SEQ ID NO 44
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (1)..(1)
<223> OTHER INFORMATION: X is (4R)-fluoro-proline

<400> SEQUENCE: 44

Xaa Phe Leu Asp Thr
1               5
```

```
<210> SEQ ID NO 45
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (1)..(1)
<223> OTHER INFORMATION: X is (4R)-fluoro-proline
<220> FEATURE:
<221> NAME/KEY: MISC_FEATURE
<222> LOCATION: (2)..(2)
<223> OTHER INFORMATION: X is biphenylalanine

<400> SEQUENCE: 45

Xaa Xaa Leu Asp Thr
1               5

<210> SEQ ID NO 46
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (1)..(1)
<223> OTHER INFORMATION: X is (4R)-fluoro-proline
<220> FEATURE:
<221> NAME/KEY: MISC_FEATURE
<222> LOCATION: (2)..(2)
<223> OTHER INFORMATION: X is [3-(3'-pyridyl)-alanine]

<400> SEQUENCE: 46

Xaa Xaa Leu Asp Thr
1               5

<210> SEQ ID NO 47
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (1)..(1)
<223> OTHER INFORMATION: X is (4R)-fluoro-proline

<400> SEQUENCE: 47

Xaa Tyr Leu Asp Thr
1               5

<210> SEQ ID NO 48
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (1)..(1)
<223> OTHER INFORMATION: X is (4S)-fluoro-proline

<400> SEQUENCE: 48

Xaa Tyr Leu Asp Thr
1               5

<210> SEQ ID NO 49
<211> LENGTH: 5
```

```
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-arginine

<400> SEQUENCE: 49

Pro Xaa Leu Asp Thr
1               5

<210> SEQ ID NO 50
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-pipecolic acid, D-homoPro

<400> SEQUENCE: 50

Pro Xaa Leu Asp Thr
1               5

<210> SEQ ID NO 51
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is (3-(4-thiazolyl)-alanine)

<400> SEQUENCE: 51

Pro Xaa Leu Asp Thr
1               5

<210> SEQ ID NO 52
<211> LENGTH: 5
<212> TYPE: PRT
<213> ORGANISM: Artificial Sequence
<220> FEATURE:
<223> OTHER INFORMATION: peptide motif

<400> SEQUENCE: 52

Pro Tyr Leu Asp Ile
1               5

<210> SEQ ID NO 53
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aza-phenylalanine

<400> SEQUENCE: 53

Pro Xaa Leu Asp Thr
1               5
```

```
<210> SEQ ID NO 54
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (5)..(5)
<223> OTHER INFORMATION: X is penicillamine, beta,beta-dimethyl-cysteine

<400> SEQUENCE: 54

Pro Tyr Leu Asp Xaa
1               5

<210> SEQ ID NO 55
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-amino-4-bromo-4-pentenoic acid

<400> SEQUENCE: 55

Pro Xaa Leu Asp Thr
1               5

<210> SEQ ID NO 56
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-benzyl-trans-4-hydroxyproline

<400> SEQUENCE: 56

Pro Xaa Leu Asp Thr
1               5

<210> SEQ ID NO 57
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is Nbeta-Z-2,3-diaminopropionic acid

<400> SEQUENCE: 57

Pro Xaa Leu Asp Thr
1               5

<210> SEQ ID NO 58
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is N-tau-benzyl-histidine
```

```
<400> SEQUENCE: 58

Pro Xaa Leu Asp Thr
1               5

<210> SEQ ID NO 59
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-amino-phenylalanine

<400> SEQUENCE: 59

Pro Xaa Leu Asp Thr
1               5

<210> SEQ ID NO 60
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aza-D-phenylalanine

<400> SEQUENCE: 60

Pro Xaa Leu Asp Thr
1               5

<210> SEQ ID NO 61
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is trans-4-hydroxyproline,
      (2S,4R)-4-hydroxypyrrolidine-2-carboxylic acid

<400> SEQUENCE: 61

Pro Xaa Leu Asp Thr
1               5

<210> SEQ ID NO 62
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-tryptophan

<400> SEQUENCE: 62

Pro Xaa Leu Asp Thr
1               5

<210> SEQ ID NO 63
<211> LENGTH: 5
<212> TYPE: PRT
<213> ORGANISM: Artificial Sequence
```

```
<220> FEATURE:
<223> OTHER INFORMATION: peptide motif

<400> SEQUENCE: 63

Pro Met Leu Asp Thr
1               5

<210> SEQ ID NO 64
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-methionine

<400> SEQUENCE: 64

Pro Xaa Leu Asp Thr
1               5

<210> SEQ ID NO 65
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-guanidino-phenylalanine

<400> SEQUENCE: 65

Pro Xaa Leu Asp Thr
1               5

<210> SEQ ID NO 66
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aza-phenylalanine

<400> SEQUENCE: 66

Pro Xaa Leu Asp Thr
1               5

<210> SEQ ID NO 67
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aza-D-phenylalanine

<400> SEQUENCE: 67

Pro Xaa Leu Asp Thr
1               5

<210> SEQ ID NO 68
<211> LENGTH: 5
```

```
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is norvaline

<400> SEQUENCE: 68

Pro Xaa Leu Asp Thr
1               5

<210> SEQ ID NO 69
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-norleucine

<400> SEQUENCE: 69

Pro Xaa Leu Asp Thr
1               5

<210> SEQ ID NO 70
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-lysine

<400> SEQUENCE: 70

Pro Xaa Leu Asp Thr
1               5

<210> SEQ ID NO 71
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-proline

<400> SEQUENCE: 71

Pro Xaa Leu Asp Thr
1               5

<210> SEQ ID NO 72
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-ornithine

<400> SEQUENCE: 72
```

Pro Xaa Leu Asp Thr
1               5

<210> SEQ ID NO 73
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-benzothienyl-alanine

<400> SEQUENCE: 73

Pro Xaa Leu Asp Thr
1               5

<210> SEQ ID NO 74
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-allyl-D-tyrosine

<400> SEQUENCE: 74

Pro Xaa Leu Asp Thr
1               5

<210> SEQ ID NO 75
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-benzyl-D-serine

<400> SEQUENCE: 75

Pro Xaa Leu Asp Thr
1               5

<210> SEQ ID NO 76
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-thiazolyl)-D-alanine

<400> SEQUENCE: 76

Pro Xaa Leu Asp Thr
1               5

<210> SEQ ID NO 77
<211> LENGTH: 5
<212> TYPE: PRT
<213> ORGANISM: Artificial Sequence
<220> FEATURE:
<223> OTHER INFORMATION: peptide motif
<220> FEATURE:

```
<221> NAME/KEY: MISC_FEATURE
<222> LOCATION: (2)..(2)
<223> OTHER INFORMATION: X is 3-benzothienyl-D-alanine

<400> SEQUENCE: 77

Pro Xaa Leu Asp Thr
1               5

<210> SEQ ID NO 78
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(2-thienyl)-D-alanine

<400> SEQUENCE: 78

Pro Xaa Leu Asp Thr
1               5

<210> SEQ ID NO 79
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-phenylalanine

<400> SEQUENCE: 79

Pro Xaa Leu Asp Thr
1               5

<210> SEQ ID NO 80
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is Ndelta-dimethyl-D-ornithine

<400> SEQUENCE: 80

Pro Xaa Leu Asp Thr
1               5

<210> SEQ ID NO 81
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-amino-D-phenylalanine

<400> SEQUENCE: 81

Pro Xaa Leu Asp Thr
1               5

<210> SEQ ID NO 82
```

```
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-D-phenylalanine

<400> SEQUENCE: 82

Pro Xaa Leu Asp Thr
1               5

<210> SEQ ID NO 83
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: O-benzyl-D-tyrosine

<400> SEQUENCE: 83

Pro Xaa Leu Asp Thr
1               5

<210> SEQ ID NO 84
<211> LENGTH: 5
<212> TYPE: PRT
<213> ORGANISM: Artificial Sequence
<220> FEATURE:
<223> OTHER INFORMATION: peptide motif

<400> SEQUENCE: 84

Pro Pro Leu Asp Thr
1               5

<210> SEQ ID NO 85
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is cyclo leucine, 1-Aminocyclopentane-1-
      carboxylic acid

<400> SEQUENCE: 85

Pro Xaa Leu Asp Thr
1               5

<210> SEQ ID NO 86
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is aminoindan-2-carboxylic acid

<400> SEQUENCE: 86

Pro Xaa Leu Asp Thr
1               5
```

```
<210> SEQ ID NO 87
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-allyl-tyrosine

<400> SEQUENCE: 87

Pro Xaa Leu Asp Thr
1               5

<210> SEQ ID NO 88
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is cyclohexyl glycine

<400> SEQUENCE: 88

Pro Xaa Leu Asp Thr
1               5

<210> SEQ ID NO 89
<211> LENGTH: 5
<212> TYPE: PRT
<213> ORGANISM: Artificial Sequence
<220> FEATURE:
<223> OTHER INFORMATION: peptide motif

<400> SEQUENCE: 89

Pro Lys Leu Asp Thr
1               5

<210> SEQ ID NO 90
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-aza-D-phenylalanine

<400> SEQUENCE: 90

Pro Xaa Leu Asp Thr
1               5

<210> SEQ ID NO 91
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2- aza-phenylalanine

<400> SEQUENCE: 91
```

```
Pro Xaa Leu Asp Thr
1               5

<210> SEQ ID NO 92
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(2-pyridyl)-4-thiazolyl-alanine

<400> SEQUENCE: 92

Pro Xaa Leu Asp Thr
1               5

<210> SEQ ID NO 93
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(3-pyridyl)-4-thiazolyl-alanine

<400> SEQUENCE: 93

Pro Xaa Leu Asp Thr
1               5

<210> SEQ ID NO 94
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(4-pyridyl)-4-thiazolyl-alanine

<400> SEQUENCE: 94

Pro Xaa Leu Asp Thr
1               5

<210> SEQ ID NO 95
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-1,2,3,4-tetrahydroisoquinoline-1-
      carboxylic acid

<400> SEQUENCE: 95

Pro Xaa Leu Asp Thr
1               5

<210> SEQ ID NO 96
<211> LENGTH: 5
<212> TYPE: PRT
<213> ORGANISM: Artificial Sequence
<220> FEATURE:
<223> OTHER INFORMATION: peptide motif
```

```
<220> FEATURE:
<221> NAME/KEY: MISC_FEATURE
<222> LOCATION: (2)..(2)
<223> OTHER INFORMATION: X is 1-(S)-isoindoline-carboxylic acid

<400> SEQUENCE: 96

Pro Xaa Leu Asp Thr
1               5

<210> SEQ ID NO 97
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is D-threonine

<400> SEQUENCE: 97

Pro Tyr Xaa Leu Asp Thr
1               5

<210> SEQ ID NO 98
<211> LENGTH: 6
<212> TYPE: PRT
<213> ORGANISM: Artificial Sequence
<220> FEATURE:
<223> OTHER INFORMATION: peptide motif

<400> SEQUENCE: 98

Pro Tyr Pro Leu Asp Thr
1               5

<210> SEQ ID NO 99
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is D-proline

<400> SEQUENCE: 99

Pro Tyr Xaa Leu Asp Thr
1               5

<210> SEQ ID NO 100
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is sarcosine, N-methyl glycine

<400> SEQUENCE: 100

Pro Tyr Xaa Leu Asp Thr
1               5

<210> SEQ ID NO 101
<211> LENGTH: 6
<212> TYPE: PRT
<213> ORGANISM: Artificial Sequence
```

```
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is cyclo leucine, 1-Aminocyclopentane-1-
      carboxylic acid

<400> SEQUENCE: 101

Pro Tyr Xaa Leu Asp Thr
1               5

<210> SEQ ID NO 102
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-iodo-phenylalanine
<220> FEATURE:
<221> NAME/KEY: MISC_FEATURE
<222> LOCATION: (3)..(3)
<223> OTHER INFORMATION: X is sarcosine, N-methyl glycine

<400> SEQUENCE: 102

Pro Xaa Xaa Leu Asp Thr
1               5

<210> SEQ ID NO 103
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-iodo-phenylalanine
<220> FEATURE:
<221> NAME/KEY: MISC_FEATURE
<222> LOCATION: (3)..(3)
<223> OTHER INFORMATION: X is sarcosine, N-methyl glycine

<400> SEQUENCE: 103

Pro Xaa Xaa Leu Asp Thr
1               5

<210> SEQ ID NO 104
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3,3-diphenyl-alanine
<220> FEATURE:
<221> NAME/KEY: MISC_FEATURE
<222> LOCATION: (3)..(3)
<223> OTHER INFORMATION: X is sarcosine, N-methyl glycine

<400> SEQUENCE: 104

Pro Xaa Xaa Leu Asp Thr
1               5

<210> SEQ ID NO 105
<211> LENGTH: 6
```

```
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is D-lysine

<400> SEQUENCE: 105

Pro Phe Xaa Leu Asp Thr
1               5

<210> SEQ ID NO 106
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is biphenylalanine
<220> FEATURE:
<221> NAME/KEY: MISC_FEATURE
<222> LOCATION: (3)..(3)
<223> OTHER INFORMATION: X is D-lysine

<400> SEQUENCE: 106

Pro Xaa Xaa Leu Asp Thr
1               5

<210> SEQ ID NO 107
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-thiazolyl)-alanine
<220> FEATURE:
<221> NAME/KEY: MISC_FEATURE
<222> LOCATION: (3)..(3)
<223> OTHER INFORMATION: X is D-lysine

<400> SEQUENCE: 107

Pro Xaa Xaa Leu Asp Thr
1               5

<210> SEQ ID NO 108
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3,3-diphenyl-alanine
<220> FEATURE:
<221> NAME/KEY: MISC_FEATURE
<222> LOCATION: (3)..(3)
<223> OTHER INFORMATION: X is D-lysine

<400> SEQUENCE: 108

Pro Xaa Xaa Leu Asp Thr
1               5

<210> SEQ ID NO 109
```

```
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is D-lysine

<400> SEQUENCE: 109

Pro Tyr Xaa Leu Asp Ile
1               5

<210> SEQ ID NO 110
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is D-arginine

<400> SEQUENCE: 110

Pro Tyr Xaa Leu Asp Thr
1               5

<210> SEQ ID NO 111
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is D-serine

<400> SEQUENCE: 111

Pro Tyr Xaa Leu Asp Thr
1               5

<210> SEQ ID NO 112
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is biphenylalanine
<220> FEATURE:
<221> NAME/KEY: MISC_FEATURE
<222> LOCATION: (3)..(3)
<223> OTHER INFORMATION: X is sarcosine, N-methyl glycine

<400> SEQUENCE: 112

Pro Xaa Xaa Leu Asp Thr
1               5

<210> SEQ ID NO 113
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
```

```
<222> LOCATION: (2)..(2)
<223> OTHER INFORMATION: X is 1-napthylalanine
<220> FEATURE:
<221> NAME/KEY: MISC_FEATURE
<222> LOCATION: (3)..(3)
<223> OTHER INFORMATION: X is sarcosine, N-methyl glycine

<400> SEQUENCE: 113

Pro Xaa Xaa Leu Asp Thr
1               5

<210> SEQ ID NO 114
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is pipecolic acid, homoPro

<400> SEQUENCE: 114

Pro Tyr Xaa Leu Asp Thr
1               5

<210> SEQ ID NO 115
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-iodo-phenylalanine
<220> FEATURE:
<221> NAME/KEY: MISC_FEATURE
<222> LOCATION: (3)..(3)
<223> OTHER INFORMATION: X is sarcosine, N-methyl glycine

<400> SEQUENCE: 115

Pro Xaa Xaa Leu Asp Thr
1               5

<210> SEQ ID NO 116
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 1-napthylalanine
<220> FEATURE:
<221> NAME/KEY: MISC_FEATURE
<222> LOCATION: (3)..(3)
<223> OTHER INFORMATION: X is D-lysine

<400> SEQUENCE: 116

Pro Xaa Xaa Leu Asp Thr
1               5

<210> SEQ ID NO 117
<211> LENGTH: 6
<212> TYPE: PRT
<213> ORGANISM: Artificial Sequence
<220> FEATURE:
<223> OTHER INFORMATION: peptide motif
<220> FEATURE:
```

```
<221> NAME/KEY: MISC_FEATURE
<222> LOCATION: (3)..(3)
<223> OTHER INFORMATION: X is D-lysine
<220> FEATURE:
<221> NAME/KEY: MISC_FEATURE
<222> LOCATION: (6)..(6)
<223> OTHER INFORMATION: X is N-methyl threonine

<400> SEQUENCE: 117

Pro Tyr Xaa Leu Asp Xaa
1               5

<210> SEQ ID NO 118
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is sarcosine, N-methyl glycine

<400> SEQUENCE: 118

Pro Phe Xaa Leu Asp Thr
1               5

<210> SEQ ID NO 119
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is (3R)-1,2,3,4-tetrahydroisoquinoline-3-
      carboxylic acid

<400> SEQUENCE: 119

Pro Tyr Xaa Leu Asp Thr
1               5

<210> SEQ ID NO 120
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 120

Pro Tyr Xaa Leu Asp Thr
1               5

<210> SEQ ID NO 121
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is D-proline

<400> SEQUENCE: 121
```

```
Pro Phe Xaa Leu Asp Thr
1               5

<210> SEQ ID NO 122
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3,4-dimethoxy-phenylalanine
<220> FEATURE:
<221> NAME/KEY: MISC_FEATURE
<222> LOCATION: (3)..(3)
<223> OTHER INFORMATION: X is D-proline

<400> SEQUENCE: 122

Pro Xaa Xaa Leu Asp Thr
1               5

<210> SEQ ID NO 123
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3,4,5-trifluoro-phenylalanine
<220> FEATURE:
<221> NAME/KEY: MISC_FEATURE
<222> LOCATION: (3)..(3)
<223> OTHER INFORMATION: X is D-proline

<400> SEQUENCE: 123

Pro Xaa Xaa Leu Asp Thr
1               5

<210> SEQ ID NO 124
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3,5-dibromo-tyrosine
<220> FEATURE:
<221> NAME/KEY: MISC_FEATURE
<222> LOCATION: (3)..(3)
<223> OTHER INFORMATION: X is D-proline

<400> SEQUENCE: 124

Pro Xaa Xaa Leu Asp Thr
1               5

<210> SEQ ID NO 125
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 125
```

```
Pro Phe Xaa Leu Asp Thr
1               5

<210> SEQ ID NO 126
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-thiazolyl)-alanine
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 126

Pro Xaa Xaa Leu Asp Thr
1               5

<210> SEQ ID NO 127
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-phenylalanine
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 127

Pro Xaa Xaa Leu Asp Thr
1               5

<210> SEQ ID NO 128
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-iodo-phenylalanine
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 128

Pro Xaa Xaa Leu Asp Thr
1               5

<210> SEQ ID NO 129
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-phenyl-phenylalanine
<220> FEATURE:
```

<221> NAME/KEY: MISC_FEATURE
<222> LOCATION: (3)..(3)
<223> OTHER INFORMATION: X is D-pipecolic acid, D-homoPro

<400> SEQUENCE: 129

Pro Xaa Xaa Leu Asp Thr
1               5

<210> SEQ ID NO 130
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(2-methoxy-phenyl)-phenylalanine
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 130

Pro Xaa Xaa Leu Asp Thr
1               5

<210> SEQ ID NO 131
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(3-methoxy-phenyl)-phenylalanine
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 131

Pro Xaa Xaa Leu Asp Thr
1               5

<210> SEQ ID NO 132
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(4-methoxy-phenyl)-phenylalanine
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 132

Pro Xaa Xaa Leu Asp Thr
1               5

<210> SEQ ID NO 133
<211> LENGTH: 6
<212> TYPE: PRT
<213> ORGANISM: Artificial Sequence
<220> FEATURE:
<223> OTHER INFORMATION: peptide motif

```
<220> FEATURE:
<221> NAME/KEY: MISC_FEATURE
<222> LOCATION: (2)..(2)
<223> OTHER INFORMATION: X is biphenylalanine
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 133

Pro Xaa Xaa Leu Asp Thr
1               5

<210> SEQ ID NO 134
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is trans-4-hydroxyproline,
      (2S,4R)-4-hydroxypyrrolidine-2-carboxylic acid

<400> SEQUENCE: 134

Pro Tyr Xaa Leu Asp Thr
1               5

<210> SEQ ID NO 135
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is trans-D-4-hydroxyproline,
      (2R,4S)-4-hydroxypyrrolidine-2-carboxylic acid

<400> SEQUENCE: 135

Pro Tyr Xaa Leu Asp Thr
1               5

<210> SEQ ID NO 136
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is cis-D-4-Hydroxyproline,
      (2R,4R)-4-Hydroxypyrrolidine-2-carboxylic acid

<400> SEQUENCE: 136

Pro Tyr Xaa Leu Asp Thr
1               5

<210> SEQ ID NO 137
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (1)..(1)
<223> OTHER INFORMATION: X is D-proline
```

```
<220> FEATURE:
<221> NAME/KEY: MISC_FEATURE
<222> LOCATION: (2)..(2)
<223> OTHER INFORMATION: X is D-tyrosine
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 137

Xaa Xaa Xaa Leu Asp Thr
1               5

<210> SEQ ID NO 138
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 1-napthylalanine
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 138

Pro Xaa Xaa Leu Asp Thr
1               5

<210> SEQ ID NO 139
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-napthylalanine
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 139

Pro Xaa Xaa Leu Asp Thr
1               5

<210> SEQ ID NO 140
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-phenylalanine
<220> FEATURE:
<221> NAME/KEY: MISC_FEATURE
<222> LOCATION: (3)..(3)
<223> OTHER INFORMATION: X is (3R)-1,2,3,4-tetrahydroisoquinoline-3-
      carboxylic acid

<400> SEQUENCE: 140

Pro Xaa Xaa Leu Asp Thr
1               5
```

-continued

```
<210> SEQ ID NO 141
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-phenylalanine
<220> FEATURE:
<221> NAME/KEY: MISC_FEATURE
<222> LOCATION: (3)..(3)
<223> OTHER INFORMATION: X is (3R)-1,2,3,4-tetrahydroisoquinoline-3-
      carboxylic acid

<400> SEQUENCE: 141

Pro Xaa Xaa Leu Asp Thr
1               5

<210> SEQ ID NO 142
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-D-phenylalanine
<220> FEATURE:
<221> NAME/KEY: MISC_FEATURE
<222> LOCATION: (3)..(3)
<223> OTHER INFORMATION: X is (3R)-1,2,3,4-tetrahydroisoquinoline-3-
      carboxylic acid

<400> SEQUENCE: 142

Pro Xaa Xaa Leu Asp Thr
1               5

<210> SEQ ID NO 143
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is N-methyl tyrosine
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 143

Pro Xaa Xaa Leu Asp Thr
1               5

<210> SEQ ID NO 144
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is D-pipecolic acid, D-homoPro
<220> FEATURE:
<221> NAME/KEY: MISC_FEATURE
<222> LOCATION: (6)..(6)
<223> OTHER INFORMATION: X is allo-threonine, (2S,3S)-2-amino-3-
``` hydroxybutyric acid

<400> SEQUENCE: 144

Pro Tyr Xaa Leu Asp Xaa
1               5

<210> SEQ ID NO 145
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is D-pipecolic acid, D-homoPro
<220> FEATURE:
<221> NAME/KEY: MISC_FEATURE
<222> LOCATION: (4)..(4)
<223> OTHER INFORMATION: X is beta-tert-butyl alanine, neopentylglycine

<400> SEQUENCE: 145

Pro Tyr Xaa Xaa Asp Thr
1               5

<210> SEQ ID NO 146
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-thiazolyl)-alanine
<220> FEATURE:
<221> NAME/KEY: MISC_FEATURE
<222> LOCATION: (3)..(3)
<223> OTHER INFORMATION: X is trans-D-4-hydroxyproline,
      (2R,4S)-4-hydroxypyrrolidine-2-carboxylic acid

<400> SEQUENCE: 146

Pro Xaa Xaa Leu Asp Thr
1               5

<210> SEQ ID NO 147
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-phenylalanine
<220> FEATURE:
<221> NAME/KEY: MISC_FEATURE
<222> LOCATION: (3)..(3)
<223> OTHER INFORMATION: X is trans-D-4-hydroxyproline,
      (2R,4S)-4-hydroxypyrrolidine-2-carboxylic acid

<400> SEQUENCE: 147

Pro Xaa Xaa Leu Asp Thr
1               5

<210> SEQ ID NO 148
<211> LENGTH: 6
<212> TYPE: PRT
<213> ORGANISM: Artificial Sequence
<220> FEATURE:
<223> OTHER INFORMATION: peptide motif

```
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 148

Pro Tyr Xaa Leu Asp Ile
1               5

<210> SEQ ID NO 149
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is N-methyl-D-Lysine

<400> SEQUENCE: 149

Pro Tyr Xaa Leu Asp Ile
1               5

<210> SEQ ID NO 150
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is D-norleucine

<400> SEQUENCE: 150

Pro Tyr Xaa Leu Asp Thr
1               5

<210> SEQ ID NO 151
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is trans-D-4-hydroxyproline,
      (2R,4S)-4-hydroxypyrrolidine-2-carboxylic acid

<400> SEQUENCE: 151

Pro Phe Xaa Leu Asp Thr
1               5

<210> SEQ ID NO 152
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is N-methyl-D-arginine

<400> SEQUENCE: 152

Pro Tyr Xaa Leu Asp Thr
1               5
```

```
<210> SEQ ID NO 153
<211> LENGTH: 6
<212> TYPE: PRT
<213> ORGANISM: Artificial Sequence
<220> FEATURE:
<223> OTHER INFORMATION: peptide motif

<400> SEQUENCE: 153

Pro Tyr Gly Leu Asp Thr
1               5

<210> SEQ ID NO 154
<211> LENGTH: 6
<212> TYPE: PRT
<213> ORGANISM: Artificial Sequence
<220> FEATURE:
<223> OTHER INFORMATION: peptide motif

<400> SEQUENCE: 154

Pro Tyr Ala Leu Asp Thr
1               5

<210> SEQ ID NO 155
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is D-alanine

<400> SEQUENCE: 155

Pro Tyr Xaa Leu Asp Thr
1               5

<210> SEQ ID NO 156
<211> LENGTH: 6
<212> TYPE: PRT
<213> ORGANISM: Artificial Sequence
<220> FEATURE:
<223> OTHER INFORMATION: peptide motif

<400> SEQUENCE: 156

Pro Met Gly Leu Asp Thr
1               5

<210> SEQ ID NO 157
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-allyl-tyrosine
<220> FEATURE:
<221> NAME/KEY: MISC_FEATURE
<222> LOCATION: (3)..(3)
<223> OTHER INFORMATION: X is sarcosine, N-methyl glycine

<400> SEQUENCE: 157

Pro Xaa Xaa Leu Asp Thr
1               5

<210> SEQ ID NO 158
```

```
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-allyl-tyrosine

<400> SEQUENCE: 158

Pro Xaa Gly Leu Asp Thr
1               5

<210> SEQ ID NO 159
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-thiazolyl)-alanine
<220> FEATURE:
<221> NAME/KEY: MISC_FEATURE
<222> LOCATION: (3)..(3)
<223> OTHER INFORMATION: X is sarcosine, N-methyl glycine

<400> SEQUENCE: 159

Pro Xaa Xaa Leu Asp Thr
1               5

<210> SEQ ID NO 160
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-phenylalanine

<400> SEQUENCE: 160

Pro Xaa Gly Leu Asp Thr
1               5

<210> SEQ ID NO 161
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-allyl-tyrosine
<220> FEATURE:
<221> NAME/KEY: MISC_FEATURE
<222> LOCATION: (3)..(3)
<223> OTHER INFORMATION: X is D-valine

<400> SEQUENCE: 161

Pro Xaa Xaa Leu Asp Thr
1               5

<210> SEQ ID NO 162
<211> LENGTH: 6
<212> TYPE: PRT
<213> ORGANISM: Artificial Sequence
```

```
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-allyl-tyrosine
<220> FEATURE:
<221> NAME/KEY: MISC_FEATURE
<222> LOCATION: (3)..(3)
<223> OTHER INFORMATION: X is D-serine

<400> SEQUENCE: 162

Pro Xaa Xaa Leu Asp Thr
1               5

<210> SEQ ID NO 163
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-allyl-tyrosine
<220> FEATURE:
<221> NAME/KEY: MISC_FEATURE
<222> LOCATION: (3)..(3)
<223> OTHER INFORMATION: X is D-alanine

<400> SEQUENCE: 163

Pro Xaa Xaa Leu Asp Thr
1               5

<210> SEQ ID NO 164
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-allyl-tyrosine

<400> SEQUENCE: 164

Pro Xaa Pro Leu Asp Thr
1               5

<210> SEQ ID NO 165
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-allyl-tyrosine
<220> FEATURE:
<221> NAME/KEY: MISC_FEATURE
<222> LOCATION: (3)..(3)
<223> OTHER INFORMATION: X is D-proline

<400> SEQUENCE: 165

Pro Xaa Xaa Leu Asp Thr
1               5

<210> SEQ ID NO 166
<211> LENGTH: 6
<212> TYPE: PRT
```

```
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-thiazolyl)-alanine
<220> FEATURE:
<221> NAME/KEY: MISC_FEATURE
<222> LOCATION: (3)..(3)
<223> OTHER INFORMATION: X is D-valine

<400> SEQUENCE: 166

Pro Xaa Xaa Leu Asp Thr
1               5

<210> SEQ ID NO 167
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-thiazolyl)-alanine
<220> FEATURE:
<221> NAME/KEY: MISC_FEATURE
<222> LOCATION: (3)..(3)
<223> OTHER INFORMATION: X is D-serine

<400> SEQUENCE: 167

Pro Xaa Xaa Leu Asp Thr
1               5

<210> SEQ ID NO 168
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-thiazolyl)-alanine
<220> FEATURE:
<221> NAME/KEY: MISC_FEATURE
<222> LOCATION: (3)..(3)
<223> OTHER INFORMATION: X is D-alanine

<400> SEQUENCE: 168

Pro Xaa Xaa Leu Asp Thr
1               5

<210> SEQ ID NO 169
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-thiazolyl)-alanine

<400> SEQUENCE: 169

Pro Xaa Pro Leu Asp Thr
1               5

<210> SEQ ID NO 170
<211> LENGTH: 6
```

```
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-thiazolyl)-alanine
<220> FEATURE:
<221> NAME/KEY: MISC_FEATURE
<222> LOCATION: (3)..(3)
<223> OTHER INFORMATION: X is D-proline

<400> SEQUENCE: 170

Pro Xaa Xaa Leu Asp Thr
1               5

<210> SEQ ID NO 171
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-phenylalanine

<400> SEQUENCE: 171

Pro Xaa Pro Leu Asp Thr
1               5

<210> SEQ ID NO 172
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-phenylalanine
<220> FEATURE:
<221> NAME/KEY: MISC_FEATURE
<222> LOCATION: (3)..(3)
<223> OTHER INFORMATION: X is D-proline

<400> SEQUENCE: 172

Pro Xaa Xaa Leu Asp Thr
1               5

<210> SEQ ID NO 173
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is cyclo leucine, 1-Aminocyclopentane-1-
      carboxylic acid

<400> SEQUENCE: 173

Pro Xaa Pro Leu Asp Thr
1               5

<210> SEQ ID NO 174
<211> LENGTH: 6
<212> TYPE: PRT
<213> ORGANISM: Artificial Sequence
```

```
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(2-pyridyl)-4-thiazolyl-alanine
<220> FEATURE:
<221> NAME/KEY: MISC_FEATURE
<222> LOCATION: (3)..(3)
<223> OTHER INFORMATION: X is sarcosine, N-methyl glycine

<400> SEQUENCE: 174

Pro Xaa Xaa Leu Asp Thr
1               5

<210> SEQ ID NO 175
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(2-pyridyl)-4-thiazolyl-alanine
<220> FEATURE:
<221> NAME/KEY: MISC_FEATURE
<222> LOCATION: (3)..(3)
<223> OTHER INFORMATION: X is D-proline

<400> SEQUENCE: 175

Pro Xaa Xaa Leu Asp Thr
1               5

<210> SEQ ID NO 176
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(3-pyridyl)-4-thiazolyl-alanine
<220> FEATURE:
<221> NAME/KEY: MISC_FEATURE
<222> LOCATION: (3)..(3)
<223> OTHER INFORMATION: X is sarcosine, N-methyl glycine

<400> SEQUENCE: 176

Pro Xaa Xaa Leu Asp Thr
1               5

<210> SEQ ID NO 177
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(3-pyridyl)-4-thiazolyl-alanine
<220> FEATURE:
<221> NAME/KEY: MISC_FEATURE
<222> LOCATION: (3)..(3)
<223> OTHER INFORMATION: X is D-proline

<400> SEQUENCE: 177

Pro Xaa Xaa Leu Asp Thr
1               5
```

```
<210> SEQ ID NO 178
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(4-pyridyl)-4-thiazolyl-alanine
<220> FEATURE:
<221> NAME/KEY: MISC_FEATURE
<222> LOCATION: (3)..(3)
<223> OTHER INFORMATION: X is D-proline

<400> SEQUENCE: 178

Pro Xaa Xaa Leu Asp Thr
1               5

<210> SEQ ID NO 179
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(2-aminobenzyl-4-thiazolyl)-alanine
<220> FEATURE:
<221> NAME/KEY: MISC_FEATURE
<222> LOCATION: (3)..(3)
<223> OTHER INFORMATION: X is sarcosine, N-methyl glycine

<400> SEQUENCE: 179

Pro Xaa Xaa Leu Asp Thr
1               5

<210> SEQ ID NO 180
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(amino-benzyl)-4-thiazolyl-alanine
<220> FEATURE:
<221> NAME/KEY: MISC_FEATURE
<222> LOCATION: (3)..(3)
<223> OTHER INFORMATION: X is D-proline

<400> SEQUENCE: 180

Pro Xaa Xaa Leu Asp Thr
1               5

<210> SEQ ID NO 181
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-tyrosine
<220> FEATURE:
<221> NAME/KEY: MISC_FEATURE
<222> LOCATION: (3)..(3)
<223> OTHER INFORMATION: X is D-pipecolic acid, D-homoPro
```

```
<400> SEQUENCE: 181

Pro Xaa Xaa Leu Asp Ile
1               5

<210> SEQ ID NO 182
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-aminomethyl-phenylalanine
<220> FEATURE:
<221> NAME/KEY: MISC_FEATURE
<222> LOCATION: (3)..(3)
<223> OTHER INFORMATION: X is azetidine-2-carboxylic acid

<400> SEQUENCE: 182

Pro Xaa Xaa Leu Asp Thr
1               5

<210> SEQ ID NO 183
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is D-pipecolic acid, D-homoPro
<220> FEATURE:
<221> NAME/KEY: MISC_FEATURE
<222> LOCATION: (6)..(6)
<223> OTHER INFORMATION: X is 2-aminobutyric acid

<400> SEQUENCE: 183

Pro Tyr Xaa Leu Asp Xaa
1               5

<210> SEQ ID NO 184
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-phenylalanine
<220> FEATURE:
<221> NAME/KEY: MISC_FEATURE
<222> LOCATION: (3)..(3)
<223> OTHER INFORMATION: X is (3R)-1,2,3,4-tetrahydroisoquinoline-3-
      carboxylic acid
<220> FEATURE:
<221> NAME/KEY: MISC_FEATURE
<222> LOCATION: (6)..(6)
<223> OTHER INFORMATION: X is 2-aminobutyric acid

<400> SEQUENCE: 184

Pro Xaa Xaa Leu Asp Xaa
1               5

<210> SEQ ID NO 185
<211> LENGTH: 6
<212> TYPE: PRT
<213> ORGANISM: Artificial Sequence
<220> FEATURE:
```

```
<223> OTHER INFORMATION: peptide motif
<220> FEATURE:
<221> NAME/KEY: MISC_FEATURE
<222> LOCATION: (2)..(2)
<223> OTHER INFORMATION: X is 2,4-dichloro-phenylalanine
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 185

Pro Xaa Xaa Leu Asp Thr
1               5

<210> SEQ ID NO 186
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-phenyl-D-phenylalanine
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 186

Pro Xaa Xaa Leu Asp Thr
1               5

<210> SEQ ID NO 187
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(5-quinolinyl)-D-phenylalanine
<220> FEATURE:
<221> NAME/KEY: MISC_FEATURE
<222> LOCATION: (3)..(3)
<223> OTHER INFORMATION: X is D-pipecolic acid, D-homoPro

<400> SEQUENCE: 187

Pro Xaa Xaa Leu Asp Thr
1               5

<210> SEQ ID NO 188
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-homolysine

<400> SEQUENCE: 188

Pro Tyr Xaa Leu Asp Thr
1               5

<210> SEQ ID NO 189
<211> LENGTH: 6
<212> TYPE: PRT
<213> ORGANISM: Artificial Sequence
```

```
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-homoproline

<400> SEQUENCE: 189

Pro Tyr Xaa Leu Asp Thr
1               5

<210> SEQ ID NO 190
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-homolysine

<400> SEQUENCE: 190

Pro Tyr Xaa Leu Asp Thr
1               5

<210> SEQ ID NO 191
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is anthranilic acid, 2-aminobenzoic acid

<400> SEQUENCE: 191

Pro Tyr Xaa Leu Asp Thr
1               5

<210> SEQ ID NO 192
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-homolysine

<400> SEQUENCE: 192

Pro Phe Xaa Leu Asp Thr
1               5

<210> SEQ ID NO 193
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-thiazolyl)-alanine
<220> FEATURE:
<221> NAME/KEY: MISC_FEATURE
<222> LOCATION: (3)..(3)
<223> OTHER INFORMATION: X is beta-homolysine
```

```
<400> SEQUENCE: 193

Pro Xaa Xaa Leu Asp Thr
1               5

<210> SEQ ID NO 194
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 194

Pro Xaa Xaa Leu Asp Thr
1               5

<210> SEQ ID NO 195
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-homolysine
<220> FEATURE:
<221> NAME/KEY: MISC_FEATURE
<222> LOCATION: (6)..(6)
<223> OTHER INFORMATION: X is O-benzyl-threonine

<400> SEQUENCE: 195

Pro Tyr Xaa Leu Asp Xaa
1               5

<210> SEQ ID NO 196
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is N-methyl tyrosine
<220> FEATURE:
<221> NAME/KEY: MISC_FEATURE
<222> LOCATION: (3)..(3)
<223> OTHER INFORMATION: X is D-beta-homolysine

<400> SEQUENCE: 196

Pro Xaa Xaa Leu Asp Thr
1               5

<210> SEQ ID NO 197
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 1-napthylalanine
```

```
<220> FEATURE:
<221> NAME/KEY: MISC_FEATURE
<222> LOCATION: (3)..(3)
<223> OTHER INFORMATION: X is beta-homolysine

<400> SEQUENCE: 197

Pro Xaa Xaa Leu Asp Thr
1               5

<210> SEQ ID NO 198
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-napthylalanine
<220> FEATURE:
<221> NAME/KEY: MISC_FEATURE
<222> LOCATION: (3)..(3)
<223> OTHER INFORMATION: X is beta-homolysine

<400> SEQUENCE: 198

Pro Xaa Xaa Leu Asp Thr
1               5

<210> SEQ ID NO 199
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is biphenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 199

Pro Xaa Xaa Leu Asp Thr
1               5

<210> SEQ ID NO 200
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-iodo-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 200

Pro Xaa Xaa Leu Asp Thr
1               5

<210> SEQ ID NO 201
<211> LENGTH: 6
<212> TYPE: PRT
<213> ORGANISM: Artificial Sequence
<220> FEATURE:
```

```
<223> OTHER INFORMATION: peptide motif
<220> FEATURE:
<221> NAME/KEY: MISC_FEATURE
<222> LOCATION: (2)..(2)
<223> OTHER INFORMATION: X is 2-(2,5-dimethyl-isoxazole)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 201

Pro Xaa Xaa Leu Asp Thr
1               5

<210> SEQ ID NO 202
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-phenyl-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 202

Pro Xaa Xaa Leu Asp Thr
1               5

<210> SEQ ID NO 203
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is (2-piperazinyl-2-phenyl)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 203

Pro Xaa Xaa Leu Asp Thr
1               5

<210> SEQ ID NO 204
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is beta-cyclohexyl alanine, (S)-2-amino-3-
      cyclohexylpropionic acid
<220> FEATURE:
<221> NAME/KEY: MISC_FEATURE
<222> LOCATION: (3)..(3)
<223> OTHER INFORMATION: X is beta-homolysine

<400> SEQUENCE: 204

Pro Xaa Xaa Leu Asp Thr
1               5
```

<210> SEQ ID NO 205
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-homolysine

<400> SEQUENCE: 205

Pro Trp Xaa Leu Asp Thr
1               5

<210> SEQ ID NO 206
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-tryptophan
<220> FEATURE:
<221> NAME/KEY: MISC_FEATURE
<222> LOCATION: (3)..(3)
<223> OTHER INFORMATION: X is beta-homolysine

<400> SEQUENCE: 206

Pro Xaa Xaa Leu Asp Thr
1               5

<210> SEQ ID NO 207
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 207

Pro Xaa Xaa Leu Asp Thr
1               5

<210> SEQ ID NO 208
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-D-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 208

Pro Xaa Xaa Leu Asp Thr
1               5

```
<210> SEQ ID NO 209
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 209

Pro Xaa Xaa Leu Asp Ile
1               5

<210> SEQ ID NO 210
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-D-homolysine

<400> SEQUENCE: 210

Pro Tyr Xaa Leu Asp Ile
1               5

<210> SEQ ID NO 211
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-arginine
<220> FEATURE:
<221> NAME/KEY: MISC_FEATURE
<222> LOCATION: (3)..(3)
<223> OTHER INFORMATION: X is beta-homolysine

<400> SEQUENCE: 211

Pro Xaa Xaa Leu Asp Thr
1               5

<210> SEQ ID NO 212
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-phenylalanine-reduced
<220> FEATURE:
<221> NAME/KEY: MISC_FEATURE
<222> LOCATION: (3)..(3)
<223> OTHER INFORMATION: X is beta-homolysine

<400> SEQUENCE: 212

Pro Xaa Xaa Leu Asp Thr
```

```
1               5
```

<210> SEQ ID NO 213
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-thiazolyl)-alanine
<220> FEATURE:
<221> NAME/KEY: MISC_FEATURE
<222> LOCATION: (3)..(3)
<223> OTHER INFORMATION: X is beta-D-homolysine

<400> SEQUENCE: 213

```
Pro Xaa Xaa Leu Asp Ile
1               5
```

<210> SEQ ID NO 214
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-D-homolysine

<400> SEQUENCE: 214

```
Pro Phe Xaa Leu Asp Ile
1               5
```

<210> SEQ ID NO 215
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-thiazolyl)-alanine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 215

```
Pro Xaa Xaa Leu Asp Thr
1               5
```

<210> SEQ ID NO 216
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-phenylalanine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 216

Pro Xaa Xaa Leu Asp Thr
1               5

<210> SEQ ID NO 217
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-thiazolyl)-alanine
<220> FEATURE:
<221> NAME/KEY: MISC_FEATURE
<222> LOCATION: (3)..(3)
<223> OTHER INFORMATION: X is beta-homolysine

<400> SEQUENCE: 217

Pro Xaa Xaa Leu Asp Ile
1               5

<210> SEQ ID NO 218
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is (3S)-1,2,3,4-tetrahydroisoquinoline-3-
      carboxylic acid
<220> FEATURE:
<221> NAME/KEY: MISC_FEATURE
<222> LOCATION: (3)..(3)
<223> OTHER INFORMATION: X is beta-homolysine

<400> SEQUENCE: 218

Pro Xaa Xaa Leu Asp Thr
1               5

<210> SEQ ID NO 219
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is (3R)-1,2,3,4-tetrahydroisoquinoline-3-
      carboxylic acid
<220> FEATURE:
<221> NAME/KEY: MISC_FEATURE
<222> LOCATION: (3)..(3)
<223> OTHER INFORMATION: X is beta-homolysine

<400> SEQUENCE: 219

Pro Xaa Xaa Leu Asp Thr
1               5

<210> SEQ ID NO 220
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is (3R)-1,2,3,4-tetrahydroisoquinoline-3-

```
                    carboxylic acid
<220> FEATURE:
<221> NAME/KEY: MISC_FEATURE
<222> LOCATION: (3)..(3)
<223> OTHER INFORMATION: X is beta-D-homolysine

<400> SEQUENCE: 220

Pro Xaa Xaa Leu Asp Thr
1               5

<210> SEQ ID NO 221
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-homoisoleucine

<400> SEQUENCE: 221

Pro Tyr Xaa Leu Asp Thr
1               5

<210> SEQ ID NO 222
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-phenylalanine
<220> FEATURE:
<221> NAME/KEY: MISC_FEATURE
<222> LOCATION: (3)..(3)
<223> OTHER INFORMATION: X is beta-homoproline

<400> SEQUENCE: 222

Pro Xaa Xaa Leu Asp Thr
1               5

<210> SEQ ID NO 223
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-D-homoproline

<400> SEQUENCE: 223

Pro Tyr Xaa Leu Asp Thr
1               5

<210> SEQ ID NO 224
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-phenylalanine
<220> FEATURE:
<221> NAME/KEY: MISC_FEATURE
```

```
<222> LOCATION: (3)..(3)
<223> OTHER INFORMATION: X is beta-D-homoproline

<400> SEQUENCE: 224

Pro Xaa Xaa Leu Asp Thr
1               5

<210> SEQ ID NO 225
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-homolysine

<400> SEQUENCE: 225

Pro Arg Xaa Leu Asp Thr
1               5

<210> SEQ ID NO 226
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 226

Pro Phe Xaa Leu Asp Thr
1               5

<210> SEQ ID NO 227
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is phenlyalanine-reduced
<220> FEATURE:
<221> NAME/KEY: MISC_FEATURE
<222> LOCATION: (3)..(3)
<223> OTHER INFORMATION: X is beta-homolysine

<400> SEQUENCE: 227

Pro Xaa Xaa Leu Asp Thr
1               5

<210> SEQ ID NO 228
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-D-phenylalanine
<220> FEATURE:
<221> NAME/KEY: MISC_FEATURE
<222> LOCATION: (3)..(3)
<223> OTHER INFORMATION: X is beta-homolysine
```

<400> SEQUENCE: 228

Pro Xaa Xaa Leu Asp Thr
1               5

<210> SEQ ID NO 229
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is {2-[3-(1-piperazinyl)phenyl]-
      phenylalanine}-beta-homolysine
<220> FEATURE:
<221> NAME/KEY: MISC_FEATURE
<222> LOCATION: (3)..(3)
<223> OTHER INFORMATION: X is beta-homolysine

<400> SEQUENCE: 229

Pro Xaa Xaa Leu Asp Thr
1               5

<210> SEQ ID NO 230
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-thiazolyl)-D-alanine
<220> FEATURE:
<221> NAME/KEY: MISC_FEATURE
<222> LOCATION: (3)..(3)
<223> OTHER INFORMATION: X is beta-homolysine

<400> SEQUENCE: 230

Pro Xaa Xaa Leu Asp Thr
1               5

<210> SEQ ID NO 231
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-bromo-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 231

Pro Xaa Xaa Leu Asp Thr
1               5

<210> SEQ ID NO 232
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)

```
<223> OTHER INFORMATION: X is 2-chloro-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 232

Pro Xaa Xaa Leu Asp Thr
1               5

<210> SEQ ID NO 233
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-fluoro-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 233

Pro Xaa Xaa Leu Asp Thr
1               5

<210> SEQ ID NO 234
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-trifluoromethyl-phenlyalanine
<220> FEATURE:
<221> NAME/KEY: MISC_FEATURE
<222> LOCATION: (3)..(3)
<223> OTHER INFORMATION: X is beta-homolysine

<400> SEQUENCE: 234

Pro Xaa Xaa Leu Asp Thr
1               5

<210> SEQ ID NO 235
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2,4-dichloro-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 235

Pro Xaa Xaa Leu Asp Thr
1               5

<210> SEQ ID NO 236
<211> LENGTH: 6
<212> TYPE: PRT
<213> ORGANISM: Artificial Sequence
```

```
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-aminomethyl-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 236

Pro Xaa Xaa Leu Asp Thr
1               5

<210> SEQ ID NO 237
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(4-quinolinyl)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 237

Pro Xaa Xaa Leu Asp Thr
1               5

<210> SEQ ID NO 238
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(5-quinolinyl)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 238

Pro Xaa Xaa Leu Asp Thr
1               5

<210> SEQ ID NO 239
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(3-quinolinyl)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 239

Pro Xaa Xaa Leu Asp Thr
1               5
```

```
<210> SEQ ID NO 240
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-homophenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 240

Pro Xaa Xaa Leu Asp Thr
1               5

<210> SEQ ID NO 241
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-iodo-D-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 241

Pro Xaa Xaa Leu Asp Thr
1               5

<210> SEQ ID NO 242
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-phenyl-D-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 242

Pro Xaa Xaa Leu Asp Thr
1               5

<210> SEQ ID NO 243
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is (2-piperazinyl-2-phenyl)-D-phenylalanine
<220> FEATURE:
<221> NAME/KEY: MISC_FEATURE
<222> LOCATION: (3)..(3)
<223> OTHER INFORMATION: X is beta-homolysine
```

```
<400> SEQUENCE: 243

Pro Xaa Xaa Leu Asp Thr
1               5

<210> SEQ ID NO 244
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-homolysine

<400> SEQUENCE: 244

Pro Tyr Xaa Leu Asp Ile
1               5

<210> SEQ ID NO 245
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-homolysine

<400> SEQUENCE: 245

Pro Tyr Xaa Leu Asp Val
1               5

<210> SEQ ID NO 246
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-tyrosine
<220> FEATURE:
<221> NAME/KEY: MISC_FEATURE
<222> LOCATION: (3)..(3)
<223> OTHER INFORMATION: X is beta-homolysine

<400> SEQUENCE: 246

Pro Xaa Xaa Leu Asp Ile
1               5

<210> SEQ ID NO 247
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-D-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 247

Pro Xaa Xaa Leu Asp Ile
```

```
1               5
```

<210> SEQ ID NO 248
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 248

```
Pro Xaa Xaa Leu Asp Val
1               5
```

<210> SEQ ID NO 249
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-iodo-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 249

```
Pro Xaa Xaa Leu Asp Thr
1               5
```

<210> SEQ ID NO 250
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-phenyl-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 250

```
Pro Xaa Xaa Leu Asp Thr
1               5
```

<210> SEQ ID NO 251
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(2-methoxy-phenyl)-phenylalanine
<220> FEATURE:
<221> NAME/KEY: MISC_FEATURE
<222> LOCATION: (3)..(3)

<223> OTHER INFORMATION: X is beta-homolysine

<400> SEQUENCE: 251

Pro Xaa Xaa Leu Asp Thr
1               5

<210> SEQ ID NO 252
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(2,6-dimthoxy-phenyl)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 252

Pro Xaa Xaa Leu Asp Thr
1               5

<210> SEQ ID NO 253
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(2-trifluoromethoxy-phenyl)-
      phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 253

Pro Xaa Xaa Leu Asp Thr
1               5

<210> SEQ ID NO 254
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-iodo-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 254

Pro Xaa Xaa Leu Asp Thr
1               5

<210> SEQ ID NO 255
<211> LENGTH: 6
<212> TYPE: PRT
<213> ORGANISM: Artificial Sequence
<220> FEATURE:
<223> OTHER INFORMATION: peptide motif
<220> FEATURE:

```
<221> NAME/KEY: MISC_FEATURE
<222> LOCATION: (2)..(2)
<223> OTHER INFORMATION: X is 4-(2-methoxy-phenyl)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 255

Pro Xaa Xaa Leu Asp Thr
1               5

<210> SEQ ID NO 256
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-(2-trifluoromethoxy-phenyl)-
      phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 256

Pro Xaa Xaa Leu Asp Thr
1               5

<210> SEQ ID NO 257
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is alpha-methyl-phenylalanine,
      (S)-(-)-2-amino-2-methyl-3-phenylpropionic acid
<220> FEATURE:
<221> NAME/KEY: MISC_FEATURE
<222> LOCATION: (3)..(3)
<223> OTHER INFORMATION: X is beta-homolysine

<400> SEQUENCE: 257

Pro Xaa Xaa Leu Asp Thr
1               5

<210> SEQ ID NO 258
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is N-methyl phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 258

Pro Xaa Xaa Leu Asp Thr
1               5
```

-continued

```
<210> SEQ ID NO 259
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(2,6-dimethyl-phenyl)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 259

Pro Xaa Xaa Leu Asp Thr
1               5

<210> SEQ ID NO 260
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(quinolin-4-yl)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 260

Pro Xaa Xaa Leu Asp Thr
1               5

<210> SEQ ID NO 261
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(3,4-difluoro-phenyl)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 261

Pro Xaa Xaa Leu Asp Thr
1               5

<210> SEQ ID NO 262
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-(2,6-dimethyl-phenyl)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 262
```

```
Pro Xaa Xaa Leu Asp Thr
1               5

<210> SEQ ID NO 263
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-(2-chloro-6-methoxy-phenyl)-
      phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 263

Pro Xaa Xaa Leu Asp Thr
1               5

<210> SEQ ID NO 264
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-thiazolyl)-alanine
<220> FEATURE:
<221> NAME/KEY: MISC_FEATURE
<222> LOCATION: (3)..(3)
<223> OTHER INFORMATION: X is beta-homolysine

<400> SEQUENCE: 264

Pro Xaa Xaa Leu Asp Thr
1               5

<210> SEQ ID NO 265
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(4-[1-piperazinyl)phenyl]-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 265

Pro Xaa Xaa Leu Asp Thr
1               5

<210> SEQ ID NO 266
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(2,6-dimethylphenyl)-phenylalanine
```

```
<220> FEATURE:
<221> NAME/KEY: MISC_FEATURE
<222> LOCATION: (3)..(3)
<223> OTHER INFORMATION: X is beta-homolysine

<400> SEQUENCE: 266

Pro Xaa Xaa Leu Asp Thr
1               5

<210> SEQ ID NO 267
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(benzolthiazol-5-yl)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 267

Pro Xaa Xaa Leu Asp Thr
1               5

<210> SEQ ID NO 268
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is homophenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 268

Pro Xaa Xaa Leu Asp Thr
1               5

<210> SEQ ID NO 269
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is piperidine-4-amino-4-carboxylic acid
<220> FEATURE:
<221> NAME/KEY: MISC_FEATURE
<222> LOCATION: (3)..(3)
<223> OTHER INFORMATION: X is beta-homolysine

<400> SEQUENCE: 269

Pro Xaa Xaa Leu Asp Thr
1               5

<210> SEQ ID NO 270
<211> LENGTH: 6
<212> TYPE: PRT
<213> ORGANISM: Artificial Sequence
<220> FEATURE:
```

```
<223> OTHER INFORMATION: peptide motif
<220> FEATURE:
<221> NAME/KEY: MISC_FEATURE
<222> LOCATION: (2)..(2)
<223> OTHER INFORMATION: X is 2-(2,5-dimethyl-isoxazole)-D-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 270

Pro Xaa Xaa Leu Asp Thr
1               5

<210> SEQ ID NO 271
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-tyrosine
<220> FEATURE:
<221> NAME/KEY: MISC_FEATURE
<222> LOCATION: (3)..(3)
<223> OTHER INFORMATION: X is beta-homolysine

<400> SEQUENCE: 271

Pro Xaa Xaa Leu Asp Val
1               5

<210> SEQ ID NO 272
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-D-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 272

Pro Xaa Xaa Leu Asp Thr
1               5

<210> SEQ ID NO 273
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(2-chloro-6-methoxyphenyl)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 273

Pro Xaa Xaa Leu Asp Thr
1               5
```

```
<210> SEQ ID NO 274
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-indanylglycine
<220> FEATURE:
<221> NAME/KEY: MISC_FEATURE
<222> LOCATION: (3)..(3)
<223> OTHER INFORMATION: X is beta-homolysine

<400> SEQUENCE: 274

Pro Xaa Xaa Leu Asp Thr
1               5

<210> SEQ ID NO 275
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-indanyl-D-glycine
<220> FEATURE:
<221> NAME/KEY: MISC_FEATURE
<222> LOCATION: (3)..(3)
<223> OTHER INFORMATION: X is beta-homolysine

<400> SEQUENCE: 275

Pro Xaa Xaa Leu Asp Thr
1               5

<210> SEQ ID NO 276
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-aminotetraline-2-carboxylic acid
<220> FEATURE:
<221> NAME/KEY: MISC_FEATURE
<222> LOCATION: (3)..(3)
<223> OTHER INFORMATION: X is beta-homolysine

<400> SEQUENCE: 276

Pro Xaa Xaa Leu Asp Thr
1               5

<210> SEQ ID NO 277
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-homolysine
<220> FEATURE:
<221> NAME/KEY: MISC_FEATURE
<222> LOCATION: (6)..(6)
<223> OTHER INFORMATION: X is allo-isoleucine, (2S,3R)-2-amino-3-
      methylpentanoic acid
```

```
<400> SEQUENCE: 277

Pro Tyr Xaa Leu Asp Xaa
1               5

<210> SEQ ID NO 278
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-tyrosine
<220> FEATURE:
<221> NAME/KEY: MISC_FEATURE
<222> LOCATION: (3)..(3)
<223> OTHER INFORMATION: X is beta-homolysine
<220> FEATURE:
<221> NAME/KEY: MISC_FEATURE
<222> LOCATION: (6)..(6)
<223> OTHER INFORMATION: X is allo-isoleucine, (2S,3R)-2-amino-3-
      methylpentanoic acid

<400> SEQUENCE: 278

Pro Xaa Xaa Leu Asp Xaa
1               5

<210> SEQ ID NO 279
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 4-aminomethyl-phenylalanine
<220> FEATURE:
<221> NAME/KEY: MISC_FEATURE
<222> LOCATION: (3)..(3)
<223> OTHER INFORMATION: X is beta-homolysine
<220> FEATURE:
<221> NAME/KEY: MISC_FEATURE
<222> LOCATION: (6)..(6)
<223> OTHER INFORMATION: X is allo-isoleucine, (2S,3R)-2-amino-3-
      methylpentanoic acid

<400> SEQUENCE: 279

Pro Xaa Xaa Leu Asp Xaa
1               5

<210> SEQ ID NO 280
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(2,5-bis(trifluoromethyl)phenyl)-
      phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 280

Pro Xaa Xaa Leu Asp Thr
1               5
```

<210> SEQ ID NO 281
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(2,5-bis(trifluoromethyl)phenyl)-
      phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 281

Pro Xaa Xaa Leu Asp Thr
1               5

<210> SEQ ID NO 282
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is aminoindan-2-carboxylic acid
<220> FEATURE:
<221> NAME/KEY: MISC_FEATURE
<222> LOCATION: (3)..(3)
<223> OTHER INFORMATION: beta-homolysine

<400> SEQUENCE: 282

Pro Xaa Xaa Leu Asp Thr
1               5

<210> SEQ ID NO 283
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-homolysine

<400> SEQUENCE: 283

Pro Pro Xaa Leu Asp Thr
1               5

<210> SEQ ID NO 284
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is D-proline
<220> FEATURE:
<221> NAME/KEY: MISC_FEATURE
<222> LOCATION: (3)..(3)
<223> OTHER INFORMATION: X is beta-homolysine

<400> SEQUENCE: 284

Pro Xaa Xaa Leu Asp Thr

```
<210> SEQ ID NO 285
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is pipecolic acid, homoPro
<220> FEATURE:
<221> NAME/KEY: MISC_FEATURE
<222> LOCATION: (3)..(3)
<223> OTHER INFORMATION: X is beta-homolysine

<400> SEQUENCE: 285

Pro Xaa Xaa Leu Asp Thr
1               5

<210> SEQ ID NO 286
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(3-pyridyl)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 286

Pro Xaa Xaa Leu Asp Thr
1               5

<210> SEQ ID NO 287
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(4-pyridyl)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 287

Pro Xaa Xaa Leu Asp Thr
1               5

<210> SEQ ID NO 288
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: 2-(3-bromo-2-pyridyl)-phenylalanine
<220> FEATURE:
<221> NAME/KEY: MISC_FEATURE
<222> LOCATION: (3)..(3)
```

```
<223> OTHER INFORMATION: beta-homolysine

<400> SEQUENCE: 288

Pro Xaa Xaa Leu Asp Thr
1               5

<210> SEQ ID NO 289
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-D-homolysine

<400> SEQUENCE: 289

Pro Tyr Xaa Leu Asp Thr
1               5

<210> SEQ ID NO 290
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is N-benzyl-glycine
<220> FEATURE:
<221> NAME/KEY: MISC_FEATURE
<222> LOCATION: (3)..(3)
<223> OTHER INFORMATION: X is beta-homolysine

<400> SEQUENCE: 290

Pro Xaa Xaa Leu Asp Thr
1               5

<210> SEQ ID NO 291
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(2-bromo-3-pyridyl)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 291

Pro Xaa Xaa Leu Asp Thr
1               5

<210> SEQ ID NO 292
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(2-chloro-6-methoxy-phenyl)-
      phenylalanine
<220> FEATURE:
```

```
<221> NAME/KEY: MISC_FEATURE
<222> LOCATION: (3)..(3)
<223> OTHER INFORMATION: X is beta-homolysine

<400> SEQUENCE: 292

Pro Xaa Xaa Leu Asp Thr
1               5

<210> SEQ ID NO 293
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(benzothiazol-5-yl)-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 293

Pro Xaa Xaa Leu Asp Thr
1               5

<210> SEQ ID NO 294
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-aminomethyl-phenylalanine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 294

Pro Xaa Xaa Leu Asp Thr
1               5

<210> SEQ ID NO 295
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-aminomethyl-D-phenylalanine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 295

Pro Xaa Xaa Leu Asp Thr
1               5

<210> SEQ ID NO 296
<211> LENGTH: 6
<212> TYPE: PRT
<213> ORGANISM: Artificial Sequence
<220> FEATURE:
<223> OTHER INFORMATION: peptide motif
```

```
<220> FEATURE:
<221> NAME/KEY: MISC_FEATURE
<222> LOCATION: (2)..(2)
<223> OTHER INFORMATION: X is 3-(4-thiazolyl)-D-alanine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 296

Pro Xaa Xaa Leu Asp Thr
1               5

<210> SEQ ID NO 297
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(2-trifluoromethoxy-phenyl)-D-
      phenylalanine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 297

Pro Xaa Xaa Leu Asp Thr
1               5

<210> SEQ ID NO 298
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is (3S)-1,2,3,4-tetrahydroisoquinoline-3-
      carboxylic acid
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 298

Pro Xaa Xaa Leu Asp Thr
1               5

<210> SEQ ID NO 299
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is (3R)-1,2,3,4-tetrahydroisoquinoline-3-
      carboxylic acid
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 299

Pro Xaa Xaa Leu Asp Thr
1               5
```

```
<210> SEQ ID NO 300
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(5-quinolinyl)-D-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 300

Pro Xaa Xaa Leu Asp Thr
1               5

<210> SEQ ID NO 301
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is beta-homolysine
<220> FEATURE:
<221> NAME/KEY: MISC_FEATURE
<222> LOCATION: (6)..(6)
<223> OTHER INFORMATION: X is allo-threonine, (2S,3S)-2-amino-3-
      hydroxybutyric acid

<400> SEQUENCE: 301

Pro Tyr Xaa Leu Asp Xaa
1               5

<210> SEQ ID NO 302
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is N-methyl beta-homoLysine
<220> FEATURE:
<221> NAME/KEY: MISC_FEATURE
<222> LOCATION: (6)..(6)
<223> OTHER INFORMATION: X is allo-threonine, (2S,3S)-2-amino-3-
      hydroxybutyric acid

<400> SEQUENCE: 302

Pro Tyr Xaa Leu Asp Xaa
1               5

<210> SEQ ID NO 303
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is N-methyl tyrosine
<220> FEATURE:
<221> NAME/KEY: MISC_FEATURE
```

```
<222> LOCATION: (3)..(3)
<223> OTHER INFORMATION: X is N-methyl beta-homoLysine

<400> SEQUENCE: 303

Pro Xaa Xaa Leu Asp Thr
1               5

<210> SEQ ID NO 304
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is N-methyl tyrosine
<220> FEATURE:
<221> NAME/KEY: MISC_FEATURE
<222> LOCATION: (3)..(3)
<223> OTHER INFORMATION: X is N-methyl beta-homoLysine
<220> FEATURE:
<221> NAME/KEY: MISC_FEATURE
<222> LOCATION: (6)..(6)
<223> OTHER INFORMATION: X is allo-threonine, (2S,3S)-2-amino-3-
      hydroxybutyric acid

<400> SEQUENCE: 304

Pro Xaa Xaa Leu Asp Xaa
1               5

<210> SEQ ID NO 305
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is N-methyl phenylalanine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 305

Pro Xaa Xaa Leu Asp Thr
1               5

<210> SEQ ID NO 306
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-fluoro-phenylalanine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 306

Pro Xaa Xaa Leu Asp Thr
1               5

<210> SEQ ID NO 307
<211> LENGTH: 6
```

```
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-fluoro-N-methyl phenylalanine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 307

Pro Xaa Xaa Leu Asp Thr
1               5

<210> SEQ ID NO 308
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2,4-dichloro-phenylalanine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 308

Pro Xaa Xaa Leu Asp Thr
1               5

<210> SEQ ID NO 309
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2,4-dichloro-N-methyl phenylalanine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 309

Pro Xaa Xaa Leu Asp Thr
1               5

<210> SEQ ID NO 310
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-aminomethyl-N-methyl-phenylalanine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 310

Pro Xaa Xaa Leu Asp Thr
```

```
1               5
```

<210> SEQ ID NO 311
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(2,6-dimethoxy-phenyl)-D-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 311

```
Pro Xaa Xaa Leu Asp Thr
1               5
```

<210> SEQ ID NO 312
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(4-quinolinyl)-D-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 312

```
Pro Xaa Xaa Leu Asp Thr
1               5
```

<210> SEQ ID NO 313
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is beta-homolysine
<220> FEATURE:
<221> NAME/KEY: MISC_FEATURE
<222> LOCATION: (3)..(3)
<223> OTHER INFORMATION: X is azetidine-2-carboxylic acid

<400> SEQUENCE: 313

```
Pro Xaa Xaa Leu Asp Thr
1               5
```

<210> SEQ ID NO 314
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-phenyl-D-phenylalanine
<220> FEATURE:
<221> NAME/KEY: MISC_FEATURE
<222> LOCATION: (3)..(3)

<223> OTHER INFORMATION: X is beta-homolysine

<400> SEQUENCE: 314

Pro Xaa Xaa Leu Asp Thr
1               5

<210> SEQ ID NO 315
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(2-trifluoromethoxy-phenyl)-D-
      phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 315

Pro Xaa Xaa Leu Asp Thr
1               5

<210> SEQ ID NO 316
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-(2-methoxy-phenyl)-D-phenylalanine
<220> FEATURE:
<221> NAME/KEY: MISC_FEATURE
<222> LOCATION: (3)..(3)
<223> OTHER INFORMATION: X is beta-homolysine

<400> SEQUENCE: 316

Pro Xaa Xaa Leu Asp Thr
1               5

<210> SEQ ID NO 317
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(5-quinolinyl)-N-methyl-phenylalanine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 317

Pro Xaa Xaa Leu Asp Thr
1               5

<210> SEQ ID NO 318
<211> LENGTH: 6
<212> TYPE: PRT
<213> ORGANISM: Artificial Sequence
<220> FEATURE:
<223> OTHER INFORMATION: peptide motif
<220> FEATURE:

```
<221> NAME/KEY: MISC_FEATURE
<222> LOCATION: (3)..(3)
<223> OTHER INFORMATION: X is beta-homonorleucine

<400> SEQUENCE: 318

Pro Phe Xaa Leu Asp Thr
1               5

<210> SEQ ID NO 319
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is N-alpha-methyl-N-epsilon-dimethyl-beta-
      homoLysine

<400> SEQUENCE: 319

Pro Phe Xaa Leu Asp Thr
1               5

<210> SEQ ID NO 320
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is N-methyl phenylalanine
<220> FEATURE:
<221> NAME/KEY: MISC_FEATURE
<222> LOCATION: (3)..(3)
<223> OTHER INFORMATION: X is N-alpha-methyl-N-epsilon-dimethyl-beta-
      homoLysine

<400> SEQUENCE: 320

Pro Xaa Xaa Leu Asp Thr
1               5

<210> SEQ ID NO 321
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 321

Pro Met Xaa Leu Asp Thr
1               5

<210> SEQ ID NO 322
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-indanylglycine
<220> FEATURE:
<221> NAME/KEY: MISC_FEATURE
```

<222> LOCATION: (3)..(3)
<223> OTHER INFORMATION: X is N-methyl beta-homoLysine

<400> SEQUENCE: 322

Pro Xaa Xaa Leu Asp Thr
1               5

<210> SEQ ID NO 323
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is homophenylalanine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 323

Pro Xaa Xaa Leu Asp Thr
1               5

<210> SEQ ID NO 324
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is O-benzyl-trans-4-hydroxyproline
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 324

Pro Xaa Xaa Leu Asp Thr
1               5

<210> SEQ ID NO 325
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is cis-2-aminocyclohexanecarboxylic acid
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 325

Pro Xaa Xaa Leu Asp Thr
1               5

<210> SEQ ID NO 326
<211> LENGTH: 6
<212> TYPE: PRT
<213> ORGANISM: Artificial Sequence
<220> FEATURE:
<223> OTHER INFORMATION: peptide motif
<220> FEATURE:

```
<221> NAME/KEY: MISC_FEATURE
<222> LOCATION: (2)..(2)
<223> OTHER INFORMATION: X is N-methyl methionine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 326

Pro Xaa Xaa Leu Asp Thr
1               5

<210> SEQ ID NO 327
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is beta-homolysine
<220> FEATURE:
<221> NAME/KEY: MISC_FEATURE
<222> LOCATION: (3)..(3)
<223> OTHER INFORMATION: X is beta-homolysine

<400> SEQUENCE: 327

Pro Xaa Xaa Leu Asp Thr
1               5

<210> SEQ ID NO 328
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is beta-homophenylalanine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 328

Pro Xaa Xaa Leu Asp Thr
1               5

<210> SEQ ID NO 329
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is beta-homomethionine
<220> FEATURE:
<221> NAME/KEY: MISC_FEATURE
<222> LOCATION: (3)..(3)
<223> OTHER INFORMATION: X is N-methyl beta-homoLysine

<400> SEQUENCE: 329

Pro Xaa Xaa Leu Asp Thr
1               5

<210> SEQ ID NO 330
<211> LENGTH: 6
```

<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is 3-aminomethyl-4-bromo-benzoic acid

<400> SEQUENCE: 330

Pro Tyr Xaa Leu Asp Thr
1               5

<210> SEQ ID NO 331
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is 3-aminomethyl-4-(4-aza-phenyl)-benzoic
      acid

<400> SEQUENCE: 331

Pro Tyr Xaa Leu Asp Thr
1               5

<210> SEQ ID NO 332
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is 3-aminomethyl-4-(2,5-dimethyl-isoxazole)-
      benzoic acid

<400> SEQUENCE: 332

Pro Tyr Xaa Leu Asp Thr
1               5

<210> SEQ ID NO 333
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (3)..(3)
<223> OTHER INFORMATION: X is 3-aminomethyl-4-(3-aminomethyl-phenyl)-
      benzoic acid

<400> SEQUENCE: 333

Pro Tyr Xaa Leu Asp Thr
1               5

<210> SEQ ID NO 334
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(4-(1-piperazinyl)- phenyl)-benzoic acid

<400> SEQUENCE: 334

Pro Xaa Leu Asp Thr
1               5

<210> SEQ ID NO 335
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(4-quinolinyl)-benzoic
    acid

<400> SEQUENCE: 335

Pro Xaa Leu Asp Thr
1               5

<210> SEQ ID NO 336
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-bromo-benzoic acid

<400> SEQUENCE: 336

Pro Xaa Leu Asp Thr
1               5

<210> SEQ ID NO 337
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(2,5-dimethyl-isoxazole)-
    benzoic acid

<400> SEQUENCE: 337

Pro Xaa Leu Asp Thr
1               5

<210> SEQ ID NO 338
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (1)..(1)
<223> OTHER INFORMATION: X is D-proline
<220> FEATURE:
<221> NAME/KEY: MISC_FEATURE
<222> LOCATION: (2)..(2)
<223> OTHER INFORMATION: X is 3-aminomethyl-4-(4-pyridyl)-benzoic acid

<400> SEQUENCE: 338

Xaa Xaa Leu Asp Thr 1               5

<210> SEQ ID NO 339
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-(4-methylpyrazole-3-yl)-
      benzoic acid

<400> SEQUENCE: 339

Pro Xaa Leu Asp Thr
1               5

<210> SEQ ID NO 340
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(3-quinolinyl)-benzoic
      acid

<400> SEQUENCE: 340

Pro Xaa Leu Asp Thr
1               5

<210> SEQ ID NO 341
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(5-quinolinyl)-benzoic
      acid

<400> SEQUENCE: 341

Pro Xaa Leu Asp Thr
1               5

<210> SEQ ID NO 342
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(2-(1-
      piperazinyl)phenyl)-benzoic acid

<400> SEQUENCE: 342

Pro Xaa Leu Asp Thr
1               5

<210> SEQ ID NO 343
<211> LENGTH: 5
<212> TYPE: PRT
<213> ORGANISM: Artificial Sequence

```
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(3-(1-
      piperzainyl)phenyl)-benzoic acid

<400> SEQUENCE: 343

Pro Xaa Leu Asp Thr
1               5

<210> SEQ ID NO 344
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is
      3-aminomethyl-4-(2-(3-(piperidin-4-ylmethoxy)phenyl))-benzoic
      acid

<400> SEQUENCE: 344

Pro Xaa Leu Asp Thr
1               5

<210> SEQ ID NO 345
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(4-pyridyl)-benzoic acid

<400> SEQUENCE: 345

Pro Xaa Leu Asp Thr
1               5

<210> SEQ ID NO 346
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(4-pyridyl)-benzoic acid
<220> FEATURE:
<221> NAME/KEY: MISC_FEATURE
<222> LOCATION: (5)..(5)
<223> OTHER INFORMATION: X is O-benzyl-threonine

<400> SEQUENCE: 346

Pro Xaa Leu Asp Xaa
1               5

<210> SEQ ID NO 347
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
```

```
<222> LOCATION: (2)..(2)
<223> OTHER INFORMATION: X is 3-aminomethyl-4-(4-quinolinyl)-benzoic
      acid
<220> FEATURE:
<221> NAME/KEY: MISC_FEATURE
<222> LOCATION: (5)..(5)
<223> OTHER INFORMATION: X is allo-threonine, (2S,3S)-2-amino-3-
      hydroxybutyric acid

<400> SEQUENCE: 347

Pro Xaa Leu Asp Xaa
1               5

<210> SEQ ID NO 348
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(4-(1-
      piperazinyl)phenyl))-benzoic acid

<400> SEQUENCE: 348

Pro Xaa Leu Asp Thr
1               5

<210> SEQ ID NO 349
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(4-quinolinyl))-benzoic
      acid
<220> FEATURE:
<221> NAME/KEY: MISC_FEATURE
<222> LOCATION: (3)..(3)
<223> OTHER INFORMATION: X is beta-tert-butyl alanine, neopentylglycine

<400> SEQUENCE: 349

Pro Xaa Xaa Asp Thr
1               5

<210> SEQ ID NO 350
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is N-benzyl-3-aminomethyl-benzoic acid

<400> SEQUENCE: 350

Pro Xaa Leu Asp Thr
1               5

<210> SEQ ID NO 351
<211> LENGTH: 5
<212> TYPE: PRT
<213> ORGANISM: Artificial Sequence
<220> FEATURE:
<223> OTHER INFORMATION: peptide motif
<220> FEATURE:
```

```
<221> NAME/KEY: MISC_FEATURE
<222> LOCATION: (2)..(2)
<223> OTHER INFORMATION: X is 3-aminomethyl-benzoic acid

<400> SEQUENCE: 351

Pro Xaa Leu Asp Thr
1               5

<210> SEQ ID NO 352
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-5-bromo-benzoic acid

<400> SEQUENCE: 352

Pro Xaa Leu Asp Thr
1               5

<210> SEQ ID NO 353
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-6-bromo-benzoic acid

<400> SEQUENCE: 353

Pro Xaa Leu Asp Thr
1               5

<210> SEQ ID NO 354
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-5-(4-aza-phenyl)-benzoic
      acid

<400> SEQUENCE: 354

Pro Xaa Leu Asp Thr
1               5

<210> SEQ ID NO 355
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(3-thiophenyl)-benzoic
      acid

<400> SEQUENCE: 355

Pro Xaa Leu Asp Thr
1               5
```

```
<210> SEQ ID NO 356
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(4-N,N-dimethyl-
      carboxamide-phenyl)-benzoic acid

<400> SEQUENCE: 356

Pro Xaa Leu Asp Thr
1               5

<210> SEQ ID NO 357
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(4-aza-phenyl)-benzoic
      acid

<400> SEQUENCE: 357

Pro Xaa Leu Asp Thr
1               5

<210> SEQ ID NO 358
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(3-aza-phenyl)-benzoic
      acid

<400> SEQUENCE: 358

Pro Xaa Leu Asp Thr
1               5

<210> SEQ ID NO 359
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(4-hydroxy-phenyl)-
      benzoic acid

<400> SEQUENCE: 359

Pro Xaa Leu Asp Thr
1               5

<210> SEQ ID NO 360
<211> LENGTH: 5
<212> TYPE: PRT
<213> ORGANISM: Artificial Sequence
<220> FEATURE:
<223> OTHER INFORMATION: peptide motif
```

```
<220> FEATURE:
<221> NAME/KEY: MISC_FEATURE
<222> LOCATION: (2)..(2)
<223> OTHER INFORMATION: X is 3-aminomethyl-4-(5-(2,4-
      dimethyl)thiazole)-benzoic acid

<400> SEQUENCE: 360

Pro Xaa Leu Asp Thr
1               5

<210> SEQ ID NO 361
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(3-N,N-
      dimethylaniline)-benzoic acid

<400> SEQUENCE: 361

Pro Xaa Leu Asp Thr
1               5

<210> SEQ ID NO 362
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(2-fluoro-pyridyl)-benzoic
      acid

<400> SEQUENCE: 362

Pro Xaa Leu Asp Thr
1               5

<210> SEQ ID NO 363
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(5-pyrimidinyl)-benzoic
      acid

<400> SEQUENCE: 363

Pro Xaa Leu Asp Thr
1               5

<210> SEQ ID NO 364
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(3-N,N-dimethyl-
      diarylether)-benzoic acid

<400> SEQUENCE: 364
```

Pro Xaa Leu Asp Thr
1               5

<210> SEQ ID NO 365
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(3-trifluoromethyl-
      phenyl)-benzoic acid

<400> SEQUENCE: 365

Pro Xaa Leu Asp Thr
1               5

<210> SEQ ID NO 366
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(2,5-dimethoxy-phenyl)-
      benzoic acid

<400> SEQUENCE: 366

Pro Xaa Leu Asp Thr
1               5

<210> SEQ ID NO 367
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-((2,3,4-tri-methoxy)-
      phenyl)-benzoic acid

<400> SEQUENCE: 367

Pro Xaa Leu Asp Thr
1               5

<210> SEQ ID NO 368
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(4-carboxy)-phenyl-
      benzoic acid

<400> SEQUENCE: 368

Pro Xaa Leu Asp Thr
1               5

<210> SEQ ID NO 369
<211> LENGTH: 5

```
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-piperonyl-benzoic acid

<400> SEQUENCE: 369

Pro Xaa Leu Asp Thr
1               5

<210> SEQ ID NO 370
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-piperidinyl-benzoic acid

<400> SEQUENCE: 370

Pro Xaa Leu Asp Thr
1               5

<210> SEQ ID NO 371
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-morpholinyl-benzoic acid

<400> SEQUENCE: 371

Pro Xaa Leu Asp Thr
1               5

<210> SEQ ID NO 372
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(N,N-dimethyl)-benzoic
      acid

<400> SEQUENCE: 372

Pro Xaa Leu Asp Thr
1               5

<210> SEQ ID NO 373
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(2-aminomethylphenyl)-
      benzoic acid
```

```
<400> SEQUENCE: 373

Pro Xaa Leu Asp Thr
1               5

<210> SEQ ID NO 374
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(3-aminomethylphenyl)-
      benzoic acid

<400> SEQUENCE: 374

Pro Xaa Leu Asp Thr
1               5

<210> SEQ ID NO 375
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(4-aminomethylphenyl)-
      benzoic acid

<400> SEQUENCE: 375

Pro Xaa Leu Asp Thr
1               5

<210> SEQ ID NO 376
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 3-aminomethyl-4-(4-quinolinyl)-benzoic
      acid
<220> FEATURE:
<221> NAME/KEY: MISC_FEATURE
<222> LOCATION: (5)..(5)
<223> OTHER INFORMATION: X is 2-aminobutyric acid

<400> SEQUENCE: 376

Pro Xaa Leu Asp Xaa
1               5

<210> SEQ ID NO 377
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (1)..(1)
<223> OTHER INFORMATION: X is norvaline
<220> FEATURE:
<221> NAME/KEY: MISC_FEATURE
<222> LOCATION: (2)..(2)
<223> OTHER INFORMATION: X is 3-aminomethyl-4-(4-quinolinyl)-benzoic
      acid
```

```
<400> SEQUENCE: 377

Xaa Xaa Leu Asp Thr
1               5

<210> SEQ ID NO 378
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is N-methyl-3-aminomethyl-benzoic acid

<400> SEQUENCE: 378

Pro Xaa Leu Asp Thr
1               5

<210> SEQ ID NO 379
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is N-methyl-3-aminomethyl-4-(4-quinolinyl)-
      benzoic acid

<400> SEQUENCE: 379

Pro Xaa Leu Asp Thr
1               5

<210> SEQ ID NO 380
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (2)..(2)
<223> OTHER INFORMATION: X is 2-(5-quinolinyl)-phenylalanine-reduced
<220> FEATURE:
<221> NAME/KEY: MISC_FEATURE
<222> LOCATION: (3)..(3)
<223> OTHER INFORMATION: X is beta-homolysine

<400> SEQUENCE: 380

Pro Xaa Xaa Leu Asp Thr
1               5
```